US012473378B2

(12) United States Patent

Dowd et al.

(10) Patent No.: US 12,473,378 B2

(45) Date of Patent: Nov. 18, 2025

(54) ANTIGEN-BINDING MOLECULES COMPRISING UNPAIRED VARIABLE DOMAINS

(71) Applicant: Kymab Limited, Cambridge (GB)

(72) Inventors: Stephen Dowd, Cambridge (GB); Andrew Lindsay Wood, Cambridge (GB); E-Chiang Lee, Cambridge (GB); Hannah Linton Craig, Cambridge (GB); Allan Bradley, Cambridge (GB)

(73) Assignee: Kymab Limited, Cambridge (GB)

(*) Notice: Subject to any disclaimer, the term of this patent is extended or adjusted under 35 U.S.C. 154(b) by 1240 days.

(21) Appl. No.: 17/274,103

(22) PCT Filed: Sep. 5, 2019

(86) PCT No.: PCT/EP2019/073767

§ 371 (c)(1),
(2) Date: Mar. 5, 2021

(87) PCT Pub. No.: WO2020/049128

PCT Pub. Date: Mar. 12, 2020

(65) Prior Publication Data

US 2021/0395397 A1 Dec. 23, 2021

(30) Foreign Application Priority Data

Sep. 6, 2018 (GB) ...................................... 1814529

(51) Int. Cl.

*C07K 16/46* (2006.01)
*A01K 67/0278* (2024.01)
*C12N 15/85* (2006.01)

(52) U.S. Cl.

CPC ........ *C07K 16/461* (2013.01); *A01K 67/0278* (2013.01); *C12N 15/8509* (2013.01); *A01K 2207/15* (2013.01); *A01K 2217/072* (2013.01); *A01K 2217/15* (2013.01); *A01K 2227/105* (2013.01); *C07K 2317/51* (2013.01); *C07K 2317/64* (2013.01)

(58) Field of Classification Search

CPC .............. C07K 16/461; C07K 2317/51; C07K 2317/64; A01K 67/0278; A01K 2207/15; A01K 2217/072; A01K 2217/15; A01K 2227/105; C12N 15/8509

See application file for complete search history.

(56) References Cited

U.S. PATENT DOCUMENTS

| | | | |
|---|---|---|---|
| 2014/0206558 A1 | 7/2014 | Zdanovsky | |
| 2018/0051307 A1 | 2/2018 | Igawa et al. | |
| 2021/0054021 A1* | 2/2021 | Deak Codarri | C07K 16/3053 |

FOREIGN PATENT DOCUMENTS

| | | | | |
|---|---|---|---|---|
| EP | 2938725 | B1 * | 8/2017 | C07K 16/00 |
| WO | 199005144 | A1 | 5/1990 | |
| WO | 199203918 | A1 | 3/1992 | |
| WO | 199404678 | A1 | 3/1994 | |
| WO | 199634103 | A1 | 10/1996 | |
| WO | 2002085944 | A2 | 10/2002 | |
| WO | 2002085945 | A2 | 10/2002 | |
| WO | 2003000737 | A2 | 1/2003 | |
| WO | 2002085945 | A3 | 3/2003 | |
| WO | 2003047336 | A2 | 6/2003 | |
| WO | 2003000737 | A3 | 9/2003 | |
| WO | 2002085944 | A3 | 3/2004 | |
| WO | 2003047336 | A3 | 6/2004 | |
| WO | 2004049794 | A2 | 6/2004 | |
| WO | 2004049794 | A3 | 12/2004 | |
| WO | 2006008548 | A2 | 1/2006 | |
| WO | 2006008548 | A3 | 6/2006 | |
| WO | 2006106905 | A1 | 12/2006 | |
| WO | 2007085837 | A1 | 8/2007 | |
| WO | 2007095338 | A2 | 8/2007 | |
| WO | 2007110205 | A2 | 10/2007 | |
| WO | 2007110205 | A3 | 2/2008 | |

(Continued)

OTHER PUBLICATIONS

Shen et al. Single Variable Domain-IgG Fusion. A Novel Recombinant Approach To Fc Domain-Containing Bispecific Antibodies. The Journal of Biological Chemistry 2006, vol. 281, No. 16, pp. 10706-10714. (Year: 2006).*

Adachi, K. et al. (Apr. 2018, e-pub. Mar. 5, 2018). "IL-7 and CCL 19 Expression In CAR-T Cells Improves Immune Cell Infiltration and CAR-T Cell Survival In The Tumor," Nature Biotech. 36(4):346-351.

Aoki-Ota, M. et al. (2012). "Skewed Primary Igk Repertoire and V-J Joining In C57BL/6 Mice: Implications For Recombination Accessibility and Receptor Editing," J Immunol. 188(5):2305-2315.

Bankovich, A.J. et al. (Apr. 13, 2007). "Structural Insight Into Pre-B Cell Receptor Function," Science 316(5822):291-294.

(Continued)

*Primary Examiner* — Shafiqul Haq

(74) *Attorney, Agent, or Firm* — MORRISON & FOERSTER LLP

(57) ABSTRACT

Antibodies comprising unpaired variable domains, e.g., heavy chain variable (VH) domains, for binding antigen. Antibody comprising two immunoglobulin (Ig) chains, wherein a first Ig chain comprises a variable domain and a constant domain, and a second Ig chain comprises a constant domain, wherein the second Ig chain lacks a variable domain, leaving the variable domain of the first Ig chain unpaired. The antibody may comprise two Ig heavy chains and two Ig light chains, each heavy chain comprising a VH domain and a constant region comprising a CH1 domain, and each light chain comprising a CL domain, wherein one or both light chains lack a VL domain, thereby leaving one or both VH domains unpaired. Non-human animals (e.g., mice) engineered to produce antibodies having unpaired VH domains, involving deletion of sequence coding for light chain variable (VL) domains. Use of unpaired VH domains to generate antigen-binding molecules.

20 Claims, 28 Drawing Sheets

Specification includes a Sequence Listing.

(56) References Cited

FOREIGN PATENT DOCUMENTS

| | | | | |
|---|---|---|---|---|
| WO | 2007095338 | A3 | 4/2008 | |
| WO | 2009068649 | A2 | 6/2009 | |
| WO | 2009143472 | A2 | 11/2009 | |
| WO | 2009068649 | A3 | 2/2010 | |
| WO | 2009143472 | A3 | 3/2010 | |
| WO | 2010109165 | A2 | 9/2010 | |
| WO | 2010151792 | A1 | 12/2010 | |
| WO | 2011004192 | A1 | 1/2011 | |
| WO | 2010109165 | A3 | 2/2011 | |
| WO | 2011072204 | A1 | 6/2011 | |
| WO | 2011143545 | A1 | 11/2011 | |
| WO | 2012089814 | A1 | 7/2012 | |
| WO | 2013061078 | A1 | 5/2013 | |
| WO | 2013157954 | A1 | 10/2013 | |
| WO | 2013171505 | A2 | 11/2013 | |
| WO | 2013171505 | A3 | 1/2014 | |
| WO | 2014022540 | A1 | 2/2014 | |
| WO | WO-2015143414 | A2 * | 9/2015 | ......... A01K 67/0278 |
| WO | 2015143414 | A3 | 12/2015 | |
| WO | 2018038469 | A1 | 3/2018 | |
| WO | 2018039180 | A1 | 3/2018 | |
| WO | 2019018770 | A1 | 1/2019 | |
| WO | 2020049128 | A1 | 3/2020 | |

OTHER PUBLICATIONS

Boroviak, K. et al. (2016, e-pub. Jan. 25, 2016). "Chromosome Engineering in Zygotes With CRISPR/Cas9," Genesis 54(2):78-85.

Davis, J.H. et al. (2010, e-pub. Feb. 4, 2010). "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies," Protein Engineering Design & Selection 23(4):195-202.

Donohoe, M.E. et al. (May 15, 2000). "Transgenic Human λ5 Rescues The Murine] λ5 Nullizygous Phenotype," The Journal of Immunology 164(10):5269-5276.

Fang, T. et al. (2001). "Conventional and Surrogate Light Chains Differentially Regulated Igμ and Dμ Heavy Chain Maturation and Surface Expression," J Immunol 167:3846-3857.

Guloglu, F.B. et al. (2005). "The Unique Region of Surrogate Light Chain Component λ5 Is a Heavy Chain-Specific Regulator of Precursor B Cell Receptor Signaling," J Immunol 175:358-366.

International Preliminary Report on Patentability, issued Mar. 9, 2021, for PCT Application No. PCT/EP2019/073767, filed Sep. 5, 2019, 9 pages.

International Search Report and Written Opinion, mailed Dec. 17, 2019, for PCT Application No. PCT/EP2019/073767, filed Sep. 5, 2019, 14 pages.

Iri-Sofla, F.J. et al. (Nov. 1, 2011, e-pub. Aug. 28, 2011). "Nanobody-based Chimeric Receptor Gene Integration in Jurkat Cells Mediated by φC31 Integrase," Experimental Cell Research 317(18):2630-2641.

Jamnani, F.R. et al. (Jan. 2014, e-pub. Sep. 27, 2013). "T Cells Expressing VHH-Directed Oligoclonal Chimeric HER2 Antigen Receptors: Towards Tumor-Directed Oligoclonal T Cell Therapy," Biochim Biophys Acta, 1840(1):378-386.

Janssens, R. et al. (Oct. 10, 2006). "Generation Of Heavy-Chain-Only Antibodies In Mice," Proc. Natl. Acad. Sci. USA 103(41): 15130-15135.

Lee, E-C. et al. (Apr. 2014, e-pub. Mar. 16, 2014). "Complete Humanization Of The Mouse Immunoglobulin Loci Enables Efficient Therapeutic Antibody Discovery," Nature Biotechnology 32(4):356-363.

Melchers, F. et al. (Feb. 1993). "The Surrogate Light Chain In B-Cell Development," Immunol Today 14(2):60-68.

Minegishi, Y. et al. (Mar. 1990). "Novel Mechanisms Control The Folding and Assembly Of λ5/14.1 and VpreB To Produce An Intact Surrogate Light Chain," PNAS 96:3041-3046.

Mårtensson, A et al. (Mar. 1999). "Partial Block In B Lymphocyte Development At The Transition Into The Pre-B Cell Receptor Stage In Vpre-B1-Deficient Mice," Int Immunol 11(3):453-460.

Papavasilou, F. et al. (Nov. 1996). "Surrogate or Conventional Light Chains Are Required for Membrane Immunoglobulin Mu to Activate the Precursor B Cell Transition," J Exp Med 184:2025-2030.

Ridgway, J.B.B. et al. (1996). "'Knobs-Into-Holes' Engineering of Antibody CH3 Domains for Heavy Chain Heterodimerization," Protein Engineering 9(7):617-621.

Sabbattini, P. et al. (Apr. 2005). "The Λ5-VpreB1 Locus—A Model System For Studying Gene Regulation During Early B Cell Development," Seminars in Immunology 17(2):121-127.

Shields, R.L. et al. (Jul. 26, 2002, e-pub. May 1, 2002). "Lack of Fucose on Human IgG1 N-Linked Oligosaccharide Improves Binding to Human FcγRIll and Antibody-dependent Cellular Toxicity," J. Biol. Chem. 277(30):26733-26740.

* cited by examiner

| Primer name | Primer sequence | Primer orientation | Primer location/details |
|---|---|---|---|
| HCP428 | gctctggctcccaggaactg | Forward | truncated Kappa fragment, also amplifies C from full length mouse Kappa light chain |
| HCP431 | gtcctgctctgtgacactct | Reverse | Mouse C coding region |
| HCP446 | ttlgtgcaggagtcagacccag | Forward | Human V -5 5' UTR |
| HCP451 | aaaagggtcagaggccaaaggat | Reverse | Mouse C 3' UTR |

FIGURE 11

Hu λ fragment CDS

Hu λ fragment translated sequence

MDMRVPAQLLGLLLLWLPGAKCVFGSGTQLTVLSQPKATPSVTLFPPSSEELQANKATLVCLMNDFYPGILTVTWKADGT 80

Signal peptide

PITQGVEMTTPSKQSNNKYAASSYLSLTPEQWRSRRSYSCQVMHEGSTVEKTVAPAECS.

FIGURE 15 (continued)

Mouse Vκ3-2 fragment translated sequence

MEKDTLLLWVLLLWVPGSTGDIVLKRADAAPTVSIFPPSSEQLTSGGASVVCFLNNFYPKDINVKWKIDGSERQNGVLNS 80

Signal peptide

WTDQDSKDSTYGMSSTLTLTKDEYERHNSYTCEATHKTSTSPIVKSFNRNEC.

FIGURE 17 (continued)

Mouse Vκ3-4 fragment CDS

Mouse Vκ3-4 fragment translated sequence

METDTILLWVLLLWVPGSTGDIVLKRADAAPTVSIFPPSSEQLTSGGASVVCFLNNFYPKDINVKWKIDGSERQNGVLNS 80

Signal peptide

WTDQDSKDSTYGMSSTLTLTKDEYERHNSYTCEATHKTSTSPIVKSFNRNEC.

FIGURE 17 (continued)

Mouse Vκ3-2 fragment translated sequence

MEKDTLLLWVLLLWVPGSTGDIVLKRADAAPTVSIFPPSSEQLTSGGASVVCFLNNFYPKDINVKWKIDGSERQNGVLNS 80

Signal peptide

WTDQDSKDSTYGMSSTLTLTKDEYERHNSYTCEATHKTSTSPIVKSFNRNEC.

FIGURE 19 (continued)

Mouse Vκ3-4 fragment CDS

Mouse Vκ3-4 fragment translated sequence

```
METDTILLWVLLLWVPGSTGDIVLKRADAAPTVSIFPPSSEQLTSGGASVVCFLNNFYPKDINVKWKIDGSERQNGVLNS  80
[Signal peptide]

WTDQDSKDSTYGMSSTLTLTKDEYERHNSYTCEATHKTSTSPIVKSFNRNEC.
```

FIGURE 19 (continued)

SEQUENCE LISTING

<160> NUMBER OF SEQ ID NOS: 101

<210> SEQ ID NO 1
<211> LENGTH: 66
<212> TYPE: DNA
<213> ORGANISM: Artificial Sequence
<220> FEATURE:
<223> OTHER INFORMATION: Nucleic acid encoding Ck signal peptide

<400> SEQUENCE: 1
atggacatga gggtccccgc tcagctcctg gggctcctgc tgctctggct cccaggaact 60
gtggct 66

<210> SEQ ID NO 2
<211> LENGTH: 22
<212> TYPE: PRT
<213> ORGANISM: Artificial Sequence

```
<220> FEATURE:
<223> OTHER INFORMATION: Ck signal peptide

<400> SEQUENCE: 2

Met Asp Met Arg Val Pro Ala Gln Leu Leu Gly Leu Leu Leu Leu Trp
1               5                   10                  15

Leu Pro Gly Thr Val Ala
            20


<210> SEQ ID NO 3
<211> LENGTH: 311
<212> TYPE: DNA
<213> ORGANISM: Homo sapiens

<400> SEQUENCE: 3

gcaccatctg tcttcatctt cccgccatct gatgagcagt tgaaatctgg aactgcctct      60

gttgtgtgcc tgctgaataa cttctatccc agagaggcca aagtacagtg gaaggtggat     120

aacgccctcc aatcgggtaa ctcccaggag agtgtcacag agcaggacag caaggacagc     180

acctacagcc tcagcagcac cctgacgctg agcaaagcag actacgagaa acacaaagtc     240

tacgcctgcg aagtcaccca tcagggcctg agctcgcccg tcacaaagag cttcaacagg     300

ggagagtgtt a                                                          311


<210> SEQ ID NO 4
<211> LENGTH: 103
<212> TYPE: PRT
<213> ORGANISM: Homo sapiens

<400> SEQUENCE: 4

Ala Pro Ser Val Phe Ile Phe Pro Pro Ser Asp Glu Gln Leu Lys Ser
1               5                   10                  15

Gly Thr Ala Ser Val Val Cys Leu Leu Asn Asn Phe Tyr Pro Arg Glu
            20                  25                  30

Ala Lys Val Gln Trp Lys Val Asp Asn Ala Leu Gln Ser Gly Asn Ser
        35                  40                  45

Gln Glu Ser Val Thr Glu Gln Asp Ser Lys Asp Ser Thr Tyr Ser Leu
    50                  55                  60

Ser Ser Thr Leu Thr Leu Ser Lys Ala Asp Tyr Glu Lys His Lys Val
65                  70                  75                  80

Tyr Ala Cys Glu Val Thr His Gln Gly Leu Ser Ser Pro Val Thr Lys
                85                  90                  95

Ser Phe Asn Arg Gly Glu Cys
            100


<210> SEQ ID NO 5
<211> LENGTH: 377
<212> TYPE: DNA
<213> ORGANISM: Artificial Sequence
<220> FEATURE:
<223> OTHER INFORMATION: Nucleic acid encoding kvC fusion with signal
      peptide

<400> SEQUENCE: 5

atggacatga gggtccccgc tcagctcctg gggctcctgc tgctctggct cccaggaact      60

gtggctgcac catctgtctt catcttcccg ccatctgatg agcagttgaa atctggaact     120

gcctctgttg tgtgcctgct gaataacttc tatcccagag aggccaaagt acagtggaag     180

gtggataacg ccctccaatc gggtaactcc caggagagtg tcacagagca ggacagcaag     240
```

gacagcacct acagcctcag cagcaccctg acgctgagca aagcagacta cgagaaacac 300
aaagtctacg cctgcgaagt cacccatcag ggcctgagct cgcccgtcac aaagagcttc 360
aacaggggag agtgtta 377

<210> SEQ ID NO 6
<211> LENGTH: 125
<212> TYPE: PRT
<213> ORGANISM: Artificial Sequence
<220> FEATURE:
<223> OTHER INFORMATION: kvC fusion with signal peptide

<400> SEQUENCE: 6

Met Asp Met Arg Val Pro Ala Gln Leu Leu Gly Leu Leu Leu Leu Trp
1 5 10 15

Leu Pro Gly Thr Val Ala Ala Pro Ser Val Phe Ile Phe Pro Pro Ser
20 25 30

Asp Glu Gln Leu Lys Ser Gly Thr Ala Ser Val Val Cys Leu Leu Asn
35 40 45

Asn Phe Tyr Pro Arg Glu Ala Lys Val Gln Trp Lys Val Asp Asn Ala
50 55 60

Leu Gln Ser Gly Asn Ser Gln Glu Ser Val Thr Glu Gln Asp Ser Lys
65 70 75 80

Asp Ser Thr Tyr Ser Leu Ser Ser Thr Leu Thr Leu Ser Lys Ala Asp
85 90 95

Tyr Glu Lys His Lys Val Tyr Ala Cys Glu Val Thr His Gln Gly Leu
100 105 110

Ser Ser Pro Val Thr Lys Ser Phe Asn Arg Gly Glu Cys
115 120 125

<210> SEQ ID NO 7
<211> LENGTH: 323
<212> TYPE: DNA
<213> ORGANISM: Homo sapiens

<400> SEQUENCE: 7
ggaactgtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg tta 323

<210> SEQ ID NO 8
<211> LENGTH: 107
<212> TYPE: PRT
<213> ORGANISM: Homo sapiens

<400> SEQUENCE: 8

Gly Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

```
Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 9
<211> LENGTH: 351
<212> TYPE: DNA
<213> ORGANISM: Homo sapiens

<400> SEQUENCE: 9

atggacatga gggtccccgc tcagctcctg gggctcctgc tgctctggct cccaggtgcc      60

aaatgtgaca tccagatgac ccagtctcct tccaccctgt ctgcatctgt aggagacaga     120

gtcaccatca cttgccgggc cagtcagagt attagtagct ggttggcctg gtatcagcag     180

aaaccaggga aagcccctaa gctcctgatc tataaggcgt ctagtttaga aagtggggtc     240

ccatcaaggt tcagcggcag tggatctggg acagaattca ctctcaccat cagcagcctg     300

cagcctgatg attttgcaac ttattactgc caacagtata atagttattc t              351


<210> SEQ ID NO 10
<211> LENGTH: 117
<212> TYPE: PRT
<213> ORGANISM: Homo sapiens

<400> SEQUENCE: 10

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Gln Ser Ile Ser Ser Trp Leu Ala Trp Tyr Gln Gln Lys Pro Gly Lys
    50                  55                  60

Ala Pro Lys Leu Leu Ile Tyr Lys Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Asp Asp Phe Ala Thr Tyr Tyr Cys Gln Gln
            100                 105                 110

Tyr Asn Ser Tyr Ser
        115


<210> SEQ ID NO 11
<211> LENGTH: 66
<212> TYPE: DNA
<213> ORGANISM: Homo sapiens

<400> SEQUENCE: 11

atggacatga gggtccccgc tcagctcctg gggctcctgc tgctctggct cccaggtgcc      60

aaatgt                                                                 66


<210> SEQ ID NO 12
<211> LENGTH: 22
<212> TYPE: PRT
<213> ORGANISM: Homo sapiens
```

<400> SEQUENCE: 12

Met Asp Met Arg Val Pro Ala Gln Leu Leu Gly Leu Leu Leu Leu Trp
1               5                   10                  15

Leu Pro Gly Ala Lys Cys
            20

<210> SEQ ID NO 13
<211> LENGTH: 990
<212> TYPE: DNA
<213> ORGANISM: Homo sapiens

<400> SEQUENCE: 13
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gggtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggatgag 720
ctgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 14
<211> LENGTH: 330
<212> TYPE: PRT
<213> ORGANISM: Homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 15
<211> LENGTH: 990
<212> TYPE: DNA
<213> ORGANISM: Homo sapiens

<400> SEQUENCE: 15

gcctccacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagaa agttgagccc     300

aaatcttgtg acaaaactca cacatgccca ccgtgcccag cacctgaact cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggatgag     720

ctgaccaaga accaggtcag cctgacctgc ctggtcaaag gcttctatcc cagcgacatc     780

gccgtggagt gggagagcaa tgggcagccg gagaacaact acaagaccac gcctcccgtg     840
```

```
ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990


<210> SEQ ID NO 16
<211> LENGTH: 330
<212> TYPE: PRT
<213> ORGANISM: Homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 17
```

<211> LENGTH: 990
<212> TYPE: DNA
<213> ORGANISM: Homo sapiens

<400> SEQUENCE: 17

```
gcctccacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagag agttgagccc     300

aaatcttgtg acaaaactca cacatgccca ccgtgcccag cacctgaact cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggaggag     720

atgaccaaga accaggtcag cctgacctgc ctggtcaaag gcttctatcc cagcgacatc     780

gccgtggagt gggagagcaa tgggcagccg gagaacaact acaagaccac gcctcccgtg     840

ctggactccg acggctcctt cttcctctat agcaagctca ccgtggacaa gagcaggtgg     900

cagcagggga acgtcttctc atgctccgtg atgcatgagg ctctgcacaa ccactacacg     960

cagaagagcc tctccctgtc cccgggtaaa                                      990
```

<210> SEQ ID NO 18
<211> LENGTH: 330
<212> TYPE: PRT
<213> ORGANISM: Homo sapiens

<400> SEQUENCE: 18

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 19
<211> LENGTH: 990
<212> TYPE: DNA
<213> ORGANISM: Homo sapiens

<400> SEQUENCE: 19

```
gcctccacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acatcttctc atgctccgtg atgcatgagg ctctgcacaa ccactacacg    960

cagaagagcc tctccctgtc tccgggtaaa                                     990
```

<210> SEQ ID NO 20
<211> LENGTH: 330
<212> TYPE: PRT
<213> ORGANISM: Homo sapiens

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 21
<211> LENGTH: 990
<212> TYPE: DNA
<213> ORGANISM: Homo sapiens

<400> SEQUENCE: 21
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180

```
ggactctact ccctcagcag cgtggtgacc gtgccctcca gcagcttggg cacccagacc    240

tacatctgca acgtgaatca caagcccagc aacaccaagg tggacaagaa agtggagccc    300

aaatcttgtg acaaaactca cacatgccca ccgtgcccag cacctgaact cgcgggggca    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                      990
```

```
<210> SEQ ID NO 22
<211> LENGTH: 330
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 23
<211> LENGTH: 978
<212> TYPE: DNA
<213> ORGANISM: Homo sapiens

<400> SEQUENCE: 23

gcctccacca agggcccatc ggtcttcccc ctggcgccct gctccaggag cacctccgag      60

agcacagccg ccctgggctg cctggtcaag gactacttcc ccgaaccggt gacggtgtcg     120

tggaactcag gcgctctgac cagcggcgtg cacaccttcc cagctgtcct acagtcctca     180

ggactctact ccctcagcag cgtggtgacc gtgccctcca gcaacttcgg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360

ctcttccccc caaaacccaa ggacaccctc atgatctccc ggacccctga ggtcacgtgc     420

gtggtggtgg acgtgagcca cgaagacccc gaggtccagt tcaactggta cgtggacggc     480

gtggaggtgc ataatgccaa gacaaagcca cgggaggagc agttcaacag cacgttccgt     540

gtggtcagcg tcctcaccgt tgtgcaccag gactggctga acggcaagga gtacaagtgc     600

aaggtctcca acaaaggcct cccagccccc atcgagaaaa ccatctccaa aaccaaaggg     660

cagccccgag aaccacaggt gtacaccctg cccccatccc gggaggagat gaccaagaac     720

caggtcagcc tgacctgcct ggtcaaaggc ttctacccca gcgacatcgc cgtggagtgg     780

gagagcaatg ggcagccgga gaacaactac aagaccacac ctcccatgct ggactccgac     840

ggctccttct tcctctacag caagctcacc gtggacaaga gcaggtggca gcaggggaac     900

gtcttctcat gctccgtgat gcatgaggct ctgcacaacc actacacgca gaagagcctc     960

tccctgtctc cgggtaaa                                                   978


<210> SEQ ID NO 24
<211> LENGTH: 326
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 25
<211> LENGTH: 978
<212> TYPE: DNA
<213> ORGANISM: Homo sapiens

<400> SEQUENCE: 25

gcctccacca agggcccatc ggtcttcccc ctggcgccct gctccaggag cacctccgag      60

agcacagcgg ccctgggctg cctggtcaag gactacttcc ccgaaccggt gacggtgtcg     120

tggaactcag gcgctctgac cagcggcgtg cacaccttcc cggctgtcct acagtcctca     180

ggactctact ccctcagcag cgtggtgacc gtgacctcca gcaacttcgg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360

ctcttccccc caaaacccaa ggacaccctc atgatctccc ggacccctga ggtcacgtgc     420

gtggtggtgg acgtgagcca cgaagacccc gaggtccagt tcaactggta cgtggacggc     480
```

atggaggtgc ataatgccaa gacaaagcca cgggaggagc agttcaacag cacgttccgt 540
gtggtcagcg tcctcaccgt cgtgcaccag gactggctga acggcaagga gtacaagtgc 600
aaggtctcca acaaaggcct cccagccccc atcgagaaaa ccatctccaa aaccaaaggg 660
cagccccgag aaccacaggt gtacaccctg cccccatccc gggaggagat gaccaagaac 720
caggtcagcc tgacctgcct ggtcaaaggc ttctacccca gcgacatcgc cgtggagtgg 780
gagagcaatg ggcagccgga gaacaactac aagaccacac ctcccatgct ggactccgac 840
ggctccttct tcctctacag caagctcacc gtggacaaga gcaggtggca gcaggggaac 900
gtcttctcat gctccgtgat gcatgaggct ctgcacaacc actacacaca gaagagcctc 960
tccctgtctc cgggtaaa 978

<210> SEQ ID NO 26
<211> LENGTH: 326
<212> TYPE: PRT
<213> ORGANISM: Homo sapiens

<400> SEQUENCE: 26

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Thr Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Met Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ala Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

```
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 27
<211> LENGTH: 978
<212> TYPE: DNA
<213> ORGANISM: Homo sapiens

<400> SEQUENCE: 27

gcctccacca agggcccatc ggtcttcccc ctggcgccct gctccaggag cacctccgag      60

agcacagcgg ccctgggctg cctggtcaag gactacttcc ccgaaccggt gacggtgtcg     120

tggaactcag gcgctctgac cagcggcgtg cacaccttcc cagctgtcct acagtcctca     180

ggactctact ccctcagcag cgtggtgacc gtgccctcca gcagcttggg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360

ctcttccccc caaaacccaa ggacaccctc atgatctccc ggacccctga ggtcacgtgc     420

gtggtggtgg acgtgagcca cgaagacccc gaggtccagt tcaactggta cgtggacggc     480

gtggaggtgc ataatgccaa gacaaagcca cgggaggagc agttcaacag cacgttccgt     540

gtggtcagcg tcctcaccgt tgtgcaccag gactggctga acggcaagga gtacaagtgc     600

aaggtctcca acaaaggcct cccagccccc atcgagaaaa ccatctccaa aaccaaaggg     660

cagccccgag aaccacaggt gtacaccctg cccccatccc gggaggagat gaccaagaac     720

caggtcagcc tgacctgcct ggtcaaaggc ttctacccca gcgacatcgc cgtggagtgg     780

gagagcaatg ggcagccgga gaacaactac aagaccacac ctcccatgct ggactccgac     840

ggctccttct tcctctacag caagctcacc gtggacaaga gcaggtggca gcaggggaac     900

gtcttctcat gctccgtgat gcatgaggct ctgcacaacc actacacgca gaagagcctc     960

tccctgtctc cgggtaaa                                                   978


<210> SEQ ID NO 28
<211> LENGTH: 326
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
```

```
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 29
<211> LENGTH: 978
<212> TYPE: DNA
<213> ORGANISM: Homo sapiens

<400> SEQUENCE: 29

gcctccacca agggcccatc ggtcttcccc ctggcgccct gctccaggag cacctccgag     60

agcacagcgg ccctgggctg cctggtcaag gactacttcc ccgaaccggt gacggtgtcg    120

tggaactcag gcgctctgac cagcggcgtg cacaccttcc cggctgtcct acagtcctca    180

ggactctact ccctcagcag cgtggtgacc gtgccctcca gcaacttcgg cacccagacc    240

tacacctgca acgtagatca caagcccagc aacaccaagg tggacaagac agttgagcgc    300

aaatgttgtg tcgagtgccc accgtgccca gcaccacctg tggcaggacc gtcagtcttc    360

ctcttccccc caaaacccaa ggacaccctc atgatctccc ggacccctga ggtcacgtgc    420

gtggtggtgg acgtgagcca cgaagacccc gaggtccagt tcaactggta cgtggacggc    480

gtggaggtgc ataatgccaa gacaaagcca cgggaggagc agttcaacag cacgttccgt    540

gtggtcagcg tcctcaccgt cgtgcaccag gactggctga acggcaagga gtacaagtgc    600

aaggtctcca acaaaggcct cccagccccc atcgagaaaa ccatctccaa aaccaaaggg    660

cagccccgag aaccacaggt gtacaccctg cccccatccc gggaggagat gaccaagaac    720

caggtcagcc tgacctgcct ggtcaaaggc ttctacccca gcgacatctc cgtggagtgg    780

gagagcaatg ggcagccgga gaacaactac aagaccacac ctcccatgct ggactccgac    840
```

```
ggctccttct tcctctacag caagctcacc gtggacaaga gcaggtggca gcaggggaac    900

gtcttctcat gctccgtgat gcatgaggct ctgcacaacc actacacaca gaagagcctc    960

tccctgtctc cgggtaaa                                                   978


<210> SEQ ID NO 30
<211> LENGTH: 326
<212> TYPE: PRT
<213> ORGANISM: Homo sapiens

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 31
<211> LENGTH: 981
<212> TYPE: DNA
<213> ORGANISM: Homo sapiens

<400> SEQUENCE: 31

```
gcttccacca agggcccatc cgtcttcccc ctggcgccct gctccaggag cacctccgag     60

agcacagccg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc atcatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaggcta accgtggaca agagcaggtg gcaggagggg    900

aatgtcttct catgctccgt gatgcatgag gctctgcaca accactacac acagaagagc    960

ctctccctgt ctctgggtaa a                                              981
```

<210> SEQ ID NO 32
<211> LENGTH: 327
<212> TYPE: PRT
<213> ORGANISM: Homo sapiens

<400> SEQUENCE: 32

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 33
<211> LENGTH: 981
<212> TYPE: DNA
<213> ORGANISM: Homo sapiens

<400> SEQUENCE: 33

```
gcttccacca agggcccatc cgtcttcccc ctggcgccct gctccaggag cacctccgag     60

agcacagccg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccgtgccc atcatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcgtgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaggcta accgtggaca agagcaggtg gcaggagggg    900

aatgtcttct catgctccgt gatgcatgag gctctgcaca accactacac gcagaagagc    960

ctctccctgt ctctgggtaa a                                              981
```

<210> SEQ ID NO 34
<211> LENGTH: 327
<212> TYPE: PRT

<213> ORGANISM: Homo sapiens

<400> SEQUENCE: 34

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 35
<211> LENGTH: 981
<212> TYPE: DNA
<213> ORGANISM: Homo sapiens

<400> SEQUENCE: 35

```
gcttccacca agggcccatc cgtcttcccc ctggcgccct gctccaggag cacctccgag      60

agcacagccg ccctgggctg cctggtcaag gactacttcc ccgaaccggt gacggtgtcg     120
```

-continued tggaactcag gcgccctgac cagcggcgtg cacaccttcc cggctgtcct acagtcctca 180
ggactctact ccctcagcag cgtggtgacc gtgccctcca gcagcttggg cacgaagacc 240
tacacctgca acgtagatca caagcccagc aacaccaagg tggacaagag agttgagtcc 300
aaatatggtc ccccatgccc atcatgccca gcacctgagt tcctgggggg accatcagtc 360
ttcctgttcc ccccaaaacc caaggacact ctcatgatct cccggacccc tgaggtcacg 420
tgcgtggtgg tggacgtgag ccaggaagac cccgaggtcc agttcaactg gtacgtggat 480
ggcgtggagg tgcataatgc caagacaaag ccgcgggagg agcagttcaa cagcacgtac 540
cgtgtggtca gcgtcctcac cgtcctgcac caggactggc tgaacggcaa ggagtacaag 600
tgcaaggtct ccaacaaagg cctcccgtcc tccatcgaga aaaccatctc caaagccaaa 660
gggcagcccc gagagccaca ggtgtacacc ctgcccccat cccaggagga gatgaccaag 720
aaccaggtca gcctgacctg cctggtcaaa ggcttctacc ccagcgacat cgccgtggag 780
tgggagagca atgggcagcc ggagaacaac tacaagacca cgcctcccgt gctggactcc 840
gacggctcct tcttcctcta cagcaagctc accgtggaca agagcaggtg gcaggagggg 900
aacgtcttct catgctccgt gatgcatgag gctctgcaca accactacac gcagaagagc 960
ctctccctgt ctctgggtaa a 981

<210> SEQ ID NO 36
<211> LENGTH: 327
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

```
Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 37
<211> LENGTH: 981
<212> TYPE: DNA
<213> ORGANISM: Homo sapiens

<400> SEQUENCE: 37

```
gcctccacca agggcccatc cgtcttcccc ctggcgccct gctccaggag cacctccgag     60

agcacggccg ccctgggctg cctggtcaag gactacttcc ccgaaccagt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc accatgccca gcgcctgaat ttgagggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtca tcgatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggatcct tcttcctcta cagcaggcta accgtggaca agagcaggtg gcaggagggg    900

aatgtcttct catgctccgt gatgcatgag gctctgcaca accactacac acagaagagc    960

ctctccctgt ctctgggtaa a                                              981
```

<210> SEQ ID NO 38
<211> LENGTH: 981
<212> TYPE: DNA
<213> ORGANISM: Homo sapiens

<400> SEQUENCE: 38

```
gcctccacca agggacctag cgtgttccct ctcgcccccct gttccaggtc cacaagcgag     60

tccaccgctg ccctcggctg tctggtgaaa gactactttc ccgagcccgt gaccgtctcc    120

tggaatagcg gagccctgac ctccggcgtg cacacatttc ccgccgtgct gcagagcagc    180

ggactgtata gcctgagcag cgtggtgacc gtgcccagct ccagcctcgg caccaaaacc    240
```

```
tacacctgca acgtggacca caagccctcc aacaccaagg tggacaagcg ggtggagagc    300

aagtacggcc ccccttgccc tccttgtcct gcccctgagt tcgagggagg accctccgtg    360

ttcctgtttc cccccaaacc caaggacacc ctgatgatct cccggacacc cgaggtgacc    420

tgtgtggtcg tggacgtcag ccaggaggac cccgaggtgc agttcaactg gtatgtggac    480

ggcgtggagg tgcacaatgc caaaaccaag cccagggagg agcagttcaa ttccacctac    540

agggtggtga gcgtgctgac cgtcctgcat caggattggc tgaacggcaa ggagtacaag    600

tgcaaggtgt ccaacaaggg actgcccagc tccatcgaga agaccatcag caaggctaag    660

ggccagccga gggagcccca ggtgtatacc ctgcctccta gccaggaaga gatgaccaag    720

aaccaagtgt ccctgacctg cctggtgaag ggattctacc cctccgacat cgccgtggag    780

tgggagagca atggccagcc cgagaacaac tacaaaacaa cccctcccgt gctcgatagc    840

gacggcagct tctttctcta cagccggctg acagtggaca agagcaggtg gcaggagggc    900

aacgtgttct cctgttccgt gatgcacgag gccctgcaca atcactacac ccagaagagc    960

ctctccctgt ccctgggcaa g                                              981
```

<210> SEQ ID NO 39
<211> LENGTH: 981
<212> TYPE: DNA
<213> ORGANISM: Homo sapiens

<400> SEQUENCE: 39

```
gccagcacca agggcccttc cgtgttcccc ctggcccctt gcagcaggag cacctccgaa     60

tccacagctg ccctgggctg tctggtgaag gactactttc ccgagcccgt gaccgtgagc    120

tggaacagcg gcgctctgac atccggcgtc cacacctttc ctgccgtcct gcagtcctcc    180

ggcctctact ccctgtcctc cgtggtgacc gtgcctagct cctccctcgg caccaagacc    240

tacacctgta acgtggacca caaaccctcc aacaccaagg tggacaaacg ggtcgagagc    300

aagtacggcc ctccctgccc tccttgtcct gcccccgagt tcgaaggcgg acccagcgtg    360

ttcctgttcc ctcctaagcc caaggacacc ctcatgatca gccggacacc cgaggtgacc    420

tgcgtggtgg tggatgtgag ccaggaggac cctgaggtcc agttcaactg gtatgtggat    480

ggcgtggagg tgcacaacgc caagacaaag ccccgggaag agcagttcaa ctccacctac    540

agggtggtca gcgtgctgac cgtgctgcat caggactggc tgaacggcaa ggagtacaag    600

tgcaaggtca gcaataaggg actgcccagc agcatcgaga agaccatctc caaggctaaa    660

ggccagcccc gggaacctca ggtgtacacc ctgcctccca gccaggagga gatgaccaag    720

aaccaggtga gcctgacctg cctggtgaag ggattctacc cttccgacat cgccgtggag    780

tgggagtcca acggccagcc cgagaacaat tataagacca cccctcccgt cctcgacagc    840

gacggatcct tctttctgta ctccaggctg accgtggata agtccaggtg gcaggaaggc    900

aacgtgttca gctgctccgt gatgcacgag gccctgcaca atcactacac ccagaagtcc    960

ctgagcctgt ccctgggaaa g                                              981
```

<210> SEQ ID NO 40
<211> LENGTH: 327
<212> TYPE: PRT
<213> ORGANISM: Homo sapiens

<400> SEQUENCE: 40

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 41
<211> LENGTH: 981
<212> TYPE: DNA
<213> ORGANISM: Homo sapiens

<400> SEQUENCE: 41

```
gcctccacca agggcccatc cgtcttcccc ctggcgccct gctccaggag cacctccgag     60

agcacggccg ccctgggctg cctggtcaag gactacttcc ccgaaccagt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300
```

```
aaatatggtc ccccatgccc accatgccca gcgcctccag ttgcgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtca tcgatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggatcct tcttcctcta cagcaggcta accgtggaca agagcaggtg gcaggagggg    900

aatgtcttct catgctccgt gatgcatgag gctctgcaca accactacac acagaagagc    960

ctctccctgt ctctgggtaa a                                              981


<210> SEQ ID NO 42
<211> LENGTH: 327
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 43
<211> LENGTH: 321
<212> TYPE: DNA
<213> ORGANISM: Homo sapiens

<400> SEQUENCE: 43

cgtacggtgg ccgctccctc cgtgttcatc ttcccacctt ccgacgagca gctgaagtcc     60

ggcaccgctt ctgtcgtgtg cctgctgaac aacttctacc cccgcgaggc caaggtgcag    120

tggaaggtgg acaacgccct gcagtccggc aactcccagg aatccgtgac cgagcaggac    180

tccaaggaca gcacctactc cctgtcctcc accctgaccc tgtccaaggc cgactacgag    240

aagcacaagg tgtacgcctg cgaagtgacc caccagggcc tgtctagccc cgtgaccaag    300

tctttcaacc ggggcgagtg t                                              321


<210> SEQ ID NO 44
<211> LENGTH: 107
<212> TYPE: PRT
<213> ORGANISM: Homo sapiens

<400> SEQUENCE: 44

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 45
<211> LENGTH: 321
<212> TYPE: DNA
<213> ORGANISM: Homo sapiens

<400> SEQUENCE: 45

cgaactgtgg ctgcaccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggag    180
```

agcaaggaca gcacctacag cctcagcagc accctgacgc tgagcaaagc agactacgag 240
aaacacaaag tctacgccgg cgaagtcacc catcagggcc tgagctcgcc cgtcacaaag 300
agcttcaaca ggggagagtg t 321

<210> SEQ ID NO 46
<211> LENGTH: 107
<212> TYPE: PRT
<213> ORGANISM: Homo sapiens

<400> SEQUENCE: 46

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Glu Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Gly Glu Val Thr His Gln Gly Leu Ser Ser
85 90 95

Pro Val Thr Lys Ser Phe Asn Arg Gly Glu Cys
100 105

<210> SEQ ID NO 47
<211> LENGTH: 321
<212> TYPE: DNA
<213> ORGANISM: Homo sapiens

<400> SEQUENCE: 47
cgaactgtgg ctgcaccatc tgtcttcatc ttcccgccat ctgatgagca gttgaaatct 60
ggaactgcct ctgttgtgtg cctgctgaat aacttctatc ccagagaggc caaagtacag 120
cggaaggtgg ataacgccct ccaatcgggt aactcccagg agagtgtcac agagcaggag 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg t 321

<210> SEQ ID NO 48
<211> LENGTH: 107
<212> TYPE: PRT
<213> ORGANISM: Homo sapiens

<400> SEQUENCE: 48

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Arg Lys Val Asp Asn Ala Leu Gln
35 40 45

Ser Gly Asn Ser Gln Glu Ser Val Thr Glu Gln Glu Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser

```
                85                  90                  95

Pro Val Thr Lys Ser Phe Asn Arg Gly Glu Cys
            100                 105


<210> SEQ ID NO 49
<211> LENGTH: 321
<212> TYPE: DNA
<213> ORGANISM: Homo sapiens

<400> SEQUENCE: 49

cgaactgtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaac tctacgcctg cgaagtcacc catcagggcc tgagctcgcc cgtcacaaag     300

agcttcaaca ggggagagtg t                                               321


<210> SEQ ID NO 50
<211> LENGTH: 107
<212> TYPE: PRT
<213> ORGANISM: Homo sapiens

<400> SEQUENCE: 50

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 51
<211> LENGTH: 321
<212> TYPE: DNA
<213> ORGANISM: Homo sapiens

<400> SEQUENCE: 51

cgaactgtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcaac accctgacgc tgagcaaagc agactacgag     240

aaacacaaag tctacgcctg cgaagtcacc catcagggcc tgagctcgcc cgtcacaaag     300

agcttcaaca ggggagagtg c                                               321


<210> SEQ ID NO 52
<211> LENGTH: 107
<212> TYPE: PRT
<213> ORGANISM: Homo sapiens
```

<400> SEQUENCE: 52

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Asn Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 53
<211> LENGTH: 312
<212> TYPE: DNA
<213> ORGANISM: Homo sapiens

<400> SEQUENCE: 53
cccaaggcca accccacggt cactctgttc ccgccctcct ctgaggagct ccaagccaac 60
aaggccacac tagtgtgtct gatcagtgac ttctacccgg gagctgtgac agtggcttgg 120
aaggcagatg gcagccccgt caaggcggga gtggagacga ccaaaccctc caaacagagc 180
aacaacaagt acgcggccag cagctacctg agcctgacgc ccgagcagtg gaagtcccac 240
agaagctaca gctgccaggt cacgcatgaa gggagcaccg tggagaagac agtggcccct 300
acagaatgtt ca 312

<210> SEQ ID NO 54
<211> LENGTH: 104
<212> TYPE: PRT
<213> ORGANISM: Homo sapiens

<400> SEQUENCE: 54

Pro Lys Ala Asn Pro Thr Val Thr Leu Phe Pro Pro Ser Ser Glu Glu
1 5 10 15

Leu Gln Ala Asn Lys Ala Thr Leu Val Cys Leu Ile Ser Asp Phe Tyr
20 25 30

Pro Gly Ala Val Thr Val Ala Trp Lys Ala Asp Gly Ser Pro Val Lys
35 40 45

Ala Gly Val Glu Thr Thr Lys Pro Ser Lys Gln Ser Asn Asn Lys Tyr
50 55 60

Ala Ala Ser Ser Tyr Leu Ser Leu Thr Pro Glu Gln Trp Lys Ser His
65 70 75 80

Arg Ser Tyr Ser Cys Gln Val Thr His Glu Gly Ser Thr Val Glu Lys
85 90 95

Thr Val Ala Pro Thr Glu Cys Ser
100

<210> SEQ ID NO 55
<211> LENGTH: 318
<212> TYPE: DNA
<213> ORGANISM: Homo sapiens

<400> SEQUENCE: 55
ggtcagccca aggccaaccc cactgtcact ctgttcccgc cctcctctga ggagctccaa 60
gccaacaagg ccacactagt gtgtctgatc agtgacttct acccgggagc tgtgacagtg 120
gcctggaagg cagatggcag ccccgtcaag gcgggagtgg agaccaccaa accctccaaa 180
cagagcaaca acaagtacgc ggccagcagc tacctgagcc tgacgcccga gcagtggaag 240
tcccacagaa gctacagctg ccaggtcacg catgaaggga gcaccgtgga gaagacagtg 300
gcccctacag aatgttca 318

<210> SEQ ID NO 56
<211> LENGTH: 318
<212> TYPE: DNA
<213> ORGANISM: Homo sapiens

<400> SEQUENCE: 56
ggtcagccca aggccaaccc cactgtcact ctgttcccgc cctcctctga ggagctccaa 60
gccaacaagg ccacactagt gtgtctgatc agtgacttct acccgggagc tgtgacagtg 120
gcctggaagg cagatggcag ccccgtcaag gcgggagtgg agaccaccaa accctccaaa 180
cagagcaaca acaagtacgc ggccagcagc tacctgagcc tgacgcccga gcagtggaag 240
tcccacagaa gctacagctg ccaggtcacg catgaaggga gcaccgtgga gaagacagtg 300
gcccctacag aatgttca 318

<210> SEQ ID NO 57
<211> LENGTH: 106
<212> TYPE: PRT
<213> ORGANISM: Homo sapiens

<400> SEQUENCE: 57

Gly Gln Pro Lys Ala Asn Pro Thr Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Gly Ser Pro
35 40 45

Val Lys Ala Gly Val Glu Thr Thr Lys Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 58
<211> LENGTH: 318
<212> TYPE: DNA
<213> ORGANISM: Homo sapiens

<400> SEQUENCE: 58
ggccagccta aggccgctcc ttctgtgacc ctgttccccc catcctccga ggaactgcag 60
gctaacaagg ccaccctcgt gtgcctgatc agcgacttct accctggcgc cgtgaccgtg 120
gcctggaagg ctgatagctc tcctgtgaag gccggcgtgg aaaccaccac cccttccaag 180
cagtccaaca acaaatacgc cgcctcctcc tacctgtccc tgacccctga gcagtggaag 240
tcccaccggt cctacagctg ccaagtgacc cacgagggct ccaccgtgga aaagaccgtg 300
gctcctaccg agtgctcc 318

<210> SEQ ID NO 59
<211> LENGTH: 318
<212> TYPE: DNA
<213> ORGANISM: Homo sapiens

<400> SEQUENCE: 59
ggccagccta aagctgcccc cagcgtcacc ctgtttcctc cctccagcga ggagctccag 60
gccaacaagg ccaccctcgt gtgcctgatc tccgacttct atcccggcgc tgtgaccgtg 120
gcttggaaag ccgactccag ccctgtcaaa gccggcgtgg agaccaccac accctccaag 180
cagtccaaca acaagtacgc cgcctccagc tatctctccc tgacccctga gcagtggaag 240
tcccaccggt cctactcctg tcaggtgacc cacgagggct ccaccgtgga aaagaccgtc 300
gcccccaccg agtgctcc 318

<210> SEQ ID NO 60
<211> LENGTH: 106
<212> TYPE: PRT
<213> ORGANISM: Homo sapiens

<400> SEQUENCE: 60

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 61
<211> LENGTH: 318
<212> TYPE: DNA
<213> ORGANISM: Homo sapiens

<400> SEQUENCE: 61
ggtcagccca aggctgcccc ctcggtcact ctgttcccgc cctcctctga ggagcttcaa 60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tatctgagcc tgacgcctga gcagtggaag 240
tcccacagaa gctacagctg ccaggtcacg catgaaggga gcaccgtgga gaagacagtg 300
gcccctacag aatgttca 318

<210> SEQ ID NO 62
<211> LENGTH: 106
<212> TYPE: PRT
<213> ORGANISM: Homo sapiens

<400> SEQUENCE: 62

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 63
<211> LENGTH: 312
<212> TYPE: DNA
<213> ORGANISM: Homo sapiens

<400> SEQUENCE: 63
cccaaggctg ccccctcggt cactctgttc ccaccctcct ctgaggagct tcaagccaac 60
aaggccacac tggtgtgtct cataagtgac ttctacccgg gagccgtgac agttgcctgg 120
aaggcagata gcagccccgt caaggcgggg gtggagacca ccacaccctc caaacaaagc 180
aacaacaagt acgcggccag cagctacctg agcctgacgc ctgagcagtg gaagtcccac 240
aaaagctaca gctgccaggt cacgcatgaa gggagcaccg tggagaagac agttgcccct 300
acggaatgtt ca 312

<210> SEQ ID NO 64
<211> LENGTH: 104
<212> TYPE: PRT
<213> ORGANISM: Homo sapiens

<400> SEQUENCE: 64

Pro Lys Ala Ala Pro Ser Val Thr Leu Phe Pro Pro Ser Ser Glu Glu
1 5 10 15

Leu Gln Ala Asn Lys Ala Thr Leu Val Cys Leu Ile Ser Asp Phe Tyr
20 25 30

Pro Gly Ala Val Thr Val Ala Trp Lys Ala Asp Ser Ser Pro Val Lys
35 40 45

Ala Gly Val Glu Thr Thr Thr Pro Ser Lys Gln Ser Asn Asn Lys Tyr
50 55 60

Ala Ala Ser Ser Tyr Leu Ser Leu Thr Pro Glu Gln Trp Lys Ser His
65 70 75 80

Lys Ser Tyr Ser Cys Gln Val Thr His Glu Gly Ser Thr Val Glu Lys
85 90 95

Thr Val Ala Pro Thr Glu Cys Ser
100

<210> SEQ ID NO 65
<211> LENGTH: 318
<212> TYPE: DNA
<213> ORGANISM: Homo sapiens

<400> SEQUENCE: 65
ggtcagccca aggctgcccc ctcggtcact ctgttcccac cctcctctga ggagcttcaa 60
gccaacaagg ccacactggt gtgtctcata agtgacttct acccggggcc agtgacagtt 120
gcctggaagg cagatagcag ccccgtcaag gcgggggtgg agaccaccac accctccaaa 180
caaagcaaca acaagtacgc ggccagcagc tacctgagcc tgacgcctga gcagtggaag 240
tcccacaaaa gctacagctg ccaggtcacg catgaaggga gcaccgtgga gaagacagtg 300
gcccctacgg aatgttca 318

<210> SEQ ID NO 66
<211> LENGTH: 106
<212> TYPE: PRT
<213> ORGANISM: Homo sapiens

<400> SEQUENCE: 66

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Pro Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Lys Ser Tyr Ser Cys Gln Val Thr His Glu Gly Ser Thr Val
85 90 95

Glu Lys Thr Val Ala Pro Thr Glu Cys Ser
100 105

<210> SEQ ID NO 67
<211> LENGTH: 318
<212> TYPE: DNA
<213> ORGANISM: Homo sapiens

<400> SEQUENCE: 67
ggtcagccca aggctgcccc ctcggtcact ctgttcccac cctcctctga ggagcttcaa 60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tacctgagcc tgacgcctga gcagtggaag 240
tcccacaaaa gctacagctg ccaggtcacg catgaaggga gcaccgtgga gaagacagtg 300
gcccctacag aatgttca 318

<210> SEQ ID NO 68
<211> LENGTH: 106
<212> TYPE: PRT
<213> ORGANISM: Homo sapiens

<400> SEQUENCE: 68

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

```
Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 69
<211> LENGTH: 318
<212> TYPE: DNA
<213> ORGANISM: Homo sapiens

<400> SEQUENCE: 69

ggtcagccca aggctgcccc ctcggtcact ctgttcccgc cctcctctga ggagcttcaa      60

gccaacaagg ccacactggt gtgtctcata agtgacttct acccgggagc cgtgacagtg     120

gcctggaagg cagatagcag ccccgtcaag gcgggagtgg agaccaccac accctccaaa     180

caaagcaaca acaagtacgc ggccagcagc tacctgagcc tgacgcctga gcagtggaag     240

tcccacagaa gctacagctg ccaggtcacg catgaaggga gcaccgtgga gaagacagtg     300

gcccctacag aatgttca                                                   318


<210> SEQ ID NO 70
<211> LENGTH: 106
<212> TYPE: PRT
<213> ORGANISM: Homo sapiens

<400> SEQUENCE: 70

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 71
<211> LENGTH: 318
<212> TYPE: DNA
<213> ORGANISM: Homo sapiens

<400> SEQUENCE: 71

ggtcagccca aggctgcccc atcggtcact ctgttcccgc cctcctctga ggagcttcaa      60

gccaacaagg ccacactggt gtgcctgatc agtgacttct acccgggagc tgtgaaagtg     120

gcctggaagg cagatggcag ccccgtcaac acgggagtgg agaccaccac accctccaaa     180

cagagcaaca acaagtacgc ggccagcagc tacctgagcc tgacgcctga gcagtggaag     240

tcccacagaa gctacagctg ccaggtcacg catgaaggga gcaccgtgga gaagacagtg     300
```

gcccctgcag aatgttca 318

<210> SEQ ID NO 72
<211> LENGTH: 106
<212> TYPE: PRT
<213> ORGANISM: Homo sapiens

<400> SEQUENCE: 72

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105
```

<210> SEQ ID NO 73
<211> LENGTH: 318
<212> TYPE: DNA
<213> ORGANISM: Homo sapiens

<400> SEQUENCE: 73

```
ggtcagccca aggctgcccc atcggtcact ctgttcccac cctcctctga ggagcttcaa     60

gccaacaagg ccacactggt gtgtctcgta agtgacttct acccgggagc cgtgacagtg    120

gcctggaagg cagatggcag ccccgtcaag gtgggagtgg agaccaccaa accctccaaa    180

caaagcaaca acaagtatgc ggccagcagc tacctgagcc tgacgcccga gcagtggaag    240

tcccacagaa gctacagctg ccgggtcacg catgaaggga gcaccgtgga gaagacagtg    300

gcccctgcag aatgctct                                                  318
```

<210> SEQ ID NO 74
<211> LENGTH: 106
<212> TYPE: PRT
<213> ORGANISM: Homo sapiens

<400> SEQUENCE: 74

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

<210> SEQ ID NO 75
<211> LENGTH: 318
<212> TYPE: DNA
<213> ORGANISM: Homo sapiens

<400> SEQUENCE: 75
ggtcagccca aggctgcccc ctcggtcact ctgttcccac cctcctctga ggagcttcaa 60
gccaacaagg ccacactggt gtgtctcgta agtgacttca acccgggagc cgtgacagtg 120
gcctggaagg cagatggcag ccccgtcaag gtgggagtgg agaccaccaa accctccaaa 180
caaagcaaca acaagtatgc ggccagcagc tacctgagcc tgacgcccga gcagtggaag 240
tcccacagaa gctacagctg ccgggtcacg catgaaggga gcaccgtgga gaagacagtg 300
gcccctgcag aatgctct 318

<210> SEQ ID NO 76
<211> LENGTH: 106
<212> TYPE: PRT
<213> ORGANISM: Homo sapiens

<400> SEQUENCE: 76

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 77
<211> LENGTH: 354
<212> TYPE: DNA
<213> ORGANISM: Artificial Sequence
<220> FEATURE:
<223> OTHER INFORMATION: Truncated human lambda 5 coding region

<400> SEQUENCE: 77
gtgtttggca gcgggaccca gctcaccgtt ttaagtcagc ccaaggccac cccctcggtc 60
actctgttcc cgccgtcctc tgaggagctc caagccaaca aggctacact ggtgtgtctc 120
atgaatgact tttatccggg aatcttgacg gtgacctgga aggcagatgg taccccccatc 180 acccagggcg tggagatgac cacgccctcc aaacagagca acaacaagta cgcggccagc 240
agctacctga gcctgacgcc cgagcagtgg aggtcccgca gaagctacag ctgccaggtc 300
atgcacgaag ggagcaccgt ggagaagacg gtggcccctg cagaatgttc atag 354

<210> SEQ ID NO 78
<211> LENGTH: 2950
<212> TYPE: DNA
<213> ORGANISM: Artificial Sequence
<220> FEATURE:
<223> OTHER INFORMATION: Human Kappa promoter and leader with intron including Human kappa intronic enhancer human Vk1-5 derived

<400> SEQUENCE: 78

```
atggacatga gggtccccgc tcagctcctg gggctcctgc tgctctggct cccaggtaag     60
taatttttca ctattgtctt ctgaaatttg ggtctgatgg ccagtattga cttttagagg    120
cttaaatagg agtttggtaa agattggtaa atgagggcat ttaagatttg ccatgggttg    180
caaaagttaa actcagcttc aaaaatggat ttggagaaaa aaagattaaa ttgctctaaa    240
ctgaatgaca caaagtaaaa aaaaaaagtg taactaaaaa ggaacccttg tatttctaag    300
gagcaaaagt aaatttattt ttgttcactc ttgccaaata ttgtattggt tgttgctgat    360
tatgcatgat acagaaaagt ggaaaaatac atttttagt ctttctccct tttgtttgat    420
aaattatttt gtcagacaac aataaaaatc aatagcacgc cctaagaaaa atcagggaaa    480
agtgaagtgt acctatttgc tatgtagaag aggcagctta cttgaaaatc agcagcaatg    540
ttgtttttag agtctgtaat aagtaataaa ctcaaaaaga cacattctat aggaataagg    600
gcttcacaga tagagctcat tttttaaaaa tccaatttgt acattagact aaacgtgaaa    660
ttatctctta ttgtaatggt ggaaaggtgg ttattcccaa aagctcaatc tcaaagaaat    720
gtgtttaaat gaaaaaaagt aaataattgc atttttaat gaccgtgggt ctgtgaaaaa    780
aataggaaat attttaaaga gtatgttctt tcattatcct ctgttattac ttgtctacat    840
ttttattctg ccaagaaggc cgtggcaccg cgagctgtag acagagccgc ggtctttctc    900
gattgagtgg ctttggtggc catgccaccg cgctcttggg gcagccgcct tgccgctagt    960
ggccgtggcc accctgtgtc tgcccgattg atgctgccgt agccagcttt cctgatgcac   1020
agtgatacaa ataatgccac taagggaaag agaacagaaa cgtaatgggc gctgagctgg   1080
gaaaaccagg gagaagactg atttattaga gatttcagaa ataaaattca cattcattat   1140
gatatctcat tagtgaaaat ttccattagg ggattgtaaa taatttaaag cttttttttt   1200
tttcagtgct atttaattat ttcaatatcc tctcatcaaa tgtatttaaa taacaaaagc   1260
tcaaccaaaa agaaagaaat atgtaattct ttcagagtaa aaatcacacc catgacctgg   1320
ccactgaggg cttgatcaat tcactttgaa tttggcatta aataccatta aggtatatta   1380
actgatttta aaataagata tattcgtgac catgttttta actttcaaaa atgtagctgc   1440
cagtgtgtga ttttatttca gttgtacaaa atatctaaac ctatagcaat gtgattaata   1500
aaaacttaaa catattttcc agtaccttaa ttctgtgata ggaaaatttt aatctgagta   1560
ttttaatttc ataatctcta aaatagttta atgatttgtc attgtgttgc tgtcgtttac   1620
cccagctgat ctcaaaagtg atatttaagg agattatttt ggtctgcaac aacttgatag   1680
gactatttta gggccttttt aaagctctat taaaactaac ttacaacgat tcaaaactgt   1740
tttaaactat ttcaaaatga ttttagagcc ttttgaaaac tcttttaaac actttttaaa   1800
ctctattaaa actaataaga taacttgaaa taattttcat gtcaaataca ttaactgttt   1860
aatgtttaaa tgccagatga aaaatgtaaa gctatcaaga attcacccag ataggagtat   1920
cttcatagca tgtttttccc tgcttatttt ccagtgatca cattattttg ctaccatggt   1980
tattttatac aattatctga aaaaaattag ttatgaagat taaaagagaa gaaaatatta   2040
aacataagag attcagtctt tcatgttgaa ctgcttggtt aacagtgaag ttagttttaa   2100
aaaaaaaaaa aactatttct gttatcagct gacttctccc tatctgttga cttctcccag   2160
caaaagattc ttattttaca ttttaactac tgctctccca cccaacgggt ggaatccccc   2220
agagggggat ttccaagagg ccacctggca gttgctgagg gtcagaagtg aagctagcca   2280
```

cttcctctta ggcaggtggc caagattaca gttgacctct cctggtatgg ctgaaaattg 2340
ctgcatatgg ttacaggcct tgaggccttt gggagggctt agagagttgc tggaacagtc 2400
agaaggtgga ggggctgaca ccacccaggc gcagaggcag ggctcagggc ctgctctgca 2460
gggaggtttt agcccagccc agccaaagta acccccggga gcctgttatc ccagcacagt 2520
cctggaagag gcacagggga aataaaagcg gacggaggct ttccttgact cagccgctgc 2580
ctggtcttct tcagacctgt tctgaattct aaactctgag gggtcggat gacgtggcca 2640 ttctttgcct aaagcattga gtttactgca aggtcagaaa agcatgcaaa gccctcagaa 2700
tggctgcaaa gagctccaac aaaacaattt agaactttat taaggaatag gggaagcta 2760 ggaagaaact caaaacatca agattttaaa tacgcttctt ggtctccttg ctataattat 2820
ctgggataag catgctgttt tctgtctgtc cctaacatgc cctgtgatta tccgcaaaca 2880
acacacccaa gggcagaact ttgttactta aacaccatcc tgtttgcttc tttcctcagg 2940
tgccaaatgt 2950

<210> SEQ ID NO 79
<211> LENGTH: 6088
<212> TYPE: DNA
<213> ORGANISM: Artificial Sequence
<220> FEATURE:
<223> OTHER INFORMATION: Full lambda 5 transgene plus homology arms

<400> SEQUENCE: 79
gctgaatctt gaatgacagc tcaagggata gggaggacag ggtgttcaga agcagagaag 60
atgccttgta aatgtggaag gctgtggcag gattggaagg actttggggt ggtaggaagg 120
ggatgggaat gggtggttac aagagaaaca agactgtagt aaataaagct gaaactcaaa 180
gcaagctttc agcatcttta attggagaca caaacttcaa aggtatcatg aatgtggttg 240
atcttggtga aagttgagct tcacctgtcc taacaacaga ccaatccatg agtgaaagct 300
tatctttctc ctttattaat ggttgctgtt gtatccataa ctcaattcca aaggatatga 360
accttaacat atagatataa ttttgtgtac cttctatgaa acagcattaa agcaaagaag 420
ttcaaataga aagactggct tagttattat taactaagag atgctagtga gttctaaatt 480
aataccattt aaaatttata atttgcagaa ttaccaccac caccaccact cagcccagga 540
aaagttacaa agaactggct atccaatttg tttgttttcc tcctttttag agttctttta 600
tttatgtgtg agtgaatgcc atgtacttat ggatgcagag gctgtcagat tccttgcagc 660
tggagtaata gacagttgtg agctacttat agtactagaa ctaagatcct atggaagagc 720
agcgagtgcc actaactgct gagccacctc tccagcccat ttctttattt ttcaatgaac 780
aaataataag cagtcctatg tgacatgctt ctaaagcaaa agatataata tttagtatta 840
tatacattaa taataaaata cattatcttc taagaattga agtctcaact atgaaaatca 900
gcagttctct gtcagagaag atgtccagtt tcatctggat ccaactgatt tctccatgta 960
catagacaat tgcttgataa gagattgagt atgtttttcc taaaggtgtt aacagggagg 1020
ctggtgtctg ggtcaggatg atgtccccat gcactgataa aaagtataag aagaaagtgt 1080
cattgatggt gcatggcagg gacatgctcc gtgcagtggc caccctcact aagacagatg 1140
aactttggga aataataccc aatggcagaa aagaaggtag actatgaagg tacccaaaac 1200
aagaataagg tgcacctcat ttagtctctg ggtattaaag agacctgcag ttcttgatag 1260
tggtggatct gtgagtgctg catgcatgga gacaacacgg tatcatcttt gtatatctgt 1320

```
aataaattgc ttgatctaat actagtaaga acaaaggcat aacaccatta cctaatactt   1380
acaaatatat agcatcatgc cgatacattt tatttttaat tttttttaga aaggaacaat   1440
gttaaactca cagaaatgtt gcaggtatag cacaattacc cccttcccta cccggaatct   1500
tatgagagtc ttttgaagac ttgagaatcc taccatctaa cattttacta tgtgtttcct   1560
acaaacaaga atattctcct aaataatcct gatacaccaa tgaaatacat tactctatcg   1620
gctcctgagg aatatttaaa attctcaaaa aaatacctaa aaattgtttc tcataataaa   1680
atagtcccca gtagaaacac attctctgca gacaaatttg tgctaccctg gtcttacctg   1740
ggacacctgg ggacactgag ctggtgctga gttactgaga tgagccagct ctgcagctgt   1800
gcccagcctg ccccatcccc tgctcatttg catgttccca gagcacaacc tcctgccctg   1860
aagccttatt aataggctgg tcacactttg tgcaggagtc agacccagtc aggacacagc   1920
atggacatga gggtccccgc tcagctcctg gggctcctgc tgctctggct cccaggtaag   1980
taatttttca ctattgtctt ctgaaatttg ggtctgatgg ccagtattga cttttagagg   2040
cttaaatagg agtttggtaa agattggtaa atgagggcat ttaagatttg ccatgggttg   2100
caaaagttaa actcagcttc aaaaatggat ttggagaaaa aaagattaaa ttgctctaaa   2160
ctgaatgaca caaagtaaaa aaaaaaagtg taactaaaaa ggaacccttg tatttctaag   2220
gagcaaaagt aaatttattt ttgttcactc ttgccaaata ttgtattggt tgttgctgat   2280
tatgcatgat acagaaaagt ggaaaaatac atttttagt ctttctccct tttgtttgat   2340
aaattatttt gtcagacaac aataaaaatc aatagcacgc cctaagaaaa atcagggaaa   2400
agtgaagtgt acctatttgc tatgtagaag aggcagctta cttgaaaatc agcagcaatg   2460
ttgtttttag agtctgtaat aagtaataaa ctcaaaaaga cacattctat aggaataagg   2520
gcttcacaga tagagctcat tttttaaaaa tccaatttgt acattagact aaacgtgaaa   2580
ttatctctta ttgtaatggt ggaaaggtgg ttattcccaa aagctcaatc tcaaagaaat   2640
gtgtttaaat gaaaaaaagt aaataattgc attttttaat gaccgtgggt ctgtgaaaaa   2700
aataggaaat attttaaaga gtatgttctt tcattatcct ctgttattac ttgtctacat   2760
ttttattctg ccaagaaggc cgtggcaccg cgagctgtag acagagccgc ggtctttctc   2820
gattgagtgg ctttggtggc catgccaccg cgctcttggg gcagccgcct tgccgctagt   2880
ggccgtggcc accctgtgtc tgcccgattg atgctgccgt agccagcttt cctgatgcac   2940
agtgatacaa ataatgccac taagggaaag agaacagaaa cgtaatgggc gctgagctgg   3000
gaaaaccagg gagaagactg atttattaga gatttcagaa ataaaattca cattcattat   3060
gatatctcat tagtgaaaat ttccattagg ggattgtaaa taatttaaag cttttttttt   3120
tttcagtgct atttaattat ttcaatatcc tctcatcaaa tgtatttaaa taacaaaagc   3180
tcaaccaaaa agaaagaaat atgtaattct ttcagagtaa aaatcacacc catgacctgg   3240
ccactgaggg cttgatcaat tcactttgaa tttggcatta aataccatta aggtatatta   3300
actgatttta aaataagata tattcgtgac catgttttta actttcaaaa atgtagctgc   3360
cagtgtgtga ttttatttca gttgtacaaa atatctaaac ctatagcaat gtgattaata   3420
aaaacttaaa catattttcc agtaccttaa ttctgtgata ggaaaatttt aatctgagta   3480
ttttaatttc ataatctcta aaatagttta atgatttgtc attgtgttgc tgtcgtttac   3540
cccagctgat ctcaaaagtg atatttaagg agattatttt ggtctgcaac aacttgatag   3600
gactatttta gggccttttt aaagctctat taaaactaac ttacaacgat tcaaaactgt   3660
tttaaactat ttcaaaatga ttttagagcc ttttgaaaac tcttttaaac actttttaaa   3720
```

-continued

```
ctctattaaa actaataaga taacttgaaa taattttcat gtcaaataca ttaactgttt   3780
aatgtttaaa tgccagatga aaaatgtaaa gctatcaaga attcacccag ataggagtat   3840
cttcatagca tgtttttccc tgcttatttt ccagtgatca cattattttg ctaccatggt   3900
tattttatac aattatctga aaaaaattag ttatgaagat taaaagagaa gaaaatatta   3960
aacataagag attcagtctt tcatgttgaa ctgcttggtt aacagtgaag ttagttttaa   4020
aaaaaaaaaa aactatttct gttatcagct gacttctccc tatctgttga cttctcccag   4080
caaaagattc ttattttaca ttttaactac tgctctccca cccaacgggt ggaatccccc   4140
agagggggat ttccaagagg ccacctggca gttgctgagg gtcagaagtg aagctagcca   4200
cttcctctta ggcaggtggc caagattaca gttgacctct cctggtatgg ctgaaaattg   4260
ctgcatatgg ttacaggcct tgaggccttt gggagggctt agagagttgc tggaacagtc   4320
agaaggtgga ggggctgaca ccacccaggc gcagaggcag ggctcagggc ctgctctgca   4380
gggaggtttt agcccagccc agccaaagta acccccggga gcctgttatc ccagcacagt   4440
cctggaagag gcacagggga aataaaagcg gacggaggct ttccttgact cagccgctgc   4500
ctggtcttct tcagacctgt tctgaattct aaactctgag gggtcggat gacgtggcca   4560
ttctttgcct aaagcattga gtttactgca aggtcagaaa agcatgcaaa gccctcagaa   4620
tggctgcaaa gagctccaac aaaacaattt agaactttat taaggaatag ggggaagcta   4680
ggaagaaact caaaacatca agattttaaa tacgcttctt ggtctccttg ctataattat   4740
ctgggataag catgctgttt tctgtctgtc cctaacatgc cctgtgatta tccgcaaaca   4800
acacacccaa gggcagaact ttgttactta aacaccatcc tgtttgcttc tttcctcagg   4860
tgccaaatgt gtgtttggca gcgggaccca gctcaccgtt ttaagtcagc ccaaggccac   4920
cccctcggtc actctgttcc cgccgtcctc tgaggagctc caagccaaca aggctacact   4980
ggtgtgtctc atgaatgact tttatccggg aatcttgacg gtgacctgga aggcagatgg   5040
tacccccatc acccagggcg tggagatgac cacgccctcc aaacagagca acaacaagta   5100
cgcggccagc agctacctga gcctgacgcc cgagcagtgg aggtcccgca gaagctacag   5160
ctgccaggtc atgcacgaag ggagcaccgt ggagaagacg gtggcccctg cagaatgttc   5220
atagagacaa aggtcctgag acgccaccac cagctcccca gctccatcct atcttccctt   5280
ctaaggtctt ggaggcttcc ccacaagcga cctaccactg ttgcggtgct ccaaacctcc   5340
tccccacctc cttctcctcc tcctcccttt ccttggcttt tatcatgcta atatttgcag   5400
aaaatattca ataaagtgag tctttgcact tgagatctct gtctttctta ctaaatggta   5460
gtaatcagtt gtttttccag ttacctgggt ttctcttcta aagaagttaa atgtttagtt   5520
gccctgaaat ccaccacact taaaggataa ataaaaccct ccacttgccc tggttggctg   5580
tccactacat ggcagtcctt tctaaggttc acgagtacta ttcatggctt atttctctgg   5640
gccatggtag gtttgaggag gcatacttcc tagttttctt cccctaagtc gtcaaagtcc   5700
tgaaggggga cagtctttac aagcacatgt tctgtaatct gattcaacct acccagtaaa   5760
cttggcgaag caaagtagaa tcattatcac aggaagcaaa ggcaacctaa atgtgcaagc   5820
aataggaaaa tgtggaagcc catcatagta cttggacttc atctgctttt gtgccttcac   5880
taagttttta aacatgagct ggctcctatc tgccattggc aaggctgggc actacccaca   5940
acctacttca aggacctcta taccgtgaga ttacacacat acatcaaaat ttgggaaaag   6000
ttctaccaag ctgagagctg atcaccccac tcttaggtgc ttatctctgt acaccagaaa   6060
```

ccttaagaag caaccagtat tgagagac 6088

<210> SEQ ID NO 80
<211> LENGTH: 9079
<212> TYPE: DNA
<213> ORGANISM: Artificial Sequence
<220> FEATURE:
<223> OTHER INFORMATION: Full lambda 5 targeting vector insert including positive negative selection cassette

<400> SEQUENCE: 80
gctgaatctt gaatgacagc tcaagggata gggaggacag ggtgttcaga agcagagaag 60
atgccttgta aatgtggaag gctgtggcag gattggaagg actttggggt ggtaggaagg 120
ggatgggaat gggtggttac aagagaaaca agactgtagt aaataaagct gaaactcaaa 180
gcaagctttc agcatcttta attggagaca caaacttcaa aggtatcatg aatgtggttg 240
atcttggtga aagttgagct tcacctgtcc taacaacaga ccaatccatg agtgaaagct 300
tatctttctc ctttattaat ggttgctgtt gtatccataa ctcaattcca aaggatatga 360
accttaacat atagatataa ttttgtgtac cttctatgaa acagcattaa agcaaagaag 420
ttcaaataga aagactggct tagttattat taactaagag atgctagtga gttctaaatt 480
aataccattt aaaatttata atttgcagaa ttaccaccac caccaccact cagcccagga 540
aaagttacaa agaactggct atccaatttg tttgttttcc tcctttttag agttctttta 600
tttatgtgtg agtgaatgcc atgtacttat ggatgcagag gctgtcagat tccttgcagc 660
tggagtaata gacagttgtg agctacttat agtactagaa ctaagatcct atggaagagc 720
agcgagtgcc actaactgct gagccacctc tccagcccat ttctttattt ttcaatgaac 780
aaataataag cagtcctatg tgacatgctt ctaaagcaaa agatataata tttagtatta 840
tatacattaa taataaaata cattatcttc taagaattga agtctcaact atgaaaatca 900
gcagttctct gtcagagaag atgtccagtt tcatctggat ccaactgatt tctccatgta 960
catagacaat tcttttaacc ctagaaagat agtctgcgta aaattgacgc atgcattctt 1020
gaaatattgc tctctctttc taaatagcgc gaatccgtcg ctgtgcattt aggacatctc 1080
agtcgccgct tggagctccc gtgaggcgtg cttgtcaatg cggtaagtgt cactgatttt 1140
gaactataac gaccgcgtga gtcaaaatga cgcatgatta tcttttacgt gacttttaag 1200
atttaactca tacgataatt atattgttat ttcatgttct acttacgtga taacttatta 1260
tatatatatt ttcttgttat agatatctac cgggtagggg aggcgctttt cccaaggcag 1320
tctggagcat gcgctttagc agccccgctg ggcacttggc gctacacaag tggcctctgg 1380
cctcgcacac attccacatc caccggtagg cgccaaccgg ctccgttctt tggtggcccc 1440
ttcgcgccac cttctactcc tcccctagtc aggaagttcc cccccgcccc gcagctcgcg 1500
tcgtgcagga cgtgacaaat ggaagtagca cgtctcacta gtctcgtgca gatggacagc 1560
accgctgagc aatggaagcg ggtaggcctt tggggcagcg gccaatagca gctttgctcc 1620
ttcgctttct gggctcagag gctgggaagg ggtgggtccg ggggcgggct caggggcggg 1680
ctcaggggcg gggcgggcgc ccgaaggtcc tccggaggcc cggcattctg cacgcttcaa 1740
aagcgcacgt ctgccgcgct gttctcctct tcctcatctc cgggcctttc gacctgcagc 1800
caacgccacc atggggaccg agtacaagcc cacggtgcgc ctcgccaccc gcgacgacgt 1860
cccccgggcc gtacgcaccc tcgccgccgc gttcgccgac taccccgcca cgcgccacac 1920
cgtcgacccg gaccgccaca tcgagcgggt caccgagctg caagaactct tcctcacgcg 1980

-continued

```
cgtcgggctc gacatcggca aggtgtgggt cgcggacgac ggcgccgcgg tggcggtctg   2040
gaccacgccg gagagcgtcg aagcgggggc ggtgttcgcc gagatcggcc cgcgcatggc   2100
cgagttgagc ggttcccggc tggccgcgca gcaacagatg gaaggcctcc tggcgccgca   2160
ccggcccaag gagcccgcgt ggttcctggc caccgtcggc gtctcgcccg accaccaggg   2220
caagggtctg ggcagcgccg tcgtgctccc cggagtggag gcggccgagc gcgccggggt   2280
gcccgccttc ctggagacct ccgcgccccg caacctcccc ttctacgagc ggctcggctt   2340
caccgtcacc gccgacgtcg aggtgcccga aggaccgcgc acctggtgca tgacccgcaa   2400
gcccggtgcc ggatccatgc ccacgctact gcgggtttat atagacggtc ctcacgggat   2460
ggggaaaacc accaccacgc aactgctggt ggccctgggt tcgcgcgacg atatcgtcta   2520
cgtacccgag ccgatgactt actggcaggt gctgggggct tccgagacaa tcgcgaacat   2580
ctacaccaca caacaccgcc tcgaccaggg tgagatatcg gccggggacg cggcggtggt   2640
aatgacaagc gcccagataa caatgggcat gccttatgcc gtgaccgacg ccgttctggc   2700
tcctcatatc ggggggggagg ctgggagctc acatgccccg cccccggccc tcaccctcat   2760
cttcgaccgc catcccatcg ccgccctcct gtgctacccg gccgcgcgat accttatggg   2820
cagcatgacc ccccaggccg tgctggcgtt cgtggccctc atcccgccga ccttgcccgg   2880
cacaaacatc gtgttggggg cccttccgga ggacagacac atcgaccgcc tggccaaacg   2940
ccagcgcccc ggcgagcggc ttgacctggc tatgctggcc gcgattcgcc gcgtttacgg   3000
gctgcttgcc aatacggtgc ggtatctgca gggcggcggg tcgtggcggg aggattgggg   3060
acagctttcg gggacggccg tgccgcccca gggtgccgag ccccagagca acgcgggccc   3120
acgaccccat atcggggaca cgttatttac cctgtttcgg gcccccgagt tgctggcccc   3180
caacggcgac ctgtacaacg tgtttgcctg ggccttggac gtcttggcca aacgcctccg   3240
tcccatgcac gtctttatcc tggattacga ccaatcgccc gccggctgcc gggacgccct   3300
gctgcaactt acctccggga tggtccagac ccacgtcacc acccccggct ccataccgac   3360
gatctgcgac ctggcgcgca cgtttgcccg ggagatgggg gaggctaact gagctctaga   3420
gctcgctgat cagcctcgac tgtgccttct agttgccagc catctgttgt ttgcccctcc   3480
cccgtgcctt ccttgaccct ggaaggtgcc actcccactg tcctttccta ataaaatgag   3540
gaaattgcat cgcattgtct gagtaggtgt cattctattc tggggggtgg ggtggggcag   3600
gacagcaagg gggaggattg ggaagacaat agcaggcatg ctggggatgc ggtgggctct   3660
atggcttctg aggcggaaag aaccagctgg ggctcgagat ccactagtta aaagttttgt   3720
tactttatag aagaaatttt gagtttttgt tttttttttaa taaataaata aacataaata   3780
aattgtttgt tgaatttatt attagtatgt aagtgtaaat ataataaaac ttaatatcta   3840
ttcaaattaa taaataaacc tcgatataca gaccgataaa acacatgcgt caattttacg   3900
catgattatc tttaacgtac gtcacaatat gattatcttt ctagggttaa tctagtataa   3960
ttgcttgata agagattgag tatgtttttc ctaaaggtgt taacagggag gctggtgtct   4020
gggtcaggat gatgtcccca tgcactgata aaaagtataa gaagaaagtg tcattgatgg   4080
tgcatggcag ggacatgctc cgtgcagtgg ccaccctcac taagacagat gaactttggg   4140
aaataatacc caatggcaga aaagaaggta gactatgaag gtacccaaaa caagaataag   4200
gtgcacctca tttagtctct gggtattaaa gagacctgca gttcttgata gtggtggatc   4260
tgtgagtgct gcatgcatgg agacaacacg gtatcatctt tgtatatctg taataaattg   4320
cttgatctaa tactagtaag aacaaaggca taacaccatt acctaatact tacaaatata   4380
```

```
tagcatcatg ccgatacatt ttatttttaa tttttttttag aaaggaacaa tgttaaactc   4440
acagaaatgt tgcaggtata gcacaattac ccccttccct acccggaatc ttatgagagt   4500
cttttgaaga cttgagaatc ctaccatcta acattttact atgtgtttcc tacaaacaag   4560
aatattctcc taaataatcc tgatacacca atgaaataca ttactctatc ggctcctgag   4620
gaatatttaa aattctcaaa aaaataccta aaaattgttt ctcataataa aatagtcccc   4680
agtagaaaca cattctctgc agacaaattt gtgctaccct ggtcttacct gggacacctg   4740
gggacactga gctggtgctg agttactgag atgagccagc tctgcagctg tgcccagcct   4800
gccccatccc ctgctcattt gcatgttccc agagcacaac ctcctgccct gaagccttat   4860
taataggctg gtcacacttt gtgcaggagt cagacccagt caggacacag catggacatg   4920
agggtccccg ctcagctcct ggggctcctg ctgctctggc tcccaggtaa gtaatttttc   4980
actattgtct tctgaaattt gggtctgatg gccagtattg acttttagag gcttaaatag   5040
gagtttggta aagattggta aatgagggca tttaagattt gccatgggtt gcaaaagtta   5100
aactcagctt caaaaatgga tttggagaaa aaaagattaa attgctctaa actgaatgac   5160
acaaagtaaa aaaaaaaagt gtaactaaaa aggaaccctt gtatttctaa ggagcaaaag   5220
taaatttatt tttgttcact cttgccaaat attgtattgg ttgttgctga ttatgcatga   5280
tacagaaaag tggaaaaata catttttttag tctttctccc ttttgtttga taaattattt   5340
tgtcagacaa caataaaaat caatagcacg ccctaagaaa aatcagggaa aagtgaagtg   5400
tacctatttg ctatgtagaa gaggcagctt acttgaaaat cagcagcaat gttgttttta   5460
gagtctgtaa taagtaataa actcaaaaag acacattcta taggaataag ggcttcacag   5520
atagagctca ttttttaaaa atccaatttg tacattagac taaacgtgaa attatctctt   5580
attgtaatgg tggaaaggtg gttattccca aaagctcaat ctcaaagaaa tgtgtttaaa   5640
tgaaaaaaag taaataattg cattttttaa tgaccgtggg tctgtgaaaa aaataggaaa   5700
tattttaaag agtatgttct ttcattatcc tctgttatta cttgtctaca tttttattct   5760
gccaagaagg ccgtggcacc gcgagctgta gacagagccg cggtctttct cgattgagtg   5820
gctttggtgg ccatgccacc gcgctcttgg ggcagccgcc ttgccgctag tggccgtggc   5880
caccctgtgt ctgcccgatt gatgctgccg tagccagctt tcctgatgca cagtgataca   5940
aataatgcca ctaagggaaa gagaacagaa acgtaatggg cgctgagctg ggaaaaccag   6000
ggagaagact gatttattag agatttcaga aataaaattc acattcatta tgatatctca   6060
ttagtgaaaa tttccattag gggattgtaa ataatttaaa gctttttttt ttttcagtgc   6120
tatttaatta tttcaatatc ctctcatcaa atgtatttaa ataacaaaag ctcaaccaaa   6180
aagaaagaaa tatgtaattc tttcagagta aaaatcacac ccatgacctg gccactgagg   6240
gcttgatcaa ttcactttga atttggcatt aaataccatt aaggtatatt aactgatttt   6300
aaaataagat atattcgtga ccatgttttt aactttcaaa aatgtagctg ccagtgtgtg   6360
attttatttc agttgtacaa aatatctaaa cctatagcaa tgtgattaat aaaaacttaa   6420
acatattttc cagtacctta attctgtgat aggaaaattt taatctgagt attttaattt   6480
cataatctct aaaatagttt aatgatttgt cattgtgttg ctgtcgttta ccccagctga   6540
tctcaaaagt gatatttaag gagattattt tggtctgcaa caacttgata ggactatttt   6600
agggcctttt taaagctcta ttaaaactaa cttacaacga ttcaaaactg ttttaaacta   6660
tttcaaaatg attttagagc cttttgaaaa ctcttttaaa cactttttaa actctattaa   6720
```

-continued aactaataag ataacttgaa ataattttca tgtcaaatac attaactgtt taatgtttaa 6780
atgccagatg aaaaatgtaa agctatcaag aattcaccca gataggagta tcttcatagc 6840
atgtttttcc ctgcttattt tccagtgatc acattatttt gctaccatgg ttattttata 6900
caattatctg aaaaaaatta gttatgaaga ttaaaagaga agaaaatatt aaacataaga 6960
gattcagtct ttcatgttga actgcttggt taacagtgaa gttagtttta aaaaaaaaaa 7020
aaactatttc tgttatcagc tgacttctcc ctatctgttg acttctccca gcaaaagatt 7080
cttattttac attttaacta ctgctctccc acccaacggg tggaatcccc cagaggggga 7140
tttccaagag gccacctggc agttgctgag ggtcagaagt gaagctagcc acttcctctt 7200
aggcaggtgg ccaagattac agttgacctc tcctggtatg gctgaaaatt gctgcatatg 7260
gttacaggcc ttgaggcctt tgggagggct tagagagttg ctggaacagt cagaaggtgg 7320
aggggctgac accacccagg cgcagaggca gggctcaggg cctgctctgc agggaggttt 7380
tagcccagcc cagccaaagt aacccccggg agcctgttat cccagcacag tcctggaaga 7440
ggcacagggg aaataaaagc ggacggaggc tttccttgac tcagccgctg cctggtcttc 7500
ttcagacctg ttctgaattc taaactctga gggggtcgga tgacgtggcc attctttgcc 7560
taaagcattg agtttactgc aaggtcagaa aagcatgcaa agccctcaga atggctgcaa 7620
agagctccaa caaaacaatt tagaacttta ttaaggaata gggggaagct aggaagaaac 7680
tcaaaacatc aagattttaa atacgcttct tggtctcctt gctataatta tctgggataa 7740
gcatgctgtt ttctgtctgt ccctaacatg ccctgtgatt atccgcaaac aacacaccca 7800
agggcagaac tttgttactt aaacaccatc ctgtttgctt ctttcctcag gtgccaaatg 7860
tgtgtttggc agcgggaccc agctcaccgt tttaagtcag cccaaggcca ccccctcggt 7920
cactctgttc ccgccgtcct ctgaggagct ccaagccaac aaggctacac tggtgtgtct 7980
catgaatgac ttttatccgg gaatcttgac ggtgacctgg aaggcagatg gtacccccat 8040
cacccagggc gtggagatga ccacgccctc caaacagagc aacaacaagt acgcggccag 8100
cagctacctg agcctgacgc ccgagcagtg gaggtcccgc agaagctaca gctgccaggt 8160
catgcacgaa gggagcaccg tggagaagac ggtggcccct gcagaatgtt catagagaca 8220
aaggtcctga gacgccacca ccagctcccc agctccatcc tatcttccct tctaaggtct 8280
tggaggcttc cccacaagcg acctaccact gttgcggtgc tccaaacctc ctccccacct 8340
ccttctcctc ctcctccctt tccttggctt ttatcatgct aatatttgca gaaaatattc 8400
aataaagtga gtctttgcac ttgagatctc tgtctttctt actaaatggt agtaatcagt 8460
tgtttttcca gttacctggg tttctcttct aaagaagtta aatgtttagt tgccctgaaa 8520
tccaccacac ttaaaggata aataaaaccc tccacttgcc ctggttggct gtccactaca 8580
tggcagtcct ttctaaggtt cacgagtact attcatggct tatttctctg ggccatggta 8640
ggtttgagga ggcatacttc ctagttttct tcccctaagt cgtcaaagtc ctgaaggggg 8700
acagtcttta caagcacatg ttctgtaatc tgattcaacc tacccagtaa acttggcgaa 8760
gcaaagtaga atcattatca caggaagcaa aggcaaccta aatgtgcaag caataggaaa 8820
atgtggaagc ccatcatagt acttggactt catctgcttt tgtgccttca ctaagttttt 8880
aaacatgagc tggctcctat ctgccattgg caaggctggg cactacccac aacctacttc 8940
aaggacctct ataccgtgag attacacaca tacatcaaaa tttgggaaaa gttctaccaa 9000
gctgagagct gatcacccca ctcttaggtg cttatctctg tacaccagaa accttaagaa 9060
gcaaccagta ttgagagac 9079

<210> SEQ ID NO 81
<211> LENGTH: 420
<212> TYPE: DNA
<213> ORGANISM: Artificial Sequence
<220> FEATURE:
<223> OTHER INFORMATION: Lambda 5 transgene-predicted spliced coding sequence

<400> SEQUENCE: 81

```
atggacatga gggtccccgc tcagctcctg gggctcctgc tgctctggct cccaggtgcc     60

aaatgtgtgt ttggcagcgg gacccagctc accgttttaa gtcagcccaa ggccaccccc    120

tcggtcactc tgttcccgcc gtcctctgag gagctccaag ccaacaaggc tacactggtg    180

tgtctcatga atgactttta tccgggaatc ttgacggtga cctggaaggc agatggtacc    240

cccatcaccc agggcgtgga gatgaccacg ccctccaaac agagcaacaa caagtacgcg    300

gccagcagct acctgagcct gacgcccgag cagtggaggt cccgcagaag ctacagctgc    360

caggtcatgc acgaagggag caccgtggag aagacggtgg cccctgcaga atgttcatag    420
```

<210> SEQ ID NO 82
<211> LENGTH: 139
<212> TYPE: PRT
<213> ORGANISM: Artificial Sequence
<220> FEATURE:
<223> OTHER INFORMATION: Lambda 5 transgene-predicted protein

<400> SEQUENCE: 82

```
Met Asp Met Arg Val Pro Ala Gln Leu Leu Gly Leu Leu Leu Leu Trp
1               5                   10                  15

Leu Pro Gly Ala Lys Cys Val Phe Gly Ser Gly Thr Gln Leu Thr Val
            20                  25                  30

Leu Ser Gln Pro Lys Ala Thr Pro Ser Val Thr Leu Phe Pro Pro Ser
        35                  40                  45

Ser Glu Glu Leu Gln Ala Asn Lys Ala Thr Leu Val Cys Leu Met Asn
    50                  55                  60

Asp Phe Tyr Pro Gly Ile Leu Thr Val Thr Trp Lys Ala Asp Gly Thr
65                  70                  75                  80

Pro Ile Thr Gln Gly Val Glu Met Thr Thr Pro Ser Lys Gln Ser Asn
                85                  90                  95

Asn Lys Tyr Ala Ala Ser Ser Tyr Leu Ser Leu Thr Pro Glu Gln Trp
            100                 105                 110

Arg Ser Arg Arg Ser Tyr Ser Cys Gln Val Met His Glu Gly Ser Thr
        115                 120                 125

Val Glu Lys Thr Val Ala Pro Ala Glu Cys Ser
    130                 135
```

<210> SEQ ID NO 83
<211> LENGTH: 399
<212> TYPE: DNA
<213> ORGANISM: Artificial Sequence
<220> FEATURE:
<223> OTHER INFORMATION: Vk3-2 fragment locus-predicted spliced coding sequence

<400> SEQUENCE: 83

```
atggagaaag acacactcct gctatgggtc ctgcttctct gggttccagg ttccacaggt     60

gacattgtgc tgaaacgggc tgatgctgca ccaactgtat ccatcttccc accatccagt    120

gagcagttaa catctggagg tgcctcagtc gtgtgcttct tgaacaactt ctaccccaaa    180
```

gacatcaatg tcaagtggaa gattgatggc agtgaacgac aaaatggcgt cctgaacagt 240
tggactgatc aggacagcaa agacagcacc tacggcatga gcagcaccct cacgttgacc 300
aaggacgagt atgaacgaca taacagctat acctgtgagg ccactcacaa gacatcaact 360
tcacccattg tcaagagctt caacaggaat gagtgttag 399

<210> SEQ ID NO 84
<211> LENGTH: 132
<212> TYPE: PRT
<213> ORGANISM: Artificial Sequence
<220> FEATURE:
<223> OTHER INFORMATION: Vk3-2 fragment locus-predicted protein

<400> SEQUENCE: 84

Met Glu Lys Asp Thr Leu Leu Leu Trp Val Leu Leu Leu Trp Val Pro
1 5 10 15

Gly Ser Thr Gly Asp Ile Val Leu Lys Arg Ala Asp Ala Ala Pro Thr
20 25 30

Val Ser Ile Phe Pro Pro Ser Ser Glu Gln Leu Thr Ser Gly Gly Ala
35 40 45

Ser Val Val Cys Phe Leu Asn Asn Phe Tyr Pro Lys Asp Ile Asn Val
50 55 60

Lys Trp Lys Ile Asp Gly Ser Glu Arg Gln Asn Gly Val Leu Asn Ser
65 70 75 80

Trp Thr Asp Gln Asp Ser Lys Asp Ser Thr Tyr Gly Met Ser Ser Thr
85 90 95

Leu Thr Leu Thr Lys Asp Glu Tyr Glu Arg His Asn Ser Tyr Thr Cys
100 105 110

Glu Ala Thr His Lys Thr Ser Thr Ser Pro Ile Val Lys Ser Phe Asn
115 120 125

Arg Asn Glu Cys
130

<210> SEQ ID NO 85
<211> LENGTH: 399
<212> TYPE: PRT
<213> ORGANISM: Artificial Sequence
<220> FEATURE:
<223> OTHER INFORMATION: Vk3-4 fragment locus-predicted spliced coding sequence

<400> SEQUENCE: 85

Ala Thr Gly Gly Ala Gly Ala Cys Ala Gly Ala Cys Ala Cys Ala Ala
1 5 10 15

Thr Cys Cys Thr Gly Cys Thr Ala Thr Gly Gly Gly Thr Gly Cys Thr
20 25 30

Gly Cys Thr Gly Cys Thr Cys Thr Gly Gly Gly Thr Thr Cys Cys Ala
35 40 45

Gly Gly Cys Thr Cys Cys Ala Cys Thr Gly Gly Thr Gly Ala Cys Ala
50 55 60

Thr Thr Gly Thr Gly Cys Thr Gly Ala Ala Ala Cys Gly Gly Gly Cys
65 70 75 80

Thr Gly Ala Thr Gly Cys Thr Gly Cys Ala Cys Cys Ala Ala Cys Thr
85 90 95

Gly Thr Ala Thr Cys Cys Ala Thr Cys Thr Thr Cys Cys Cys Ala Cys
100 105 110

Cys Ala Thr Cys Cys Ala Gly Thr Gly Ala Gly Cys Ala Gly Thr Thr 115 120 125

Ala Ala Cys Ala Thr Cys Thr Gly Gly Ala Gly Gly Thr Gly Cys Cys
130 135 140

Thr Cys Ala Gly Thr Cys Gly Thr Gly Thr Gly Cys Thr Thr Cys Thr
145 150 155 160

Thr Gly Ala Ala Cys Ala Ala Cys Thr Thr Cys Thr Ala Cys Cys Cys
165 170 175

Cys Ala Ala Ala Gly Ala Cys Ala Thr Cys Ala Ala Thr Gly Thr Cys
180 185 190

Ala Ala Gly Thr Gly Gly Ala Ala Gly Ala Thr Thr Gly Ala Thr Gly
195 200 205

Gly Cys Ala Gly Thr Gly Ala Ala Cys Gly Ala Cys Ala Ala Ala Ala
210 215 220

Thr Gly Gly Cys Gly Thr Cys Cys Thr Gly Ala Ala Cys Ala Gly Thr
225 230 235 240

Thr Gly Gly Ala Cys Thr Gly Ala Thr Cys Ala Gly Gly Ala Cys Ala
245 250 255

Gly Cys Ala Ala Ala Gly Ala Cys Ala Gly Cys Ala Cys Cys Thr Ala
260 265 270

Cys Gly Gly Cys Ala Thr Gly Ala Gly Cys Ala Gly Cys Ala Cys Cys
275 280 285

Cys Thr Cys Ala Cys Gly Thr Thr Gly Ala Cys Cys Ala Ala Gly Gly
290 295 300

Ala Cys Gly Ala Gly Thr Ala Thr Gly Ala Ala Cys Gly Ala Cys Ala
305 310 315 320

Thr Ala Ala Cys Ala Gly Cys Thr Ala Thr Ala Cys Cys Thr Gly Thr
325 330 335

Gly Ala Gly Gly Cys Cys Ala Cys Thr Cys Ala Cys Ala Ala Gly Ala
340 345 350

Cys Ala Thr Cys Ala Ala Cys Thr Thr Cys Ala Cys Cys Cys Ala Thr
355 360 365

Thr Gly Thr Cys Ala Ala Gly Ala Gly Cys Thr Thr Cys Ala Ala Cys
370 375 380

Ala Gly Gly Ala Ala Thr Gly Ala Gly Thr Gly Thr Thr Ala Gly
385 390 395

<210> SEQ ID NO 86
<211> LENGTH: 132
<212> TYPE: PRT
<213> ORGANISM: Artificial Sequence
<220> FEATURE:
<223> OTHER INFORMATION: Vk3-4 fragment locus-predicted protein

<400> SEQUENCE: 86

Met Glu Thr Asp Thr Ile Leu Leu Trp Val Leu Leu Leu Trp Val Pro
1 5 10 15

Gly Ser Thr Gly Asp Ile Val Leu Lys Arg Ala Asp Ala Ala Pro Thr
20 25 30

Val Ser Ile Phe Pro Pro Ser Ser Glu Gln Leu Thr Ser Gly Gly Ala
35 40 45

Ser Val Val Cys Phe Leu Asn Asn Phe Tyr Pro Lys Asp Ile Asn Val
50 55 60

Lys Trp Lys Ile Asp Gly Ser Glu Arg Gln Asn Gly Val Leu Asn Ser
65 70 75 80

Trp Thr Asp Gln Asp Ser Lys Asp Ser Thr Tyr Gly Met Ser Ser Thr

```
                85                  90                  95

Leu Thr Leu Thr Lys Asp Glu Tyr Glu Arg His Asn Ser Tyr Thr Cys
            100                 105                 110

Glu Ala Thr His Lys Thr Ser Thr Ser Pro Ile Val Lys Ser Phe Asn
        115                 120                 125

Arg Asn Glu Cys
    130


<210> SEQ ID NO 87
<211> LENGTH: 399
<212> TYPE: DNA
<213> ORGANISM: Artificial Sequence
<220> FEATURE:
<223> OTHER INFORMATION: Vk6-17 fragment locus-predicted spliced coding
      sequence

<400> SEQUENCE: 87

atggagtcac agattcaggt ctttgtattc gtgtttctct ggttgtctgg tgttgacgga     60

gacattgtgc tgaaacgggc tgatgctgca ccaactgtat ccatcttccc accatccagt    120

gagcagttaa catctggagg tgcctcagtc gtgtgcttct tgaacaactt ctaccccaaa    180

gacatcaatg tcaagtggaa gattgatggc agtgaacgac aaaatggcgt cctgaacagt    240

tggactgatc aggacagcaa agacagcacc tacggcatga gcagcaccct cacgttgacc    300

aaggacgagt atgaacgaca taacagctat acctgtgagg ccactcacaa gacatcaact    360

tcacccattg tcaagagctt caacaggaat gagtgttag                           399


<210> SEQ ID NO 88
<211> LENGTH: 132
<212> TYPE: PRT
<213> ORGANISM: Artificial Sequence
<220> FEATURE:
<223> OTHER INFORMATION: Vk6-17 fragment locus-predicted protein

<400> SEQUENCE: 88

Met Glu Ser Gln Ile Gln Val Phe Val Phe Val Phe Leu Trp Leu Ser
1               5                   10                  15

Gly Val Asp Gly Asp Ile Val Leu Lys Arg Ala Asp Ala Ala Pro Thr
            20                  25                  30

Val Ser Ile Phe Pro Pro Ser Ser Glu Gln Leu Thr Ser Gly Gly Ala
        35                  40                  45

Ser Val Val Cys Phe Leu Asn Asn Phe Tyr Pro Lys Asp Ile Asn Val
    50                  55                  60

Lys Trp Lys Ile Asp Gly Ser Glu Arg Gln Asn Gly Val Leu Asn Ser
65                  70                  75                  80

Trp Thr Asp Gln Asp Ser Lys Asp Ser Thr Tyr Gly Met Ser Ser Thr
                85                  90                  95

Leu Thr Leu Thr Lys Asp Glu Tyr Glu Arg His Asn Ser Tyr Thr Cys
            100                 105                 110

Glu Ala Thr His Lys Thr Ser Thr Ser Pro Ile Val Lys Ser Phe Asn
        115                 120                 125

Arg Asn Glu Cys
    130


<210> SEQ ID NO 89
<211> LENGTH: 399
<212> TYPE: DNA
<213> ORGANISM: Artificial Sequence
<220> FEATURE:
```

<223> OTHER INFORMATION: Vk10-96 fragment locus-predicted spliced coding
      sequence

<400> SEQUENCE: 89
atgatgtcct ctgctcagtt ccttggtctc ctgttgctct gttttcaagg taccagatgt 60
gatatccagc tgaaacgggc tgatgctgca ccaactgtat ccatcttccc accatccagt 120
gagcagttaa catctggagg tgcctcagtc gtgtgcttct tgaacaactt ctaccccaaa 180
gacatcaatg tcaagtggaa gattgatggc agtgaacgac aaaatggcgt cctgaacagt 240
tggactgatc aggacagcaa agacagcacc tacggcatga gcagcaccct cacgttgacc 300
aaggacgagt atgaacgaca taacagctat acctgtgagg ccactcacaa gacatcaact 360
tcacccattg tcaagagctt caacaggaat gagtgttag 399

<210> SEQ ID NO 90
<211> LENGTH: 132
<212> TYPE: PRT
<213> ORGANISM: Artificial Sequence
<220> FEATURE:
<223> OTHER INFORMATION: Vk10-96 fragment locus-predicted protein

<400> SEQUENCE: 90

Met Met Ser Ser Ala Gln Phe Leu Gly Leu Leu Leu Leu Cys Phe Gln
1               5                   10                  15

Gly Thr Arg Cys Asp Ile Gln Leu Lys Arg Ala Asp Ala Ala Pro Thr
            20                  25                  30

Val Ser Ile Phe Pro Pro Ser Ser Glu Gln Leu Thr Ser Gly Gly Ala
        35                  40                  45

Ser Val Val Cys Phe Leu Asn Asn Phe Tyr Pro Lys Asp Ile Asn Val
    50                  55                  60

Lys Trp Lys Ile Asp Gly Ser Glu Arg Gln Asn Gly Val Leu Asn Ser
65                  70                  75                  80

Trp Thr Asp Gln Asp Ser Lys Asp Ser Thr Tyr Gly Met Ser Ser Thr
                85                  90                  95

Leu Thr Leu Thr Lys Asp Glu Tyr Glu Arg His Asn Ser Tyr Thr Cys
            100                 105                 110

Glu Ala Thr His Lys Thr Ser Thr Ser Pro Ile Val Lys Ser Phe Asn
        115                 120                 125

Arg Asn Glu Cys
    130

<210> SEQ ID NO 91
<211> LENGTH: 1257
<212> TYPE: DNA
<213> ORGANISM: Artificial Sequence
<220> FEATURE:
<223> OTHER INFORMATION: Vk6-17 full transgene, promoter and leader,
      including intron and J5 fragment

<400> SEQUENCE: 91
gggttaggtg catcgatatc tctgaatgaa cacagaccca gcagtactct tctgtatgtg 60
tgttggtggc atcatatcag ctggtgtatg ctgcctgttt ggtgatccag tgtttgagag 120
atctcggggg tccagattaa ttgagacagt tggacttcct acagggtcac tgtcctcctc 180
aacttctttc agtctttccc taattcaaca acaggagtca gctgcttctg tccattggtt 240
gggtgcaaat acctgcatct agctcaactg cttgttgtat cttctagagt gaggtcatgc 300
taggtccctt tctgtgagtt cttcatagcc tcaatgatag tgtcaggcct tgtggctgcc 360
acttgagctg gattccactt tggacctgtc gctggacctt cttttcttca ggctcccctc 420
catttccatc cctgtaattc tttcagacag gaacaattat gggtcagagt tgtaactgta 480
ggatggcacc ccctccctca tttgatgccc tgtcttcctg ctggaggtgg gctctagaag 540
ttccctctcc ctactgttgg gcattttatc cctttgattc ctgagagtct ctcacctgca 600
aggtctctgg tgcattctgg agggtcctcc caacctccta cctcctgagg ttgcctgctt 660
ccattctttc agctggccct cagtgcttca gtcctttacc ctcacccaat atctgatttt 720
gatggaagcc tatcatgaga gcatctatac acttgtggtt tcagagcttt aaattggtcc 780
ttgagcttct attttgactt ccttcccagt gattacttcc tgtctttggt tgtacttttg 840
actgtttatt taacctggat actctcaaac cgctgtgtaa tttacttcct tatttgatga 900
ctcctttgca tagatcccta gaggccagcc cagctgctca tgatttataa accaggtctt 960
tgcagtgaga tatgaaatgc atcacaccag catgggcatc aaaatggagt cacagattca 1020
ggtctttgta ttcgtgtttc tctggttgtc tggtgagaca tgtaaaactt ttataatatc 1080
ttaaaagtaa ttcatttaaa tatctatttc ctataagaag ccaatattag gcagacaatg 1140
ctattagata agacattttg gattctaaca tttgtatcat gaagtctttg tatgtgtaag 1200
tgtatacaca ttatctgttt ctgtttgcag gtgttgacgg agacattgtg ctgaaac 1257

<210> SEQ ID NO 92
<211> LENGTH: 3177
<212> TYPE: DNA
<213> ORGANISM: Artificial Sequence
<220> FEATURE:
<223> OTHER INFORMATION: Vk6-17 full targeting vector insert including homology arms

<400> SEQUENCE: 92
gctgaatctt gaatgacagc tcaagggata gggaggacag ggtgttcaga agcagagaag 60
atgccttgta aatgtggaag gctgtggcag gattggaagg actttggggt ggtaggaagg 120
ggatgggaat gggtggttac aagagaaaca agactgtagt aaataaagct gaaactcaaa 180
gcaagctttc agcatcttta attggagaca caaacttcaa aggtatcatg aatgtggttg 240
atcttggtga aagttgagct tcacctgtcc taacaacaga ccaatccatg agtgaaagct 300
tatctttctc ctttattaat ggttgctgtt gtatccataa ctcaattcca aaggatatga 360
accttaacat atagatataa ttttgtgtac cttctatgaa acagcattaa agcaaagaag 420
ttcaaataga aagactggct tagttattat taactaagag atgctagtga gttctaaatt 480
aataccattt aaaatttata atttgcagaa ttaccaccac caccaccact cagcccagga 540
aaagttacaa agaactggct atccaatttg tttgttttcc tcctttttag agttctttta 600
tttatgtgtg agtgaatgcc atgtacttat ggatgcagag gctgtcagat tccttgcagc 660
tggagtaata gacagttgtg agctacttat agtactagaa ctaagatcct atggaagagc 720
agcgagtgcc actaactgct gagccacctc tccagcccat ttctttattt ttcaatgaac 780
aaataataag cagtcctatg tgacatgctt ctaaagcaaa agatataata tttagtatta 840
tatacattaa taataaaata cattatcttc taagaattga agtctcaact atgaaaatca 900
gcagttctct gtcagagaag ggttaggtg catcgatatc tctgaatgaa cacagaccca 960
gcagtactct tctgtatgtg tgttggtggc atcatatcag ctggtgtatg ctgcctgttt 1020
ggtgatccag tgtttgagag atctcggggg tccagattaa ttgagacagt tggacttcct 1080
acagggtcac tgtcctcctc aacttctttc agtctttccc taattcaaca acaggagtca 1140
gctgcttctg tccattggtt gggtgcaaat acctgcatct agctcaactg cttgttgtat 1200
cttctagagt gaggtcatgc taggtccctt tctgtgagtt cttcatagcc tcaatgatag 1260
tgtcaggcct tgtggctgcc acttgagctg gattccactt tggacctgtc gctggacctt 1320
cttttcttca ggctcccctc catttccatc cctgtaattc tttcagacag gaacaattat 1380
gggtcagagt tgtaactgta ggatggcacc ccctccctca tttgatgccc tgtcttcctg 1440
ctggaggtgg gctctagaag ttccctctcc ctactgttgg gcattttatc cctttgattc 1500
ctgagagtct ctcacctgca aggtctctgg tgcattctgg agggtcctcc caacctccta 1560
cctcctgagg ttgcctgctt ccattctttc agctggccct cagtgcttca gtcctttacc 1620
ctcacccaat atctgatttt gatggaagcc tatcatgaga gcatctatac acttgtggtt 1680
tcagagcttt aaattggtcc ttgagcttct attttgactt ccttcccagt gattacttcc 1740
tgtctttggt tgtacttttg actgtttatt taacctggat actctcaaac cgctgtgtaa 1800
tttacttcct tatttgatga ctcctttgca tagatcccta gaggccagcc cagctgctca 1860
tgatttataa accaggtctt tgcagtgaga tatgaaatgc atcacaccag catgggcatc 1920
aaaatggagt cacagattca ggtctttgta ttcgtgtttc tctggttgtc tggtgagaca 1980
tgtaaaactt ttataatatc ttaaaagtaa ttcatttaaa tatctatttc ctataagaag 2040
ccaatattag gcagacaatg ctattagata agacattttg gattctaaca tttgtatcat 2100
gaagtctttg tatgtgtaag tgtatacaca ttatctgttt ctgtttgcag gtgttgacgg 2160
agacattgtg ctgaaacgta agtacacttt tctcatcttt ttttatgtgt aagacacagg 2220
ttttcatgtt aggagttaaa gtcagttcag aaaatcttga gaaaatggag agggctcatt 2280
atcagttgac gtggcataca gtgtcagatt ttctgtttat caagctagtg agattagggg 2340
caaaaagagg ctttagttga gaggaaagta attaatacta tggtcaccat ccaagagatt 2400
ggatcggaga ataagcatga gtagttattg agatctgggt ctgactgcag gtagcgtggt 2460
cttctagacg tttaagtggg agatttggag gggatgagga atgaaggaac ttcaggatag 2520
aaaagggctg aagtcaagtt cagctcctaa aatggatgtg ggagcaaact ttgaagataa 2580
actgaatgac ccagaggatg aaacagcgca gatcaaagag gggcctggag ctctgagaag 2640
agaaggagac tcatccgtgt tgagtttcca caagtactgt cttgagtttt gcaataaaag 2700
tgggatagca gagttgagtg agccgtaggc tgagttctct cttttgtctc ctaagttttt 2760
atgactacaa aaatcagtag tatgtcctga aataatcatt aagctgtttg aaagtatgac 2820
tgcttgccat gtagatacca tggcttgctg aataatcaga agaggtgtga ctcttattct 2880
aaaatttgtc acaaaatgtc aaaatgagag actctgtagg aacgagtcct tgacagacag 2940
ctcaaggggt ttttttcctt tgtctcattt ctacatgaaa gtaaatttga aatgatcttt 3000
tttattataa gagtagaaat acagttgggt ttgaactata tgttttaatg gccacggttt 3060
tgtaagacat ttggtccttt gttttcccag ttattactcg attgtaattt tatatcgcca 3120
gcaatggact gaaacggtcc gcaacctctt ctttacaact gggtgacctc gcggctg 3177

<210> SEQ ID NO 93
<211> LENGTH: 1199
<212> TYPE: DNA
<213> ORGANISM: Artificial Sequence
<220> FEATURE:
<223> OTHER INFORMATION: Vk10-96 full transgene, promoter and leader, including intron and J5 fragment

<400> SEQUENCE: 93

```
acagtgggta atagtctctg gcaggacagc gctgatgatc atgagggctt cctctcagca      60
attaaagact acaatgggaa catatccata acacagtgat cagtgttgac tggtatacta     120
gggatgtcct tttacactgt gcttaatttt gttgggattc attatttatc caatcgtagg     180
aaccaaatgt aacatccaga gtacccagta gcagtgtttt ctgttatagt attcaaggat     240
atcttcacta gtcaaacgtg tatgctgaag aattgtggta aatattagca agtacaagaa     300
aagtgtttaa gtagatgatc ccaaactgag caaagggtac atcccattat tcccaagaga     360
ataaatatac tttcatattc atgtggacaa agaattcctt gtgatatagg ttgctgggat     420
caggaattat atgtgcccat attttgcatt tactcattat actgtattaa acacggctaa     480
ttctgttaaa tcttactttt taattcacca aaaagagtcc tgataaatta tactcttaat     540
taaaagacat gattactcta atcacacaaa tggttcacaa ggataaatatg tagtatttta    600
aaagcaattg aattattaat ctgattaata atctcctgtt tgaataatat tcctagaaac     660
aagattgttt tttatattac acccaatgta tatttgatat atagtattac aattagagct     720
catgtatagt agaatttttc aaataacctt caaaatgaca tctgtaattt taaaacctta     780
aaaatgaagt gtgatctcca aagccatatg ttcactctga ccttgggcaa agaggggtca     840
ctgtgcttgt gctaagtcct gagaagagtt agccttgcag ctgtgctcag ccctaaatag     900
ttcccaaaaa tttgcatgct ctcacttcct atctttgggt actttttcat ataccagtca     960
gattgtgagc cattgtaatt gaagtcaaga ctcagcctgg acatgatgtc ctctgctcag    1020
ttccttggtc tcctgttgct ctgttttcaa ggtaaaattt actacaatgg gaattttgct    1080
gttgcacagt gattcttgtt gactggaatt ttggaggggt cctttctttt cctgcttaac    1140
tctgtgggta tttattatgt ctccactcct aggtaccaga tgtgatatcc agctgaaac     1199
```

<210> SEQ ID NO 94
<211> LENGTH: 3119
<212> TYPE: DNA
<213> ORGANISM: Artificial Sequence
<220> FEATURE:
<223> OTHER INFORMATION: Vk10-96 full targeting vector insert including homology arms

<400> SEQUENCE: 94

```
gctgaatctt gaatgacagc tcaagggata gggaggacag ggtgttcaga agcagagaag      60
atgccttgta aatgtggaag gctgtggcag gattggaagg actttggggt ggtaggaagg     120
ggatgggaat gggtggttac aagagaaaca agactgtagt aaataaagct gaaactcaaa     180
gcaagctttc agcatcttta attggagaca caaacttcaa aggtatcatg aatgtggttg     240
atcttggtga aagttgagct tcacctgtcc taacaacaga ccaatccatg agtgaaagct     300
tatctttctc ctttattaat ggttgctgtt gtatccataa ctcaattcca aaggatatga     360
accttaacat atagatataa ttttgtgtac cttctatgaa acagcattaa agcaaagaag     420
ttcaaataga aagactggct tagttattat taactaagag atgctagtga gttctaaatt     480
aataccattt aaaatttata atttgcagaa ttaccaccac caccaccact cagcccagga     540
aaagttacaa agaactggct atccaatttg tttgttttcc tcctttttag agttctttta     600
tttatgtgtg agtgaatgcc atgtacttat ggatgcagag gctgtcagat tccttgcagc     660
tggagtaata gacagttgtg agctacttat agtactagaa ctaagatcct atggaagagc     720
agcgagtgcc actaactgct gagccacctc tccagcccat ttctttattt ttcaatgaac     780
aaataataag cagtcctatg tgacatgctt ctaaagcaaa agatataata tttagtatta     840
```

```
tatacattaa taataaaata cattatcttc taagaattga agtctcaact atgaaaatca    900
gcagttctct gtcagagaag acagtgggta atagtctctg gcaggacagc gctgatgatc    960
atgagggctt cctctcagca attaaagact acaatgggaa catatccata acacagtgat   1020
cagtgttgac tggtatacta gggatgtcct tttacactgt gcttaatttt gttgggattc   1080
attatttatc caatcgtagg aaccaaatgt aacatccaga gtacccagta gcagtgtttt   1140
ctgttatagt attcaaggat atcttcacta gtcaaacgtg tatgctgaag aattgtggta   1200
aatattagca agtacaagaa aagtgtttaa gtagatgatc ccaaactgag caaagggtac   1260
atcccattat tcccaagaga ataaatatac tttcatattc atgtggacaa agaattcctt   1320
gtgatatagg ttgctgggat caggaattat atgtgcccat attttgcatt tactcattat   1380
actgtattaa acacggctaa ttctgttaaa tcttactttt taattcacca aaaagagtcc   1440
tgataaatta tactcttaat taaaagacat gattactcta atcacacaaa tggttcacaa   1500
ggataaatatg tagtatttta aaagcaattg aattattaat ctgattaata atctcctgtt   1560
tgaataatat tcctagaaac aagattgttt tttatattac acccaatgta tatttgatat   1620
atagtattac aattagagct catgtatagt agaatttttc aaataacctt caaaatgaca   1680
tctgtaattt taaaacctta aaaatgaagt gtgatctcca aagccatatg ttcactctga   1740
ccttgggcaa agaggggtca ctgtgcttgt gctaagtcct gagaagagtt agccttgcag   1800
ctgtgctcag ccctaaatag ttcccaaaaa tttgcatgct ctcacttcct atctttgggt   1860
actttttcat ataccagtca gattgtgagc cattgtaatt gaagtcaaga ctcagcctgg   1920
acatgatgtc ctctgctcag ttccttggtc tcctgttgct ctgttttcaa ggtaaaattt   1980
actacaatgg gaattttgct gttgcacagt gattcttgtt gactggaatt ttggaggggt   2040
cctttctttt cctgcttaac tctgtgggta tttattatgt ctccactcct aggtaccaga   2100
tgtgatatcc agctgaaacg taagtacact tttctcatct ttttttatgt gtaagacaca   2160
ggttttcatg ttaggagtta aagtcagttc agaaaatctt gagaaaatgg agagggctca   2220
ttatcagttg acgtggcata cagtgtcaga ttttctgttt atcaagctag tgagattagg   2280
ggcaaaaaga ggctttagtt gagaggaaag taattaatac tatggtcacc atccaagaga   2340
ttggatcgga gaataagcat gagtagttat tgagatctgg gtctgactgc aggtagcgtg   2400
gtcttctaga cgtttaagtg ggagatttgg aggggatgag gaatgaagga acttcaggat   2460
agaaaagggc tgaagtcaag ttcagctcct aaaatggatg tgggagcaaa ctttgaagat   2520
aaactgaatg acccagagga tgaaacagcg cagatcaaag aggggcctgg agctctgaga   2580
agagaaggag actcatccgt gttgagtttc cacaagtact gtcttgagtt ttgcaataaa   2640
agtgggatag cagagttgag tgagccgtag gctgagttct ctcttttgtc tcctaagttt   2700
ttatgactac aaaaatcagt agtatgtcct gaaataatca ttaagctgtt tgaaagtatg   2760
actgcttgcc atgtagatac catggcttgc tgaataatca gaagaggtgt gactcttatt   2820
ctaaaatttg tcacaaaatg tcaaaatgag agactctgta ggaacgagtc cttgacagac   2880
agctcaaggg gttttttttcc tttgtctcat ttctacatga aagtaaattt gaaatgatct   2940
tttttattat aagagtagaa atacagttgg gtttgaacta tatgttttaa tggccacggt   3000
tttgtaagac atttggtcct ttgttttccc agttattact cgattgtaat tttatatcgc   3060
cagcaatgga ctgaaacggt ccgcaacctc ttctttacaa ctgggtgacc tcgcggctg    3119
```

<210> SEQ ID NO 95
<211> LENGTH: 20

<212> TYPE: DNA
<213> ORGANISM: Artificial Sequence
<220> FEATURE:
<223> OTHER INFORMATION: Primer HCP428

<400> SEQUENCE: 95
gctctggctc ccaggaactg 20

<210> SEQ ID NO 96
<211> LENGTH: 20
<212> TYPE: DNA
<213> ORGANISM: Artificial Sequence
<220> FEATURE:
<223> OTHER INFORMATION: Primer HCP431

<400> SEQUENCE: 96
gtcctgctct gtgacactct 20

<210> SEQ ID NO 97
<211> LENGTH: 22
<212> TYPE: DNA
<213> ORGANISM: Artificial Sequence
<220> FEATURE:
<223> OTHER INFORMATION: Primer HCP446

<400> SEQUENCE: 97
tttgtgcagg agtcagaccc ag 22

<210> SEQ ID NO 98
<211> LENGTH: 23
<212> TYPE: DNA
<213> ORGANISM: Artificial Sequence
<220> FEATURE:
<223> OTHER INFORMATION: Primer HCP451

<400> SEQUENCE: 98
aaaagggtca gaggccaaag gat 23

<210> SEQ ID NO 99
<211> LENGTH: 20
<212> TYPE: DNA
<213> ORGANISM: Artificial Sequence
<220> FEATURE:
<223> OTHER INFORMATION: Primer HCP428

<400> SEQUENCE: 99
gctctggctc ccaggaactg 20

<210> SEQ ID NO 100
<211> LENGTH: 354
<212> TYPE: DNA
<213> ORGANISM: Artificial Sequence
<220> FEATURE:
<223> OTHER INFORMATION: Mouse lambda 5 gene fragment, truncated to include just the J-segment-like and C-segment-like domains

<400> SEQUENCE: 100
gtctttggtg gtgggaccca gctcacaatc ctaggtcagc ccaagtctga ccccttggtc 60
actctgttcc tgccttcctt aaagaatctt cagccaacaa ggccacacgt agtgtgtttg 120
gtgagcgaat tctacccagg tactttggtg gtggactgga aggtagatgg ggtccctgtc 180
actcagggtg tagagacaac ccaaccctcc aaacagacca acaacaaata catggtcagc 240
agctacctga cactgatatc tgaccagtgg atgcctcaca gtagatacag ctgccgggtc 300
actcatgaag gaaacactgt ggagaagagt gtgtcacctg ctgagtgttc ttag 354

-continued

```
<210> SEQ ID NO 101
<211> LENGTH: 117
<212> TYPE: PRT
<213> ORGANISM: Artificial Sequence
<220> FEATURE:
<223> OTHER INFORMATION: Mouse lambda 5 gene fragment, truncated to
      include just the J-segment-like and C-segment-like domains-
      translated

<400> SEQUENCE: 101

Val Phe Gly Gly Gly Thr Gln Leu Thr Ile Leu Gly Gln Pro Lys Ser
1               5                   10                  15

Asp Pro Leu Val Thr Leu Phe Leu Pro Ser Leu Lys Asn Leu Gln Ala
            20                  25                  30

Asn Lys Ala Thr Leu Val Cys Leu Val Ser Glu Phe Tyr Pro Gly Thr
        35                  40                  45

Leu Val Val Asp Trp Lys Val Asp Gly Val Pro Val Thr Gln Gly Val
    50                  55                  60

Glu Thr Thr Gln Pro Ser Lys Gln Thr Asn Asn Lys Tyr Met Val Ser
65                  70                  75                  80

Ser Tyr Leu Thr Leu Ile Ser Asp Gln Trp Met Pro His Ser Arg Tyr
                85                  90                  95

Ser Cys Arg Val Thr His Glu Gly Asn Thr Val Glu Lys Ser Val Ser
            100                 105                 110

Pro Ala Glu Cys Ser
        115
```

ANTIGEN-BINDING MOLECULES COMPRISING UNPAIRED VARIABLE DOMAINS

CROSS REFERENCE TO RELATED APPLICATIONS

This application is a national stage application under 35 U.S.C. § 371 of International Application No. PCT/EP2019/073767, filed internationally on Sep. 5, 2019, which claims benefit of United Kingdom Application No. 1814529.2, filed Sep. 6, 2018, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165062000500SEQLIST.TXT, date recorded: Mar. 1, 2021, size: 145 KB).

FIELD OF THE INVENTION

The present invention relates to polypeptides comprising unpaired antibody variable domains, e.g., unpaired VH domains, for binding antigen. The invention also relates to animals, e.g., mice, that express antibodies comprising one or more heavy chains or heavy chain variable domains, wherein the antibodies are devoid of light chain variable domains that pair with the heavy chain variable domains to form paired antigen binding sites.

BACKGROUND

The antigen-binding region of a native human immunoglobulin is composed of two variable domains—the heavy chain variable (VH) domain and the light chain variable (VL) domain—which pair together to form an Fv region. The Fv region has an antigen-binding site provided by six loops of variable amino acid sequence—the complementarity determining regions (CDRs). The VH domain comprises HCDR1, HCDR2 and HCDR3 interspersed with framework regions (FRs) and the VL domain comprises LCDR1, LCDR2 and LCDR3 interspersed with FRs. One or more CDRs of the VH domain and/or of the VL domain bind to the antigen. Binding may be mediated by CDRs of both the VH and the VL domain, or by CDRs of one domain alone. HCDR3 of the VH domain often has a major role in antigen-binding, although other CDRs of both domains can and often do contribute. Even where an antigen binds solely or mainly to CDRs of the VH domain, the presence of the VL domain in the Fv may stabilise the VH in a functional binding conformation.

Antibody variable domains are generated in vivo through combinatorial rearrangement of gene segments at the immunoglobulin (Ig) loci within cells of B lymphocyte lineage, which provides a repertoire of encoded amino acid sequences capable of binding to the diverse immunogenic stimuli encountered by the immune system. The Ig heavy chain locus in humans has approximately 41 functional V gene segments, 27 functional D gene segments and 6 functional J gene segments, depending on haplotype. Nucleic acid encoding a VH domain is generated through V-D-J gene segment recombination. The V gene segment encodes the N terminal region of the polypeptide chain comprising FR1, HCDR1, FR2, HCDR2, FR3 and the start of HCDR3, while the D gene segment is encompassed within HCDR3 and the J gene segment provides the end of HCDR3 and the C terminal framework region FR4. The highly variable nature of HCDR3 sequences in an antibody repertoire reflects the combinatorial diversity generated by rearrangement of the many different V, D and J segments. Humans have two Ig light chain loci, kappa (κ) and lambda (λ). The human Ig light chain loci have approximately 40 functional Vκ segments, 5 functional Jκ segments, 29 functional Vλ segments and 4 functional Jλ segments, depending on haplotype. Nucleic acid encoding a VL domain is produced by the recombination of two gene segments, V and J, at either the kappa (κ) or lambda (λ) locus. The v gene segment encodes the FR1, LCDR1, FR2, LCDR2, FR3 and the first part of LCDR3, while the J gene segment forms the second part of LCDR3 and the FR4. In addition to the combinatorial diversity arising from V-D-J and V-J recombination and from VH/VL pairing, further antibody sequence diversity is generated by junctional mutations at the point of gene segment joining and by the in vivo process of somatic hypermutation in response to antigen binding.

WO90/05144 (MRC) disclosed that VH domains, when isolated from complete antibodies comprising heavy and light chains, were able to bind to antigen in a 1:1 ratio and with binding constants of equivalent magnitude to those of complete antibody molecules.

Camelids (the animal family including camels and llamas) naturally produce antibodies which bind antigen with unpaired VH domains in the absence of a VL. These antibodies completely lack the immunoglobulin light chain, and are bivalent binders composed of homodimeric heavy chains each comprising an antigen-binding single VH or "VHH" domain, a hinge region and a dimerising constant region comprising CH2 and CH3 domains. While homologous to the heavy chains of classical mammalian antibodies, these "heavy chain antibodies" ("HCAbs") lack the first domain of the constant region (CH1), which is spliced out during mRNA processing (WO94/04678 Casterman & Hamers; WO96/34103 Hamers & Muyldermans).

An analogous mutation occurs in a pathological setting in humans, known as heavy chain disease. Immunoglobulin heavy chains are expressed comprising the VH, CH2 and CH3 domains, but lacking a CH1 domain. In patients with this disease the heavy chains are found to accumulate instead of pairing with light chains to form normal antibodies.

Cartilaginous fish such as sharks also have antibodies composed of heavy chains and lacking any light chain. These antibodies are termed IgNAR (immunoglobulin new antigen receptor) and have been used as a source of single domain antibodies called VNAR fragments.

Researchers have worked to develop single variable domain antibodies into pharmaceutical products. These molecules, known as domain antibodies (dAbs), are bioactive as monomers and, owing to their small size and inherent stability, are also well suited for incorporation into larger molecules to create drugs with prolonged serum half lives and/or other pharmacological activities. Antigen-binding molecules comprising single variable domains of antibodies include immunoconjugates (e.g., dAb-toxin) and chimaeric antigen receptors (CARs). To this end, antibody single variable domain binders have been cloned and expressed in recombinant systems, and in vitro libraries of such binders have been generated for selection and screening using systems such as phage display.

Laboratory animals such as mice have been genetically engineered to express heavy chain antibodies as a further source of single antigen-binding variable domains. One can begin by knocking out (deleting or inactivating) the endogenous Ig light chain loci of the animal (WO92/03918 Genpharm; WO03/000737 The Babraham Institute). The heavy chain alone is then expressed, and homodimerises (FIG. 1*a*). However, the CH1 domain of the heavy chain is intrinsically disordered and adopts the typical immunoglobulin fold only upon interaction with its cognate partner, the Cκ or Cλ domain of the light chain. Expression of Ig heavy chains has been reported to be non-productive owing to misfolding and aggregation of the CH1 domain. Nevertheless, in light chain deficient mice, some functional HCAbs are spontaneously produced through a variation of the class switch mechanism. In class switching, nucleic acid encoding the VH is normally joined to nucleic acid encoding a CH1-CH2-CH3 constant region, but in the aberrant mechanism the VH is joined to only CH2-CH3. The resulting HCAbs, like those of camelids, lack the CH1 domain and can be expressed and selected for antigen binding. However, functional HCAbs are generated only at low efficiency by this method, since the normal mechanism of class switching predominates and produces a full Ig heavy chain including the CH1.

Mouse strains used for producing heavy chain antibodies have therefore been engineered to have a genetic deletion of the CH1 domain of the immunoglobulin heavy chain and knockout of the light chains. Such mice produce antibodies comprising dimeric heavy chains and lacking light chains, each heavy chain having a variable (VH) domain and constant regions CH2 and CH3. The constant regions dimerise to form an Fc region, while the two VH domains are available for divalent antigen binding (FIG. 1*b*). Following immunisation of the mice with a target antigen, heavy chain antibodies specific for the antigen are generated, selected and affinity matured in vivo, and can be isolated. Nucleic acid encoding the VH domains can then be expressed recombinantly and cloned as desired to provide polypeptides comprising the VH domain, optionally in the context of larger molecules such as CARs or other products for therapeutic or diagnostic use.

Erasmus Universiteit Rotterdam have described transgenic mice whose genomes comprise exons from camelid VHH domains or "camelised" VH domains and heavy chain constant region genes which did not express a functional CH1 domain (WO02/085944, WO02/085945, WO2006/008548, WO2010/109165). "Camelised" VH are human (or other non-camelid) VH sequences which have been mutated to resemble camelid VHH. In these transgenic platforms, the heavy chain genes are engineered to exclude functional CH1 domains. As reported in WO02/085944, the absence of the CH1 rendered the heavy chain antibodies unable to associate with light chains to form "conventional" antibodies, since the CH1 was the natural partner for the constant domain of the light chain. WO2006/008548 reported that normal B-cell maturation and antibody production in the mice was dependent on the complete absence of CH1 sequences from each heavy chain constant region present in the transgenic locus. WO2004/049794 (The Babraham Institute) describes production of HCAbs from a YAC transgene in mice, in which the CH1 domain of the heavy chain is spliced out during mRNA processing. The resulting mice could then be crossed with mice in which endogenous heavy and light chain genes had been knocked out, to generate mice which only expressed the desired HCAbs.

Unfortunately, "heavy chain only" mice carrying CH1 deletions in their Ig heavy chains do not have normal B cell populations. Mice in which DNA encoding the CH1 domain was deleted from both the μ and the γ heavy chain constant region genes produced IgM heavy chains lacking CH1 (CH1Δμ) and IgG heavy chains lacking CH1 (CH1Δγ), but the proportion of immature B cells in these mice was increased, with impaired differentiation into follicular zone B cells and marginal zone B cells. Nevertheless, the deletion of CH1 was essential for the expression of both IgM and IgG antibodies in the mice, since the inclusion of the CH1 domain in either the μ or γ heavy chain resulted in non-productive expression[1].

Human VH domains are desirable for administration to humans since they are associated with lower immunogenic side effects in patients compared with administration of polypeptides of non-human origin such as camelid VHH. Transgenic mice expressing human antibody heavy chains are a source of human VH domains that undergo in vivo selection for antigen-binding. However, human antibodies naturally contain both heavy and light chains, and only a subset of heavy chain variable regions are able to generate functional heavy chain antibodies in the absence of the light chain. Human VH domains from heavy chain antibodies produced in heavy chain only mice therefore lack the sequence diversity of VH domains from full immunoglobulins. The limitation of the human VH domain repertoire in such mice is compounded where the human Ig heavy chain genes are introduced at a random insertion point in the mouse genome, since the ectopic transgenic locus produces VH domains with HCDR3 sequences which are shorter than in humans (believed to result from limited N-addition occurring during VDJ recombination) and which undergo limited hypermutation, resulting in an already low diversity of VH domains. This appears to be an intrinsic limitation of known random insertion transgenic platforms for human antibody generation. The latter issue can be addressed by integrating the human immunoglobulin genes at the endogenous immunoglobulin locus of the host animal, rather than at a random position in the genome[2]. Recombination and somatic hypermutation at the native loci in such mice generate a broader diversity of sequences from which to evolve less soluble VH domains into ones with improved biophysical properties (such as solubility) in vivo.

WO2011/072204 (Regeneron Pharmaceuticals) described mice expressing heavy chain antibodies comprising human VH domains and mouse constant regions with deleted CH1 domains. These mice were said to comprise a germline deletion of the sequence encoding CH1 in an endogenous Ig constant region gene, rendering them incapable of expressing an IgG mRNA that comprised a sequence encoding a CH1 domain, but the mice retained the ability to express normal functional IgM antibody as the CH1 domain of the IgM isotype constant domain was not deleted. WO2013/171505 (Kymab Limited) described a mouse engineered to express normal IgM antibodies and CH1-deleted IgG antibodies, where stage-specific class switching from IgM to IgG in lymphocytes was accompanied by inactivation of the endogenous Ig light chain loci and genetic deletion of CH1 from the IgG constant region, so that IgG antibodies were expressed by the cell in the absence of light chain expression. This modification enabled antibody and B-cell compartment development to pass through a favourable 4-chain (H2L2) endogenous IgM stage before proceeding to a subsequent IgG stage which selected solely heavy chain only (H2) antibodies from the good pool of heavy chain VDJ recombinations provided by the earlier 4-chain IgM stage, this subsequent stage essentially eliminating the possibility for 4-chain antibodies.

WO2018/039180 (Teneobio, Inc.) reported that HCAbs with less propensity for aggregation could be prepared by replacement of the native amino acid residue at the first position of FR4 of an HCAb by another amino acid residue to disrupt a surface-exposed hydrophobic patch which, in a normal Fv, would be buried in the VH-VL interface. The exposure of the hydrophobic patch was identified as being a causal factor in the unwanted aggregation of heavy chains in the absence of light chain, as well as in VH-VL domain pairing in the presence of light chain. Rats were genetically engineered to express HCAbs including identified VH residue mutations, and heavy chain homodimerisation was enforced by inactivation of the endogenous light chain loci.

Although less common than heavy chain only antibodies, the art has also described production of antibodies comprising unpaired VL domains. WO2009/143472 (Aliva Biopharmaceuticals) and WO2015/143414 (Regeneron Pharmaceuticals) described a method of generating antibodies with unpaired VL domains in transgenic animals, by linking gene sequences encoding a human VL domain to heavy chain constant regions with a deletion of the CH1 domain.

SUMMARY OF THE INVENTION

In the field of antibodies comprising unpaired variable domains and transgenic animals for producing them, the present invention represents a shift away from "heavy chain only" antibodies and "heavy chain only mice" which have to date been the theme of this technical area. The inventors realised that neither CH1 deletion nor light chain absence were necessary to produce antibodies which bind antigen through their VH domain alone. In the present invention, the VL domain of an antibody is deleted, while the CL domain is retained. This produces an antibody comprising a heavy chain and a light chain, wherein the heavy chain comprises an unpaired VH domain for binding antigen and a constant region including a CH1 domain, and wherein the light chain comprises a CL domain and no VL domain (FIG. 2). The absence of the VL domain leaves the VH domain unpaired. The retained CL domain binds the CH1 of the heavy chain, stabilising the antibody molecule and inhibiting heavy chain aggregation. The heavy chain CH1 domain can thus be retained, optionally as part of a full heavy chain constant region (e.g., CH1-CH2-CH3 or CH1-CH2-CH3-CH4). The heavy chain and the (residual) light chain are paired through association of the CH1 with the CL.

Through analogous modifications it is also possible to generate antibodies that bind antigen through the VL domain in the absence of a paired VH domain. Further modifications may optionally be included in antibodies comprising unpaired VH and/or VL domains, e.g., changes in antibody format and design.

Transgenic animals such as mice can be engineered to produce antibodies according to the present invention, for in vivo generation and selection of antigen-specific variable domains that are capable of binding antigen outside the context of a VH-VL pair (Fv). By retaining CH1 and permitting its pairing and stabilisation with a shield domain, the antibody repertoire that can be generated in animals expressing antibodies of the present invention may be significantly greater than CH1-deleted antibody platforms in which the in vivo immune response was limited in some respects. On immunisation with a target antigen of interest, an animal according to the present invention generates antibodies against the target, wherein the antibodies comprise unpaired variable domains that bind the target. These antibodies and/or their encoding nucleic acid may be recovered from the animal, and DNA encoding the variable domain can then be recombinantly expressed, optionally incorporating the unpaired variable domain into a binding molecule (e.g., antibody or chimaeric antigen receptor) comprising the variable domain and one or more further protein domains. The unpaired variable domains, antibodies and other binding molecules comprising them, their encoding nucleic acid, cells and transgenic animals containing such nucleic acid, and methods of generating and using the foregoing are all aspects of the present invention.

In a first aspect, the invention provides an antibody comprising an unpaired variable domain (VH domain or VL domain) linked to a constant region, wherein the constant region comprises a CH1 domain and a domain which pairs with the CH1 domain. The domain which pairs with the CH1 domain is herein termed "shield domain", and its interface with the heavy chain CH1 domain may serve to stabilise the CH1 domain, promoting solubility and/or inhibiting aggregation of the antibodies. The shield domain may be a polypeptide domain, e.g., an immunoglobulin domain, i.e., a polypeptide domain comprising an immunoglobulin fold. It may be a CL domain (Cκ or Cλ) or the Ig domain of a surrogate light chain λ5 protein. An example of a λ5 protein may be a human λ5 domain that is devoid of the 50 amino acid unique region at the N-terminal end of human λ5, or an example of a λ5 protein may be a non-human λ5 domain that is devoid of the region that corresponds to the 50 amino acid unique region at the N-terminal end of human λ5. Preferably, the shield domain is a CL domain, e.g., Cκ, so that the constant region comprises a CH1:CL domain pair. The unpaired variable domain may be linked to either the CH1 domain or the shield domain, e.g., as a fusion protein. This core structure of an unpaired variable domain linked to a constant region comprising a CH1:CL or CH1:λ5 domain pair may be provided in isolation (a protein consisting of that structure) or as part of a larger polypeptide molecule, optionally comprising further antibody constant domains and/or functional moieties. Although such further domains and moieties may be included, the antibody of the present invention characteristically comprises an unpaired variable domain for binding antigen and so is devoid of any polypeptide domain that pairs with said variable domain to provide an antigen-binding site.

The constant region may comprise two polypeptide chains, one comprising the CH1 domain and one comprising the shield domain. Thus, the antibody may comprise

- a first polypeptide comprising an unpaired variable domain, and
- a second polypeptide,
- wherein the first polypeptide comprises a CH1 domain and the second polypeptide comprises a shield domain which pairs with the CH1 domain, or wherein the first polypeptide comprises the shield domain and the second polypeptide comprises the CH1 domain.

For example, the antibody may comprise

- a first polypeptide comprising an unpaired variable domain (e.g., VH domain) and a CH1 domain, and
- a second polypeptide comprising a shield domain which pairs with the CH1 domain (e.g., CL or λ5). In the first polypeptide, the variable domain is preferably an N-terminal domain, followed by an adjacent CH1 domain. The second polypeptide lacks an N-terminal variable domain, thereby leaving the variable domain of the first polypeptide unpaired. The second polypeptide may comprise the shield domain and be devoid of additional domains, or it may consist of the shield domain and a C terminal extension of one or more further domains (e.g., Ig constant domains) and/or functional moieties. Optionally the second polypeptide consists of the shield domain.

Alternatively, the antibody may comprise a first polypeptide comprising a variable domain (e.g., VH domain) and a shield domain, and a second polypeptide comprising a CH1 domain which pairs with said shield domain, wherein the second polypeptide lacks a variable domain, thereby leaving the variable domain of the first polypeptide unpaired. In the first polypeptide, the variable domain is preferably an N-terminal domain, followed by an adjacent shield domain. The second polypeptide lacks an N-terminal variable domain, thereby leaving the variable domain of the first polypeptide unpaired. The second polypeptide may comprise the CH1 domain and be devoid of additional domains, or may consist of the CH1 domain and a C terminal extension of one or more further domains (e.g., Ig constant domains) and/or functional moieties. Optionally the second polypeptide consists of the CH1 domain.

Pairing of the CH1 domain with its shield domain forms a constant region, which may additionally comprise further domains such as CH2, CH3 and/or CH4, typically as C-terminal domains. The first or second polypeptide may comprise CH2-CH3 linked to the C terminus of the CH1 or shield domain respectively. A first polypeptide may comprise (in an N to C direction) the unpaired variable domain linked to CH1-CH2-CH3 (e.g., VH-CH1-CH2-CH3) and a second polypeptide may comprise or consist of the shield domain (e.g., CL or λ5), lacking an N terminal variable domain. As another example, a first polypeptide may comprise (in an N to C direction) the unpaired variable domain linked to CH1 (e.g., VH-CH1) and a second polypeptide may comprise or consist of (in an N to C direction) the shield domain linked to CH2-CH3 (e.g., CL or λ5 linked to CH2-CH3). Domains may be directly linked by a peptide bond, or by a peptide linker. A hinge region is usually present immediately upstream of the CH2 domain, so the polypeptide may comprise the CH1 or shield domain linked via an antibody hinge region to CH2-CH3. The constant region of an antibody according to the present invention may be a human constant region. It may comprise or consist of the amino acid sequence of the constant region of a native human IgG, e.g., human IgG1. Alternatively, the constant region may be from a non-human animal such as a rodent (e.g., a mouse constant region or rat constant region). In a non-human animal as herein described, the constant region may be an endogenous constant region encoded by the endogenous immunoglobulin locus in the non-human animal's genome.

Exemplary pairings of first and second polypeptides (showing domains in an N to C direction) in antibodies of the present invention are shown in Table 1 below.

TABLE 1

Pairs of first and second polypeptides

| First polypeptide | Second polypeptide |
|---|---|
| VH-CH1—CH2—CH3 | CL |
| VH-CH1—CH2—CH3 | λ5 |
| VH-CH1 | CL-CH2—CH3 |
| VH-CH1 | λ5-CH2—CH3 |
| VL-CH1—CH2—CH3 | CL |
| VL-CH1—CH2—CH3 | λ5 |
| VL-CH1 | CL-CH2—CH3 |
| VL-CH1 | λ5-CH2—CH3 |
| VH-CL | CH1—CH2—CH3 |
| VH-λ5 | CH1—CH2—CH3 |
| VH-CL-CH2—CH3 | CH1 |
| VH-λ5-CH2—CH3 | CH1 |
| VL-CL | CH1—CH2—CH3 |
| VL-λ5 | CH1—CH2—CH3 |
| VL-CL-CH2—CH3 | CH1 |
| VL-λ5-CH2—CH3 | CH1 |

A polypeptide comprising CH2-CH3 may comprise further domains, e.g., some antibody isotypes include CH4.

In a given CH1:shield domain pair, any further constant domains (e.g., CH2-CH3) are normally linked to only one of either the CH1 domain and the shield domain. However, CH2-CH3 constant regions naturally dimerise to form an antibody Fc region. A polypeptide comprising CH2-CH3 may associate with a second polypeptide comprising CH2-CH3 via inter-chain pairing between the CH2 and/or CH3 regions, to form an Fc region comprising dimerised CH2-CH3. Inter-chain disulphide bonds may form, and these are normally present in naturally occurring antibodies. Such dimerisation may produce an antibody comprising multiple antigen binding sites. For example, an antibody may comprise two unpaired variable domains, each linked to a constant region comprising CH2 and/or CH3.

An antibody may comprise two first polypeptides and two second polypeptides. Pairs of first and second polypeptides may be independently selected from those shown in Table 1 above. The antibody may comprise two first polypeptides and two second polypeptides, wherein each first polypeptide comprises an unpaired variable domain and a CH1 domain, and each second polypeptide comprises a shield domain which pairs with the CH1 domain, wherein one or both of said second polypeptides lacks a variable domain.

Preferably, the antibody comprises two unpaired variable domains. For example, a four chain antibody may comprise two unpaired variable domains (e.g., two VH domains), each linked to a CH1:shield domain pair, and an Fc region. Optionally, a four-chain antibody comprises two first polypeptides and two second polypeptides, wherein the first and second polypeptides both consist of the same domain structure, e.g., two first polypeptides VH-CH1-CH2-CH3 and two second polypeptides CL. The four-chain antibody may thus comprise two first polypeptides, wherein the first polypeptide is any of the first polypeptides shown in Table 1, and two second polypeptides, wherein the second polypeptide is the corresponding second polypeptide shown in Table 1. The two first polypeptides may have identical amino acid sequences, i.e., the antibody may comprise two copies of the same first polypeptide. The two second polypeptides may have identical amino acid sequences, i.e., the antibody may comprise two copies of the same second polypeptide. Alternatively, the sequences of the two first polypeptides may differ from each other and/or the sequences of the two second polypeptides may differ from each other. Differences in sequence are optionally in (e.g., only in) variable domains, e.g., an antibody may comprise two different unpaired variable domains.

With reference to the structure of a full four chain immunoglobulin comprising two heavy-light chain pairs, each heavy chain comprising VH-CH1-CH2-CH3 and each light chain comprising VL-CL, antibodies with unpaired VH domains can be produced by removing one or both VL domains, leaving the CL domains in place. An antibody according to the present invention may comprise two heavy chains and two light chains, each heavy chain comprising a VH domain and a constant region comprising a CH1 domain, and each light chain comprising a CL domain, wherein one or both light chains lack a VL domain, thereby leaving one or both VH domains unpaired. Conversely, antibodies with unpaired VL domains can be produced by removing one or both VH domains, leaving the CH1 domains in place. Variations may be described with reference to other antibody formats, a number of which are discussed herein. Expression in transgenic animals and selection for antigen-binding is facilitated when the four-chain antibody is composed of two identical first polypeptides (e.g., two identical heavy chains) and two identical second polypeptides (e.g., two identical light chains), since this affects the natural mode of expression, assembly and display of antibodies on the surface of antibody-producing cells in animals such as mice and humans.

In a preferred embodiment, both VL domains of an antibody are deleted, thereby producing a four-chain immunoglobulin having the natural structure of an immunoglobulin (e.g., IgG or IgM) except for the absence of the VL domains (FIG. 2). Similarly, an antibody with unpaired VL domains may be generated by deleting the VH domains, retaining paired CH1:CL domains.

An antibody according to the present invention may comprise two heavy chains and two light chains, wherein

- each heavy chain comprises an unpaired VH domain for binding a target antigen, and a heavy chain constant region comprising a CH1 domain, and wherein
- each light chain comprises a shield domain (e.g., CL domain), wherein the light chain lacks a VL domain.

The light chain may comprise the shield domain and be devoid of additional domains, or may consist of the shield domain and a C-terminal extension of one or more further domains (e.g., Ig constant domains) and/or functional moieties. Optionally, the light chain consists of the shield domain. The antibody is devoid of VL domains or other domains that pair with the VH domain to form an antigen-binding site, so that the unpaired VH domain provides a binding site for a target antigen.

Optionally, the positions of the CH1 and shield domain (e.g., CL) may be interchanged relative to their positions in a natural human antibody. In a four-chain antibody comprising two binding arms, the positions of the CH1 and shield domain may be interchanged in one arm only, or in both arms. Thus, the overall format of the molecule may be symmetrical or asymmetrical.

Similarly, the natural positions of the VH and VL domains are interchangeable, so that optionally a VH domain is linked to a shield domain or a VL domain is linked to a CH1 domain.

Different antibody chain formats may be combined to form heterodimers (e.g., each half of the heterodimer comprising an unpaired variable domain and two-chain constant region), optionally wherein the heterodimer is bispecific for antigen-binding. An antibody may comprise one unpaired variable domain specific for one antigen or epitope and a second unpaired variable domain specific for a different antigen or epitope. Bispecific antibodies comprising unpaired variable domains capable of binding first and second antigens or epitopes respectively may also be assembled by dimerisation of polypeptides of identical format (each half of the dimer comprising an unpaired variable domain and two-chain constant region). Thus, optionally only the unpaired variable domains differ in amino acid sequence and the antibody molecule is otherwise symmetrical. Additional antigen-binding regions may optionally be incorporated to provide trispecificity or further-order multispecific binding.

Polypeptide domains and antibodies according to the present invention are preferably human. Unpaired variable domains may be human. Antibodies may be fully human.

Non-human animal genomes may be engineered to produce the antibodies according the present invention. For generation of antibodies comprising unpaired human variable domains, these will be transgenic animals comprising genomes into which human immunoglobulin genes have been incorporated. A non-human animal may have a genome comprising immunoglobulin loci engineered to express antibodies comprising unpaired variable domains according to the present invention. B-lymphocytes of such animals are capable of expressing antibodies according to the invention in response to antigenic stimulation, and antibodies comprising unpaired variable domains can be generated by administering a target antigen to the animal. Non-human animals and cells thereof for the production of antibodies with unpaired variable domains, methods of producing them by genetic engineering, and use of the animals or cells for generating the antibodies all represent further aspects of the invention. Suitable non-human animals include laboratory animals such as rodents, e.g., mice and rats.

In one embodiment, an animal according to the present invention, e.g., a mouse, expresses an antibody comprising one or more heavy chains or VH domains, wherein the antibody is devoid of VL domains that pair with the VH domains to form Fv regions, characterised in that the heavy chain comprises a CH1 domain (or the VH domain is linked to a CH1 domain) and the antibody comprises a shield domain that pairs with the CH1 domain.

The genome of a non-human animal or a non-human animal cell may be engineered for expression of an antibody according to the present invention, e.g., it may be engineered to comprise

- a plurality of variable region gene segments capable of rearrangement to encode a variable domain, upstream of DNA encoding an immunoglobulin constant region comprising a CH1 domain, and
- a gene encoding a shield domain, e.g., CL domain, which lacks functional expression of variable region gene segments.

In another embodiment, an animal according to the present invention, e.g., a mouse, expresses an antibody comprising one or more heavy chains or VH domains, wherein the antibody is devoid of VL domains that pair with the VH domains to form Fv regions, characterised in that the heavy chain comprises a shield domain (or the VH domain is linked to a shield domain), and the antibody comprises a CH1 domain that pairs with the shield domain.

The genome of a non-human animal or a non-human animal cell may be engineered to comprise

- a plurality of variable region gene segments capable of rearrangement to encode a variable domain, upstream of DNA encoding a shield domain (e.g., CL domain), which lacks functional expression of variable region gene segments, and a gene encoding an immunoglobulin constant region comprising a CH1 domain, which lacks functional expression of variable region gene segments.

For expression of antibodies comprising unpaired VH domains for binding antigen, functional expression of endogenous light chain variable domains may be inactivated in the animal, e.g., by knocking out endogenous expression of variable region gene segments from the lambda and/or kappa loci. Preferably, VJ rearrangement of light chain gene segments does not occur, or is non-productive, in B-lymphocytes of animals according to the present invention. Functional expression of VpreB may be inactivated in the animal if desired, e.g., by deleting or mutating the endogenous VpreB gene to render it non-functional, so that the animal does not functionally express a VpreB polypeptide. Animals, cells (e.g., B-lymphocytes) and antibodies according to the present invention may be devoid of VL domains and VpreB. Alternatively, the expression of VL domains and/or VpreB in a cell or animal (e.g., in B-lymphocytes of the animal) may be minimal, e.g., less than 10%, optionally less than 5%, compared with their expression of antibodies comprising unpaired VH domains.

Animals according to the present invention represent a change of direction from prior art platforms for producing antibodies with unpaired variable domains. Until now, binding molecules comprising or consisting of single binding domains were made in the context of heavy chain only (or light chain only) antibodies, expressing the heavy (or light) chain in isolation and engineering the molecule to counter the loss of stability, solubility and/or other properties compared with antibodies in which the binding site is provided by a VH-VL pair. The problem of aggregation caused by the heavy chain CH1 domain was previously resolved by deleting that domain, and a variety of different antibody discovery platforms were produced based on a CH1-deletion approach. The present invention uniquely provides an antibody discovery platform in which the CH1 domain is retained and stabilised through pairing with a shield domain, reflecting the CL:CH1 pairing of a natural four-chain antibody and enabling single binding domains to be selected in vivo from a repertoire of immunoglobulins which present unpaired antibody variable domains in the context of an otherwise native antibody structure. Antibodies of interest can be selected directly from repertoires of antibodies generated in transgenic animals according to the present invention. The unpaired variable domains of such antibodies can also be selected and used as binders, in the form of single domain binding molecules, or they can be incorporated into larger binding molecules such as chimaeric antigen receptors (CARs) in which the unpaired variable domain provides the antigen binding site.

The genome of a non-human animal or a non-human animal cell may be engineered to comprise a first immunoglobulin locus capable of expressing a heavy chain or first polypeptide according to the present invention, the heavy chain or first polypeptide comprising a variable domain (e.g., VH domain) and a CH1 domain, and a second immunoglobulin locus capable of expressing a light chain or second polypeptide according to the present invention, the light chain or second polypeptide comprising a shield domain (e.g., Cκ domain) which pairs with said CH1 domain, wherein the light chain or second polypeptide lacks a variable domain, wherein the heavy chain or first polypeptide and the light chain or second polypeptide expressed from said respective loci are capable of pairing through association of the CH1 domain with the shield domain, wherein the absence of a variable domain in the light chain or second polypeptide leaves the variable domain of the heavy chain or first polypeptide unpaired.

For example, the genome of a non-human animal or non-human animal cell may be engineered to comprise an immunoglobulin heavy chain locus encoding or capable of rearrangement to encode an immunoglobulin heavy chain comprising a human VH domain and a CH1 domain, and an immunoglobulin locus which is engineered to express a polypeptide comprising a shield domain (e.g., lambda or kappa CL domain, or λ5) that pairs with CH1, wherein the polypeptide does not comprise a variable domain. Nucleic acid encoding the VL domain of the light chain may be absent and/or V-J rearrangement at the locus may be inactivated. Preferably the animal entirely lacks functional expression of light chains comprising a VL domain—thus the endogenous light chain loci may be modified to prevent functional expression of VL domains.

Preferably, the immunoglobulin heavy and/or light chain locus is the endogenous immunoglobulin locus in the animal. Thus, the endogenous immunoglobulin heavy chain locus (or loci) on chromosome 12 of a mouse may be engineered to contain DNA of the human heavy chain locus, expressing a heavy chain comprising the human VH. The immunoglobulin light chain locus (or loci) may be the endogenous immunoglobulin kappa light chain locus on mouse chromosome 6 and/or the endogenous immunoglobulin lambda light chain locus (or loci) on mouse chromosome 16. The immunoglobulin domain for pairing with CH1 (shield domain) may be expressed under control of human or endogenous transcriptional control elements (promoter/enhancers) at an endogenous immunoglobulin locus of the animal, e.g., a polypeptide comprising a CL domain may be expressed at an endogenous light chain locus. The light chain locus may be lambda or kappa. Optionally, both the lambda and kappa loci are engineered to express a light chain comprising a CL domain and lacking a VL domain.

A non-human animal according to the present invention may comprise B-lymphocytes expressing an antibody comprising an unpaired VH domain for binding antigen, wherein the genome of the animal comprises a plurality of variable region gene segments capable of rearrangement to encode a variable domain, upstream of DNA encoding an immunoglobulin constant region comprising a CH1 domain, and a gene encoding a CL domain which lacks functional expression of variable region gene segments.

Within B-lymphocytes of the animal, the genome is functional to express antibody comprising an antigen-binding variable domain linked to the CH1 domain and a light chain comprising a CL domain, wherein the light chain lacks a VL domain, thereby leaving the antigen-binding variable domain unpaired.

For the generation of a non-human animal comprising B-lymphocytes expressing an antibody comprising an unpaired VH domain for binding antigen, a suitable method comprises:

engineering the genome of a non-human animal cell (e.g., an embryonic stem cell or a zygote) to comprise a plurality of variable region gene segments capable of rearrangement to encode a variable domain, upstream of DNA encoding an immunoglobulin constant region comprising a CH1 domain, and a gene encoding a CL domain which lacks functional expression of variable region gene segments, and generating an animal from said cell or from a group of cells comprising said cell.

Variable region gene segments are capable of rearrangement to encode a VH or VL domain for binding a target antigen. A VH domain is generated through rearrangement of one V gene segment, one D gene segment and one J gene segment, and the genome may be engineered to comprise one or more V gene segments, one or more D gene segments and one or more J gene segments for rearrangement to encode a VH domain. A minimum would be one V, one D and one J, but the inclusion of a larger number of V, D and/or J gene segments provides a greater diversity of encodable VH domains. Alternatively, where the unpaired variable domain of the antibody is to be a VL domain, the genome may be engineered to comprise one or more V gene segments and one or more J gene segments for rearrangement to encode the VL domain. A minimum would be one V and one J, but the inclusion of a larger number of V and J gene segments provides a greater diversity of encodable VL domains.

Preferably the gene segments are human. For example, a full set of human heavy chain V, D and J gene segments may be included, or a full set of human light chain V and J gene segments may be included. The genome may comprise 41 human heavy chain V gene segments. It may comprise human heavy chain D gene segments. It may comprise 6 human heavy chain J gene segments. The genome may comprise 38 light chain κ V gene segments. It may comprise 5 human light chain κ J gene segments. Preferably the CL domain is a human CL domain, e.g., human Cκ or human Cλ.

The gene encoding the CL domain may comprise inserted DNA of a human Ig light chain locus, comprising an exon encoding a light chain variable region leader sequence (e.g., human vκ leader sequence) and an exon encoding the CL domain (e.g., human Cκ domain), separated by an intron comprising a J-C intron enhancer element. Transcription of the DNA results in splicing out of the intron thereby joining the two exons, resulting in nucleic acid (e.g., comprising nucleotide sequence SEQ ID NO: 5) encoding the CL domain linked to an upstream (5') leader sequence encoding a signal peptide. Human light chain variable region gene segments are not functionally expressed, and may be absent (deleted from or not included in the animal genome) or inactivated. The encoded CL domain may be a human Cκ domain comprising SEQ ID NO: 4. The encoded sequence may comprise or consist of SEQ ID NO: 6 which includes the N-terminal signal peptide SEQ ID NO: 2, which may be post-translationally cleaved to leave the Cκ domain sequence SEQ ID NO: 4. FIG. 3.

Human variable region gene segments may be inserted at the endogenous immunoglobulin heavy chain locus of the genome. The gene encoding the human CL domain may be inserted at the endogenous light chain locus (e.g., Igκ locus) of the genome. In an embodiment, human transcriptional control elements are included together with the coding sequence. However, optionally the inserted human DNA may be placed under control of endogenous transcriptional control elements in the animal genome. In an embodiment, the inserted human DNA is under the control of one or more control elements (e.g., a promoter and/or enhancer (such as an intronic enhancer and/or 3' locus enhancer) selected from:

(i) Endogenous control elements;
(ii) Rodent control elements;
(iii) Mouse control elements;
(iv) Rat control elements;
(v) Primate control elements;
(vi) Non-human primate (e.g., monkey) control elements;
(vii) Human control elements; or
(viii) A mixture of two of (i) to (vii), such human and rodent (e.g., mouse or rat) elements (e.g., a human promoter and a rodent intronic and/or 3' locus enhancer).

In another example, the control element(s) may be mammalian.

Expression of the endogenous Ig heavy and/or light chains may be inactivated, e.g., by deletion or inactivation of variable region gene segments. In an example, the endogenous lambda loci comprise a deletion of at least 100, 150 or 200 kb of DNA to inactivate endogenous lambda variable domain expression (optionally, this is in combination with endogenous kappa loci that have been modified to encode a shield domain as described herein). In an example, the endogenous kappa loci comprise a deletion of at least 100, 150 or 200 kb of DNA to inactivate endogenous kappa variable domain expression (optionally, this is in combination with endogenous lambda loci that have been modified to encode a shield domain as described herein).

The genome of a mouse or a mouse cell may be modified by insertion of a plurality of human variable region gene segments capable of rearrangement to encode a human variable domain, upstream of human DNA encoding an immunoglobulin constant region comprising a human CH1 domain, at the endogenous immunoglobulin heavy chain locus on mouse chromosome 12. Similarly, DNA encoding a human CL domain (e.g., Cκ) may be inserted at the endogenous Igκ light chain locus on mouse chromosome 6. DNA encoding a human CL domain (e.g., Cλ) may alternatively or additionally be inserted at the endogenous IgA locus on mouse chromosome 16. Expression of mouse heavy and light chains (κ and/or λ) may be inactivated, e.g., by deletion of encoding DNA or by rendering its expression non-functional.

Antibodies according to the present invention may be generated in the animals. The antibodies will generally be expressed in B-lymphocytes of the animal. A naïve repertoire of unpaired variable domains is obtainable from the animal before immunisation with an antigen. An antigen-specific repertoire is obtainable after immunisation with an antigen. At least 50% of antibody-expressing B-lymphocytes in the animal (e.g., 75% or more, or all antibody-expressing B-lymphocytes) may express antibodies comprising unpaired variable domains in accordance with the invention. Following immunogenic exposure of the animal to a target antigen, B-lymphocytes expressing antibodies comprising unpaired variable domains that bind the target antigen will be positively selected by the immune system and will undergo expansion and somatic hypermutation, generating a repertoire of variable domains that recognise the target antigen. One or more such antibodies, or the antigen-binding variable domains thereof, or their encoded nucleic acid, can then be recovered from the animal and used in downstream steps such as recombinant expression, incorporation into larger antigen-binding polypeptides, and/or therapeutic use, examples of which are described herein.

A method of generating an antibody comprising an unpaired variable domain for binding antigen may comprise exposing a non-human animal of the present invention to immunogenic stimulation with target antigen. The antibody and/or its encoding nucleic acid can then be isolated from the animal (e.g., by isolating B-lymphocytes from blood, bone marrow and/or spleen), enabling identification of the variable domain sequence (nucleotide and/or amino acid sequence). Optionally, mutations may be introduced into the sequence, such as reversion of non-germline framework residues to germline, insertion, substitution or deletion of residues within the variable domain, e.g., in one or more CDRs, or in one or more FRs, to refine properties of the variable domain such as binding affinity or physical properties such as stability and solubility. DNA encoding the variable domain comprising one or more mutations may then be provided, e.g., in a vector such as a plasmid, expression vector, transfection vector or cloning vector. The sequence encoding the variable domain may be provided as part of larger sequence encoding a polypeptide comprising the variable domain and one or more additional domains. Examples of such polypeptides include antibodies and CARs, which are detailed elsewhere herein. Preferably, the variable domain is the N-terminal domain of such a polypeptide, as this is its natural position in an immunoglobulin and exposes the CDRs of the variable domain binding site, although other formats are possible and the variable domain may be connected to an N-terminal domain, optionally via a peptide linker, and still retain its antigen-binding ability. The encoding nucleic acid may be introduced into the genome of a host cell, and the cells comprising the recombinant DNA can then be cultured for expression of the antibody, isolated variable domain or the polypeptide comprising the unpaired variable domain. The antibody, isolated variable domain or polypeptide is then purified from the cells or from the cell culture medium, and may be formulated into a composition comprising a pharmaceutically acceptable excipient and may be used therapeutically in treatment (optionally preventative treatment) of diseases and conditions amenable to treatment by binding the target antigen recognised by the unpaired variable domain. The encoding nucleic acid, and/or cells comprising it, also represent potential therapeutic products themselves. For example, a T-lymphocyte may be engineered to express a CAR comprising the unpaired variable domain, and the T-lymphocyte may be used for immunotherapy through targeting the antigen recognised by the unpaired variable domain.

Antibodies according to the present invention may also be used in vitro, e.g., in diagnostic methods, for binding antigen. An antibody which binds a target antigen may be used in a method of detecting whether a target antigen is present in a sample, optionally for quantifying the target antigen, or for selecting a target antigen from a mixture (optionally in solution) comprising that antigen among other molecules. The antibody may optionally be immobilised on a surface, e.g., a bead, or a matrix, optionally within a column) to facilitate isolation of antibody:antigen complex. Conversely, a target antigen (optionally immobilised on a surface, e.g., a bead, or a matrix, optionally within a column) may be used to select an antibody of the present invention that is capable of binding that target antigen, by contacting a mixture (e.g., a solution) comprising that antibody among other molecules (e.g., other antibodies with different unpaired variable domains). Binding of the unpaired variable domain of the antibody to the target antigen forms an antibody:antigen complex, which may then be isolated (e.g., separated from the solution). One or more washing steps may be performed to remove unbound antibody or unbound antigen. In general, a method of preparing an antibody:antigen complex may comprise

- exposing a target antigen to an antibody according to the present invention in vitro,
- allowing binding of the unpaired variable domain to the target antigen, thereby forming an antibody:antigen complex, and
- isolating the antibody:antigen complex.

The method may further comprise determining the sequence or identity of the antibody or antigen in the antibody:antigen complex, and/or quantifying the number of antibody:antigen complexes formed.

The invention will now be described in more detail, with reference to the accompanying drawings. Headings within this document are included solely to assist navigation and should not be construed as limiting. Embodiments of the invention that are separately described may be combined, except where the context indicates otherwise. Those skilled in the art will additionally recognise, or be able to ascertain using no more than routine experimentation, many equivalents to the specific embodiments of the invention described herein. Such equivalents are intended to be within the scope of protection of the appended claims.

BRIEF DESCRIPTION OF THE DRAWINGS

FIG. 11 shows primers used for RT-PCR amplification of kappa light chain (KLC) and/or truncated kappa light chain fragment (KCF) from mouse lymphocyte RNA.

DETAILED DESCRIPTION

Polypeptides Comprising Unpaired Variable Domains

Figure 1A:
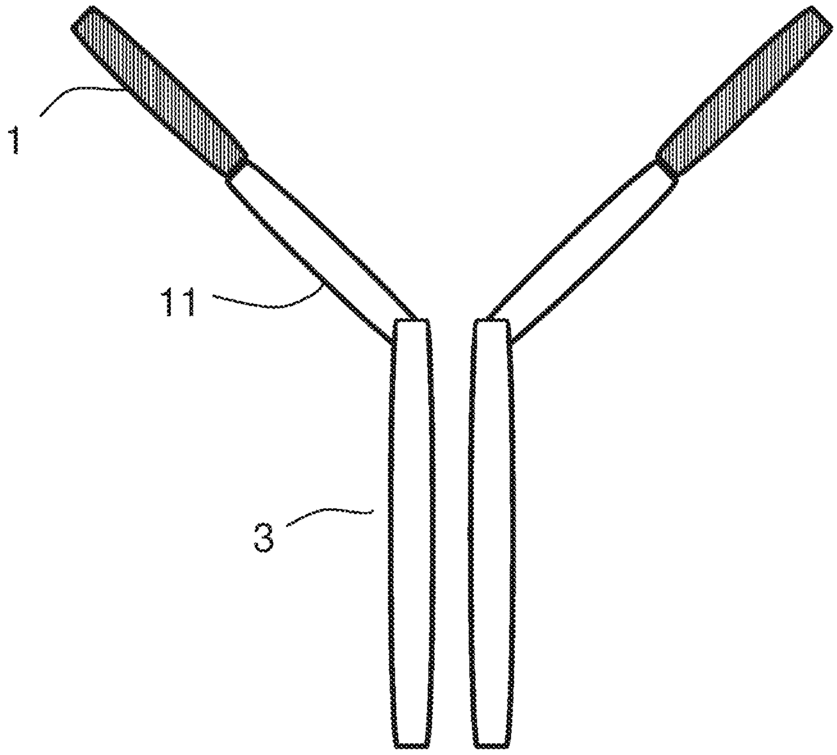
FIG. 1 shows: (a) a heavy chain only antibody (HCAb) comprising two heavy chains and lacking light chains. Each heavy chain has (in the N- to C-terminal direction) a VH domain (1) and a constant region comprising domains CH1 (11), CH2 and CH3. The CH2-CH3 regions of the two heavy chains dimerise to form an Fc region (3), while the VH domain (1) and CH1 domain (11) are unpaired; (b) a CH1-deleted HCAb comprising two heavy chains and lacking light chains. Each heavy chain has (in the N- to C-terminal direction) a VH domain (1) fused to a constant region comprising domains CH2 and CH3 but lacking domain CH1. The constant regions of two heavy chains dimerise to form an Fc region (3), while the two unpaired VH domains (1) are available for divalent antigen binding.
Figure 1B:
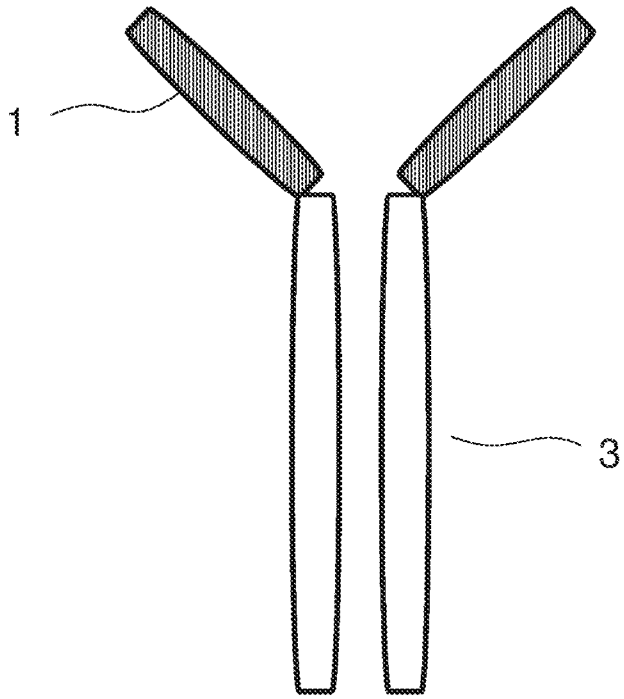

Pairing between polypeptide domains refers to a molecular association at an interface between spatially adjacent domains. Pairing generally involves non-covalent bonding (e.g., hydrophobic and/or electrostatic interactions) although the domains may additionally be covalently linked e.g., via one or more disulphide bonds or other molecular linkers. Paired domains may optionally be part of the same polypeptide, and therefore covalently linked as well as non-covalently paired, and may be adjacent in the primary polypeptide sequence or separated by one or more other domains. Examples of paired domains are a VH:VL pair of an antibody Fv region (whether formed by separate polypeptides comprising the VH and VL domain respectively, or by a single chain Fv (scFv)), a CH1:CL pair between heavy and light chains of an antibody, and a (CH2-CH3):(CH2-CH3) pair between constant regions in an antibody Fc region. Paired domains may be heterodimeric or homodimeric. By extension, the concept of paired polypeptides involves molecular association between two polypeptides, e.g., via pairing of domains of the respective polypeptides. For example, an antibody can be referred to as comprising paired heavy and light chains (or "a heavy:light chain pair"), wherein for example the CH1 domain of the heavy chain pairs with the CL domain of the light chain.

An unpaired domain is a domain which is not paired with another domain. An unpaired variable domain corresponds to an antibody Fv region from which either the VH or VL domain has been removed. The unpaired variable domain may be a VH or a VL. The unpaired variable domain may be capable of binding antigen outside the context of an Fv. Thus, a VH domain may not require the presence of a paired VL domain for antigen-binding. Conversely, a VL domain may not require the presence of a paired VH domain for antigen-binding. Indeed, in many cases, especially where variable domains are selected for antigen-binding in their unpaired state (as described in methods herein, such as methods of generating antigen-specific antibodies in vivo by immunisation of transgenic mice), an unpaired variable domain may specifically bind its target antigen with affinity that is comparable to the affinity of Fv regions from "normal" antibodies raised against that target. Moreover, for at least certain categories of antigen, including those with clefts or deep binding pockets in their three dimensional structure, antibodies comprising unpaired variable domains according to the present invention are preferred over whole Fv regions since the narrower structure of an unpaired variable domain presents a smaller binding site which may reach epitopes buried within antigens whereas such epitopes may be inaccessible or less accessible to binding by a full Fv region. Example target antigens and the raising of antibodies against them are discussed in more detail elsewhere herein.

While pairing indicates non-covalent interaction (optionally supplemented by inter-domain covalent bonding), reference to linking herein generally indicates a covalent attachment. Domains of a polypeptide may be linked via a peptide bond or peptide linker. Moieties may be linked by other suitable covalent attachment, a range of which will be apparent to the protein chemist.

A domain of a polypeptide comprises a sequence which adopts a folded structure, e.g., an immunoglobulin fold or other stable conformation. Where a polypeptide comprises a domain as part of a longer polypeptide sequence, the domain will generally have a tertiary structure independent of or distinguishable from the rest of the polypeptide. Generally, domains are responsible for discrete functional properties of proteins and in many cases may be added, removed or transferred to other proteins without loss of function of the remainder of the protein and/or of the domain.

Antibodies comprise immunoglobulin domains, which have an "immunoglobulin fold" of two β-sheets of antiparallel β-strands linked by a disulphide bond and hydrophobic interactions. A constant domain referred to herein may be an immunoglobulin constant domain, e.g., a CH1, CH2, CH3 or CL domain. A constant region may comprise one or more constant domains, linked and/or paired with each other. Antibody constant regions are described in more detail elsewhere herein.

Where multiple domains of a polypeptide are recited herein, they will usually be ordered in the standard N- to C-terminal direction, unless the context indicates otherwise. E.g., unless indicated to the contrary, a polypeptide comprising a VH domain and a CH1 domain comprises the VH domain "upstream of" the CH1 domain. A polypeptide may be represented by its domain structure such as VH-CH1, where the domains are shown in an N- to C-terminal direction from left to right.

Optionally, antibodies or polypeptide chains according to the present invention may be fused or conjugated to additional polypeptide sequences and/or to labels, tags, toxins or other molecules, e.g., to form immunocytokines. For example, an antibody constant region or shield domain may be linked to a cytokine such as IL-2. Linkage between polypeptide or peptide sequences can conveniently be made by generating a fusion protein comprising their two (or more) sequences in series.

Antibodies, Variable Domains and Specific Antigen-Binding

The term "antibody" herein includes monoclonal antibodies (including full length antibodies which have an immunoglobulin Fc region), antibody compositions with polyepitopic specificity, multispecific antibodies (e.g., bispecific antibodies), and single-chain molecules, as well as antibody fragments. Antibodies comprising unpaired variable domains according to the present invention may comprise a natural or known antibody structure, subject to the modification that one or more Fv region of the antibody is replaced with an unpaired variable domain. This may be envisaged as the removal of either a VL (or VH) domain from the Fv, leaving the remaining VH (or VL) domain unpaired.

Antibodies and polypeptide domains herein may be human. Human variable domains are preferred for their lower immunogenicity in compositions intended for administration to humans. Constant regions of antibodies may be human (especially in the context of antibodies for administration to humans, as noted), although they may be generated in transgenic non-human animals as chimaeric antibodies comprising human variable regions and non-human animal constant regions, followed by exchange of the non-human animal constant regions for human constant regions to provide fully human antibodies. Alternatively, fully human antibodies may be generated directly from transgenic animals whose genomes have been engineered to contain human variable region gene segments and human constant region genes. Accordingly, an antibody of the invention may be a human antibody or a chimaeric antibody comprising one or more human variable regions and one or more non-human (e.g., mouse) constant regions. It may comprise at least one unpaired human variable region linked to a human constant region.

An antibody variable domain (e.g., unpaired variable domain as described herein) provides a binding site for antigen. Recognition between an antibody and its cognate antigen may be referred to as specific binding, contrasting with non-specific binding whereby an antibody or other polypeptide binds non-target molecules through relatively low affinity interactions. Antigen-binding of a variable domain is via contact between the antigen and one or (usually) multiple residues in the CDRs (HCDRs or LCDRs). One or more FR residues of the variable domain may also make contact with the antigen. The region of the antigen bound by the antibody is referred to as its epitope. The region of the antibody which binds the antigen is referred to as its paratope.

A variable domain or binding site that "specifically binds to" or is "specific for" a particular antigen or epitope may be one that binds to that particular antigen or epitope without substantially binding to other antigens or epitopes. For example, binding to the antigen or epitope is specific when the antibody binds with a $K_D$ of 1 mM or less, e.g., 100 μM or less, 10 μM or less, 1 μM or less, 100 nM or less, e.g., 10 nM or less, 1 nM or less, 500 μM or less, 100 μM or less, or 10 μM or less. The binding affinity ($K_D$) can be determined using standard procedures as will be known by the skilled person, e.g., binding in ELISA and/or affinity determination using surface plasmon resonance (SPR) (e.g., Biacore™, Proteon™ or KinExA™ solution phase affinity measurement which can detect down to fM affinities (Sapidyne Instruments, Idaho)). In one embodiment, SPR is carried out at 25° C. In another embodiment, the SPR is carried out at 37° C. In one embodiment, the SPR is carried out at physiological pH, such as about pH 7 or at pH 7.6 (e.g., using Hepes buffered saline at pH 7.6 (also referred to as HBS-EP)). In one embodiment, the SPR is carried out at a physiological salt level, e.g., 150 mM NaCl. In one embodiment, the SPR is carried out at a detergent level of no greater than 0.05% by volume, e.g., in the presence of P20 (polysorbate 20; eg, Tween-20™) at 0.05% and EDTA at 3 mM. The SPR may be carried out at 25° C. or 37° C. in a buffer at pH 7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity is determined using SPR by

1. Coupling anti-human or anti-mouse (or other relevant non-human vertebrate, to match the C region of an antibody for example) IgG (eg, Biacore BR-1008-38) to a biosensor chip (e.g., GLM chip) such as by primary amine coupling;

2. Exposing the IgG to a test antibody (or heavy chain thereof) comprising a constant region to capture the test antibody (or heavy chain thereof) on the chip;
3. Passing the test antigen over the chip's capture surface at 1024 nM, 256 nM, 64 nM, 16 nM, 4 nM with a 0 nM (i.e., buffer alone) control; and
4. Determining the affinity of binding of test antibody/chain to test antigen using surface plasmon resonance, eg, under an SPR condition discussed above (e.g., at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH 1.7. This removes the captured antibody and allows the surface to be used for another interaction. The binding data can be fitted to 1:1 model inherent using standard techniques, eg, using a model inherent to the ProteOn XPR36™ analysis software.

Antibody Constant Regions

A constant region of an antibody may comprise one or more human constant domains, and may be a human constant region. For example, an unpaired variable domain (e.g., VL domain) may be attached at its C-terminal end to an antibody light chain κ or λ constant domain. An unpaired variable domain (e.g., VH domain) may be attached at its C-terminal end to all or part (e.g. a CH1 domain or Fc region) of an immunoglobulin heavy chain constant region derived from any antibody isotype, e.g. IgG, IgA, IgE and IgM and any of the isotype sub-classes, such as IgG1 or IgG4.

An antibody constant region may comprise a human IgG, IgM, IgA, IgD or IgE constant region. An antibody heavy chain constant region may comprise a human heavy chain IgG, IgM, IgA, IgD or IgE constant region.

Sequences of exemplary human constant regions are provided in the appended Table A.

Constant regions of antibodies of the invention may alternatively be non-human constant regions. For example, when antibodies are generated in transgenic animals (examples of which are described elsewhere herein), chimaeric antibodies may be produced comprising human variable regions and non-human (host animal) constant regions. Some transgenic animals generate fully human antibodies. Others have been engineered to generate antibodies comprising chimaeric heavy chains and fully human light chains. Where antibodies comprise one or more non-human constant regions, these may be replaced with human constant regions to provide antibodies more suitable for administration to humans as therapeutic compositions, as their immunogenicity is thereby reduced.

Digestion of whole immunoglobulins with the enzyme papain results in two identical antigen-binding fragments, known also as "Fab" fragments, and a "Fc" fragment, having no antigen-binding activity but having the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulphides. The effector functions of antibodies are determined by sequences in the Fc region, the region which is also recognised by Fc receptors (FcR) found on certain types of cells.

Transgenic Animals Containing Human Immunoglobulin Loci

A non-human animal genome may be engineered to contain one or more human heavy chain V gene segments, one or more human heavy chain D gene segments and one or more human heavy chain J gene segments, for expression of a human VH domain. It may contain a full set of all human heavy chain V, D and J gene segments. The human VDJ gene segments may be inserted upstream of a constant region, for production of VH domains linked to a constant region.

Similarly, the non-human animal genome may be engineered to contain one or more human light chain V gene segments and one or more human light chain J gene segments, for expression of a human VL domain. Gene segments may be κ or λ. The non-human animal genome may contain a full set of all human κ or λ gene segments. The human VJ gene segments may be inserted upstream of a constant region, for production of VL domains linked to a constant region.

Since antibodies of the present invention comprise the VH or VL domain in unpaired form, the genome may comprise heavy chain gene segments in the absence of light chain gene segments (or wherein expression of light chain gene segments is inactivated), or it may comprise light chain gene segments in the absence heavy chain gene segments (or wherein expression of heavy chain gene segments is inactivated).

Recombination of V(D)J gene segments generates combinatorial diversity in each variable domain. With the inclusion of a full set of human heavy (or light) chain gene segments, the full combinatorial diversity of human variable domains can be incorporated into a transgenic animal platform. Affinity maturation of these variable domains then proceeds through the natural in vivo processes of somatic hypermutation and selection, providing an extensive and diverse sequence repertoire from which antigen-specific variable domains with desirable properties may be identified and their sequences recovered. The antibody production platforms described herein take advantage of the natural ability of CH1 to pair with a shield domain, enabling a complete human heavy chain repertoire to be maintained and avoiding the need to re-engineer the human heavy chain. Preferably the heavy chain immunoglobulin locus is or comprises an unmodified human heavy chain locus and/or expresses human immunoglobulin heavy chains that are comparable in all respects to those generated in humans. Such a platform can deliver a full repertoire of antibodies comprising unpaired human VH domains for binding antigen, enabling selection of desired molecules of interest, suitable for development into pharmaceutical products.

Methods of generating transgenic animals having genomes comprising all or part of human immunoglobulin loci are well known in this technical field. Such animals have been used to discover and produce several antibodies comprising human variable domains which are currently on the market as pharmaceutical products, with a great many more in the development pipeline. Methods of engineering the non-human animal genome to contain human immunoglobulin gene segments are described for example in WO2011/004192 (Genome Research Limited), which is incorporated herein by reference. Examples of transgenic non-human animals include Kymouse™ (e.g., as described in WO2011/004192), VelociMouse®, OmniMouse®, Omnirat®, XenoMouse®, HuMab Mouse® and MeMo Mouse®.

In addition to the variable region, the genome of the non-human animal encodes the constant region of an antibody described herein. The locus comprising the variable region gene segments further comprises a constant region gene or genes, e.g., a heavy chain constant region comprising CH1 (e.g., comprising domains CH1, CH2 and CH3), or a constant region comprising CL (e.g., comprising domains CL, CH2 and CH3). The constant region at a locus may be a human constant region, i.e., wherein the domains are of human origin. The non-human animal genome may be engineered to contain one or more human constant region genes. It may contain the full repertoire of human constant region genes: M, D, G3, G1, A1, G2, G4, E and A2 respectively, optionally by insertion of a fragment of human genomic DNA containing these genes.

A constant region may comprise a fragment of a human IgH locus including the Cμ to (and optionally including) the 5'-most yl exon; optionally including all γ1 CH1-3 or CH1-M2 exons. In an alternative, the fragment is from and including Sp or Ep. In an alternative, the fragment is from a point within the first 400, 500, 600, 700 800 or 900 nucleotides of the IgH J-C intron, wherein the fragment comprises intronic DNA 5' of and contiguous with Eμ and Cμ.

The constant region may comprise at least one IgH C gene segment, e.g., a Cmu gene segment, and optionally also one or more of an alpha, delta, epsilon and gamma (eg, gamma-1) C gene segment. In an embodiment, the constant region comprises a Cmu and a Cgamma (e.g., gamma-1, human gamma-1, mouse gamma-1 or rat gamma-1 C segment). One or both of the Cmu and Cgamma can be endogenous to the non-human animal; e.g., the Cmu is endogenous and Cgamma is endogenous or human. In an example, the gene segments of the C region are in germline order of C segments found in an IgH or IgL locus of a human, rodent, rat or mouse genome. In an example, the gene segments of the C region are in germline order of C segments found in an IgH or IgL locus of a mouse genome. This order is known to the skilled addressee.

In an example, the antibody C gene segment(s) are endogenous segments of the non-human animal, optionally wherein the constant region is an endogenous heavy chain constant region at an endogenous heavy chain locus, or an endogenous light chain (kappa or lambda) constant region at an endogenous light chain locus. Thus, when the animal is a mouse, the C segment(s) are those on chromosome 12 (for IgH C segment(s)), 6 (for Igκ C segment(s)) or 16 (for Igλ C segment(s)).

A non-human animal genome may be engineered to comprise first and second loci, wherein the first locus is engineered to express a first polypeptide or a heavy chain according to the present invention and wherein the second locus is engineered to express a second polypeptide or a light chain according to the present invention. The first and second loci may be on the same or different chromosomes.

The first locus may be engineered to comprise a fragment of the human immunoglobulin heavy chain locus, comprising VDJ segments and constant region genes together with intergenic regions and regulatory elements. Alternatively, the first locus may be engineered to comprise a fragment of the human immunoglobulin K or A light chain locus, comprising VJ segments and constant region genes together with intergenic regions and regulatory elements.

The V(D)J gene segments may be linked to a constant region which is the endogenous non-human animal constant region. This can be achieved by inserting the human variable region gene segments into the non-human animal genome upstream of the endogenous constant region at the endogenous immunoglobulin locus. Alternatively, the constant region is human, and human DNA comprising V(D)J gene segments and human constant region may be inserted at the endogenous locus, thereby fully humanising that locus. Intergenic and regulatory elements of the human immunoglobulin locus are preferably also included.

Figure 7:
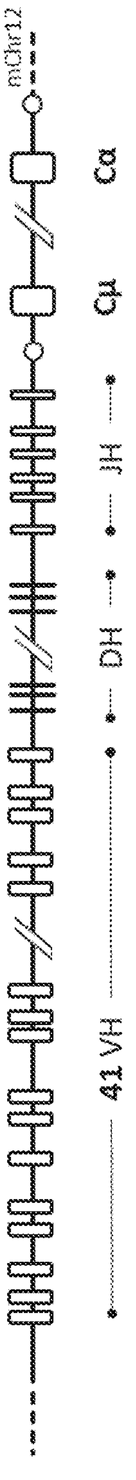
FIG. 7 shows an overview of a mouse Ig heavy chain locus on mouse chromosome 12, containing a large fragment of the human Ig heavy chain locus. The human DNA comprises (in 5' to 3' order) a set of 41 V gene segments, a set of D gene segments, and a set of 6 J gene segments, upstream of genes encoding a set of heavy chain constant genes from M (Cμ) to A2 (Cα). This locus may be present in a transgenic animal or animal cell according to the present invention.

Human heavy chain genes may be inserted at the mouse heavy chain locus on chromosome 12 to provide a first locus encoding a first polypeptide or heavy chain locus as described herein. FIG. 7.

Figure 8:
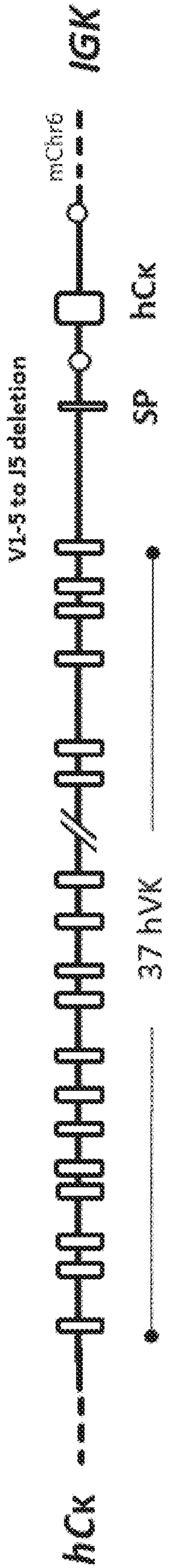
FIG. 8 shows an overview of a mouse Ig κ chain locus at the endogenous locus of the mouse chromosome 6, containing a large fragment of the human Ig κ light chain locus comprising a deletion from vκ1-5 to jκ5. The human DNA comprises (in 5' to 3' order) a set of Vκ gene segments and the leader sequence for vκ1-5 encoding signal peptide SP, upstream of the Cκ gene. This locus may be present in a transgenic animal or animal cell according to the present invention.

The second locus may be engineered for expression of a shield domain. It may comprise DNA of a human κ light chain locus comprising the human κ constant region gene and optionally the associated human intergenic and regulatory elements. Thus, the non-human animal genome may be engineered to comprise a fragment of the human κ locus comprising the constant region genes and regulatory elements. Productive rearrangement of the variable region gene segments is inactivated, e.g., by deletion of all Jκ gene segments. The human Cκ gene may be inserted at the mouse κ locus on chromosome 6. FIG. 8.

Figure 9:
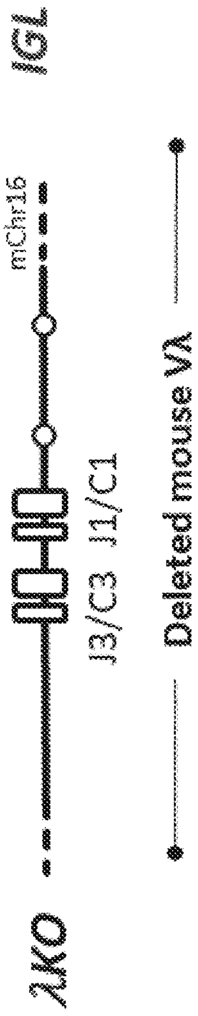
FIG. 9 shows an overview of an inactivated mouse A locus on mouse chromosome 16.

Expression of endogenous variable region gene segments from an endogenous Ig locus or loci in the non-human animal may be inactivated, e.g., by deletion or inversion of a stretch of DNA comprising endogenous V(D)J regions. Optionally the endogenous A locus is unmodified. However, it too may be inactivated if desired (FIG. 9).

In an example, the human heavy chain variable region and/or constant region DNA is integrated at an endogenous antibody locus of the non-human animal (e.g., mouse). Optionally the donor and recipient loci are matched, thus human heavy chain locus DNA may be integrated at the endogenous heavy chain locus, and human κ light chain locus DNA may be integrated at an endogenous κ light chain locus and human λ light chain locus DNA may be integrated at an endogenous λ light chain locus, although such matching is not essential.

A constant region may comprise an endogenous (e.g., mouse) antibody constant gene segment. It may additionally comprise one or more human constant gene segments. The antibody locus may be an IgH locus and the constant region comprise an endogenous Cμ constant gene segment and human Cγ constant gene segments. The antibody locus may be an IgH locus and comprise an endogenous Sμ operably linked upstream of a Cμ (e.g., an endogenous Cμ). For example, the locus comprises an endogenous intronic enhancer (e.g., Eμ when the antibody locus is an IgH; or iEκ when the antibody locus is an Igκ). The locus may comprise an endogenous 3' enhancer of the antibody locus.

Alternatives to targeted integration of human DNA at an endogenous immunoglobulin locus of the non-human animal include random integration of the human DNA into the animal genome, or targeted integration of the human DNA at a locus separate from (optionally on a different chromosome from) the endogenous immunoglobulin loci. The Rosa26 locus may be a convenient target. Optionally therefore the first and/or second locus is not an endogenous antibody locus, e.g., the DNA may have been randomly inserted into the germline genome of the animal. In an embodiment, the constant region comprises an exogenous antibody constant gene segment (so the antibody does not comprise an endogenous antibody constant gene segment). The exogenous constant gene segment may be of the same or a different species to the animal, e.g., a human or rodent (such as mouse or rat) constant gene segment.

Transgenic non-human animals and non-human animal cell genomes preferably comprise a fully humanised heavy chain locus containing the full repertoire of human V, D and J gene segments and all human constant region genes plus human enhancers. In situ targeting of the human immunoglobulin locus DNA to the endogenous immunoglobulin loci of the non-human animal, in contrast with random insertion, facilitates the correct and precise regulation of the immune response. Transgenic animals of the present invention can thus display a robust immune response, including somatic hypermutation and affinity maturation of antibody variable domains, following exposure to an immunogenic composition comprising target antigen. Expression of mouse heavy chains from the endogenous mouse heavy chain locus may be inactivated by inversion of the variable region and replacement of the mouse constant region with the human heavy chain constant region genomic fragment. Deletion of mouse variable region gene segments is an alternative to displacement and/or inversion of the endogenous DNA. For example, the mouse heavy chain V and/or J gene segments may be deleted.

Well validated methods are now available for genomic engineering of animals and the available techniques continue to improve. Engineering of ES cells may be performed by homologous recombination or recombinase cassette exchange [2; WO2011/004192] and chromosomal engineering may also be performed in zygotes [3].

In one embodiment, the first locus is produced by insertion of variable region gene segments at an endogenous IgH locus of an embryonic stem cell (ES cell) or iPS cell of the species of said animal (e.g., mouse cell). Subsequently, the second locus can be introduced as a transgene into the genome of the cell (or a progeny cell or zygote thereof), wherein the transgene is inserted into the genome of the cell or zygote. The non-human animal is then developed from the cell, zygote or a progeny thereof. Alternatively, as is known in the art, loci can be engineered in separate non-human animal cells (e.g., ES cells, iPS cells or zygotes), which are developed into animals comprising the engineered loci in their germline DNA, and the separate animals are bred together to combine the loci in the germline genome of a progeny animal. Thus, a first animal whose germline genome comprises the first locus and a second animal whose germline genome comprises the second locus are mated to produce a progeny animal whose germline genome comprises both loci. The progeny animal can be observed to produce lymphocytes expressing antibodies as described herein.

An animal according to the present invention may be homozygous for the first locus or heavy chain locus and/or homozygous for the second locus or light chain locus as described herein. In an alternative, the vertebrate is heterozygous for the or each such locus. Preferably the animals are homozygous at humanised heavy and light chain loci. They may be homozygous at all three immunoglobulin loci, i.e., heavy locus, A locus and K locus. As noted, heterozygous animals can be generated initially for each locus and bred to generate double or triple homozygous animals (depending on the number of modified loci) and a stable breeding population is thus produced. A breeding colony of transgenic animals may be housed in an animal house, optionally under sterile or specific pathogen free (SPF) conditions. Male and female mice may be grouped separately or together.

Figure 3A:
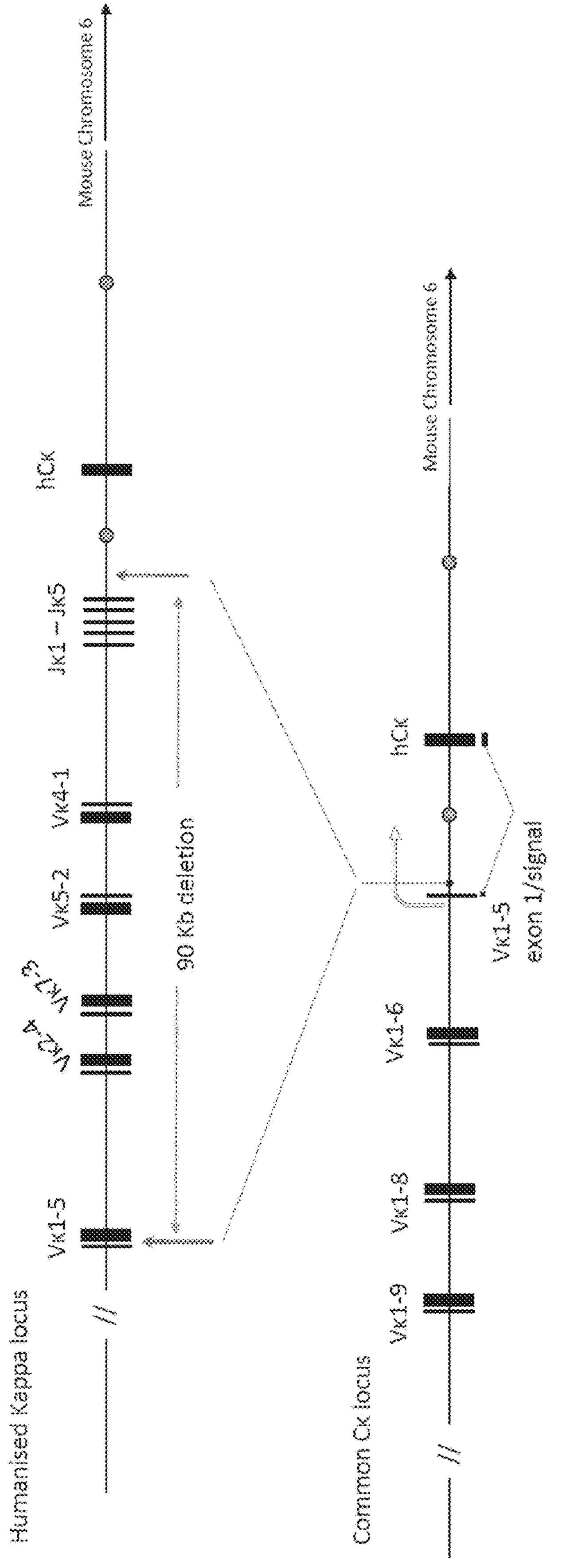
FIG. 3 shows construction of an immunoglobulin locus for expression of a Cκ shield domain, and the resulting Cκ sequence, according to the present invention. a) Generation of gene encoding Cκ shield domain through humanisation of mouse κ locus with human κ locus DNA comprising a 90 kb deletion. b) Human Cκ shield domain cDNA with signal peptide. Nucleic acid encoding signal peptide SEQ ID NO: 1. Nucleic acid encoding isolated Cκ shield domain SEQ ID NO: 3. Nucleic acid encoding Cκ including signal peptide SEQ ID NO: 5. c) Translated Cκ shield domain. Signal peptide SEQ ID NO: 2. Isolated Cκ sequence following predicted cleavage of signal peptide SEQ ID NO: 4. Encoded Cκ sequence including signal peptide SEQ ID NO: 6.
Figure 3B:
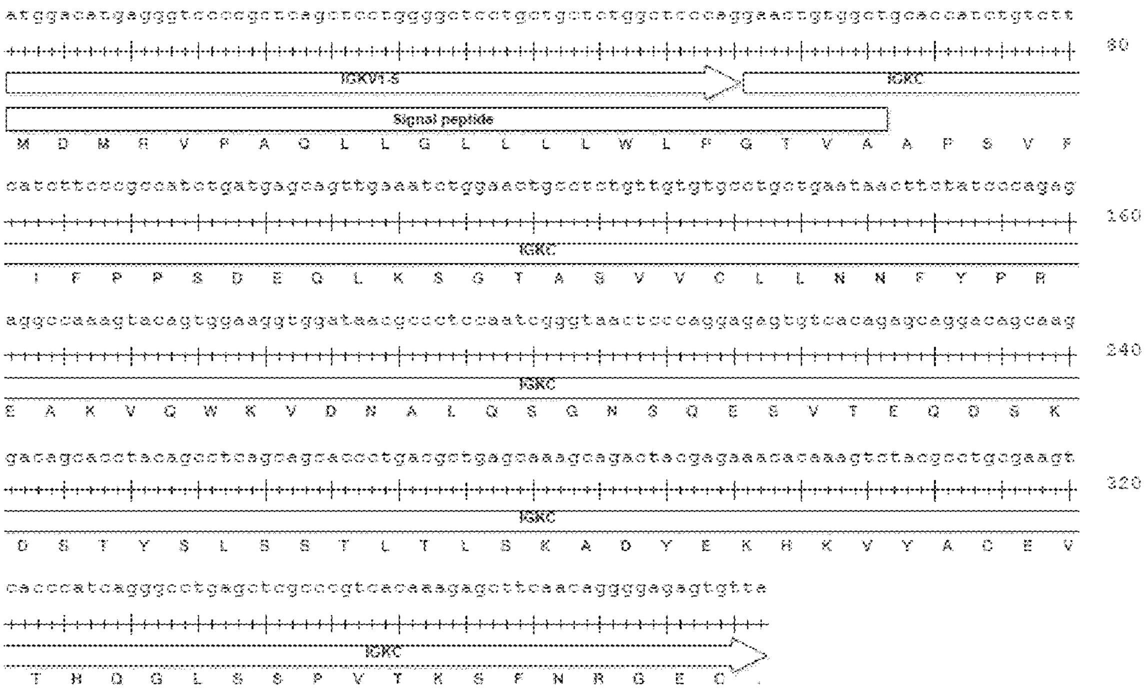
Figure 3C:
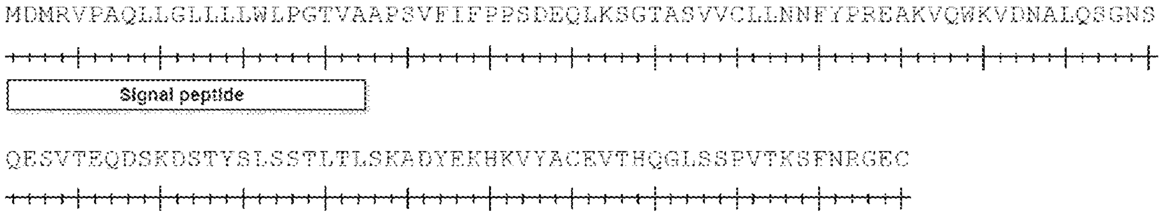

In one example, mice comprising a humanised heavy chain locus described herein, animals comprising a humanised K locus as described herein, and optionally animals comprising an inactivated A locus as described herein, are generated separately and then bred together to produce a strain in which fully human heavy chains are expressed at the endogenous Ig heavy locus, the VJ rearrangement at the endogenous κ locus is inactivated by deletion of the J region, and the locus expresses a Cκ fragment (e.g., SEQ ID NO: 4). FIG. 3*c*. The Cκ contains no variable domain sequence. It acts as a shield domain, stabilising CH1 of the heavy chain in expressed antibodies.

The endogenous λ locus of a mouse may be inactivated (e.g., deleted in whole or in part) so that it does not express a light chain comprising a VL domain. There may be no functional polypeptide expression from the λ locus. However, in other embodiments the λ locus of the mouse may be unmodified. Expression from the λ locus naturally occurs at only a low level in the mouse. Moreover, where the κ locus is active, for example where the κ locus encodes and expresses a shield domain (e.g., a CL or λ5 domain), the λ locus may be silenced through the natural process of allelic exclusion in B-lymphocytes. Thus, expression from the λ locus may be silenced in B-lymphocytes of animals (e.g., mice) according to the present invention, whether naturally by allelic exclusion, by engineering of the genome or in any other way. Inactivation of the locus by deletion is illustrated in Example 3.

Aspects herein may be expressed in terms of the non-human animal being a mouse, but it is to be understood that other laboratory or livestock animal or any other non-human vertebrate may be suitable for performing the present invention. The vertebrate may be a rodent, e.g., a mouse or rat. In other examples, the vertebrate is a bird (e.g., chicken), fish (e.g., shark or zebrafish), mammal (e.g., rabbit), livestock animal (e.g., cow, sheep, pig or goat), or camelid (e.g., llama, alpaca or camel). In an embodiment, the mouse strain is 129 (or a 129 hybrid), C57BL6 (or C57BL6 hybrid), or derived from an AB2.1, AB2.2, JM8, BALB/c, or F1H4 ES cell line.

Knockouts can be used to provide access to human/non-human (e.g., human/mouse) cross-reactive antibodies. Thus, in addition to the modifications above, expression of an endogenous target may be inactivated in the genome of the non-human animal. The resulting knockout animals can be used for immunisation with the target antigen and may generate a stronger immune response (e.g., higher antibody titre and/or greater antibody diversity) to the target compared with animals that express the endogenous target. This is because, where a target antigen (e.g., human protein X) shares homology with the endogenous target in the non-human animal (e.g., mouse protein X), the non-human animal's immune repertoire will have undergone negative selection against the self-antigen, so that immunisation with the human protein predominantly generates antibodies that are selective for the human protein and are not cross-reactive with the endogenous protein from the non-human animal. Use of a knockout animal thus increases the diversity of antibodies obtained from immunisation, including those that recognise epitopes conserved between species, and can generate potentially useful cross-reactive antibodies.

λ5 and B Cell Development

Development of B-lymphocytes (B cells) is characterised by the ordered rearrangement of immunoglobulin variable region genes. After the VDJ rearrangement of heavy chain gene segments, a precursor B cell (pre-B cell) is generated. After the VJ rearrangement of light chain gene segments, pre-B cells develop into mature B cells bearing IgM on the cell surface where it can be presented to antigen. Assembled antibodies comprising heavy and light chains are transported to the B cell surface, while free heavy chains are retained in the endoplasmic reticulum (ER) in association with the 70 kDa heat shock protein chaperone BiP.

A critical step in B cell differentiation is the selective expansion of cells with a functional μ heavy chain resulting from productive rearrangement of heavy chain gene segments. This is achieved by the association of the μ heavy chain with surrogate light chain proteins λ5 and VpreB and a signal transducing heterodimer Igαβ to form a pre-B-cell receptor (pre-BCR). The surrogate light chain has the overall structure of a light chain but is a non-covalent heterodimer of VpreB (homologous to VL) and λ5 (homologous to CL). The N-terminal region of λ5 represents an extra 3 strand which is not part of the typical Ig domain, while the Ig domain in VpreB lacks one of the canonical p strands. Complementation of the incomplete Ig domain in VpreB by the extra p strand in λ5 is necessary and sufficient for the folding and assembly of these proteins to make the surrogate light chain[4]. λ5 can be disulphide bonded to μ heavy chains in pre-B cells. A high-resolution structure of a pre-BCR Fab-like fragment was published in 2007, showing that the unique regions of VpreB and λ5 interact with each other and with the heavy chain CDR3, potentially influencing selection of the antibody repertoire[5].

The surrogate light chain acts as a chaperone, displacing the ER-resident BiP from the CH1 domain and escorting the heavy chain μ to the cell surface together with Igαβ[6]. The expression and formation of the pre-BCR dramatically improves the efficiency of pre-B and B cell production, by signalling proliferative expansion of pre-B cells. The surface display of membrane-bound p chains is essential for the clonal expansion of these cells and their initiation of light chain gene rearrangement.

The surrogate light chain is then repressed while the light chain gene segments undergo rearrangement. The product of a successfully rearranged light chain gene will pair with the heavy chain to form a BCR with antigen-binding capability on the surface of immature B-cells. These cells migrate to the peripheral blood and secondary lymphoid organs, and develop into mature B cells ready for subsequent encounter with antigen[7]. Since expression of VpreB and λ5 is silenced after the pro- and pre-B cell stages, these proteins are not naturally present in B-lymphocytes.

In 1996, Papavasiliou, Jankovic and Nussenzweig[8] described evidence for the two pathways for induction of B cell development; one activated through surrogate light chain (λ5) and IgM and one through conventional light chain (κ or λ) and IgM. In the absence of κ and λ light chain expression in the mice under study, λ5 expression rescued surface display of IgM which delivered the signal for B cell development. Guloglu et al[9] also later reported that although heavy chains were not expressed in B cells of RAG/λ5 double knockout mice transfected with heavy chain DNA, they could be expressed on the mouse surface of B cells if co-transfected with either λ5 or a truncated λ5 excluding the N-terminal unique region preceding the λ5 immunoglobulin fold.

Using VpreB knockout mice, it has been shown that VpreB is required for efficient B cell development, particularly for the transition to pre-BCR bearing cells (pre-BII stage)[7, 10]. In HEK cells expressing a heavy chain mutant that did not require Igαβ for signalling, expression of a complete λ5 polypeptide without VpreB did not result in surface presentation of IgM. However, expression of truncated λ5 without VpreB did enable surface presentation of IgM. Indeed, surface presentation of IgM in cells expressing only the truncated λ5 surpassed surface presentation of IgM in cells expressing a full surrogate light chain (both VpreB and λ5). Surface presentation of IgM was even higher if Igκ light chain was expressed[11].

Selective Deletion of CH1 Domain in Class-Switched Isotypes

Co-expression of a shield domain with a polypeptide comprising a CH1 domain provides significant immunological advantages and greatly facilitates discovery of antibodies comprising unpaired variable domains. However, there are situations in which it is nevertheless still desirable to generate antibodies that comprise unpaired variable domains linked to constant regions bearing CH1 deletions. Where this is desired, it is best achieved after the antibodies have undergone affinity maturation (rather than having a CH1 deletion present in the pre-BCR). Accordingly, heavy chain constant regions present in class-switched antibodies may be selectively engineered to carry CH1 deletions.

The CH1 domain is optionally deleted from heavy chain constant region genes other than IgM, and retained in the μ constant region gene. IgM heavy chains may be expressed and combined with a shield domain of the present invention (e.g., λ5, or Cκ, from an engineered K locus as detailed elsewhere herein). A CH1-deleted non-mu heavy chain (e.g., IgG or IgA heavy chain) may then subsequently be expressed following class switching in the lymphocytes. In B-lymphocytes comprising this combination of genome modifications, the shield domain pairs with CH1 of the μ heavy chain to form IgM antibodies, and class-switching in the B-lymphocytes then generates heavy chain only antibodies having a heavy chain comprising an unpaired VH domain and a constant region lacking a CH1 domain, e.g., CH1-deleted IgG and CH1-deleted IgA. WO2013/171505 (Kymab Limited) described non-human animals expressing normal IgM antibodies and CH1-deleted IgG antibodies, where stage-specific class switching from IgM to IgG in lymphocytes was accompanied genetic deletion of CH1 from the IgG constant region, so that IgG heavy chain only antibodies were expressed. The methods and embodiments of WO2013/171505, incorporated herein by reference, may be employed in the present invention.

In one embodiment, the CH1-encoding region is deleted from the IgA constant region gene in the heavy chain locus of the non-human animal (e.g., humanised heavy chain locus in a transgenic animal). The CH1 domain is optionally deleted in the context of the complete human heavy chain locus inserted at the endogenous heavy chain locus of the non-human animal. IgA is highly abundant, and switching from IgG to IgA is frequently observed. Thus, selective CH1 deletion in the IgA isotype while retaining the full heavy chain in the IgM isotype will allow initial B cell development with complete heavy chains, which will undergo affinity maturation in the normal way, followed by isotype switching to IgA antibodies comprising heavy chains with a CH1 deletion. The antibodies may comprise the unpaired variable domain (e.g., VH domain) throughout this in vivo evolution, ensuring selection for repertoires of variable domains that are effective as single isolated antigen-binding domains.

Bispecific Antibodies

An antibody according to the present invention may exhibit bispecific or multispecific antigen-binding. Thus, it may comprise first and second unpaired variable domains, wherein the first unpaired variable domain specifically binds a first antigen or epitope and the second unpaired variable domain specifically binds a second antigen or epitope. The first and second variable domains may have amino acid sequences that differ from one another, for binding to different first and second antigens/epitopes respectively. The different epitopes may be epitopes of one antigen or of different antigens. Thus, for example the first unpaired variable domain may specifically bind antigen A (and not antigen B) and the second unpaired variable domain may specifically bind antigen B (and not antigen A).

Just as the "heavy chain only" antibodies of the prior art were a format that was often chosen for bispecific and multispecific antibodies, so too the antibodies of the present invention also lend themselves to this purpose.

There are advantages to providing an antigen-binding site within an unpaired variable domain which is expressible as part of a single polypeptide chain, since a bispecific antibody can be generated through the association (e.g., following coexpression) of two such polypeptides comprising different variable domains (and thus different antigen-binding sites). This contrasts with the more complex generation of a typical four-chain bispecific antibody which comprises two different heavy:light chain pairs and thus 4 different polypeptide chains, which if expressed together could assemble into 10 different potential antibody molecules including homodimers (homodimeric anti-A binding arms and homodimeric anti-B binding arms), molecules in which one or both light chains are swapped between the H-L pairs, as well as the "correct" bispecific heterodimeric structure.

The antibody format of the present invention allows the antibody to be expressed as a relatively simple two-chain or three-chain molecule. This may be combined with design of the constant region to strongly favour assembly into the desired bispecific format.

"Knobs into holes" technology for making bispecific antibodies was described in [12] and in U.S. Pat. No. 5,731,168, both incorporated herein by reference. The principle is to engineer paired CH3 domains of heterodimeric heavy chains so that one CH3 domain contains a "knob" and the other CH3 domains contains a "hole" at a sterically opposite position. Knobs are created by replacing small amino acid side chain at the interface between the CH3 domains, while holes are created by replacing large side chains with smaller ones. The knob is designed to insert into the hole, to favour heterodimerisation of the different CH3 domains while destabilising homodimer formation. In in a mixture of antibody heavy and light chains that assemble to form a bispecific antibody, the proportion of IgG molecules having paired heterodimeric heavy chains is thus increased, raising yield and recovery of the active molecule Mutations Y349C and/or T366W may be included to form "knobs" in an IgG CH3 domain. Mutations E356C, T366S, L368A and/or Y407V may be included to form "holes" in an IgG CH3 domain. Knobs and holes may be introduced into any human IgG CH3 domain, e.g., an IgG1, IgG2, IgG3 or IgG4 CH3 domain. A preferred example is IgG4. The IgG4 may include further modifications such as the "P" and/or "E" mutations. A "P" substitution at position 228 in the hinge (S228P) stabilises the hinge region of the heavy chain. An "E" substitution in the CH2 region at position 235 (L235S) abolishes binding to FcγR. A bispecific antibody of the present invention may contain an IgG4 PE human heavy chain constant region, optionally comprising two such paired constant regions, optionally wherein one has "knobs" mutations and one has "holes" mutations.

While knobs-into-holes technology involves engineering amino acid side chains to create complementary molecular shapes at the interface of the paired CH3 domains in the bispecific heterodimer, another way to promote heterodimer formation and hinder homodimer formation is to engineer the amino acid side chains to have opposite charges. Association of CH3 domains in the heavy chain heterodimers is favoured by the pairing of oppositely charged residues, while paired positive charges or paired negative charges would make homodimer formation less energetically favourable. WO2006/106905 described a method for producing a heteromultimer composed of more than one type of polypeptide (such a heterodimer of two different antibody heavy chains) comprising a substitution in an amino acid residue forming an interface between said polypeptides such that heteromultimer association will be regulated, the method comprising:

(a) modifying a nucleic acid encoding an amino acid residue forming the interface between polypeptides from the original nucleic acid, such that the association between polypeptides forming one or more multimers will be inhibited in a heteromultimer that may form two or more types of multimers;
(b) culturing host cells such that a nucleic acid sequence modified by step (a) is expressed; and
(c) recovering said heteromultimer from the host cell culture, wherein the modification of step (a) is modifying the original nucleic acid so that one or more amino acid residues are substituted at the interface such that two or more amino acid residues, including the mutated residue(s), forming the interface will carry the same type of positive or negative charge.

An example of this is to suppress association between heavy chains by introducing electrostatic repulsion at the interface of the heavy chain homodimers, for example by modifying amino acid residues that contact each other at the interface of the CH3 domains, including:

positions 356 and 439
positions 357 and 370
positions 399 and 409, the residue numbering being according to the EU numbering system.

By modifying one or more of these pairs of residues to have like charges (both positive or both negative) in the CH3 domain of a first heavy chain, the pairing of heavy chain homodimers is inhibited by electrostatic repulsion. By engineering the same pair or pairs of residues in the CH3 domain of a second (different) heavy chain to have an opposite charge compared with the corresponding residues in the first heavy chain, the heterodimeric pairing of the first and second heavy chains is promoted by electrostatic attraction.

In one example, amino acids at the heavy chain constant region CH3 interface are modified to introduce charge pairs, the mutations being listed in Table 1 of WO2006/106905. It was reported that modifying the amino acids at heavy chain positions 356, 357, 370, 399, 409 and 439 to introduce charge-induced molecular repulsion at the CH3 interface had the effect of increasing efficiency of formation of the intended bispecific antibody. WO2006/106905 also exemplified bispecific IgG antibodies in which the CH3 domains of IgG4 were engineered with knobs-into-holes mutations.

Further examples of charge pairs are disclosed in WO2013/157954, which described a method for producing a heterodimeric CH3 domain-comprising molecule from a single cell, the molecule comprising two CH3 domains capable of forming an interface. The method comprised providing in the cell (a) a first nucleic acid molecule encoding a first CH3 domain-comprising polypeptide chain, this chain comprising a K residue at position 366 according to the EU numbering system and (b) a second nucleic acid molecule encoding a second CH3 domain-comprising polypeptide chain, this chain comprising a D residue at position 351 according to the EU numbering system, the method further comprising the step of culturing the host cell, allowing expression of the two nucleic acid molecules and harvesting the heterodimeric CH3 domain-comprising molecule from the culture.

Further methods of engineering electrostatic interactions in polypeptide chains to promote heterodimer formation over homodimer formation were described in WO2011/143545.

Another example of engineering at the CH3-CH3 interface is strand-exchange engineered domain (SEED) CH3 heterodimers. The CH3 domains are composed of alternating segments of human IgA and IgG CH3 sequences, which form pairs of complementary SEED heterodimers referred to as "SEED-bodies" [13; WO2007/110205].

Bispecifics have also been produced with heterodimerised heavy chains that are differentially modified in the CH3 domain to alter their affinity for binding to a purification reagent such as Protein A. WO2010/151792 described a heterodimeric bispecific antigen-binding protein comprising a first polypeptide comprising, from N-terminal to C-terminal, a first epitope-binding region that selectively binds a first epitope, an immunoglobulin constant region that comprises a first CH3 region of a human IgG selected from IgG1, IgG2, and IgG4; and a second polypeptide comprising, from N-terminal to C-terminal, a second epitope-binding region that selectively binds a second epitope, an immunoglobulin constant region that comprises a second CH3 region of a human IgG selected from IgG1, IgG2, and IgG4, wherein the second CH3 region comprises a modification that reduces or eliminates binding of the second CH3 domain to Protein A.

Antibodies of the present invention may employ any of these techniques and molecular formats as desired.

Immunisation

Further aspects of the invention are the use of non-human animals described herein for producing antibodies comprising unpaired variable domains that specifically bind target antigens. An antibody comprising an unpaired variable domain may be produced by exposing a non-human animal as described herein to immunogenic stimulation with the target antigen.

A method of producing an antibody that binds a target antigen may comprise providing a non-human animal having a genome as described herein and (a) immunising the animal with the target antigen (e.g., with cells expressing the antigen or with purified recombinant antigen);

(b) isolating antibodies generated by the animal;

(c) testing the antibodies for ability to bind the antigen; and (d) selecting one or more antibodies that binds the antigen.

The non-human animal may be a knockout animal wherein endogenous expression of the target (e.g., of an orthologue of a human target antigen) has been inactivated.

A non-human animal as described herein can be challenged with the target antigen, and lymphatic cells (such as B cells) can then recovered from animals that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. Nucleic acid encoding the variable regions may be isolated and linked to desirable isotypic constant regions. Such an antibody may be produced in a cell, such as a CHO cell. Alternatively, nucleic acid encoding the variable domains may be isolated directly from lymphocytes.

Nucleic acid encoding an antibody heavy chain variable domain and/or an antibody light chain variable domain of a selected antibody may be isolated. Such nucleic acid may encode the full antibody heavy chain and/or light chain, or the variable domain without associated constant region. As noted, encoding nucleotide sequences may be obtained from lymphocytes.

Antibody discovery is made significantly easier by working with antibodies comprising unpaired variable domains (provided by either a heavy chain or a light chain) rather than paired antigen-binding domains (provided by heavy: light chain pairs) because the identification of correctly paired sequences is not required. Leading techniques of antibody discovery in vivo involve bulk sequencing of variable domains from B cells, which in a "classical" system generates vast numbers of VH and VL domain sequences for which it is strongly desirable to keep track of which VH domain sequence was paired with which VL domain sequence. Pairwise tracking can add an extra layer of complexity, e.g., requiring sorting of single cells into individual wells of a plate for analysis, so that VH and VL sequence information are co-identified from each cell. By contrast, where the variable domain sequence information is contained in a single VH or VL domain sequence per B cell, antibody sequences may conveniently be processed in bulk rather than as individual cells. Bulk sequencing of B cells of immunised animals may be performed with or without a step of antigen-specific cell sorting.

Optionally, once nucleic acid encoding the variable domain has been obtained it is conjugated to a nucleotide sequence encoding a desired constant region or other polypeptide domain(s) to provide nucleic acid encoding a polypeptide comprising an unpaired variable domain.

Where the immunised mammal produces chimaeric antibodies with non-human constant regions, these may be replaced with human constant regions to generate an antibody that will be less immunogenic when administered to humans as a medicament. Provision of particular human isotype constant regions is also significant for determining the effector function of the antibody, and a number of suitable heavy chain constant regions are discussed herein. Nucleic acid encoding the variable domain may alternatively be linked to non-antibody polypeptide domains e.g., to encode a CAR.

Other alterations to nucleic acid encoding the antibody heavy and/or light chain variable domain may be performed, such as mutation of residues and generation of variants. There are many reasons why it may be desirable to create variants, which include optimising the sequence for large-scale manufacturing, facilitating purification, enhancing stability or improving suitability for inclusion in a desired pharmaceutical formulation. Protein engineering work can be performed at one or more chosen residues in the sequence, e.g., to substituting one amino acid with an alternative amino acid (optionally, generating variants containing all naturally occurring amino acids at this position, with the possible exception of Cys and Met), and monitoring the impact on function and expression to determine the best substitution. It is in some instances undesirable to substitute a residue with Cys or Met, or to introduce these residues into a sequence, as to do so may generate difficulties in manufacturing—for instance through the formation of new intramolecular or intermolecular cysteine-cysteine bonds. Where a lead candidate has been selected and is being optimised for manufacturing and clinical development, it will generally be desirable to change its antigen-binding properties as little as possible, or at least to retain the affinity and potency of the parent molecule. However, variants may also be generated in order to modulate key antibody characteristics such as affinity, cross-reactivity or neutralising potency.

The isolated (optionally mutated) nucleic acid may be introduced into host cells, e.g., CHO cells. Host cells are then cultured under conditions for expression of a polypeptide comprising the variable domain.

The antibody may bind a cell-surface receptor, e.g., the extracellular domain of such a receptor. Cells expressing the antigen or a desired fragment thereof on their cell surface (e.g., cells transfected with nucleic acid encoding the antigen or fragment, and expressing that antigen or fragment at high level), may be used for immunisation.

Example categories of antigens include transmembrane receptors such as 7-pass transmembrane receptors, e.g., G-protein coupled receptors (GPCRs). A receptor may comprise an extracellular (EC) domain, a transmembrane domain and a cytosolic domain. It is common to target an EC domain of a receptor using an antibody, since the EC domain is more accessible to antibody that has been injected into a patient. Receptors of interest may bind ligands such as hormones, neurotransmitters, cytokines, growth factors, cell adhesion molecules, or nutrients. The target antigen may be an antigen of a pathogen, for generation of antibodies (and isolated unpaired variable domains) binding to the pathogen or to infected cells.

In many envisaged situations the target antigen is a human antigen.

Antibodies produced according to the present invention may bind a human antigen and a non-human orthologue of the antigen, e.g., may bind both human and rodent (e.g., mouse or rat) antigen. Antibodies generated by methods described herein may be tested to confirm specific binding to human and non-human animal target antigen. Cross-reactive antibodies can thus be selected, which may be screened for other desirable properties as described herein.

Methods of generating antibodies to an antigen (e.g., a human antigen), through immunisation of animals with the antigen where expression of the endogenous antigen (e.g., endogenous mouse antigen) has been knocked-out in the animal, may be performed in animals capable of generating antibodies comprising human variable domains. The genomes of such animals can be engineered to comprise a human or humanised immunoglobulin locus encoding human variable region gene segments, and optionally an endogenous constant region or a human constant region. Recombination of the human variable region gene segments generates human antibodies, which may have either a non-human or human constant region. Non-human constant regions may subsequently be replaced by human constant regions where the antibody is intended for in vivo use in humans. Such methods and knockout transgenic animals are described elsewhere herein and in WO2013/061078.

Encoding Nucleic Acids and Methods of Expression

Isolated nucleic acid may be provided, encoding antibodies according to the present invention. Nucleic acid may be DNA and/or RNA. Genomic DNA, cDNA, mRNA or other RNA, of synthetic origin, or any combination thereof can encode an antibody.

The present invention provides constructs in the form of plasmids, vectors, transcription or expression cassettes which comprise at least one polynucleotide as above. Exemplary nucleotide sequences are included in the sequence listing. Reference to a nucleotide sequence as set out herein encompasses a DNA molecule with the specified sequence, and encompasses an RNA molecule with the specified sequence in which U is substituted for T, unless context requires otherwise.

The present invention also provides a recombinant host cell that comprises one or more nucleic acids encoding the antibody. Methods of producing the encoded antibody may comprise expression from the nucleic acid, e.g., by culturing recombinant host cells containing the nucleic acid. The antibody may thus be obtained, and may be isolated and/or purified using any suitable technique, then used as appropriate. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals.

The expression of antibodies and antibody fragments in prokaryotic cells is well established in the art. A common bacterial host is E co/i. Expression in eukaryotic cells in culture is also available to those skilled in the art as an option for production. Mammalian cell lines available in the art for expression of a heterologous polypeptide include Chinese hamster ovary (CHO) cells, HeLa cells, baby hamster kidney cells, NSO mouse melanoma cells, YB2/0 rat myeloma cells, human embryonic kidney cells, human embryonic retina cells and many others.

Vectors may contain appropriate regulatory sequences, including promoter sequences, terminator sequences, polyadenylation sequences, enhancer sequences, marker genes and other sequences as appropriate. Nucleic acid encoding an antibody can be introduced into a host cell. Nucleic acid can be introduced to eukaryotic cells by various methods, including calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid-based system. The plasmid system may be maintained episomally or may be incorporated into the host cell or into an artificial chromosome. Incorporation may be either by random or targeted integration of one or more copies at single or multiple loci. For bacterial cells, suitable techniques include calcium chloride transformation, electroporation and transfection using bacteriophage. The introduction may be followed by expressing the nucleic acid, e.g., by culturing host cells under conditions for expression of the gene, then optionally isolating or purifying the antibody.

Nucleic acids of the invention may be integrated into the genome (e.g. chromosome) of the host cell. Integration may be promoted by inclusion of sequences that promote recombination with the genome, in accordance with standard techniques.

The present invention also provides a method that comprises using nucleic acid described herein in an expression system in order to express an antibody.

Compositions

Antibodies and their encoding nucleic acid according to the present invention may be provided in isolated form and/or in solution, e.g., aqueous solution.

The invention further provides a composition (eg, a pharmaceutical composition or a composition for medical use) comprising an antibody, bispecific antibody, polypeptide, antibody heavy or light chain, VH domain, VL domain or nucleotide sequence thereof obtained or obtainable by a method of the invention as disclosed herein.

Antibodies may be monoclonal or polyclonal, but are preferably provided as monoclonal antibodies for therapeutic use. They may be provided as part of a mixture of other antibodies, optionally including antibodies of different binding specificity.

Antibodies according to the invention, and encoding nucleic acids, will usually be provided in isolated form. Thus, the antibodies, VH and/or VL domains, and nucleic acids may be provided purified from their natural environment or their production environment. Isolated antibodies and isolated nucleic acid will be free or substantially free of material with which they are naturally associated, such as other polypeptides or nucleic acids with which they are found in vivo, or the environment in which they are prepared (e.g., cell culture) when such preparation is by recombinant DNA technology in vitro. Optionally, an isolated antibody or nucleic acid (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature.

Antibodies or nucleic acids may be formulated with diluents or adjuvants and still for practical purposes be isolated—for example they may be mixed with carriers if used to coat microtitre plates for use in immunoassays, and may be mixed with pharmaceutically acceptable carriers or diluents when used in therapy. As described elsewhere herein, other active ingredients may also be included in therapeutic preparations. Antibodies may be glycosylated, either naturally in vivo or by systems of heterologous eukaryotic cells such as CHO cells, or they may be (for example if produced by expression in a prokaryotic cell) unglycosylated. The invention encompasses antibodies having a modified glycosylation pattern. In some applications, modification to remove undesirable glycosylation sites may be useful, or e.g., removal of a fucose moiety to increase ADCC function [14]. In other applications, modification of galactosylation can be made in order to modify CDC.

Typically, an isolated product constitutes at least about 5%, at least about 10%, at least about 25%, or at least about 50% of a given sample. An antibody may be substantially free from proteins or polypeptides or other contaminants that are found in its natural or production environment that would interfere with its therapeutic, diagnostic, prophylactic, research or other use.

An antibody may have been identified, separated and/or recovered from a component of its production environment (e.g., naturally or recombinantly). The isolated antibody may be free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated antibody or its encoding nucleic acid will be prepared by at least one purification step.

The polypeptides comprising unpaired variable domains (e.g., antibodies), or their encoding nucleic acids, may be formulated for the desired route of administration to a patient, e.g., in liquid (optionally aqueous solution) for injection. Compositions may comprise a polypeptide or nucleic acid in combination with medical injection buffer and/or with adjuvant. Various delivery systems are known and can be used to administer the pharmaceutical composition of the invention. Methods of introduction include, but are not limited to, intradermal, intramuscular, intraperitoneal, intravenous, subcutaneous, intranasal, epidural, and oral routes.

The composition may comprise a diluent, excipient or carrier. When the composition is a pharmaceutical composition or a composition for medical use, the diluent, excipient or carrier is pharmaceutically acceptable. "Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to a carrier, excipient, or adjuvant that can be administered to a subject, together with an agent, e.g., any antibody, VL or antibody chain described herein, and which does not destroy the pharmacological activity thereof and is nontoxic when administered in doses sufficient to deliver a therapeutic amount of the agent.

Compositions comprising polypeptides or nucleic acids described herein may be contained in a sterile container in vitro. A composition may be in a bag or other medical container connected to an IV syringe. It may be within a phial, syringe or an injection device. In an example, a kit is provided comprising the antibody, polypeptide or nucleic acid, plus packaging and instructions for use in a therapeutic method as described herein.

The invention provides therapeutic compositions comprising polypeptides comprising unpaired variable domains as described herein. Therapeutic compositions comprising nucleic acid encoding such polypeptides are also provided. Encoding nucleic acids are described in more detail elsewhere herein and include DNA and RNA, e.g., mRNA. In therapeutic methods described herein, use of nucleic acid encoding the antibody, and/or of cells containing such nucleic acid, may be used as alternatives (or in addition) to compositions comprising the antibody itself. Cells (e.g., human cells, e.g., human lymphocytes) containing nucleic acid encoding the antibody, optionally wherein the nucleic acid is stably integrated into the genome, thus represent medicaments for therapeutic use in a patient. Cells expressing CARs, e.g., CAR-T cells, are an example. Alternatively, nucleic acid encoding an antibody of the present invention may be introduced into human B lymphocytes, optionally B lymphocytes derived from the intended patient and modified ex vivo. Optionally, memory B cells are used. Administration of cells containing the encoding nucleic acid to the patient provides a reservoir of cells capable of expressing the antibody, which may provide therapeutic benefit over a longer term compared with administration of isolated nucleic acid or isolated antibody.

Chimaeric Antigen Receptors (CARs)

Antibodies and non-human animals according to the present invention represent a source of unpaired antigen-binding variable domains which may be incorporated into a variety of modular molecular designs, one of which is the chimaeric antigen receptor (CAR). A CAR comprises an antigen-binding moiety fused to a T-cell activating moiety, typically in a transmembrane receptor which also includes a cytosolic T-cell activating domain. CAR-T structures comprising VH domains for binding target antigen have been described [15, 16].

Thus, an unpaired variable domain may be linked to a T-cell activating moiety to provide a CAR. Optionally a T-lymphocyte is engineered to express the CAR on its surface. CARs and cells are preferably human.

It may be desirable to engineer CAR-T cells to express IL-7 and CCL19 as these factors have been reported to be important for the maintenance of T cell zones in lymphoid organs [17].

Following construction of nucleic acid encoding a human CAR using an unpaired variable domain produced as described herein, it may be transfected into human T cells and/or integrated into a T cell genome. Activity of a CAR may be assessed e.g., by introducing CAR-T cells into animals bearing syngenic tumours and/or human cell lines and observing effects on the target cells.

Unless otherwise specified herein or the context does not allow, any unpaired variable domain herein may be a VH (heavy chain variable domain, eg, a human, dog, cat, horse, fish or bird VH domain), VHH (e.g., Camelid variable domain with or without humanisation) or VL (light chain variable domain, such as a kappa or lambda VL, e.g., a human, dog, cat, horse, fish or bird VL domain), Unless otherwise specified herein or the context does not allow, any unpaired variable domain may be a human, humanised, chimaeric (e.g., mouse-human or rat-human chimaeric), rodent (e.g., mouse or rat), dog, cat, horse, fish or bird variable domain.

Unless otherwise specified herein or the context does not allow, any inserted DNA (e.g., human variable region DNA in a heavy chain locus) and/or shield domain-encoding DNA may be human, humanised, chimaeric (e.g., mouse-human or rat-human chimaeric), rodent (e.g., mouse or rat), dog, cat, horse, fish or bird DNA, preferably human DNA. For example, any heavy chain locus herein may comprise one or more variable region gene segments disclosed in Table C(a), or may comprise at least 50%, 60% or 90% of such gene segments, or may comprise all of such gene segments.

An example shield domain is a CK encoded by the gene segment shown in Table C(b).

An example of a suitable antigen (eg, an antigen with which an animal of the invention is immunised or to which an antibody or variable domain of the invention binds) is selected from the group consisting of ABCF1; ACVR1; ACVR1B; ACVR2; ACVR2B; ACVRL1; ADORA2A; Aggrecan; AGR2; AICDA; AWI; AIG1; AKAP1; AKAP2; AIYIH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BA11; BCL2; BCL6; BDNF; BLNK; BLR1 (MDR15); B1yS; BMP1; BMP2; BMP3B (GDF10); BMP4; BMP6; BMP8; BMPR1A; BMPR1B; BMPR2; BPAG1 (plectin); BRCA1; Cl9orflO (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-id); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2 I eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1 RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wapl/Cip1); CDKN1B (p27Kip1); CDKNIC; CDKN2A (p161NK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYDi); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78 I LIX); CXCL6 (GCP-2); CXCL9 (MIG); CXCR3 (GPR9/CKR-L2); CXCR4; CXCR6 (TYMSTR ISTRL33 I Bonzo); CYB5; CYC1; CYSLTR1; DAB21P; DES; DKFZp451J0118; DNCL1; DPP4; E2F1; ECGF1; EDG1; EFNAI; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF2O; FGF21; FGF22; FGF23; FGF3 (int-2); FGF4 (HST); FGF5; FGF6 (HST-2); FGF7 (KGF); FGF8; FGF9; FGFR3; FIGF (VEGFD); FILL (EPSILON); FILL (ZETA); FLJ12584; FLJ25530; FLRT1 (fibronectin); FLT1; FOS; FOSL1 (FRA-1); FY (DARC); GABRP (GABAa); GAGEBI; GAGEC1; GALNAC4S-65T; GATA3; GDF5; GFI1; GGT1; GM-CSF; GNAS1; GNRH1; GPR2 (CCR1O); GPR31; GPR44; GPR81 (FKSG80); GRCC10 (C10); GRP; GSN (Gelsolin); GSTP1; HAVCR2; HDAC4; EDAC5; HDAC7A; HDAC9; HGF; HIF1A; HIP1; histamine and histamine receptors; HLA-A; HLA-DRA; HM74; HMOX1; HUMCYT2A; ICEBERG; ICOSL; 1D2; IFN-a; IFNA1; IFNA2; IFNA4; IFNA5; IFNA6; IFNA7; IFNB1; I FNgamma; TFNW1; IGBP1; IGF1; IGF1R; IGF2; IGFBP2; I GFBP3; IGFBP6; IL-1; IL10; IL10RA; IL10RB; IL11; IL11RA; IL-12;

IL12A; IL12B; IL12RB1; IL12RB2; 1L13; IL13RA1; IL13RA2; 1L14; 1115; IL15RA; IL16; 1L17; IL17B; IL17C; IL17R; 1L18; IL18BP; IL18R1; IL18RAP; 1L19; IL1A; IL1B; IL1F1O; IL1F5; IL1F6; IL1F7; IL1F8; IL1F9; IL1HY1; IL1R1; IL1R2; ILiRAP; IL1RAPL1; IL1RAPL2; IL1RL1; IL1RL2 IL1RN; 1L2; 1L20; IL20RA; IL21R; 1L22; 1L22R; 1L22RA2; IL23; 1L24; 1L25; 1L26; 1L27; 1L28A; 1L28B; 1L29; IL2RA; IL2RB; IL2RG; 1L3; 1L30; IL3RA; 1L4; IL4R; 1L5; IL5RA; 1L6; IL6R; IL6ST (glycoprotein 130); 1L7; TL7R; 1L8; IL8RA; IL8RB; IL8RB; 1L9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; MTLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MK167 (Ki-67); MMP2; MMP9; MS4A1; MSMB; MT3 (metallothionectin-ifi); MTSS 1; MUC 1 (mucin); MYC; MYD88; NCK2; neurocan; NFKB 1; NFKB2; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NR112; NR113; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PART1; PATE; PAWR; PCA3; PCNA; PDGFA; PDGFB; PECAMi; PF4 (CXCL4); PGF; PGR; phosphacan; PIAS2; PIK3CG; PLAU (uPA); PLG; PLXDC1; PPBP (CXCL7); PPI D; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; S100A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINIA3; SERPINB5 (maspin); SERPINE1 (PAT-i); SERPINF1; SHBG; SLA2; SLC2A2; SLC33A1; SLC43A1; SLIT2; SPP1; SPRR1B (Spri); ST6GAL1; STAB1; STAT6; STEAP; STEAP2; TB4R2; TBX21; TCP10; TDGF1; TEK; TGFA; TGFB1; TGFB1I1; TGFB2; TGFB3; TGFBI; TGFBR1; TGFBR2; TGFBR3; TH1 L; THBS1 (thrombospondin-1); THBS2; THBS4; THPO; TIE (Tie-i); T]MP3; tissue factor; TLR10; TLR2; TLR3; TLR4; TLR5; TLR6; TLR7; TLR8; TLR9; TNF; TNF-a; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSF1O (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase lia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-Ib); XCR1 (GPR5/CCXCR1); YY1; and ZFPM2.

For example the antigen is selected from the following list (e.g., wherein the antibody or variable domain is for administration to a human or animal subject for treating a cancer or autoimmune condition): immune checkpoint inhibitors (such as PD-L1, PD-1, CTLA-4, TIGIT, TIM-3, LAG-3 and VISTA, e.g. TIGIT, TIM-3 and LAG-3), immune modulators (such as BTLA, hHVEM, CSF1R, CCR4, CD39, CD40, CD73, CD96, CXCR2, CXCR4, CD200, GARP, SIRPα, CXCL9, CXCL10, CXCL11 and CD155, e.g. GARP, SIRPα, CXCR4, BTLA, hVEM and CSF1R), immune activators (such as CD137, GITR, OX40, CD40, CXCR3 (e.g. agonistic anti-CXCR3 antibodies), CD27, CD3, ICOS (e.g. agonistic anti-ICOS antibodies), for example. ICOS, CD137, GITR and OX40).

In an example, a λ5 shield domain herein comprises or consists of an amino acid sequence encoded by SEQ ID NO: 77.

In an example herein, an animal of the invention comprises a light chain locus (a kappa or lambda locus) that comprises SEQ ID NO: 77, 78, 81, 83, 85, 87, 89, 91, 93 or 100.

In an example herein, an animal of the invention expresses SEQ ID NO: 82, 84, 86, 88 90 or 101.

In an example, the animal of the invention comprises a kappa light chain locus (in heterozygous or homozygous state) as herein described. Optionally, the locus comprises a deletion between an endogenous Vκ gene and an endogenous Jκ gene, but retaining the Vκ exon 1 plus endogenous splice junctions at the 5' end of the Vκ exon 2 and the 3' end of the J. In another example, the animal of the invention comprises a replacement of endogenous Jκ genes with a targeting vector encoding a variable region promoter, leader (exon 1, intron, partial exon 2) of a mouse or human Vκ plus a fragment of a Jκ retaining endogenous splice junctions at the 5' end of the Vκ exon 2 and the 3' end of the J. The result of either of these strategies is a locus that expresses a transcript, under endogenous or human Vκ promoter control, that is spliced to generate a Cκ with a Vκ leader sequence and partial J sequence. This strategy can utilise any Vκ and J of the mouse Kappa repertoire. For strategy one, we will use Vκ3-2 or Vκ3-4 with Jκ5. The reason for this is that Vκ3-2 or Vκ3-4 are close to the 3' end of the locus, reducing the size of deletion required, plus have been shown in literature to have a fairly high frequency of usage in the mice. See FIG. 16 for Kappa locus structure overview and FIG. 4 for predicted expressed sequences from the two example modified loci. One may use Vκ6-17 or Vκ10-96 with Jκ5 as these Vs have been shown to be the most highly used in the mouse repertoire (see reference 18). See FIG. 18 for example targeting strategy/locus summary and FIG. 19 for predicted expressed sequence using Vκ6-17 and Vκ10-96.

In an example, all non-coding and regulatory elements in the modified locus are endogenous. For a modified kappa locus, this includes the specific promoter for the Vκ/Jκ/Cκ fragment, the endogenous κ intronic enhancer (located between Jκ5 and Cκ) and the endogenous κ 3' enhancer. Interaction of these endogenous promoters/enhancers with the endogenous (eg, mouse) effectors involved in expression from the κ locus is likely to be more effective than that of endogenous effectors with the human regulatory sequences, thus potentially resulting a more active locus.

Clauses

The following numbered clauses, setting out embodiments of the present invention, are part of the description.

1. A composition comprising an isolated antibody in solution, the antibody comprising an unpaired variable domain for binding a target antigen, wherein the unpaired variable domain is linked to a constant region, wherein the constant region comprises a CH1 domain and a shield domain which binds the CH1 domain.

2. A composition according to clause 1, wherein the unpaired variable domain is linked to the CH1 domain of the constant region.

3. A composition comprising
 a first polypeptide comprising a human variable domain and a CH1 domain, and
 a second polypeptide comprising a shield domain which pairs with said CH1 domain, wherein the second polypeptide lacks a variable domain, thereby leaving the variable domain of the first polypeptide unpaired.

4. A composition according to clause 3, wherein the first polypeptide is an immunoglobulin heavy chain comprising VH-CH1-CH2-CH3.

5. A composition according to clause 3 or clause 4, wherein the second polypeptide consists of the shield domain.

6. A composition according to any of clauses 1 to 5, wherein the shield domain is a CL domain.

7. A composition according to clause 6, wherein the CL is Cκ.

8. A composition according to clause 6, wherein the CL is Cλ.

9. A composition according to any of clauses 1 to 5, wherein the shield domain is a λ5 immunoglobulin domain.

10. A composition according to any preceding clause, comprising an Fc region.

11. A composition according to any preceding clause wherein the unpaired variable domain is a VH domain.

12. A composition according to any preceding clause, which is a four-chain antibody comprising two of said unpaired variable domains.

13. A composition comprising an isolated antibody in solution, the antibody comprising two first polypeptides and two second polypeptides, wherein
 each first polypeptide comprises a human variable domain and a CH1 domain, and
 each second polypeptide comprises a shield domain which pairs with the CH1 domain of the first polypeptide, wherein
 one or both of said second polypeptides lacks a variable domain, thereby leaving one or both variable domains of the first polypeptide unpaired.

14. A composition according to clause 13, wherein the variable domains of both first polypeptides are unpaired variable domains.

15. A composition according to clause 13 or clause 14, each said first polypeptide comprises a VH domain.

16. A composition according to any of clauses 13 to 15, wherein each said first polypeptide comprises VH-CH1-CH2-CH3.

17. A composition according to any of clauses 13 to 16, wherein the two first polypeptides are identical.

18. A composition according to any of clauses 13 to 17, wherein the two second polypeptides are identical.

19. A composition according to any of clauses 13 to 18, wherein each said second polypeptide consists of the shield domain.

20. A composition according to any of clauses 13 to 19, wherein the shield domain is a CL domain.

21. A composition according to clause 20, wherein the CL is Cκ.

22. A composition according to clause 20, wherein the CL is Cλ.

23. A composition according to any of clauses 13 to 19, wherein the shield domain is a λ5 immunoglobulin domain.

24. An antibody comprising a heavy chain and a light chain, wherein
 the heavy chain comprises an unpaired human VH domain for binding a target antigen and a heavy chain constant region comprising a CH1 domain, and wherein
 the light chain comprises a CL domain, wherein the light chain lacks a VL domain, thereby leaving the VH domain unpaired.

25. An antibody according to clause 24, comprising two heavy chains and two light chains,
 each heavy chain comprising a human VH domain and a heavy chain constant region comprising a CH1 domain, and
 each light chain comprising a CL domain, wherein
 one or both light chains lack a VL domain, thereby leaving one or both VH domains unpaired.

26. An antibody according to clause 25, comprising two heavy chains and two light chains, wherein
 each heavy chain comprises an unpaired human VH domain for binding a target antigen, and a heavy chain constant region comprising a CH1 domain, and wherein
 each light chain comprises a CL domain, wherein the light chain lacks a VL domain.

27. An antibody according to clause 26, wherein the two unpaired VH domains bind the same antigen or epitope.

28. An antibody according to clause 26 or clause 27, wherein the two unpaired VH domains are identical in amino acid sequence.

29. An antibody according to any of clauses 25 to 28, wherein the two first polypeptides are identical in sequence and/or wherein the two second polypeptides are identical in sequence.

30. An antibody according to any of clauses 24 to 29, wherein the heavy chain constant region comprises the CH1 domain and one or more further CH domains.

31. An antibody according to clause 30, wherein the heavy chain constant region comprises a CH2 domain and a CH3 domain.

32. An antibody according to any of clauses 24 to 31, wherein the CL is Cκ.

33. An antibody according to any of clauses 24 to 28, wherein the CL is Cλ.

34. An antibody according to any of clauses 24 to 33, wherein the light chain consists of the CL domain.

35. An antibody according to any of clauses 24 to 34, wherein the heavy chain constant region is a human heavy chain constant region.

36. An antibody according to any of clauses 24 to 35, wherein the CL is human Cκ or human Cλ.

37. An antibody according to clause 36, wherein the CL comprises human Cκ sequence SEQ ID NO: 4.

38. An antibody according to clause 37, wherein the CL consists of human Cκ sequence SEQ ID NO: 4.

39. A composition according to any of clauses 1 to 23 or an antibody according to any of clauses 24 to 38, wherein the antibody is an IgG.

40. An antibody according to any of clauses 24 to 38, wherein the antibody is an IgM.

41. A composition or an antibody according to any preceding clause, wherein the antibody is a fully human antibody.

43. A composition or an antibody according to any preceding clause, wherein the unpaired variable domain binds a human antigen.

43. A composition or an antibody according to any preceding clause, wherein the unpaired variable domain binds an extracellular domain of a receptor.

44. Nucleic acid encoding an antibody as defined in any preceding clause or a polypeptide or unpaired variable domain thereof.

45. Nucleic acid according to clause 44, comprising nucleotide sequences encoding a heavy chain comprising a human VH domain for binding a target antigen and a heavy chain constant region comprising a CH1 domain, and a light chain comprising a CL domain, wherein the light chain lacks a variable domain.

46. Nucleic acid according to clause 45, wherein the light chain comprises a signal peptide fused to a Cκ constant domain.

47. Nucleic acid according to clause 46, wherein the light chain comprises SEQ ID NO: 6.

48. Nucleic acid according to clause 47, comprising a nucleotide sequence SEQ ID NO: 5 encoding the light chain.

49. A non-human animal, or cell thereof, whose genome comprises nucleic acid according to any of clauses 44 to 48.

50. A non-human animal comprising B-lymphocytes expressing an antibody as defined in any of clauses 1 to 43.

51. An animal according to clause 50 wherein, upon immunogenic stimulation, at least 50% of antibody-expressing B-lymphocytes in the animal express an antibody according to any of clauses 1 to 43.

52. An animal according to clause 50 or clause 51, wherein the B-lymphocytes lack functional expression of light chains comprising a VL domain.

53. A non-human animal cell having a genome comprising a plurality of human variable region gene segments capable of rearrangement to encode a variable domain, upstream of DNA encoding an immunoglobulin constant region comprising a CH1 domain, and a gene encoding a CL domain which lacks functional expression of variable region gene segments, or a gene encoding the immunoglobulin domain of λ5.

54. A non-human animal comprising B-lymphocytes expressing an antibody comprising an unpaired human VH domain for binding antigen, wherein the genome of the animal comprises a plurality of human variable region gene segments capable of rearrangement to encode a variable domain, upstream of DNA encoding an immunoglobulin constant region comprising a CH1 domain, and a gene encoding a CL domain which lacks functional expression of variable region gene segments, or a gene encoding the immunoglobulin domain of λ5.

A λ5 immunoglobulin domain may be a human, rodent, mouse, rat, rabbit or mammalian, vertebrate domain. It may be a domain that has a truncation as described herein.

55. A method of generating a non-human animal comprising B-lymphocytes expressing an antibody comprising an unpaired human VH domain for binding antigen, comprising engineering the genome of a non-human animal cell to comprise a plurality of human variable region gene segments capable of rearrangement to encode a variable domain, upstream of DNA encoding an immunoglobulin constant region comprising a CH1 domain, and a gene encoding a CL domain which lacks functional expression of variable region gene segments, or a gene encoding the immunoglobulin domain of λ5, and generating an animal from said cell or from a group of cells comprising said cell.

56. A cell according to clause 53 or a method according to clause 55, wherein the cell is an embryonic stem cell or a zygote.

57. An animal, cell or method according to any of clauses 53 to 56, wherein the plurality of variable region gene segments comprises one or more V gene segments, one or more D gene segments and one or more J gene segments capable of rearrangement to encode a VH domain.

58. An animal, cell or method according to clause 57, wherein the one or more V gene segments, one or more D gene segments and one or more J gene segments comprise multiple human V gene segments, multiple human D gene segments and multiple human J gene segments.

59. An animal, cell or method according to any of clauses 53 to 58, wherein the plurality of variable region gene segments are at the endogenous immunoglobulin heavy chain locus of the animal.

60. An animal, cell or method according to any of clauses 53 to 59, wherein the CL domain is a human CL domain.

61. An animal, cell or method according to clause 60, wherein the human CL domain is human Cκ.

62. An animal, cell or method according to any of clauses 53 to 61, wherein the gene encoding the CL domain comprises an exon encoding a light chain variable region leader sequence and an exon encoding the CL domain, separated by an intron comprising a J-C intron enhancer element, wherein the encoded CL domain comprises an N-terminal signal peptide.

63. An animal, cell or method according to clause 62, wherein the gene encoding the CL domain comprises an exon encoding a human Vκ leader sequence and an exon encoding a human Cκ domain, separated by an intron comprising a human J-Cκ intron enhancer element, wherein the encoded CL domain is a human Cκ domain comprising an N-terminal signal peptide.

64. An animal, cell or method according to clause 63, wherein the human Cκ domain comprises SEQ ID NO: 4 or SEQ ID NO: 6.

65. An animal, cell or method according to clause 64, wherein transcription of the gene encoding the CL domain produces nucleic acid comprising SEQ ID NO: 5.

66. An animal, cell or method according to any of clauses 53 to 66, wherein the gene encoding the CL domain is at an endogenous immunoglobulin light chain locus of the animal.

67. An animal, cell or method according to clause 66, wherein the endogenous immunoglobulin light chain locus is the endogenous Igκ locus.

68. An animal, cell or method according to any of clauses 53 to 67, wherein expression of endogenous immunoglobulin light chain variable region gene segments is inactivated.

69. An animal, cell or method according to clause 69, wherein expression of endogenous immunoglobulin light chains is inactivated.

70. An animal, cell or method according to any of clauses 53 to 66, wherein expression of endogenous immunoglobulin heavy chain variable region gene segments is inactivated.

71. An animal, cell or method according to clause 70, wherein expression of endogenous immunoglobulin heavy chains is inactivated.

72. An animal, cell or method according to any of clauses 53 to 71, wherein the animal is a rodent.

73. An animal, cell or method according to clause 72, wherein the animal is a mouse or rat.

74. An animal, cell or method according to clause 73, wherein a plurality of human variable region gene segments capable of rearrangement to encode a human variable domain, upstream of human DNA encoding an immunoglobulin constant region comprising a human CH1 domain, are inserted at the endogenous immunoglobulin heavy chain locus on mouse chromosome 12, and expression of mouse heavy chains is inactivated.

75. An animal, cell or method according to clause 73 or clause 74, wherein a gene encoding a human Cκ domain is inserted at the endogenous Igκ light chain locus on mouse chromosome 6, and expression of mouse Igκ light chains is inactivated.

76. An animal produced by the method of any of clauses 55 to 75.

77. An animal or method according to any of clauses 54 to 76, wherein B-lymphocytes of the animal express antibodies as defined in any of clauses 1 to 43.

78. An animal or method according to clause 77 wherein, upon immunogenic stimulation, at least 50% of antibody-expressing B-lymphocytes in the animal express antibodies as defined in any of clauses 1 to 43.

79. A method of generating an antibody comprising an unpaired VH domain for binding antigen, comprising exposing an animal according to any of clauses 49 to 52, 54 or 57 to 78 to immunogenic stimulation with target antigen.

80. A method according to clause 79, comprising isolating the antibody or its encoding nucleic acid from the animal.

81. A method according to clause 79 or clause 80, comprising identifying the sequence of the unpaired variable domain of the antibody or its encoding nucleic acid.

82. A method according to clause 80 or clause 81 comprising introducing one or more mutations into the nucleotide sequence of nucleic acid encoding the variable domain.

83. A method according to clause 81 or clause 82, comprising providing a DNA vector comprising the encoding nucleic acid.

84. A method according to clause 83, wherein the nucleic acid encodes a polypeptide comprising the variable domain and one or more further domains.

85. A method according to any of clauses 80 to 84, further comprising cloning the encoding nucleic acid into a recombinant host cell.

86. A method according to clause 85, further comprising culturing the cell for expression of a polypeptide comprising the variable domain.

87. A method according to clause 86, comprising recovering and purifying the polypeptide from the cell or culture medium.

88. A method according to any of clauses 84 to 87, wherein the polypeptide is an isolated variable domain, an antibody or a chimaeric antigen receptor.

89. A method according to clause 87 or clause 88, comprising formulating the polypeptide into a composition comprising a pharmaceutically acceptable excipient.

90. An antibody according to any of clauses 1 to 43 for use in treatment of the human body by therapy.

91. A method of preparing an antibody:antigen complex, comprising
- exposing a target antigen to an antibody as defined in any of clauses 1 to 43 in vitro,
- allowing binding of the unpaired variable domain to the target antigen, thereby forming an antibody:antigen complex, and
- isolating the antibody:antigen complex.

EXPERIMENTAL EXAMPLES

Figure 2:
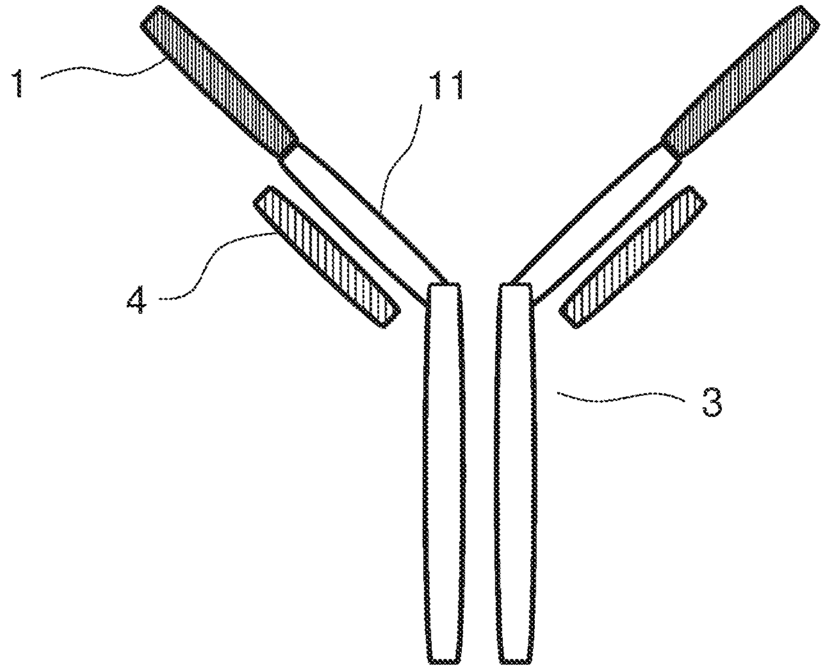
FIG. 2 shows an embodiment of an antibody according to the present invention. The antibody comprises two heavy chains and two light chains. Each heavy chain has (in the N- to C-terminal direction) a VH domain (1) and a constant region comprising domains CH1 (11), CH2 and CH3. The CH2-CH3 regions of the two heavy chains dimerise to form an Fc region (3). Each light chain comprises a CL domain (4) and lacks any further domains. CL domain (4) pairs with CH1 domain (11), so the antibody comprises two heavy: light chain pairs, dimerised into the four-chain antibody molecule via the CH2-CH3 of Fc region (3). The VH domain (1) of each heavy chain is unpaired, and the two VH domains of the antibody are available for divalent antigen binding.

Example 1: Mouse Genome Engineered to Express Human Ig Light Chain Comprising Cκ and Devoid of VL Domain Mice are engineered to express antibodies in which a truncated K light chain comprising a Cκ domain fragment pairs with the CH1 of fully human heavy chains comprising unpaired VH domains. FIG. 2.

The mouse contains a humanised heavy chain locus on mouse chromosome 12 (FIG. 7), a modified fully humanised K locus on mouse chromosome 6 (FIG. 8) and an active or inactivated endogenous or inactivated humanised λ locus on chromosome 16 (FIG. 9).

In this mouse the humanised K locus is modified to inactivate normal vj rearrangement and instead express a Cκ domain fragment.

A large deletion (~90 kb) of the human κ locus removes a 90 kb fragment encompassing exon 2 of Vκ1-5 to Jκ5. This removes all of Vκ2-4, Vκ7-3, Vκ5-2, Vκ4-1, Jκ1, Jκ2, Jκ3, Jκ4 and Jκ5 but leaves exon 1 of Vκ1-5 which encodes the majority of the Vκ1-5 signal peptide, the κ enhancers and the Cκ gene. The latter elements are therefore left intact. Upstream V gene segments cannot rearrange in the absence of the complete set of J gene segments. The normal κ VJ recombination is thus inactivated. The remaining Vκ1-5 exon 1 (i.e., the leader sequence) will therefore be spliced onto the Cκ, creating a novel transcript encoding a Cκ polypeptide comprising a signal peptide (FIG. 3).

Figure 4A:
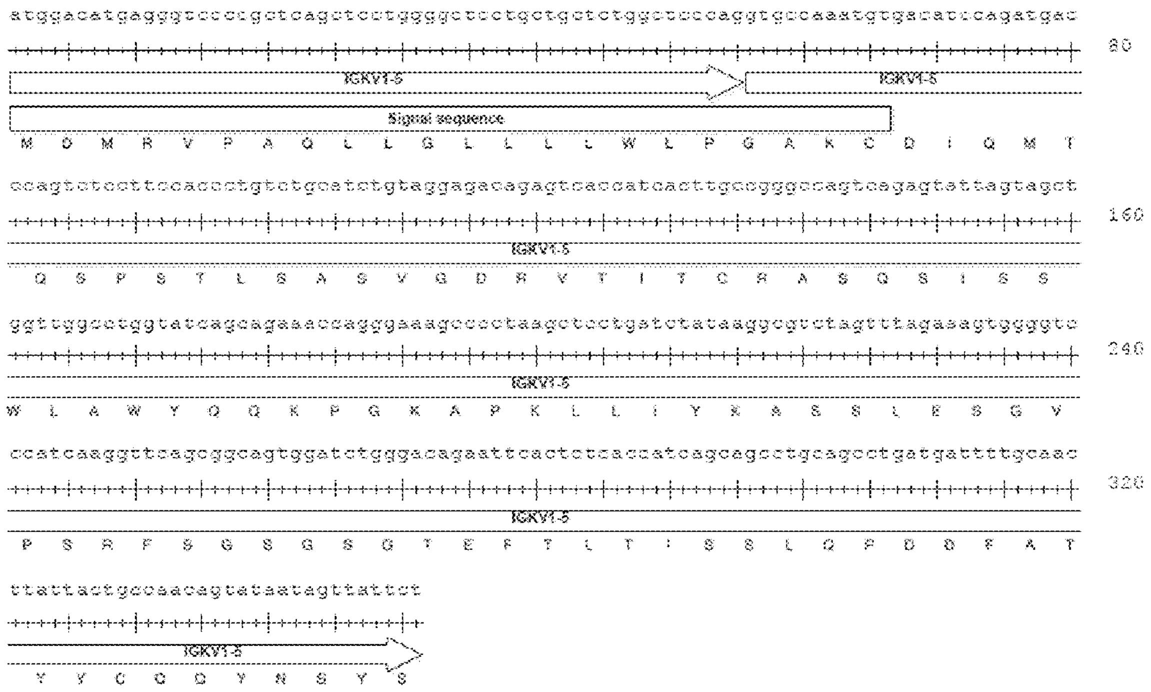
FIG. 4 shows the human vκ1-5 sequence of an unmodified human κ locus. a) cDNA of vκ1-5 SEQ ID NO: 9. Nucleic acid of vκ1-5 leader sequence SEQ ID NO: 11. b) Translated vκ1-5. Encoded vκ1-5 including signal peptide SEQ ID NO: 10. Signal peptide SEQ ID NO: 12.
Figure 4B:
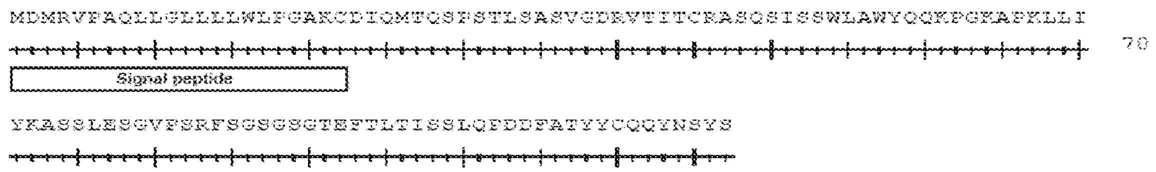

The nucleotide and protein sequence of the modified K locus of the present invention (FIG. 3*b*, 3c) may be compared with unmodified human Vκ1-5 sequence (FIG. 4*a*, 4b).

Figure 5:
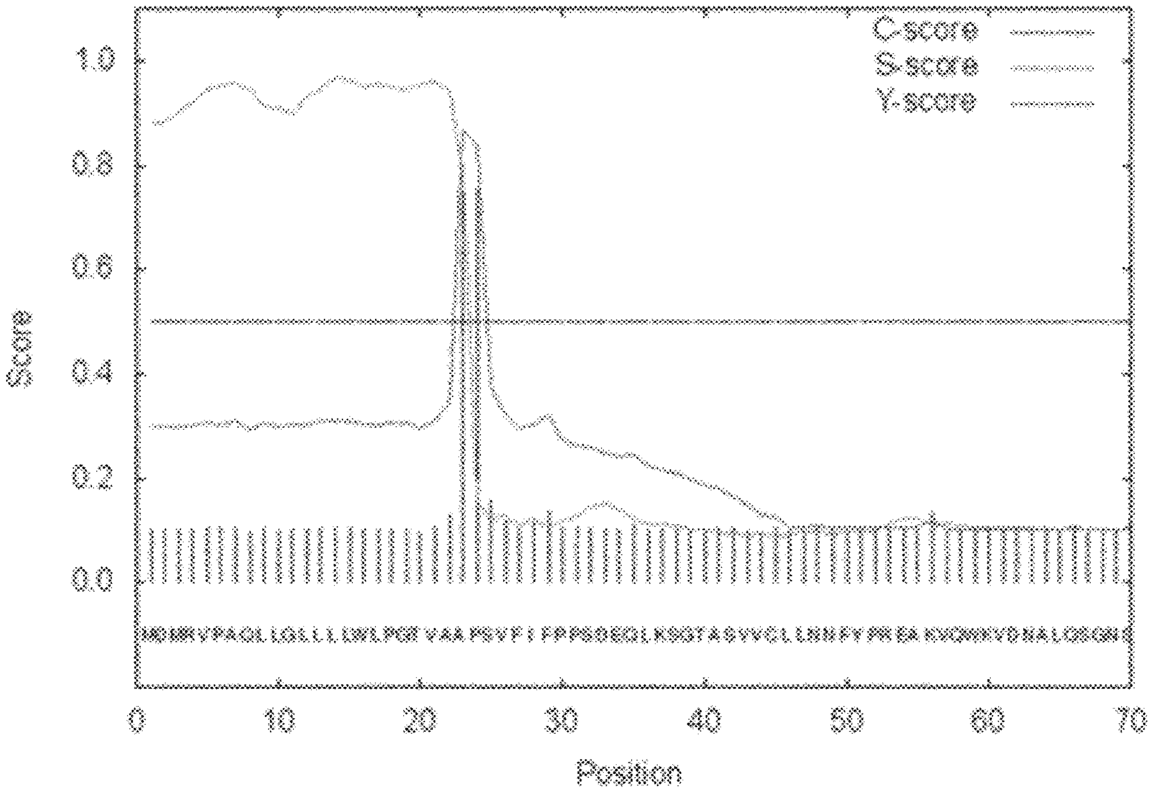
FIG. 5 shows prediction of signal peptide cleavage in a Cκ shield domain according to the present invention, generated using SignalP software. The N-terminal sequence is a predicted signal peptide with a cleavage site between residues 22 and 23.

The sequence of the Cκ fragment transcript and resulting protein includes a predicted cleavage site of the signal peptide (FIG. 5). After cleavage of the signal peptide, the Cκ is available to pair with the CH1 domain of an antibody heavy chain, allowing its proper folding and stabilisation.

The modified K locus can be generated by creating double strand breaks at defined locations in the κ genomic locus and providing a repair template to promote the desired deletion. The genetic deletion can be performed in mouse cells comprising a humanised K locus, for example in mouse embryonic stem cells containing a humanised K locus, or reagents may be injected into zygotes from mice whose genomes comprise a humanised K locus.

Animals with the desired Cκ locus are then mated with animals containing a fully human heavy chain locus to produce mice that are able to generate fully human antibodies comprising unpaired VH domains.

The λ locus can be either unmodified or inactivated in this platform.

Data are presented in Example 4.

Example 2: Pairing CH1 with λ5 Shield Domain

It is known that Ig heavy chain is not expressed on the B cell surface in the absence of light chain. However, λ5 can rescue the surface expression of Ig heavy chains if expressed at stages beyond early B cell development in the bone marrow. A truncated λ5 protein, which is able to rescue surface IgM display in the absence of VpreB[11], appears especially suitable. The 50 amino acid unique region at the N-terminal end of human λ5 is believed to limit the rate of λ5 folding in the absence of VpreB[4]. The immunoglobulin domain of λ5, lacking this N-terminal unique region, binds the heavy chain constant domain CH1 and thus represents a shield domain in the present invention. The λ5 comprises its native signal peptide or a non-native signal peptide such as that encoded by the Vκ1-5 leader or the λ1 leader sequence. Signal peptides may be post-translationally cleaved.

Replacement of the Jκ region of the light chain κ immunoglobulin locus with a gene encoding the λ5 immunoglobulin domain places λ5 expression under control of the Igκ locus. A 5 kb replacement would suffice. The β strand (J) preceding the λ5 Ig fold can be retained. Alternatively, this is omitted, including only the Ig domain itself. In the context of the surrogate light chain this J strand supplies the missing B strand of the VpreB Ig domain[4, 5]. VpreB is not expressed during Igκ (or Igλ) light chain expression, therefore the λ5 will be expressed in the absence of VpreB.

Figure 6A:
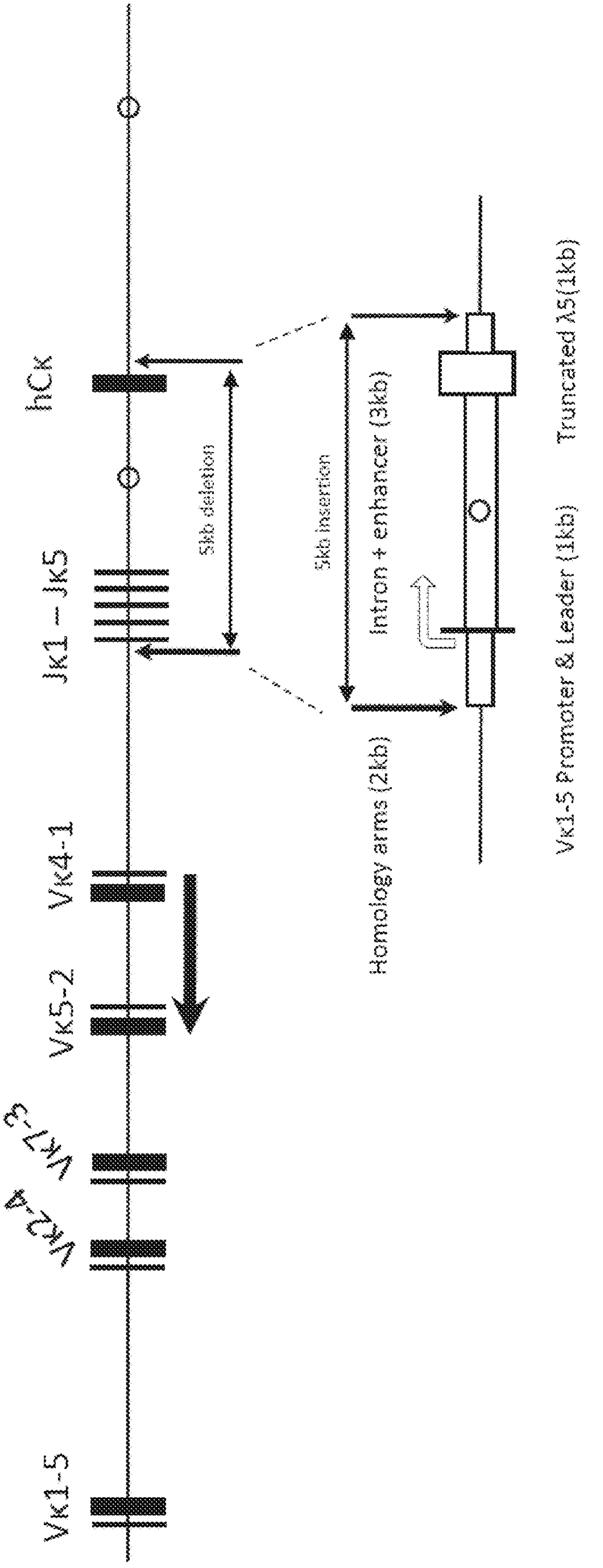
FIG. 6 shows construction of an immunoglobulin locus for expression of a λ5 shield domain according to the present invention.
Figure 6B:
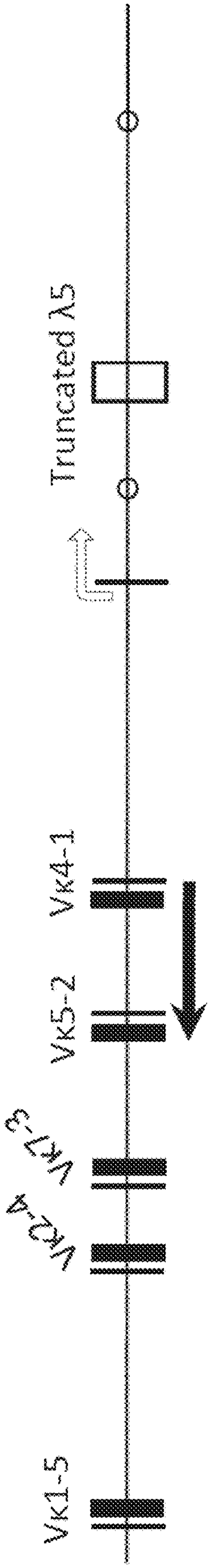

FIG. 6 shows the modification of the humanised Kappa locus with a targeting vector to introduce a human λ5 transgene. The vector includes mouse 3' and 5 homology arms, human Vκ promoter, human intron and intronic enhancer and truncated human λ5. Targeting of this vector replaces the human Jκ1-Jκ5, intron and intronic enhancer and Cκ with the vector insert.

A human Igκ locus comprising the above modification is inserted into the genome of a non-human animal, e.g., mouse, to generate a transgenic animal expressing the human λ5 gene under control of human Igκ transcriptional control elements. The human DNA is inserted at the endogenous Igκ locus of the animal or at an independent (ectopic) locus in the animal genome. Inactivation of κ and/or λ light chain loci in an animal genome can be combined with insertion of a transgene encoding all or part of the human λ5 gene or a mutant thereof. Here the λ5 transgene is inserted in the inactivated κ and/or λ light chain locus and is placed under control of the human κ or A gene control elements including promoter/enhancer elements.

Example 3: Inactivation of Endogenous λ Light Chain

Figure 10:
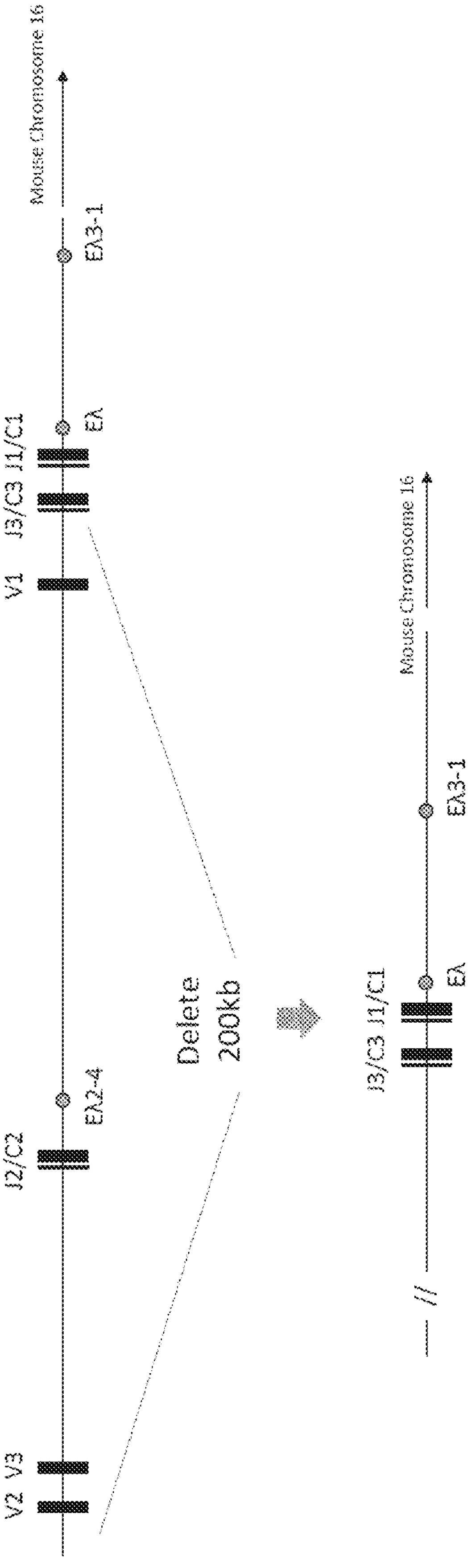
FIG. 10 shows a more detailed plan for inactivation of the endogenous mouse λ locus by deletion of a large (200 kb) genomic fragment from chromosome 16. Inactivation has been achieved by a large deletion, removing Vλ2, Vλ3, Vλ1 plus Jλ2/Cλ2 cluster, leaving Jλ3/Cλ3 and Jλ1/Cλ1 clusters.

A large deletion (200 kb) of the λ locus removes v2 to v1 (the segment comprising V2, V3, J2C2 and V1) but leaves J3C3, J1C1 and downstream enhancers intact. This inactivates expression of the A light chain. FIG. 9 and FIG. 10.

The locus is generated by creating double strand breaks at defined locations in the A genomic locus and providing a repair template to promote the desired deletion.

The inactivated λ locus is combined by breeding an animal comprising this genomic modification with an animal comprising the fully humanised heavy chain locus and a modified kappa locus as described herein. This ensures that, even in the absence of allelic exclusion, no light chains are expressed from the endogenous λ locus.

In the absence of λ light chain, the Cκ domain pairs with heavy chain CH1 in expressed antibodies.

Example 4: Performance of Mice Containing a Truncated K Light Chain Locus Comprising a Cκ Region Mosaic F0 animals generated by cytoplasmic injection, containing the desired fully human Kappa locus with a deletion to enable expression of a truncated Kappa Cκ fragment, which we call a KCF locus (see Example 1), plus a mixture of WT alleles and uncharacterised indel mutations, were mated individually to segregate this mosaicism, generating F1 animals each with a single F0-derived allele. In order to generate F1 animals suitable for early analysis, each mosaic F0 was bred with an animal containing an inactivated Kappa locus (inactivation by insertion of a Neomycin cassette within the Kappa locus, between Jκ5 and Cκ, preventing normal Kappa recombination). The resulting heterozygous animals, containing the desired modified Kappa locus plus inactivated mouse Kappa locus, were analysed at the transcript and protein level.

Figure 12:
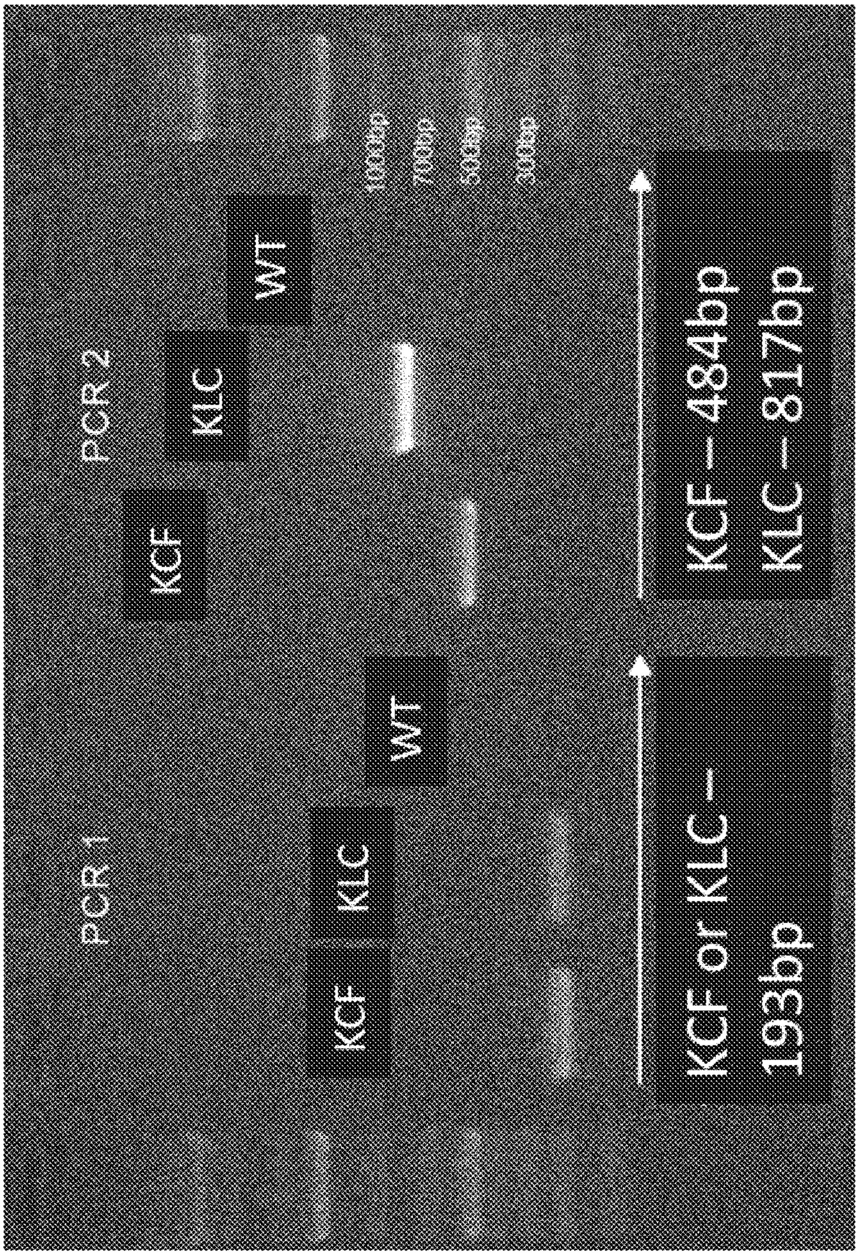
FIG. 12 shows RT-PCR analysis of human Kappa fragment locus (KCF), unmodified humanised Kappa locus (KLC) plus WT control. PCR 1 uses forward and reverse oligos in human Cκ (primers HCP428/HCP431) and therefore gives the same product from both loci. PCR 2 uses forward oligo in human Vκ1-5 5' UTR and reverse oligo in human Cκ 3' UTR (primers HCP446/HCP451). PCR 2 shows expected smaller size product for KCF compared to full length Kappa light chain from KLC locus.
Figure 13:
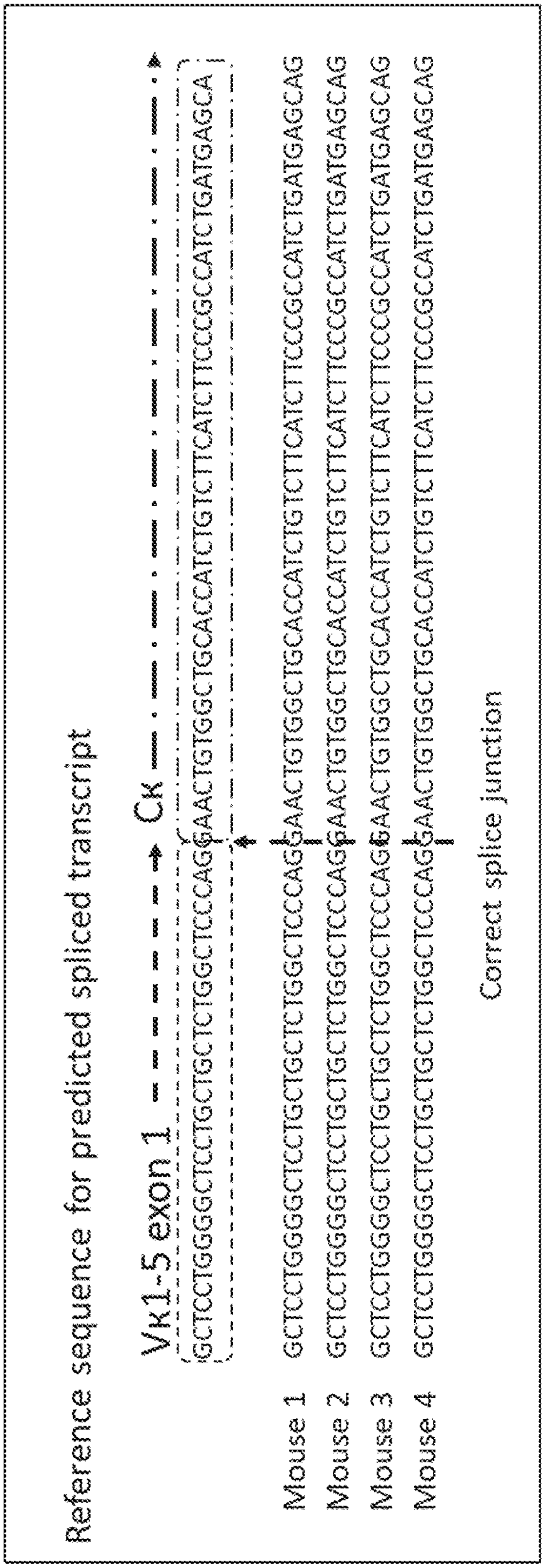
FIG. 13 shows a sequence alignment of RT-PCR product (PCR 2) from multiple KCF animals with the reference sequence for predicted KCF transcript, showing presence of correct Vκ1-5 exon 1/Cκ splice junction.

RNA was extracted from splenocytes, from these heterozygotes and from control animals with an unmodified fully human Kappa locus, using TRIzol® Reagent (Invitrogen™) and a standard protocol. First strand DNA synthesis was performed using a SuperScript III First-Strand Synthesis SuperMix kit (Invitrogen™) and either an oligo specific for the human Cκ coding region or an Oligo(dT) primer. The first strand DNA was then used as a template for PCR with primers specific for the human Kappa constant coding region or 3' UTR in combination with oligos specific for the human Vκ1-5 leader sequence or 5' UTR. A single PCR product, with the expected size for the predicted truncated Kappa fragment, was identified from the modified Kappa locus with oligos in the human Vκ1-5 5'UTR and human Cκ 3'UTR. Sequencing of this PCR product confirmed that this transcript contained the predicted splice junction between the human Vκ1-5 exon 1 and the human Cκ gene. This is evidence that the large deletion created in the humanised Kappa locus does indeed result in expression of the predicted truncated Kappa fragment transcript—see FIG. 11 for primer details, FIG. 12 for PCR results and FIG. 13 for sequencing results.

The presence of the correctly spliced transcript for the truncated human Kappa shield domain was confirmed for samples from multiple animals containing the KCF locus.

Example 5: Mice with Human λ5 Shield Domain

Embodiments of the invention provide a mouse containing an inactivated Kappa and/or Lambda light chain locus, either endogenous or humanised, combined with insertion of a transgene encoding all or part of the human, rodent, non-human primate or other mammalian Lambda 5 (λ5) gene, or mutant thereof. The λ5 transgene is inserted in the inactivated Kappa and/or Lambda light chain locus and is under the control of endogenous and/or exogenous light chain promoter and enhancers. For example, human promoters and enhancers are used; or mouse promoters and enhancers; or human variable region promoter(s) and mouse enhancers (such as the mouse intronic and 3' light chain locus enhancers).

Inactivation of the Kappa locus can be achieved by:

1) Deletion or replacement of Jκ1-Jκ5 genes (Example 6)
2) Deletion or replacement of Jκ1-Jκ5 and Cκ gene (Example 5)
3) Deletion or replacement of C gene
4) Deletion or replacement of all Vκ genes
5) Deletion or replacement of all Vκ genes, Jκ1-Jκ5 plus Cκ gene
6) Insertion of a cassette preventing normal splicing between Jκ1-Jκ5 and the Cκ gene (Kappa ‘KO’ allele bred with mosaic animals for analysis)

Figure 14:
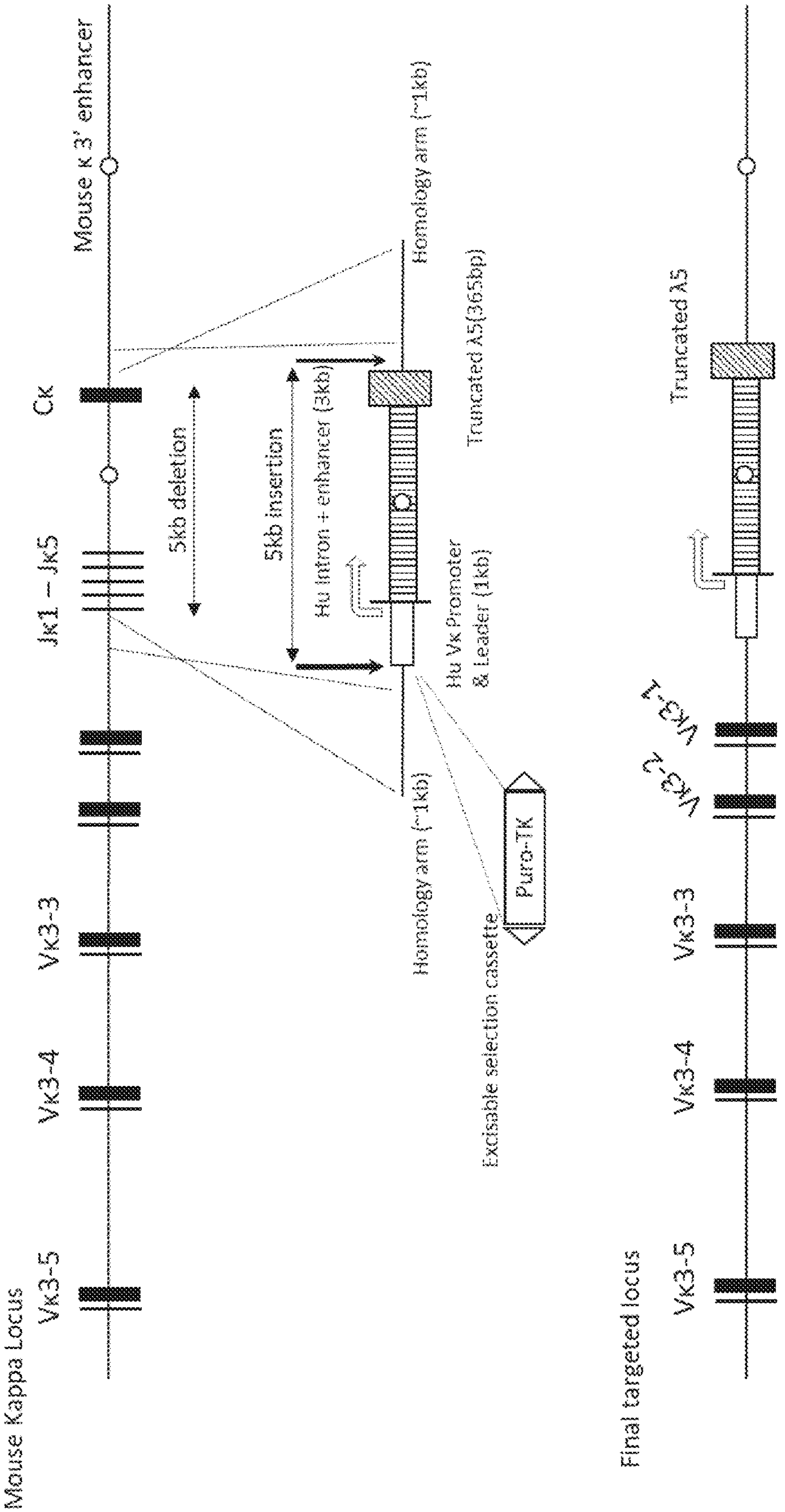
FIG. 14 shows the modification of WT mouse Kappa locus to introduce human λ5 transgene. Vector includes 1 kb mouse 3' and 5 homology arms, human Vκ promoter (white box), human intron and intronic enhancer (vertical hashed box) and truncated human λ5 (diagonal hashed box). Vector can also include an excisable positive/negative selection cassette which is removed from the final targeted locus. Targeting of this vector replaces the endogenous mouse Jκ1-Jκ5, intron and intronic enhancer and Cκ with the vector insert.
Figure 15:
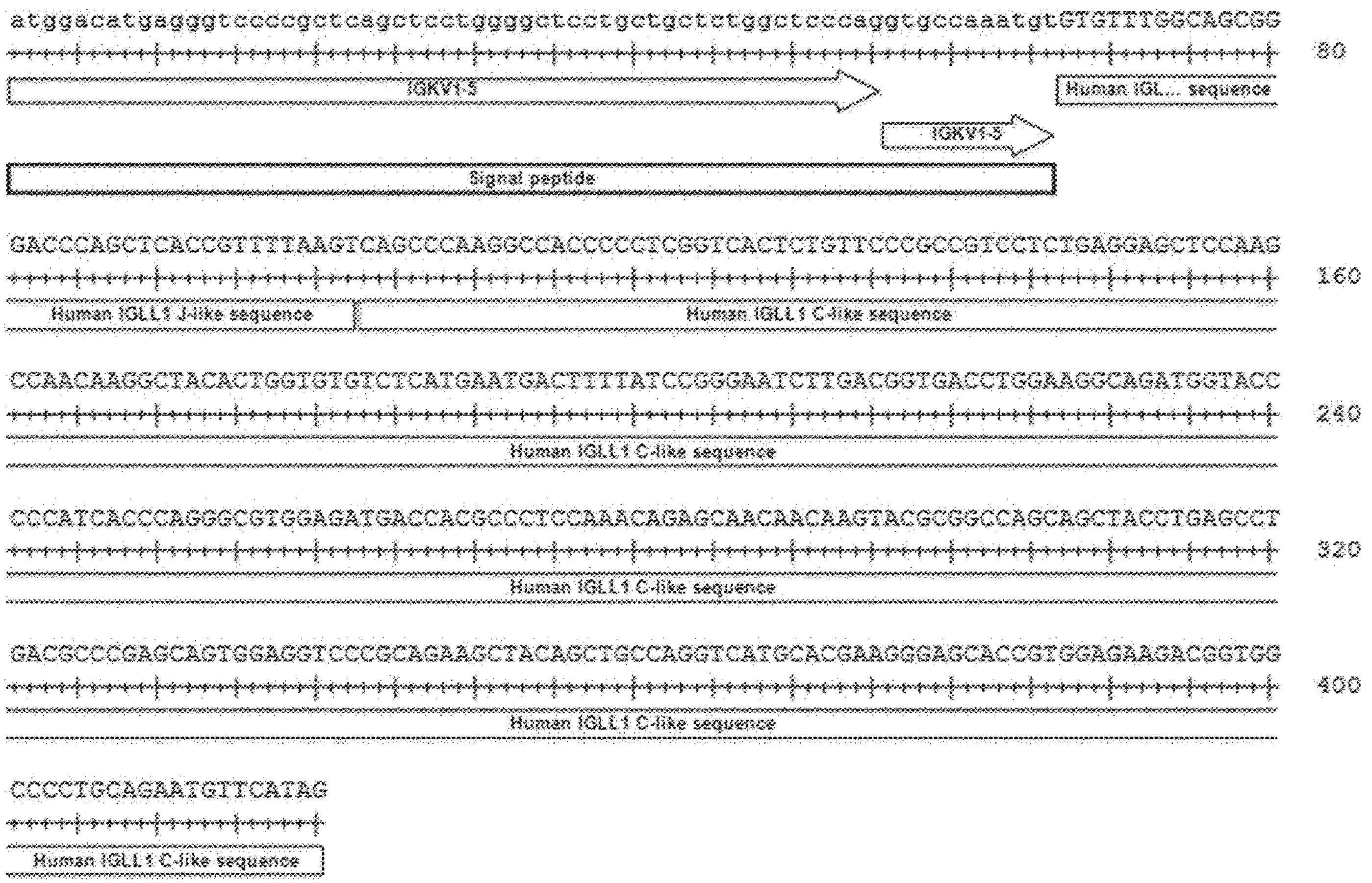
FIG. 15 shows transcript and protein generated by mouse Kappa/human λ5 locus.

Inactivation of the Lambda locus can be achieved by:

1) Deletion or replacement of Vλ2, Vλ3, Vλ1 plus Jλ2/Cλ2 cluster, leaving Jλ3/Cλ3 and Jλ1/Cλ1 clusters (Example 3)
2) Deletion or replacement of Vλ1 plus Jλ2/Cλ2, Jλ3/Cλ3 and Jλ1/Cλ1 clusters, leaving Vλ2 and Vλ3,
3) Deletion or replacement of Vλ1, Vλ3, Vλ1 plus Jλ2/Cλ2, Jλ3/Cλ3 and Jλ1/Cλ1 clusters A targeting vector encoding a truncated human λ5 coding region (SEQ ID NO:77) and human Kappa intronic region, including human Kappa intronic enhancer, preceded by a human Kappa promoter and leader (human Vκ1-5 derived) (SEQ ID NO: 78), flanked by 800-1 kb arms homologous to the mouse genomic sequence upstream of Kappa J1 and downstream of Kappa Cκ (full transgene including homology arms, SEQ ID NO:79). This sequence was synthesised as a single fragment and cloned into a pUC vector (by Genscript™). See FIG. 14.

This vector can be used in one of two ways:

1) Modification of mouse embryos to introduce the λ5 transgene: This will be achieved by injecting mouse 2 cell embryos with the required reagents to create double strand breaks at defined locations in the κ genomic locus and providing the above plasmid vector as a repair template to promote the desired deletion/insertion by homologous recombination.
2) Modification of mouse embryonic stem cells (mESCs) to introduce the λ5 transgene: This was achieved by transfecting mESCs with the required reagents to create double strand breaks at defined locations in the κ genomic locus and providing the above plasmid vector as a repair template to promote the desired deletion/insertion by homologous recombination. A positive/negative selection cassette was cloned into the vector, just downstream of the 5' homology arm. This cassette confers Puromycin resistance, and Fialuridine sensitivity (thymidine kinase gene) flanked by PiggyBac transposase-compatible 3' and 5' inverted terminal repeats. This ensured efficient targeting of the vector under positive Puromycin selection in mouse embryonic stem cells, followed by PiggyBac-induced excision of this cassette under negative Fialuridine selection. This vector was designed to target the WT mouse Kappa locus and was used in 129 strain mouse embryonic stems cells (mESCs) (AB2.1 cell line). Full targeting vector insert sequence including selection cassette, SEQ ID NO:80 Diagram summarising this modification of the mouse Kappa locus included in FIG. 14. Sequences of predicted transgene products: SEQ ID NO: 81 and SEQ ID NO: 82.

This vector was designed to target the WT mouse Kappa locus and was used in 129 strain mouse embryonic stems cells (mESCs) (AB2.1 cell line). A similar approach, with a modified vector, could be used to target the humanised Kappa locus in mESCs containing such a locus. A similar vector could be used to perform direct modification in mouse 2 cell stage embryos by cytoplasmic injection, modifying either the WT mouse Lambda locus or a humanised Lambda locus.

An alternative strategy would involve modification of the WT mouse Kappa or Lambda locus, or a humanised Kappa/Lambda locus, with a vector containing a truncated λ5 sequence from mouse (see SEQ ID NO: 100 and SEQ ID NO: 101), another rodent, non-human primate or other mammalian source.

mESCs containing the inactivated Kappa locus/human λ5 transgene were microinjected into blastocysts derived from RAG-1−/− (B6.129S7-Rag1<tm1Mom>/J) mice. Mice homozygous for this RAG-1 mutation have no mature B or T cells due to failure of V(D)J recombination. This allows for early analysis of the functionality of the introduced locus in chimeras generated in this background, as any mature lymphocytes present in the lymphoid organs of these animals will be derived from the transgene-containing mESC line injected. The same mESC lines were also injected into WT CB7bl/6 blastocysts, for generation of stable mouse lines with germline transmission of the transgene.

An additional step was performed in some λ5 mESC lines in order to inactivate the endogenous mouse λ light chain locus. This was achieved by transfecting mESCs with the required reagents to create double strand breaks at defined locations in the A genomic locus and providing a small single stranded DNA donor fragment as a repair template to promote the desired deletion. The region deleted is the same as described in Example 3 (removes V2 to V1 (the segment comprising V2, V3, J2C2 and V1) but leaves J3C3, J1C1 and downstream enhancers intact).

Analysis of initial chimeras generated in RAG-1−/− background will be performed as follows: —

Lymphoid organs from chimaeric mice generated by injection of λ5 transgene into RAG-1−/− mESCs, either without or with the mouse λ light chain knockout locus are disassociated and the resulting cells are incubated with a staining panel containing markers for mouse lymphocytes along with an anti-human λ5 antibody, followed by flow cytometry analysis. A positive result would suggest successful expression of the human λ5 transgene and assembly with the endogenous mouse Heavy chain to allow cell-surface expression of a '$V_H$-only' antibody in vivo.

Mouse lines positive for λ5 expression on surface of lymphocytes will be cross-bred with other mouse strains to introduce both the fully human Heavy locus and the mouse Lambda knockout. This will result in animals generating fully human $V_H$-only antibodies.

Example 6: Mouse Kappa Constant Fragment Shield Domain with Endogenous Regulatory Control This embodiment is a mouse containing a Kappa locus that has been modified to inactivate normal Kappa light chain rearrangement and to instead express a truncated Kappa chain composed of the Kappa constant region (Ck) plus Vκ leader and partial J fragment. This is achieved by either:

1) Creating a deletion between a mouse endogenous Vκ gene and a mouse Jκ gene, removing most of the coding sequence for the Vκ and Jκ but retaining the Vκ exon 1 plus endogenous splice junctions at the 5' end of the Vκ exon 2 and the 3' end of the J.
2) Replacing the mouse Jκ genes with a targeting vector encoding the promoter, leader (exon 1, intron, partial exon 2) of a mouse Vκ plus a small fragment of a Jκ gene, again retaining endogenous splice junctions at the 5' end of the Vκ exon 2 and the 3' end of the J.

The result of either of these strategies is a locus that expresses a transcript, under endogenous Vκ promoter control, that is spliced to generate a Cκ with a Vκ leader sequence and partial J sequence. This strategy can utilise any Vκ and J of the mouse Kappa repertoire. For strategy one, we will use Vκ3-2 or Vκ3-4 with Jκ5. The reason for this is that Vκ3-2 or Vκ3-4 are close to the 3' end of the locus, reducing the size of deletion required, plus have been shown in literature to have a fairly high frequency of usage in the mice. See FIG. 16 for Kappa locus structure overview and FIG. 4 for predicted expressed sequences from the two modified loci. For strategy 2, we will use Vκ6-17 or Vκ10-96 with Jκ5 as these Vs have been shown to be the most highly used in the mouse repertoire (see reference 18). See FIG. 18 for targeting strategy/locus summary and FIG. 19 for predicted expressed sequence using Vκ6-17 and Vκ10-96.

This mouse differs from versions with human control elements, in that in the current example all non-coding and regulatory elements in the modified locus are endogenous. This includes the specific promoter for the Vκ/Jκ/Cκ fragment, the mouse κ intronic enhancer (located between Jκ5 and Cκ) and the mouse κ 3' enhancer. Interaction of these endogenous promoters/enhancers with the mouse effectors involved in expression from the κ locus is likely to be more effective than that of mouse effectors with the human regulatory sequences present in Examples 2 and 4, thus potentially resulting a more active locus.

Figure 16A:
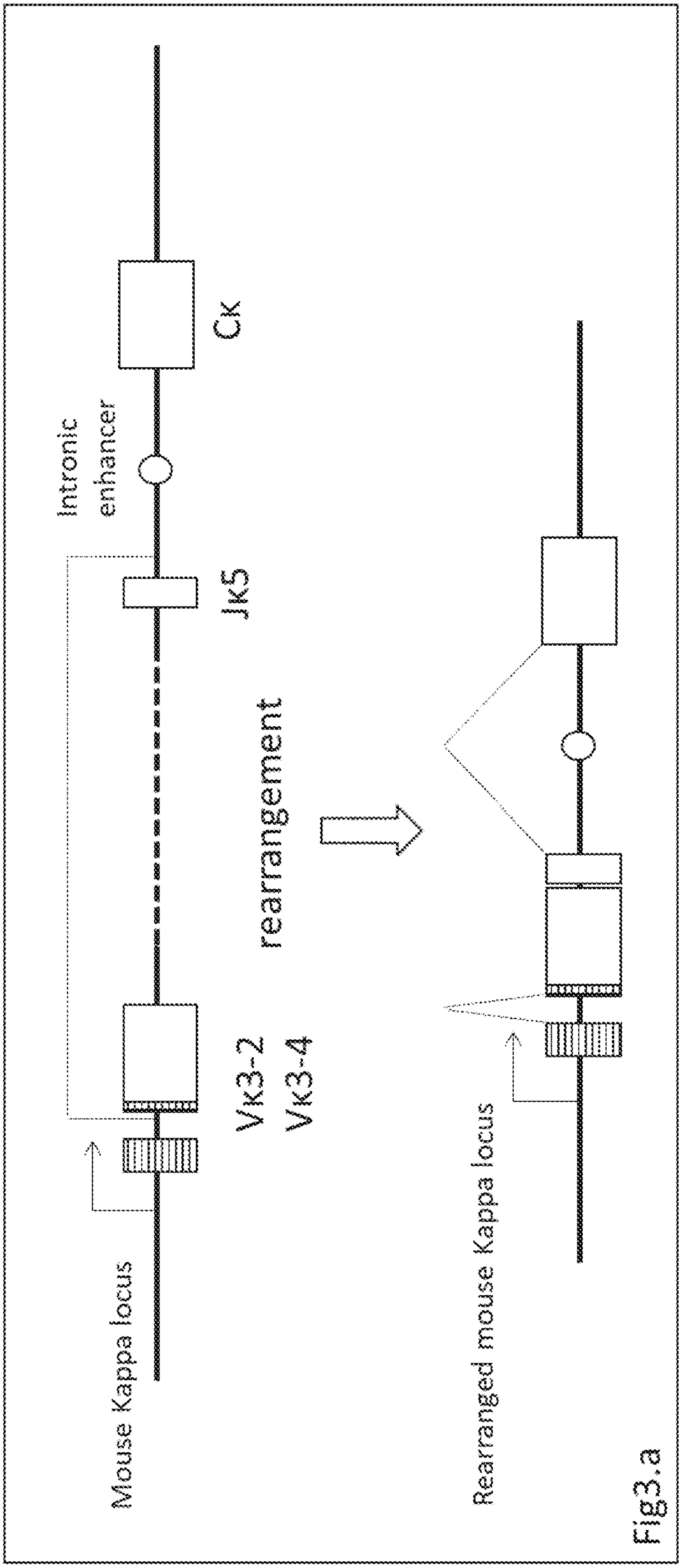
FIG. 16 shows mouse Kappa locus after normal rearrangement (a) and deletion to generate Kappa fragment locus (b).
Figure 16B:
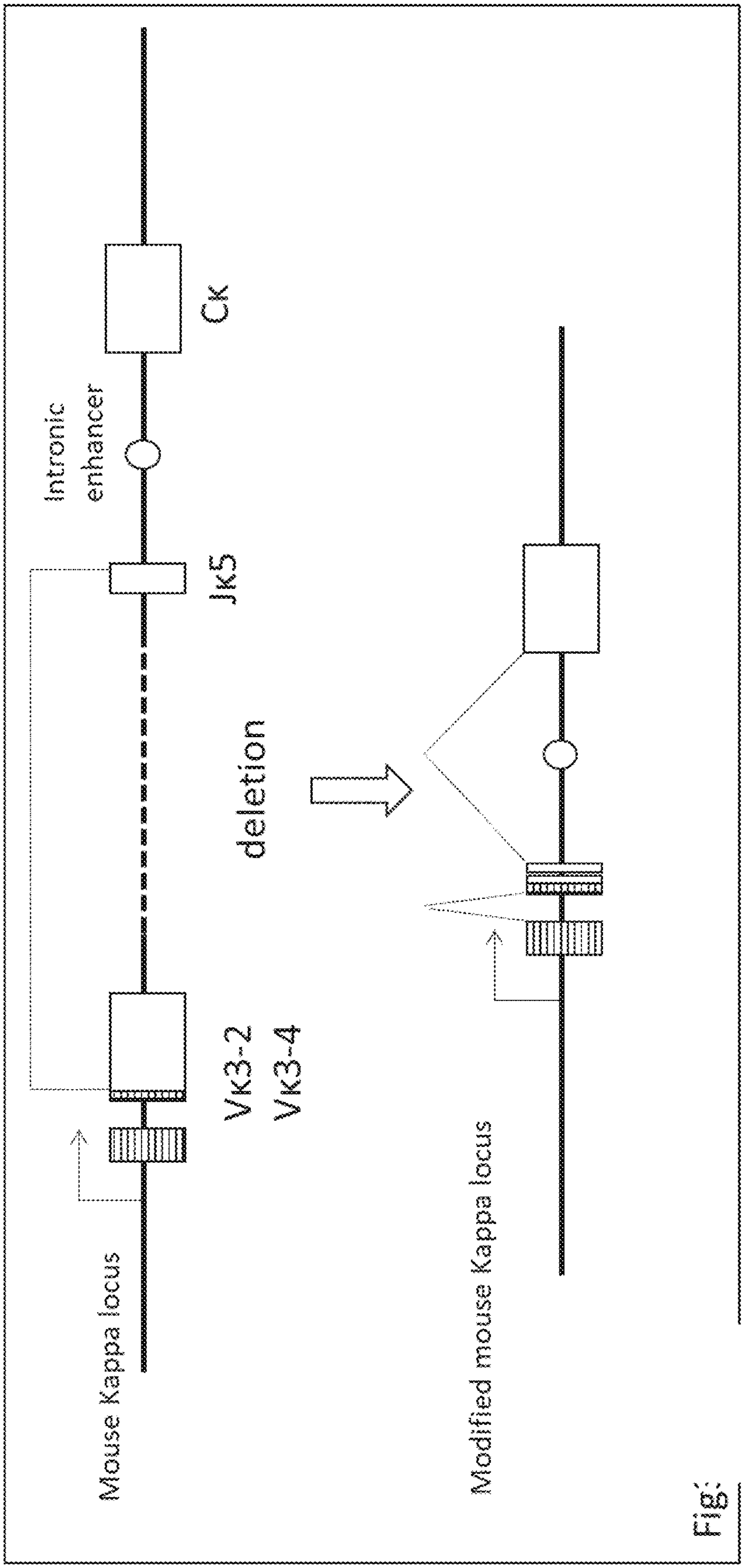
Figure 17:
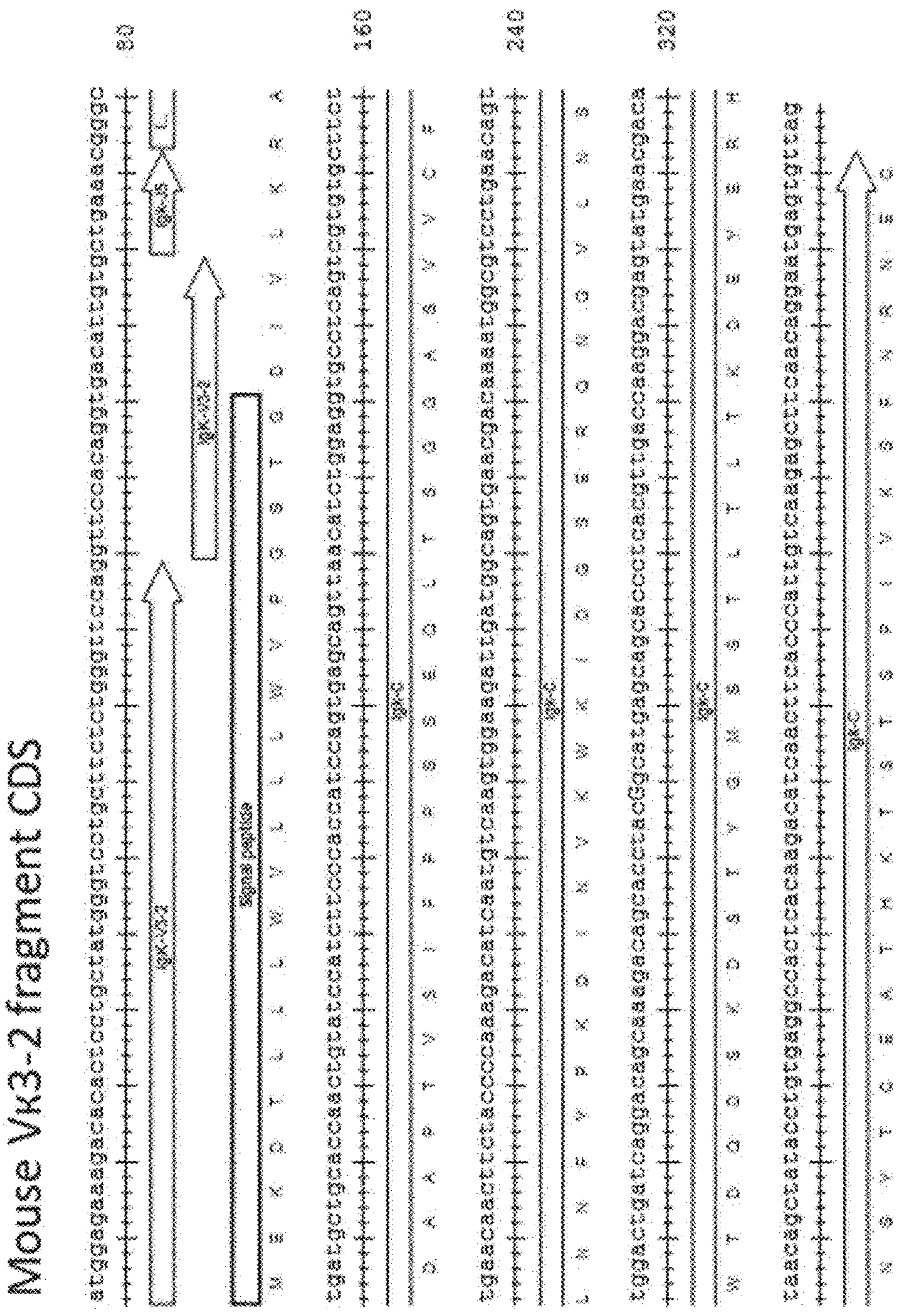
FIG. 17 shows spliced coding sequence and protein for Vκ3-2 and Vκ3-4 versions of Kappa fragment locus.
Figure 17:
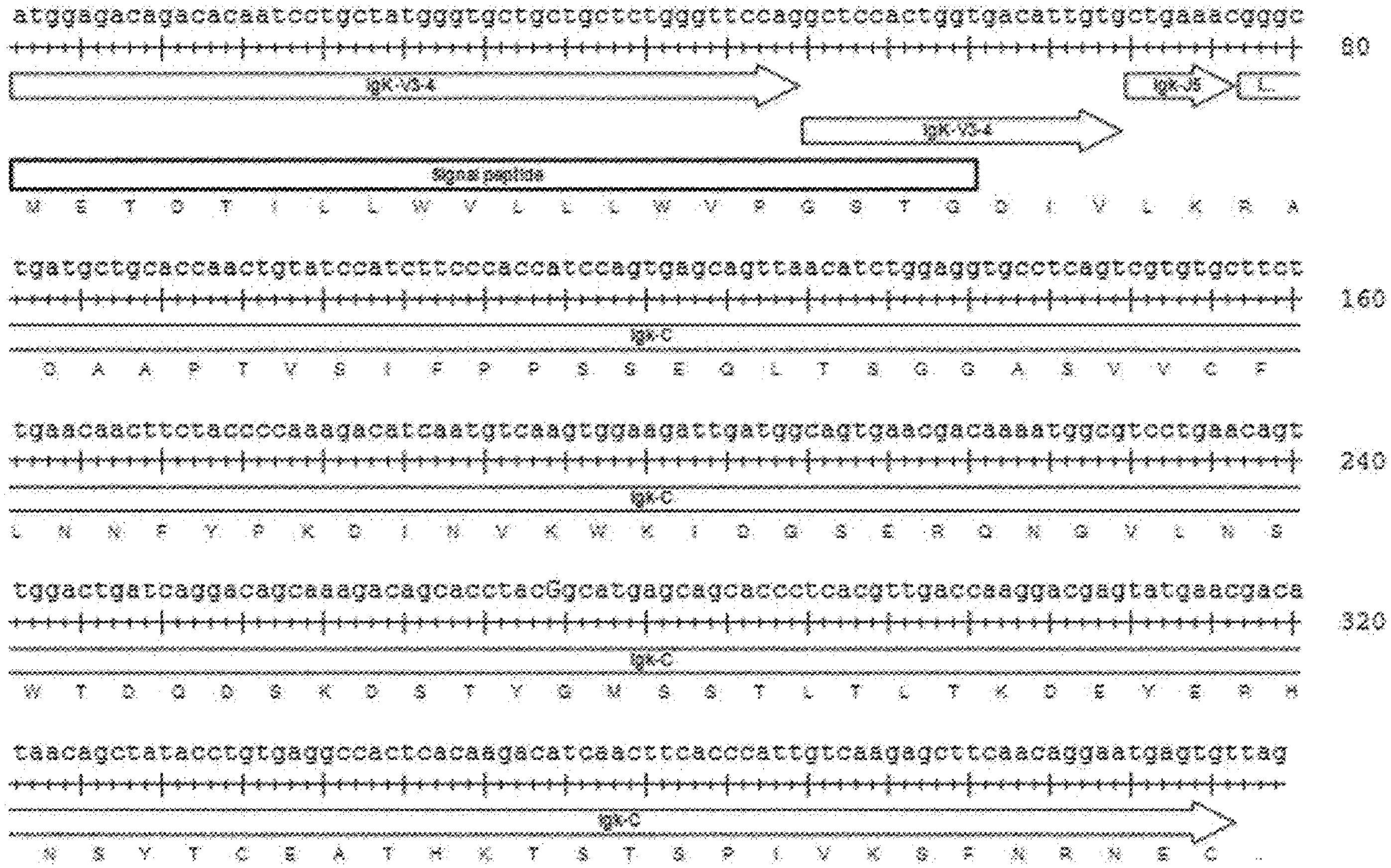

Generation of the modified locus by strategy 1 involves a large, precise deletion of either 25 kb (for Vκ3-2 version) or 54 kb (Vκ3-4 version). This mouse locus could be generated in multiple ways:

1) Direct modification of the mouse Kappa Locus by cytoplasmic injection: this will be achieved by injecting mouse 1 cell zygotes or 2 cell embryos with the required reagents to create double strand breaks at defined locations in the κ genomic locus and providing a repair template to promote the desired deletion.
2) Modification of the mouse Kappa Locus in mESCs: this will be achieved by transfecting mESCs with the required reagents to create double strand breaks at defined locations in the κ genomic locus and providing a repair template to promote the desired deletion FIG. 16. Summarises the modification of the κ locus by this method and FIG. 17. contains annotated sequence diagrams for the predicted coding and translated sequences expressed by the modified loci. The predicted gene products, coding sequence and translated protein sequence, for the two versions are provided in SEQ ID NO: 83, SEQ ID NO: 84, SEQ ID NO: 85 and SEQ ID NO: 86.

Generation of the modified locus by strategy 2 involves replacement of a 1.5 kb region of the mouse Kappa locus (Jκ1-5) with a 1.3 kb sequence encoding the partial Vκ/Jκ fragment. This could be achieved by:

1) Modification of the Kappa locus in mouse embryos by cytoplasmic injection: This will be achieved by injecting mouse 2 cell embryos with the required reagents to create double strand breaks at defined locations in the κ genomic locus and providing a plasmid vector as a repair template to promote the desired deletion/insertion by homologous recombination.
2) Modification of the Kappa locus in mouse embryonic stem cells (mESCs): This will be achieved by transfecting mESCs with the required reagents to create double strand breaks at defined locations in the κ genomic locus and providing a plasmid vector as a repair template to promote the desired deletion/insertion by homologous recombination. A positive/negative selection cassette was cloned into the vector, just downstream of the 5' homology arm.

Figure 18:
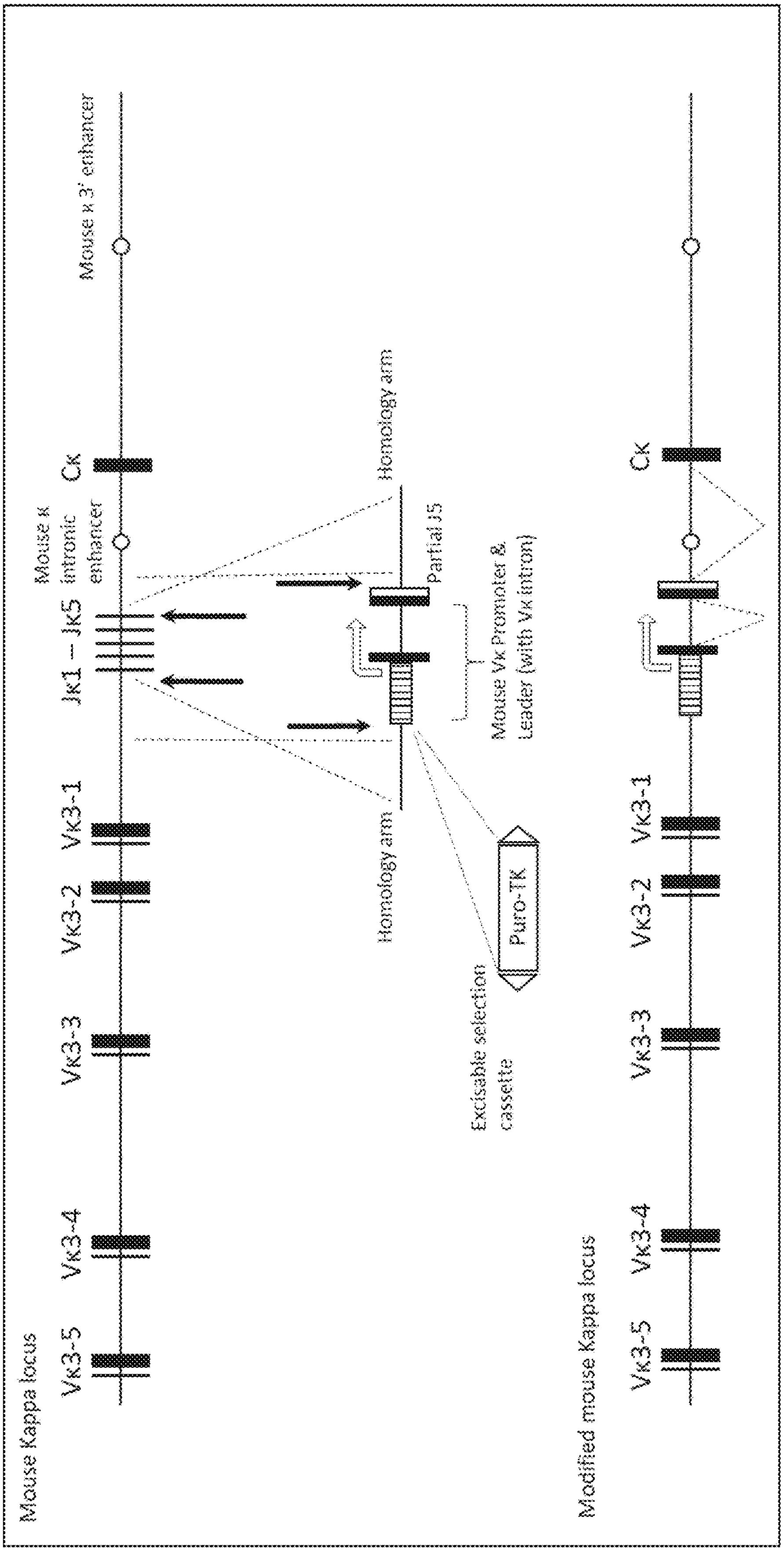
FIG. 18 shows modification of the mouse Kappa locus by targeting vector to express a truncated Mouse κ fragment. Vector includes ~1 kb mouse 3' and 5 homology arms, mouse Vκ promoter (vertical hashed box), mouse Vκ leader (black boxes) including mouse Vκ intron, and partial mouse Jκ5 (white box). Vector can also include an excisable positive/negative selection cassette which is removed from the final targeted locus. Targeting of this vector replaces the endogenous mouse Jκ1-Jκ5 only, leaving the rest of the mouse Kappa locus, including mouse κ intronic enhancer, intact.
Figure 19:
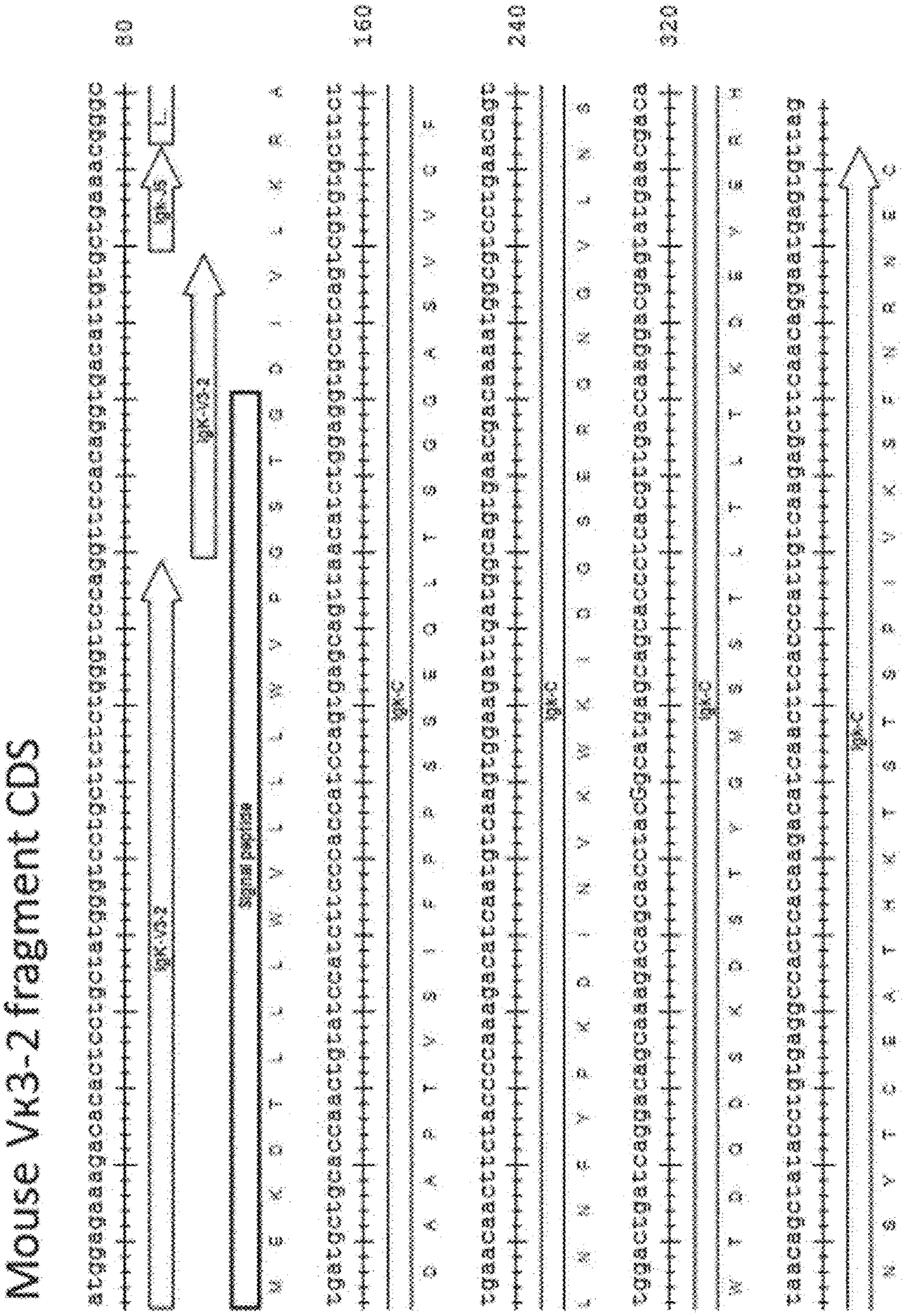
FIG. 19 shows spliced coding sequence and protein product from Mouse locus targeted with truncated Kappa Vκ6-17 or Vκ10-96 fragment.
Figure 19:
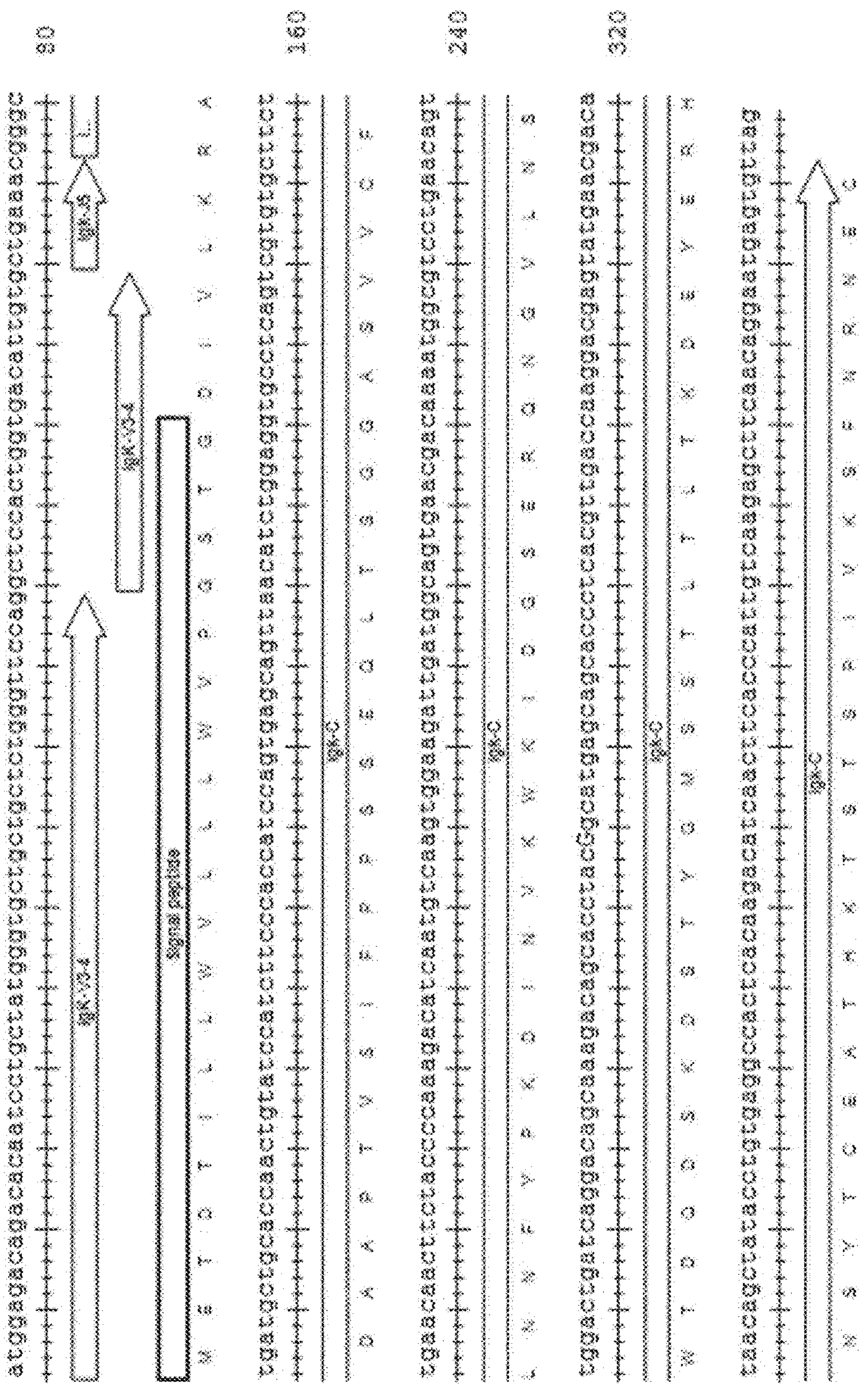

Targeting vector inserts will be synthesised as single fragments and cloned into a pUC vector (by Genscript™). FIG. 18 summarises the modification of the κ locus by this method and FIG. 19 contains annotated sequence diagrams for the predicted coding and translated sequences expressed by the modified loci. The targeting vector insert sequences (minus selection cassette) plus predicted gene products, coding sequence and translated protein sequence, for the two versions (Vκ6-17 and Vκ10-96) are provided in SEQ ID NO: 87, SEQ ID NO: 88, SEQ ID NO: 89, SEQ ID NO: 90, SEQ ID NO: 91, SEQ ID NO: 92, SEQ ID NO: 93 and SEQ ID NO: 94.

Initial analysis of mESC lines generated by this method will be performed in the same way as in Example 5 i.e. injection into RAG-1−/− blastocysts followed by analysis of chimera-derived lymphocytes for expression of the truncated Kappa fragment. Mouse lines expressing the truncated mouse Kappa fragment, paired with a Heavy chain, on surface of lymphocytes, will be cross-bred with other lines to introduce both the fully human Heavy locus and the mouse Lambda knockout (as detailed in Example 3). This will result in animals generating VH-only antibodies with a fully human Heavy chain and mouse Kappa Cκ fragment.

REFERENCES

1 Janssens et al. PNAS 103(41):15130-15135 2006

2 Lee et al., Nature Biotech 32(4):356-363 2014

3 Boroviak et al., Genesis 54(2):78-85 2016

4 Minegishi, Hendershot & Conley PNAS 96:3041 1998

5 Bankovich et al., Science 316(5822):291-294 2007

6 Melchers et al., Immunol Today 14(2):60-68 1993

7 Sabbattini & Dillon, Seminars in Immunology 17(2):121-127 2005

8 Papavasilou, Jankovic & Nussenzweig, J Exp Med 184: 2025-2030 1996

9 Guloglu et al., J Immunol 175:358-366 2005

10 Mirtensson et al, Int Immunol 11(3):453-460 1999

11 Fang, Smith & Roman, J Immunol 167:3846-3857 2001

12 Ridgway et al., Protein Eng. 9:617-621 1996

13 Davis J H et al., PEDS 23:195-202)

14 Shields et al. (2002) JBC 277:26733

15 Iri-Sofla et al., Experimental Cell Research 317:2630-2641 2011

16 Jamnani et al., Biochim BiophysActa, 1840:378-386 2014

17 Adachi et al., Nature Biotech. 36(4):346-351 2018

18 Aoki-Ota M, Torkamani A, Ota T, Schork N, Nemazee D. Skewed primary Igκ repertoire and V-J joining in C57BL/6 mice: implications for recombination accessibility and receptor editing. J Immunol. 2012; 188(5): 2305-2315

Sequences

SEQ ID NO: 1 Nucleic acid encoding Cκ signal peptide
Artificial sequence
atggacatgagggtccccgctcagctcctggggctcctgctgctctggctcccaggaactgtggct SEQ ID NO: 2 Cκ signal peptide
Artificial sequence
MDMRVPAQLLGLLLLWLPGTVA SEQ ID NO: 3 Nucleic acid encoding isolated Cκ sequence
*Homo sapiens*
gcaccatctgtcttcatcttcccgccatctgatgagcagttgaaatctggaactgcctctgttgtgtgcctgctgaataacttctatcccagagagg
ccaaagtacagtggaaggtggataacgccctccaatcgggtaactcccaggagagtgtcacagagcaggacagcaaggacagcacctaca
gcctcagcagcaccctgacgctgagcaaagcagactacgagaaacacaaagtctacgcctgcgaagtcacccatcagggcctgagctcgcc
cgtcacaaagagcttcaacaggggagagtgtta SEQ ID NO: 4 Isolated Cκ sequence
*Homo sapiens*

-continued

| Sequences |
| --- |
| APSVFIFPPSDEQLKSGTASVVCLLNNFYPREAKVQWKVDNALQSGNSQESVTEQDSKDSTYSLSSTLTLSKADY<br>EKHKVYACEVTHQGLSSPVTKSFNRGEC |
| SEQ ID NO: 5 Nucleic acid encoding κvC fusion with signal peptide<br>Artificial sequence<br>atggacatgagggtccccgctcagctcctggggctcctgctgctctggctcccaggaactgtggctgcaccatctgtcttcatcttcccgccatct<br>gatgagcagttgaaatctggaactgcctctgttgtgtgcctgctgaataacttctatcccagagaggccaaagtacagtggaaggtggataac<br>gccctccaatcgggtaactcccaggagagtgtcacagagcaggacagcaaggacagcacctacagcctcagcagcaccctgacgctgagc<br>aaagcagactacgagaaacacaaagtctacgcctgcgaagtcacccatcagggcctgagctcgcccgtcacaaagagcttcaacagggga<br>gagtgtta |
| SEQ ID NO: 6 κvC fusion with signal peptide<br>Artificial sequence<br>MDMRVPAQLLGLLLLWLPGTVAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| SEQ ID NO: 7 Nucleic acid encoding full Cκ domain<br>*Homo sapiens*<br>ggaactgtggctgcaccatctgtcttcatcttcccgccatctgatgagcagttgaaatctggaactgcctctgttgtgtgcctgctgaataacttcta<br>tcccagagaggccaaagtacagtggaaggtggataacgccctccaatcgggtaactcccaggagagtgtcacagagcaggacagcaagga<br>cagcacctacagcctcagcagcaccctgacgctgagcaaagcagactacgagaaacacaaagtctacgcctgcgaagtcacccatcagggc<br>ctgagctcgcccgtcacaaagagcttcaacaggggagagtgtta |
| Note: the initial nucleotide g of SEQ ID NO: 7 is provided by the vκ exon which splices to nucleic<br>acid encoding the CL domain. |
| SEQ ID NO: 8 Full Cκ domain<br>*Homo sapiens*<br>GTVAAPSVFIFPPSDEQLKSGTASVVCLLNNFYPREAKVQWKVDNALQSGNSQESVTEQDSKDSTYSLSSTLTLS<br>KADYEKHKVYACEVTHQGLSSPVTKSFNRGEC<br>Note: the N terminal amino acid G of SEQ ID NO: 8 is encoded by the gga codon formed by splicing<br>of the Vκ exon to nucleic acid encoding the CL domain. The initial g is provided by the 3' end of the<br>vκ exon while the remainder of the codon (ga) is provided by the 5' end of the CK exon. Under some<br>definitions the CK domain is considered to start from the second residue of SEQ ID NO: 8, i.e.,<br>TVA.... |
| SEQ ID NO: 9 cDNA of spliced Vκ1-5 gene segment<br>*Homo sapiens*<br>atggacatgagggtccccgctcagctcctggggctcctgctgctctggctcccaggtgccaaatgtgacatccagatgacccagtctccttccac<br>cctgtctgcatctgtaggagacagagtcaccatcacttgccgggccagtcagagtattagtagctggttggcctggtatcagcagaaaccagg<br>gaaagcccctaagctcctgatctataaggcgtctagtttagaaagtggggtcccatcaaggttcagcggcagtggatctgggacagaattcact<br>ctcaccatcagcagcctgcagcctgatgattttgcaacttattactgccaacagtataatagttattct |
| SEQ ID NO: 10 Vκ encoded segment including signal peptide<br>*Homo sapiens*<br>MDMRVPAQLLGLLLLWLPGAKCDIQMTQSPSTLSASVGDRVTITCRASQSISSWLAWYQQKPGKAPKLLIYKAS<br>SLESGVPSRFSGSGSGTEFTLTISSLQPDDFATYYCQQYNSYS |
| SEQ ID NO: 11 Nucleic acid encoding Vκ1-5 signal peptide<br>*Homo sapiens*<br>atggacatgagggtccccgctcagctcctggggctcctgctgctctggctcccaggtgccaaatgt |
| SEQ ID NO: 12 Vκ1-5 signal peptide<br>*Homo sapiens*<br>MDMRVPAQLLGLLLLWLPGAKC |

TABLE A

Sequences of human antibody constant regions

| | | | Description | Sequence |
|---|---|---|---|---|
| SEQ ID NO: 13 | Human IgG1 constant region | IGHG1* 01 | Human Heavy Chain Constant Region (IGHG1*01) Nucleotide Sequence | gcctccaccaagggcccatcggtcttccccctggcaccctcctccaagagcacctctgggggcacagcgg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacccagacctacatctgcaacgtgaatcacaagcccagcaacaccaagg<br>tggacaagaaagttgagcccaaatcttgtgacaaaactcacacatgcccaccgtgcccagcacctgaact<br>cctggggggaccgtcagtcttcctcttccccccaaaacccaaggacaccctcatgatctcccggacccctg<br>aggtcacatgcgtggtggtggacgtgagccacgaagaccctgaggtcaagttcaactggtacgtggacg<br>gcgtggaggtgcataatgccaagacaaagccgcgggaggagcagtacaacagcacgtaccgggtggt<br>cagcgtcctcaccgtcctgcaccaggactggctgaatggcaaggagtacaagtgcaaggtctccaacaa<br>agccctcccagcccccatcgagaaaaccatctccaaagccaaagggcagccccgagaaccacaggtgt<br>acaccctgcccccatcccgggatgagctgaccaagaaccaggtcagcctgacctgcctggtcaaaggctt<br>ctatcccagcgacatcgccgtggagtgggagagcaatgggcagccggagaacaactacaagaccacg<br>cctcccgtgctggactccgacggctccttcttcctctacagcaagctcaccgtggacaagagcaggtggca<br>gcaggggaacgtcttctcatgctccgtgatgcatgaggctctgcacaaccactacacgcagaagagcctc<br>tccctgtctccgggtaaa |
| SEQ ID NO: 14 | | | Human Heavy Chain Constant Region (IGHG1*01) Protein Sequence (P01857) | ASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNTKVDKKVEPKSCDKTHTCPPCP<br>APELLGGPSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |
| SEQ ID NO: 15 | Human IgG1 constant region | IGHG1* 02 or IGHG1* 05 | Human Heavy Chain Constant Region (IGHG1*02 or IGHG1*05) Nucleotide Sequence | gcctccaccaagggcccatcggtcttccccctggcaccctcctccaagagcacctctgggggcacagcgg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacccagacctacatctgcaacgtgaatcacaagcccagcaacaccaagg<br>tggacaagaaagttgagcccaaatcttgtgacaaaactcacacatgcccaccgtgcccagcacctgaact<br>cctggggggaccgtcagtcttcctcttccccccaaaacccaaggacaccctcatgatctcccggacccctg<br>aggtcacatgcgtggtggtggacgtgagccacgaagaccctgaggtcaagttcaactggtacgtggacg<br>gcgtggaggtgcataatgccaagacaaagccgcgggaggagcagtacaacagcacgtaccgtgtggt<br>cagcgtcctcaccgtcctgcaccaggactggctgaatggcaaggagtacaagtgcaaggtctccaacaa<br>agccctcccagcccccatcgagaaaaccatctccaaagccaaagggcagccccgagaaccacaggtgt<br>acaccctgcccccatcccgggatgagctgaccaagaaccaggtcagcctgacctgcctggtcaaaggctt<br>ctatcccagcgacatcgccgtggagtgggagagcaatgggcagccggagaacaactacaagaccacg<br>cctcccgtgctggactccgacggctccttcttcctctacagcaagctcaccgtggacaagagcaggtggca<br>gcaggggaacgtcttctcatgctccgtgatgcatgaggctctgcacaaccactacacgcagaagagcctc<br>tccctgtctccgggtaaa |
| SEQ ID NO: 16 | | | Human Heavy Chain Constant Region (IGHG1*02) Protein Sequence | ASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNTKVDKKVEPKSCDKTHTCPPCP<br>APELLGGPSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |

TABLE A-continued

| Sequences of human antibody constant regions | | | | |
| --- | --- | --- | --- | --- |
| | | | Description | Sequence |
| SEQ ID NO: 17 | Human IgG1 constant region | IGHG1* 03 | Human Heavy Chain Constant Region (IGHG1*03) Nucleotide Sequence (Y14737) | gcctccaccaagggcccatcggtcttccccctggcaccctcctccaagagcacctctgggggcacagcgg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacccagacctacatctgcaacgtgaatcacaagcccagcaacaccaagg<br>tggacaagagagttgagcccaaatcttgtgacaaaactcacacatgcccaccgtgcccagcacctgaact<br>cctggggggaccgtcagtcttcctcttccccccaaaacccaaggacaccctcatgatctcccggacccctg<br>aggtcacatgcgtggtggtggacgtgagccacgaagaccctgaggtcaagttcaactggtacgtggacg<br>gcgtggaggtgcataatgccaagacaaagccgcgggaggagcagtacaacagcacgtaccgtgtggt<br>cagcgtcctcaccgtcctgcaccaggactggctgaatggcaaggagtacaagtgcaaggtctccaacaa<br>agccctcccagcccccatcgagaaaaccatctccaaagccaaagggcagccccgagaaccacaggtgt<br>acaccctgcccccatcccgggaggagatgaccaagaaccaggtcagcctgacctgcctggtcaaaggct<br>tctatcccagcgacatcgccgtggagtgggagagcaatgggcagccggagaacaactacaagaccac<br>gcctcccgtgctggactccgacggctccttcttcctctatagcaagctcaccgtggacaagagcaggtggc<br>agcaggggaacgtcttctcatgctccgtgatgcatgaggctctgcacaaccactacacgcagaagagcct<br>ctccctgtccccgggtaaa |
| SEQ ID NO: 18 | | | Human Heavy Chain Constant Region (IGHG1*03) Protein Sequence | ASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNTKVDKRVEPKSCDKTHTCPPCP<br>APELLGGPSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQ<br>PREPQVYTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |
| SEQ ID NO: 19 | Human IgG1 constant region | IGHG1* 04 | Human Heavy Chain Constant Region (IGHG1*04) Nucleotide Sequence | gcctccaccaagggcccatcggtcttccccctggcaccctcctccaagagcacctctgggggcacagcgg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacccagacctacatctgcaacgtgaatcacaagcccagcaacaccaagg<br>tggacaagaaagttgagcccaaatcttgtgacaaaactcacacatgcccaccgtgcccagcacctgaact<br>cctggggggaccgtcagtcttcctcttccccccaaaacccaaggacaccctcatgatctcccggacccctg<br>aggtcacatgcgtggtggtggacgtgagccacgaagaccctgaggtcaagttcaactggtacgtggacg<br>gcgtggaggtgcataatgccaagacaaagccgcgggaggagcagtacaacagcacgtaccgtgtggt<br>cagcgtcctcaccgtcctgcaccaggactggctgaatggcaaggagtacaagtgcaaggtctccaacaa<br>agccctcccagcccccatcgagaaaaccatctccaaagccaaagggcagccccgagaaccacaggtgt<br>acaccctgcccccatcccgggatgagctgaccaagaaccaggtcagcctgacctgcctggtcaaaggctt<br>ctatcccagcgacatcgccgtggagtgggagagcaatgggcagccggagaacaactacaagaccacg<br>cctcccgtgctggactccgacggctccttcttcctctacagcaagctcaccgtggacaagagcaggtggca<br>gcaggggaacatcttctcatgctccgtgatgcatgaggctctgcacaaccactacacgcagaagagcctc<br>tccctgtctccgggtaaa |
| SEQ ID NO: 20 | | | Human Heavy Chain Constant Region (IGHG1*04) Protein Sequence | ASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNTKVDKKVEPKSCDKTHTCPPCP<br>APELLGGPSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVL<br>DSDGSFFLYSKLTVDKSRWQQGNIFSCSVMHEALHNHYTQKSLSLSPGK |

TABLE A-continued

| Sequences of human antibody constant regions | | | | |
|---|---|---|---|---|
| | | | Description | Sequence |
| SEQ ID NO: 21 | Disabled Human IgG1 heavy chain constant region | Disabled human IGHG1*01 | Disabled Human IGHG1*01 Heavy Chain Constant Region Nucleotide Sequence. | gcctccaccaagggcccatcggtcttccccctggcaccctcctccaagagcacctctgggggcacagcgg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacccagacctacatctgcaacgtgaatcacaagcccagcaacaccaagg<br>tggacaagaaagtggagcccaaatcttgtgacaaaactcacacatgcccaccgtgcccagcacctgaac<br>tcgcgggggcaccgtcagtcttcctcttccccccaaaacccaaggacaccctcatgatctcccggacccct<br>gaggtcacatgcgtggtggtggacgtgagccacgaagaccctgaggtcaagttcaactggtacgtggac<br>ggcgtggaggtgcataatgccaagacaaagccgcgggaggagcagtacaacagcacgtaccgtgtgg<br>tcagcgtcctcaccgtcctgcaccaggactggctgaatggcaaggagtacaagtgcaaggtctccaaca<br>aagccctcccagcccccatcgagaaaaccatctccaaagccaaagggcagccccgagaaccacaggtg<br>tacaccctgcccccatcccgggatgagctgaccaagaaccaggtcagcctgacctgcctggtcaaaggct<br>tctatcccagcgacatcgccgtggagtgggagagcaatgggcagccggagaacaactacaagaccac<br>gcctcccgtgctggactccgacggctccttcttcctctacagcaagctcaccgtggacaagagcaggtggc<br>agcaggggaacgtcttctcatgctccgtgatgcatgaggctctgcacaaccactacacgcagaagagcct<br>ctccctgtctccgggtaaa |
| SEQ ID NO: 22 | | | Disabled Human IGHG1*01 Heavy Chain Constant Region Amino Acid Sequence. Two residues that differ from the wild-type sequence are identified in bold. | ASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNTKVDKKVEPKSCDKTHTCPPCP<br>APEL**A**G**A**PSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |
| SEQ ID NO: 23 | Human IgG2 constant region | IGHG2*01 or IGHG2*04 or IGHG2*05 | Human Heavy Chain Constant Region (IGHG2*01 or IGHG2*03 or IGHG2*05) Nucleotide Sequence | gcctccaccaagggcccatcggtcttccccctggcgccctgctccaggagcacctccgagagcacagccg<br>ccctgggctgcctggtcaaggactacttccccgaaccggtgacggtgtcgtggaactcaggcgctctgac<br>cagcggcgtgcacaccttcccagctgtcctacagtcctcaggactctactccctcagcagcgtggtgaccg<br>tgccctccagcaacttcggcacccagacctacacctgcaacgtagatcacaagcccagcaacaccaagg<br>tggacaagacagttgagcgcaaatgttgtgtcgagtgcccaccgtgcccagcaccacctgtggcaggac<br>cgtcagtcttcctcttccccccaaaacccaaggacaccctcatgatctcccggacccctgaggtcacgtgcg<br>tggtggtggacgtgagccacgaagaccccgaggtccagttcaactggtacgtggacggcgtggaggtg<br>cataatgccaagacaaagccacgggaggagcagttcaacagcacgttccgtgtggtcagcgtcctcacc<br>gttgtgcaccaggactggctgaacggcaaggagtacaagtgcaaggtctccaacaaaggcctcccagc<br>ccccatcgagaaaaccatctccaaaaccaaagggcagccccgagaaccacaggtgtacaccctgcccc<br>catcccgggaggagatgaccaagaaccaggtcagcctgacctgcctggtcaaaggcttctaccccagcg<br>acatcgccgtggagtgggagagcaatgggcagccggagaacaactacaagaccacacctcccatgctg<br>gactccgacggctccttcttcctctacagcaagctcaccgtggacaagagcaggtggcagcaggggaac<br>gtcttctcatgctccgtgatgcatgaggctctgcacaaccactacacgcagaagagcctctccctgtctccg<br>ggtaaa |
| SEQ ID NO: 24 | | | Human Heavy Chain Constant Region (IGHG2*01) Protein Sequence | ASTKGPSVFPLAPCSRSTSESTAALGCLVKDYFPEPVTVSWNSGALTSGVHTFPAVL<br>QSSGLYSLSSVVTVPSSNFGTQTYTCNVDHKPSNTKVDKTVERKCCVECPPCPAPP<br>VAGPSVFLFPPKPKDTLMISRTPEVTCVVVDVSHEDPEVQFNWYVDGVEVHNAKTK<br>PREEQFNSTFRVVSVLTVVHQDWLNGKEYKCKVSNKGLPAPIEKTISKTKGQPREP<br>QVYTLPPSREEMTKNQVSLTCLVKGFYPSDIAVEWESNGQPENNYKTTPPMLDSD<br>GSFFLYSKLTVDKSRWQQGNVFSCSVMHEALHNHYTQKSLSLSPGK |

TABLE A-continued

Sequences of human antibody constant regions

| | | | Description | Sequence |
|---|---|---|---|---|
| SEQ ID NO: 25 | Human IgG2 constant region | IGHG2*02 | Human Heavy Chain Constant Region (IGHG2*02) Nucleotide Sequence | GCCTCCACCAAGGGCCCATCGGTCTTCCCCCTGGCGCCCTGCTCCAGGAGCACC<br>TCCGAGAGCACAGCGGCCCTGGGCTGCCTGGTCAAGGACTACTTCCCCGAACCG<br>GTGACGGTGTCGTGGAACTCAGGCGCTCTGACCAGCGGCGTGCACACCTTCCCG<br>GCTGTCCTACAGTCCTCAGGACTCTACTCCCTCAGCAGCGTGGTGACCGTGACC<br>TCCAGCAACTTCGGCACCCAGACCTACACCTGCAACGTAGATCACAAGCCCAGCA<br>ACACCAAGGTGGACAAGACAGTTGAGCGCAAATGTTGTGTCGAGTGCCCACCGT<br>GCCCAGCACCACCTGTGGCAGGACCGTCAGTCTTCCTCTTCCCCCCAAAACCCAA<br>GGACACCCTCATGATCTCCCGGACCCCTGAGGTCACGTGCGTGGTGGTGGACGT<br>GAGCCACGAAGACCCCGAGGTCCAGTTCAACTGGTACGTGGACGGCATGGAGG<br>TGCATAATGCCAAGACAAAGCCACGGGAGGAGCAGTTCAACAGCACGTTCCGTG<br>TGGTCAGCGTCCTCACCGTCGTGCACCAGGACTGGCTGAACGGCAAGGAGTACA<br>AGTGCAAGGTCTCCAACAAAGGCCTCCCAGCCCCCATCGAGAAAACCATCTCCAA<br>AACCAAAGGGCAGCCCCGAGAACCACAGGTGTACACCCTGCCCCCATCCCGGGA<br>GGAGATGACCAAGAACCAGGTCAGCCTGACCTGCCTGGTCAAAGGCTTCTACCC<br>CAGCGACATCGCCGTGGAGTGGGAGAGCAATGGGCAGCCGGAGAACAACTACA<br>AGACCACACCTCCCATGCTGGACTCCGACGGCTCCTTCTTCCTCTACAGCAAGCT<br>CACCGTGGACAAGAGCAGGTGGCAGCAGGGGAACGTCTTCTCATGCTCCGTGAT<br>GCATGAGGCTCTGCACAACCACTACACACAGAAGAGCCTCTCCCTGTCTCCGGG<br>TAAA |
| SEQ ID NO: 26 | | | Human Heavy Chain Constant Region (IGHG2*02) Protein Sequence | ASTKGPSVFPLAPCSRSTSESTAALGCLVKDYFPEPVTVSWNSGALTSGVHTFPAVL<br>QSSGLYSLSSVVTVTSSNFGTQTYTCNVDHKPSNTKVDKTVERKCCVECPPCPAPP<br>VAGPSVFLFPPKPKDTLMISRTPEVTCVVVDVSHEDPEVQFNWYVDGMEVHNAKT<br>KPREEQFNSTFRVVSVLTVVHQDWLNGKEYKCKVSNKGLPAPIEKTISKTKGQPRE<br>PQVYTLPPSREEMTKNQVSLTCLVKGFYPSDIAVEWESNGQPENNYKTTPPMLDS<br>DGSFFLYSKLTVDKSRWQQGNVFSCSVMHEALHNHYTQKSLSLSPGK |
| SEQ ID NO: 27 | Human IgG2 constant region | IGHG2*04 | Human Heavy Chain Constant Region (IGHG2*04) Nucleotide Sequence | gcctccaccaagggcccatcggtcttccccctggcgccctgctccaggagcacctccgagagcacagcg<br>gccctgggctgcctggtcaaggactacttccccgaaccggtgacggtgtcgtggaactcaggcgctctga<br>ccagcggcgtgcacaccttcccagctgtcctacagtcctcaggactctactccctcagcagcgtggtgacc<br>gtgccctccagcagcttgggcacccagacctacacctgcaacgtagatcacaagcccagcaacaccaag<br>gtggacaagacagttgagcgcaaatgttgtgtcgagtgcccaccgtgcccagcaccacctgtggcagga<br>ccgtcagtcttcctcttccccccaaaacccaaggacaccctcatgatctcccggacccctgaggtcacgtgc<br>gtggtggtggacgtgagccacgaagaccccgaggtccagttcaactggtacgtggacggcgtggaggt<br>gcataatgccaagacaaagccacgggaggagcagttcaacagcacgttccgtgtggtcagcgtcctcac<br>cgttgtgcaccaggactggctgaacggcaaggagtacaagtgcaaggtctccaacaaaggcctcccag<br>cccccatcgagaaaaccatctccaaaaccaaagggcagccccgagaaccacaggtgtacaccctgccc<br>ccatcccgggaggagatgaccaagaaccaggtcagcctgacctgcctggtcaaaggcttctaccccagc<br>gacatcgccgtggagtgggagagcaatgggcagccggagaacaactacaagaccacacctcccatgct<br>ggactccgacggctccttcttcctctacagcaagctcaccgtggacaagagcaggtggcagcaggggaa<br>cgtcttctcatgctccgtgatgcatgaggctctgcacaaccactacacgcagaagagcctctccctgtctcc<br>gggtaaa |
| SEQ ID NO: 28 | | | Human Heavy Chain Constant Region (IGHG2*04) Protein Sequence | ASTKGPSVFPLAPCSRSTSESTAALGCLVKDYFPEPVTVSWNSGALTSGVHTFPAVL<br>QSSGLYSLSSVVTVPSSSLGTQTYTCNVDHKPSNTKVDKTVERKCCVECPPCPAPP<br>VAGPSVFLFPPKPKDTLMISRTPEVTCVVVDVSHEDPEVQFNWYVDGVEVHNAKTK<br>PREEQFNSTFRVVSVLTVVHQDWLNGKEYKCKVSNKGLPAPIEKTISKTKGQPREP<br>QVYTLPPSREEMTKNQVSLTCLVKGFYPSDIAVEWESNGQPENNYKTTPPMLDSD<br>GSFFLYSKLTVDKSRWQQGNVFSCSVMHEALHNHYTQKSLSLSPGK |

TABLE A-continued

Sequences of human antibody constant regions

| | | | Description | Sequence |
|---|---|---|---|---|
| SEQ ID NO: 29 | Human IgG2 constant region | IGHG2*06 | Human Heavy Chain Constant Region (IGHG2*06) Nucleotide Sequence | GCCTCCACCAAGGGCCCATCGGTCTTCCCCCTGGCGCCCTGCTCCAGGAGCACC<br>TCCGAGAGCACAGCGGCCCTGGGCTGCCTGGTCAAGGACTACTTCCCCGAACCG<br>GTGACGGTGTCGTGGAACTCAGGCGCTCTGACCAGCGGCGTGCACACCTTCCCG<br>GCTGTCCTACAGTCCTCAGGACTCTACTCCCTCAGCAGCGTGGTGACCGTGCCC<br>TCCAGCAACTTCGGCACCCAGACCTACACCTGCAACGTAGATCACAAGCCCAGCA<br>ACACCAAGGTGGACAAGACAGTTGAGCGCAAATGTTGTGTCGAGTGCCCACCGT<br>GCCCAGCACCACCTGTGGCAGGACCGTCAGTCTTCCTCTTCCCCCCAAAACCCAA<br>GGACACCCTCATGATCTCCCGGACCCCTGAGGTCACGTGCGTGGTGGTGGACGT<br>GAGCCACGAAGACCCCGAGGTCCAGTTCAACTGGTACGTGGACGGCGTGGAGG<br>TGCATAATGCCAAGACAAAGCCACGGGAGGAGCAGTTCAACAGCACGTTCCGTG<br>TGGTCAGCGTCCTCACCGTCGTGCACCAGGACTGGCTGAACGGCAAGGAGTACA<br>AGTGCAAGGTCTCCAACAAAGGCCTCCCAGCCCCCATCGAGAAAACCATCTCCAA<br>AACCAAAGGGCAGCCCCGAGAACCACAGGTGTACACCCTGCCCCCATCCCGGGA<br>GGAGATGACCAAGAACCAGGTCAGCCTGACCTGCCTGGTCAAAGGCTTCTACCC<br>CAGCGACATCTCCGTGGAGTGGGAGAGCAATGGGCAGCCGGAGAACAACTACAA<br>GACCACACCTCCCATGCTGGACTCCGACGGCTCCTTCTTCCTCTACAGCAAGCTC<br>ACCGTGGACAAGAGCAGGTGGCAGCAGGGGAACGTCTTCTCATGCTCCGTGATG<br>CATGAGGCTCTGCACAACCACTACACACAGAAGAGCCTCTCCCTGTCTCCGGGT<br>AAA |
| SEQ ID NO: 30 | | | Human Heavy Chain Constant Region (IGHG2*06) Protein Sequence | ASTKGPSVFPLAPCSRSTSESTAALGCLVKDYFPEPVTVSWNSGALTSGVHTFPAVL<br>QSSGLYSLSSVVTVPSSNFGTQTYTCNVDHKPSNTKVDKTVERKCCVECPPCPAPP<br>VAGPSVFLFPPKPKDTLMISRTPEVTCVVVDVSHEDPEVQFNWYVDGVEVHNAKTK<br>PREEQFNSTFRVVSVLTVVHQDWLNGKEYKCKVSNKGLPAPIEKTISKTKGQPREP<br>QVYTLPPSREEMTKNQVSLTCLVKGFYPSDISVEWESNGQPENNYKTTPPMLDSD<br>GSFFLYSKLTVDKSRWQQGNVFSCSVMHEALHNHYTQKSLSLSPGK |
| SEQ ID NO: 31 | Human IgG4 constant region | IGHG4*01 or IGHG4*04 | Human Heavy Chain Constant Region (IGHG4*01 or IGHG4*04) Nucleotide Sequence | gcttccaccaagggcccatccgtcttccccctggcgccctgctccaggagcacctccgagagcacagccg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacgaagacctacacctgcaacgtagatcacaagcccagcaacaccaagg<br>tggacaagagagttgagtccaaatatggtcccccatgcccatcatgcccagcacctgagttcctgggggg<br>accatcagtcttcctgttccccccaaaacccaaggacactctcatgatctcccggacccctgaggtcacgtg<br>cgtggtggtggacgtgagccaggaagaccccgaggtccagttcaactggtacgtggatggcgtggagg<br>tgcataatgccaagacaaagccgcgggaggagcagttcaacagcacgtaccgtgtggtcagcgtcctca<br>ccgtcctgcaccaggactggctgaacggcaaggagtacaagtgcaaggtctccaacaaaggcctcccgt<br>cctccatcgagaaaaccatctccaaagccaaagggcagccccgagagccacaggtgtacaccctgcccc<br>catcccaggaggagatgaccaagaaccaggtcagcctgacctgcctggtcaaaggcttctaccccagcg<br>acatcgccgtggagtgggagagcaatgggcagccggagaacaactacaagaccacgcctcccgtgctg<br>gactccgacggctccttcttcctctacagcaggctaaccgtggacaagagcaggtggcaggaggggaat<br>gtcttctcatgctccgtgatgcatgaggctctgcacaaccactacacacagaagagcctctccctgtctctg<br>ggtaaa |
| SEQ ID NO: 32 | | | Human Heavy Chain Constant Region (IGHG4*01) Protein Sequence (P01861) | ASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPSCPAPEF<br>LGGPSVFLFPPKPKDTLMISRTPEVTCVVVDVSQEDPEVQFNWYVDGVEVHNAKTK<br>PREEQFNSTYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSLGK |

TABLE A-continued

| Sequences of human antibody constant regions | | | | |
|---|---|---|---|---|
| | | | Description | Sequence |
| SEQ ID NO: 33 | Human IgG4 constant region | IGHG4*02 | Human Heavy Chain Constant Region (IGHG4*02) Nucleotide Sequence | gcttccaccaagggcccatccgtcttccccctggcgccctgctccaggagcacctccgagagcacagccg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacgaagacctacacctgcaacgtagatcacaagcccagcaacaccaagg<br>tggacaagagagttgagtccaaatatggtcccccgtgcccatcatgcccagcacctgagttcctgggggg<br>accatcagtcttcctgttccccccaaaacccaaggacactctcatgatctcccggacccctgaggtcacgtg<br>cgtggtggtggacgtgagccaggaagaccccgaggtccagttcaactggtacgtggatggcgtggagg<br>tgcataatgccaagacaaagccgcgggaggagcagttcaacagcacgtaccgtgtggtcagcgtcctca<br>ccgtcgtgcaccaggactggctgaacggcaaggagtacaagtgcaaggtctccaacaaaggcctcccg<br>tcctccatcgagaaaaccatctccaaagccaaagggcagccccgagagccacaggtgtacaccctgccc<br>ccatcccaggaggagatgaccaagaaccaggtcagcctgacctgcctggtcaaaggcttctaccccagc<br>gacatcgccgtggagtgggagagcaatgggcagccggagaacaactacaagaccacgcctcccgtgct<br>ggactccgacggctccttcttcctctacagcaggctaaccgtggacaagagcaggtggcaggaggga<br>atgtcttctcatgctccgtgatgcatgaggctctgcacaaccactacacgcagaagagcctctccctgtctct<br>gggtaaa |
| SEQ ID NO: 34 | | | Human Heavy Chain Constant Region (IGHG4*02) Protein Sequence | ASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPSCPAPEF<br>LGGPSVFLFPPKPKDTLMISRTPEVTCVWDVSQEDPEVQFNWYVDGVEVHNAKTK<br>PREEQFNSTYRVVSVLTVVHQDWLNGKEYKCKVSNKGLPSSIEKTISKAKGQPREP<br>QVYTLPPSQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSLGK |
| SEQ ID NO: 35 | Human IgG4 constant region | IGHG4*03 | Human Heavy Chain Constant Region (IGHG4*03) Nucleotide Sequence | gcttccaccaagggcccatccgtcttccccctggcgccctgctccaggagcacctccgagagcacagccg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacgaagacctacacctgcaacgtagatcacaagcccagcaacaccaagg<br>tggacaagagagttgagtccaaatatggtcccccatgcccatcatgcccagcacctgagttcctgggggg<br>accatcagtcttcctgttccccccaaaacccaaggacactctcatgatctcccggacccctgaggtcacgtg<br>cgtggtggtggacgtgagccaggaagaccccgaggtccagttcaactggtacgtggatggcgtggagg<br>tgcataatgccaagacaaagccgcgggaggagcagttcaacagcacgtaccgtgtggtcagcgtcctca<br>ccgtcctgcaccaggactggctgaacggcaaggagtacaagtgcaaggtctccaacaaaggcctcccgt<br>cctccatcgagaaaaccatctccaaagccaaagggcagccccgagagccacaggtgtacaccctgcccc<br>catcccaggaggagatgaccaagaaccaggtcagcctgacctgcctggtcaaaggcttctaccccagcg<br>acatcgccgtggagtgggagagcaatgggcagccggagaacaactacaagaccacgcctcccgtgctg<br>gactccgacggctccttcttcctctacagcaagctcaccgtggacaagagcaggtggcaggaggggaac<br>gtcttctcatgctccgtgatgcatgaggctctgcacaaccactacacgcagaagagcctctccctgtctctg<br>ggtaaa |
| SEQ ID NO: 36 | | | Human Heavy Chain Constant Region (IGHG4*03) Protein Sequence | ASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPSCPAPEF<br>LGGPSVFLFPPKPKDTLMISRTPEVTCVWDVSQEDPEVQFNWYVDGVEVHNAKTK<br>PREEQFNSTYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTTPPVLDSD<br>GSFFLYSKLTVDKSRWQEGNVFSCSVMHEALHNHYTQKSLSLSLGK |
| SEQ ID NO: 37 | Human IgG4-PE constant region | IGHG4-PE | Human Heavy Chain Constant Region (IGHG4-PE) Nucleotide Sequence Version A | gcctccaccaagggcccatccgtcttccccctggcgccctgctccaggagcacctccgagagcacggccg<br>ccctgggctgcctggtcaaggactacttccccgaaccagtgacggtgtcgtggaactcaggcgccctgac<br>cagcggcgtgcacaccttcccggctgtcctacagtcctcaggactctactccctcagcagcgtggtgaccg<br>tgccctccagcagcttgggcacgaagacctacacctgcaacgtagatcacaagcccagcaacaccaagg<br>tggacaagagagttgagtccaaatatggtcccccatgcccaccatgcccagcgcctgaatttgaggggg |

TABLE A-continued

| Sequences of human antibody constant regions | | |
|---|---|---|
| | Description | Sequence |
| | | gaccatcagtcttcctgttcccccaaaacccaaggacactctcatgatctcccggacccctgaggtcacgt<br>gcgtggtggtggacgtgagccaggaagaccccgaggtccagttcaactggtacgtggatggcgtggag<br>gtgcataatgccaagacaaagccgcgggaggagcagttcaacagcacgtaccgtgtggtcagcgtcctc<br>accgtcctgcaccaggactggctgaacggcaaggagtacaagtgcaaggtctccaacaaaggcctccc<br>gtcatcgatcgagaaaaccatctccaaagccaaagggcagccccgagagccacaggtgtacaccctgc<br>ccccatcccaggaggagatgaccaagaaccaggtcagcctgacctgcctggtcaaaggcttctacccca<br>gcgacatcgccgtggagtgggagagcaatgggcagccggagaacaactacaagaccacgcctcccgt<br>gctggactccgacggatccttcttcctctacagcaggctaaccgtggacaagagcaggtggcaggaggg<br>gaatgtcttctcatgctccgtgatgcatgaggctctgcacaaccactacacacagaagagcctctccctgtc<br>tctgggtaaa |
| SEQ ID NO: 38 | Human Heavy Chain Constant Region (IGHG4-PE) Nucleotide Sequence Version B | gcctccaccaagggacctagcgtgttccctctcgcccccctgttccaggtccacaagcgagtccaccgctgc<br>cctcggctgtctggtgaaagactactttcccgagcccgtgaccgtctcctggaatagcggagccctgacct<br>ccggcgtgcacacatttcccgccgtgctgcagagcagcggactgtatagcctgagcagcgtggtgaccgt<br>gcccagctccagcctcggcaccaaaacctacacctgcaacgtggaccacaagccctccaacaccaaggt<br>ggacaagcgggtggagagcaagtacggcccccccttgccctccttgtcctgcccctgagttcgagggagg<br>accctccgtgttcctgtttcccccaaacccaaggacaccctgatgatctcccggacacccgaggtgacct<br>gtgtggtcgtggacgtcagccaggaggaccccgaggtgcagttcaactggtatgtggacggcgtggag<br>gtgcacaatgccaaaaccaagcccagggaggagcagttcaattccacctacagggtggtgagcgtgct<br>gaccgtcctgcatcaggattggctgaacggcaaggagtacaagtgcaaggtgtccaacaagggactgc<br>ccagctccatcgagaagaccatcagcaaggctaagggccagccgagggagccccaggtgtataccctg<br>cctcctagccaggaagagatgaccaagaaccaagtgtccctgacctgcctggtgaagggattctacccct<br>ccgacatcgccgtggagtgggagagcaatggccagcccgagaacaactacaaaacaacccctcccgtg<br>ctcgatagcgacggcagcttctttctctacagccggctgacagtggacaagagcaggtggcaggagggc<br>aacgtgttctcctgttccgtgatgcacgaggccctgcacaatcactacacccagaagagcctctccctgtcc<br>ctgggcaag |
| SEQ ID NO: 39 | Human Heavy Chain Constant Region (IGHG4-PE) Nucleotide Sequence Version C | gccagcaccaagggcccttccgtgttcccccctggccccttgcagcaggagcacctccgaatccacagctg<br>ccctgggctgtctggtgaaggactactttcccgagcccgtgaccgtgagctggaacagcggcgctctgac<br>atccggcgtccacacctttcctgccgtcctgcagtcctccggcctctactccctgtcctccgtggtgaccgtg<br>cctagctcctccctcggcaccaagacctacacctgtaacgtggaccacaaaccctccaacaccaaggtgg<br>acaaacgggtcgagagcaagtacggccctccctgccctccttgtcctgcccccgagttcgaaggcggacc<br>cagcgtgttcctgttccctcctaagcccaaggacaccctcatgatcagccggacacccgaggtgacctgc<br>gtggtggtggatgtgagccaggaggaccctgaggtccagttcaactggtatgtggatggcgtggaggtg<br>cacaacgccaagacaaagccccgggaagagcagttcaactccacctacagggtggtcagcgtgctgac<br>cgtgctgcatcaggactggctgaacggcaaggagtacaagtgcaaggtcagcaataagggactgccca<br>gcagcatcgagaagaccatctccaaggctaaaggccagccccgggaacctcaggtgtacaccctgcctc<br>ccagccaggaggagatgaccaagaaccaggtgagcctgacctgcctggtgaagggattctacccttccg<br>acatcgccgtggagtgggagtccaacggccagcccgagaacaattataagaccacccctcccgtcctcg<br>acagcgacggatccttctttctgtactccaggctgaccgtggataagtccaggtggcaggaaggcaacgt<br>gttcagctgctccgtgatgcacgaggccctgcacaatcactacacccagaagtccctgagcctgtccctgg<br>gaaag |
| SEQ ID NO: 40 | Human Heavy Chain Constant Region (IGHG4-PE) Protein Sequence | ASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPPCPAPEF<br>EGGPSVFLFPPKPKDTLMISRTPEVTCVVVDVSQEDPEVQFNWYVDGVEVHNAKT<br>KPREEQFNSTYRVVSVLTVLHQDWLNGKEYKCKVSNKGLPSSIEKTISKAKGQPRE<br>PQVYTLPPSQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSLGK |

TABLE A-continued

Sequences of human antibody constant regions

| | | | Description | Sequence |
|---|---|---|---|---|
| SEQ ID NO: 41 | In-activated Human IgG4 constant region | In-activated IGHG4 | Inactivated Human Heavy Chain Constant Region (IGHG4) Nucleotide Sequence | gcctccaccaagggcccatccgtcttccccctggcgccctgctccaggagcacctccgagagcacggccg<br>ccctgggctgcctggtcaaggactacttccccgaaccagtgacggtgtcgtggaactcaggcgccctgac<br>cagcggcgtgcacaccttcccggctgtcctacagtcctcaggactctactccctcagcagcgtggtgaccg<br>tgccctccagcagcttgggcacgaagacctacacctgcaacgtagatcacaagcccagcaacaccaagg<br>tggacaagagagttgagtccaaatatggtcccccatgcccaccatgcccagcgcctccagttgcgggggg<br>gaccatcagtcttcctgttccccccaaaacccaaggacactctcatgatctcccggacccctgaggtcacgt<br>gcgtggtggtggacgtgagccaggaagaccccgaggtccagttcaactggtacgtggatggcgtggag<br>gtgcataatgccaagacaaagccgcgggaggagcagttcaacagcacgtaccgtgtggtcagcgtcctc<br>accgtcctgcaccaggactggctgaacggcaaggagtacaagtgcaaggtctccaacaaaggcctccc<br>gtcatcgatcgagaaaaccatctccaaagccaaagggcagccccgagagccacaggtgtacaccctgc<br>ccccatcccaggaggagatgaccaagaaccaggtcagcctgacctgcctggtcaaaggcttctacccca<br>gcgacatcgccgtggagtgggagagcaatgggcagccggagaacaactacaagaccacgcctcccgt<br>gctggactccgacggatccttcttcctctacagcaggctaaccgtggacaagagcaggtggcaggaggg<br>gaatgtcttctcatgctccgtgatgcatgaggctctgcacaaccactacacacagaagagcctctccctgtc<br>tctgggtaaa |
| SEQ ID NO: 42 | | | Inactivated Human Heavy Chain Constant Region (IGHG4) Protein Sequence (inactivating mutations from human IgG4 shown in bold) | ASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPPCPAPP<br>VAGGPSVFLFPPKPKDTLMISRTPEVTCVVVDVSQEDPEVQFNWYVDGVEVHNAK<br>TKPREEQFNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKTTPPVLDS<br>DGSFFLYSRLTVDKSRWQEGNVFSCSVMHEALHNHYTQKSLSLSLGK |
| SEQ ID NO: 43 | Human constant region | Cκ IGKC*01 | Human Cκ Light Chain Constant Region (IGKC*01) Nucleotide Sequence | cgtacggtggccgctccctccgtgttcatcttcccaccttccgacgagcagctgaagtccggcaccgcttct<br>gtcgtgtgcctgctgaacaacttctacccccgcgaggccaaggtgcagtggaaggtggacaacgccctg<br>cagtccggcaactcccaggaatccgtgaccgagcaggactccaaggacagcacctactccctgtcctcca<br>ccctgaccctgtccaaggccgactacgagaagcacaaggtgtacgcctgcgaagtgacccaccagggc<br>ctgtctagccccgtgaccaagtctttcaaccggggcgagtgt |
| SEQ ID NO: 44 | | | Cκ Light Chain Constant Region (IGKC*01) Amino Acid Sequence | RTVAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| SEQ ID NO: 45 | Human constant region | Cκ IGKC*02 | Cκ Light Chain Constant Region (IGKC*02) Nucleotide Sequence | cgaactgtggctgcaccatctgtcttcatcttcccgccatctgatgagcagttgaaatctggaactgcctctg<br>ttgtgtgcctgctgaataacttctatcccagagaggccaaagtacagtggaaggtggataacgccctcca<br>atcgggtaactcccaggagagtgtcacagagcaggagagcaaggacagcacctacagcctcagcagc<br>accctgacgctgagcaaagcagactacgagaaacacaaagtctacgccggcgaagtcacccatcaggg<br>cctgagctcgcccgtcacaaagagcttcaacaggggagagtgt |
| SEQ ID NO: 46 | | | Cκ Light Chain Constant Region (IGKC*02) Amino Acid Sequence | RTVAAPSVFIFPPSDEQLKSGTASVVCLLNNFYPREAKVQWKVDNALQSGNSQESV<br>TEQESKDSTYSLSSTLTLSKADYEKHKVYAGEVTHQGLSSPVTKSFNRGEC |
| SEQ ID NO: 47 | Human constant region | Cκ IGKC*03 | Cκ Light Chain Constant Region (IGKC*03) Nucleotide Sequence | cgaactgtggctgcaccatctgtcttcatcttcccgccatctgatgagcagttgaaatctggaactgcctctg<br>ttgtgtgcctgctgaataacttctatcccagagaggccaaagtacagcggaagtggataacgccctcca<br>atcgggtaactcccaggagagtgtcacagagcaggagagcaaggacagcacctacagcctcagcagc<br>accctgacgctgagcaaagcagactacgagaaacacaaagtctacgcctgcgaagtcacccatcaggg<br>cctgagctcgcccgtcacaaagagcttcaacaggggagagtgt |
| SEQ ID NO: 48 | | | Cκ Light Chain Constant Region (IGKC*03) Amino Acid Sequence | RTVAAPSVFIFPPSDEQLKSGTASVVCLLNNFYPREAKVQRKVDNALQSGNSQESV<br>TEQESKDSTYSLSSTLTLSKADYEKHKVYACEVTHQGLSSPVTKSFNRGEC |

TABLE A-continued

| Sequences of human antibody constant regions | | | | |
|---|---|---|---|---|
| | | | Description | Sequence |
| SEQ ID NO: 49 | Human constant region | Cκ IGKC*04 | Cκ Light Chain Constant Region (IGKC*04) Nucleotide Sequence | cgaactgtggctgcaccatctgtcttcatcttcccgccatctgatgagcagttgaaatctggaactgcctctg ttgtgtgcctgctgaataacttctatcccagagaggccaaagtacagtggaaggtggataacgccctcca atcgggtaactcccaggagagtgtcacagagcaggacagcaaggacagcacctacagcctcagcagc accctgacgctgagcaaagcagactacgagaaacacaaactctacgcctgcgaagtcacccatcaggg cctgagctcgcccgtcacaaagagcttcaacaggggagagtgt |
| SEQ ID NO: 50 | | | Cκ Light Chain Constant Region (IGKC*04) Amino Acid Sequence | RTVAAPSVFIFPPSDEQLKSGTASVVCLLNNFYPREAKVQWKVDNALQSGNSQESV TEQDSKDSTYSLSSTLTLSKADYEKHKLYACEVTHQGLSSPVTKSFNRGEC |
| SEQ ID NO: 51 | Human constant region | Cκ IGKC*05 | Cκ Light Chain Constant Region (IGKC*05) Nucleotide Sequence | cgaactgtggctgcaccatctgtcttcatcttcccgccatctgatgagcagttgaaatctggaactgcctctg ttgtgtgcctgctgaataacttctatcccagagaggccaaagtacagtggaaggtggataacgccctcca atcgggtaactcccaggagagtgtcacagagcaggacagcaaggacagcacctacagcctcagcaac accctgacgctgagcaaagcagactacgagaaacacaaagtctacgcctgcgaagtcacccatcaggg cctgagctcgcccgtcacaaagagcttcaacaggggagagtgc |
| SEQ ID NO: 52 | | | Cκ Light Chain Constant Region (IGKC*05) Amino Acid Sequence | RTVAAPSVFIFPPSDEQLKSGTASVVCLLNNFYPREAKVQWKVDNALQSGNSQESV TEQDSKDSTYSLSNTLTLSKADYEKHKVYACEVTHQGLSSPVTKSFNRGEC |
| SEQ ID NO: 53 | Human Cλ constant region | IGLC1* 01 | Cλ Light Chain Constant Region (IGLC1*01) Nucleotide Sequence (ENST00000390321.2) | cccaaggccaaccccacggtcactctgttcccgccctcctctgaggagctccaagccaacaaggccacac tagtgtgtctgatcagtgacttctacccgggagctgtgacagtggcttggaaggcagatggcagccccgt caaggcgggagtggagacgaccaaaccctccaaacagagcaacaacaagtacgcggccagcagcta cctgagcctgacgcccgagcagtggaagtcccacagaagctacagctgccaggtcacgcatgaaggga gcaccgtggagaagacagtggcccctacagaatgttca |
| SEQ ID NO: 54 | | | Cλ Light Chain Constant Region (IGLC1*01) Amino Acid Sequence (A0A075B6K8) | PKANPTVTLFPPSSEELQANKATLVCLISDFYPGAVTVAWKADGSPVKAGVETTKPS KQSNNKYAASSYLSLTPEQWKSHRSYSCQVTHEGSTVEKTVAPTECS |
| SEQ ID NO: 55 | Human Cλ constant region | IGLC1* 02 | Cλ Light Chain Constant Region (IGLC1*02) Nucleotide Sequence Version A | ggtcagcccaaggccaaccccactgtcactctgttcccgccctcctctgaggagctccaagccaacaagg ccacactagtgtgtctgatcagtgacttctacccgggagctgtgacagtggcctggaaggcagatggcag ccccgtcaaggcgggagtggagaccaccaaaccctccaaacagagcaacaacaagtacgcggccagc agctacctgagcctgacgcccgagcagtggaagtcccacagaagctacagctgccaggtcacgcatga agggagcaccgtggagaagacagtggcccctacagaatgttca |
| SEQ ID NO: 56 | | | Cλ Light Chain Constant Region (IGLC1*02) Nucleotide Sequence Version B | ggtcagcccaaggccaaccccactgtcactctgttcccgccctcctctgaggagctccaagccaacaagg ccacactagtgtgtctgatcagtgacttctacccgggagctgtgacagtggcctggaaggcagatggcag ccccgtcaaggcgggagtggagaccaccaaaccctccaaacagagcaacaacaagtacgcggccagc agctacctgagcctgacgcccgagcagtggaagtcccacagaagctacagctgccaggtcacgcatga agggagcaccgtggagaagacagtggcccctacagaatgttca |
| SEQ ID NO: 57 | | | Cλ Light Chain Constant Region (IGLC1*02) Amino Acid Sequence | GQPKANPTVTLFPPSSEELQANKATLVCLISDFYPGAVTVAWKADGSPVKAGVETT KPSKQSNNKYAASSYLSLTPEQWKSHRSYSCQVTHEGSTVEKTVAPTECS |
| SEQ ID NO: 58 | Human Cλ constant region | IGLC2* 01 | Cλ Light Chain Constant Region (IGLC2*01) Nucleotide Sequence Version A | ggccagcctaaggccgctccttctgtgaccctgttcccccatcctccgaggaactgcaggctaacaaggc caccctcgtgtgcctgatcagcgacttctaccctggcgccgtgaccgtggcctggaaggctgatagctctc ctgtgaaggccggcgtggaaaccaccacccccttccaagcagtccaacaacaaatacgccgcctcctccta cctgtccctgacccctgagcagtggaagtcccaccggtcctacagctgccaagtgacccacgagggctcc accgtggaaaagaccgtggctcctaccgagtgctcc |
| SEQ ID NO: 59 | | | Cλ Light Chain Constant Region (IGLC2*01) Nucleotide Sequence Version B | ggccagcctaaagctgcccccagcgtcaccctgtttcctccctccagcgaggagctccaggccaacaagg ccaccctcgtgtgcctgatctccgacttctatcccggcgctgtgaccgtggcttggaaagccgactccagcc ctgtcaaagccggcgtggagaccaccacaccctccaagcagtccaacaacaagtacgccgcctccagct atctctccctgacccctgagcagtggaagtcccaccggtcctactcctgtcaggtgacccacgagggctcc accgtggaaaagaccgtcgcccccaccgagtgctcc |

TABLE A-continued

| Sequences of human antibody constant regions | | | | |
|---|---|---|---|---|
| | | | Description | Sequence |
| SEQ ID NO: 60 | | | Cλ Light Chain Constant Region (IGLC1*02) Amino Acid Sequence | GQPKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| SEQ ID NO: 61 | Human Cλ constant region | IGLC2* 02 or IGLC2* 03 | Cλ Light Chain Constant Region (IGLC2*02 or IGLC2*03) Nucleotide Sequence | ggtcagcccaaggctgccccctcggtcactctgttcccgccctcctctgaggagcttcaagccaacaaggc<br>cacactggtgtgtctcataagtgacttctacccgggagccgtgacagtggcctggaaggcagatagcag<br>ccccgtcaaggcgggagtggagaccaccacaccctccaaacaaagcaacaacaagtacgcggccagc<br>agctatctgagcctgacgcctgagcagtggaagtcccacagaagctacagctgccaggtcacgcatgaa<br>gggagcaccgtggagaagacagtggcccctacagaatgttca |
| SEQ ID NO: 62 | | | Cλ Light Chain Constant Region (IGLC2*02) Amino Acid Sequence | GQPKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| SEQ ID NO: 63 | Human Cλ constant region | IGLC3* 01 | Cλ Light Chain Constant Region (IGLC3*01) Nucleotide Sequence | cccaaggctgccccctcggtcactctgttcccaccctcctctgaggagcttcaagccaacaaggccacact<br>ggtgtgtctcataagtgacttctacccgggagccgtgacagttgcctggaaggcagatagcagccccgtc<br>aaggcgggggtggagaccaccacaccctccaaacaaagcaacaacaagtacgcggccagcagctacc<br>tgagcctgacgcctgagcagtggaagtcccacaaaagctacagctgccaggtcacgcatgaagggagc<br>accgtggagaagacagttgcccctacggaatgttca |
| SEQ ID NO: 64 | | | Cλ Light Chain Constant Region (IGLC3*01) Amino Acid Sequence | PKAAPSVTLFPPSSEELQANKATLVCLISDFYPGAVTVAWKADSSPVKAGVETTTPS<br>KQSNNKYAASSYLSLTPEQWKSHKSYSCQVTHEGSTVEKTVAPTECS |
| SEQ ID NO: 65 | Human Cλ constant region | IGLC3* 02 | Cλ Light Chain Constant Region (IGLC3*02) Nucleotide Sequence | ggtcagcccaaggctgccccctcggtcactctgttcccaccctcctctgaggagcttcaagccaacaaggc<br>cacactggtgtgtctcataagtgacttctacccggggccagtgacagttgcctggaaggcagatagcagc<br>cccgtcaaggcgggggtggagaccaccacaccctccaaacaaagcaacaacaagtacgcggccagca<br>gctacctgagcctgacgcctgagcagtggaagtcccacaaaagctacagctgccaggtcacgcatgaag<br>ggagcaccgtggagaagacagtggcccctacggaatgttca |
| SEQ ID NO: 66 | | | Cλ Light Chain Constant Region (IGLC1*02) Amino Acid Sequence | GQPKAAPSVTLFPPSSEELQANKATLVCLISDFYPGPVTVAWKADSSPVKAGVETTT<br>PSKQSNNKYAASSYLSLTPEQWKSHKSYSCQVTHEGSTVEKTVAPTECS |
| SEQ ID NO: 67 | Human Cλ constant region | IGLC3* 03 | Cλ Light Chain Constant Region (IGLC3*03) Nucleotide Sequence | ggtcagcccaaggctgccccctcggtcactctgttcccaccctcctctgaggagcttcaagccaacaaggc<br>cacactggtgtgtctcataagtgacttctacccgggagccgtgacagtggcctggaaggcagatagcag<br>ccccgtcaaggcgggagtggagaccaccacaccctccaaacaaagcaacaacaagtacgcggccagc<br>agctacctgagcctgacgcctgagcagtggaagtcccacaaaagctacagctgccaggtcacgcatgaa<br>gggagcaccgtggagaagacagtggcccctacagaatgttca |
| SEQ ID NO: 68 | | | Cλ Light Chain Constant Region (IGLC3*03) Amino Acid Sequence | GQPKAAPSVTLFPPSSEELQANKATLVCLISDFYPGAVTVAWKADSSPVKAGVETTT<br>PSKQSNNKYAASSYLSLTPEQWKSHKSYSCQVTHEGSTVEKTVAPTECS |
| SEQ ID NO: 69 | Human Cλ constant region | IGLC3* 04 | Cλ Light Chain Constant Region (IGLC3*04) Nucleotide Sequence | ggtcagcccaaggctgccccctcggtcactctgttcccgccctcctctgaggagcttcaagccaacaaggc<br>cacactggtgtgtctcataagtgacttctacccgggagccgtgacagtggcctggaaggcagatagcag<br>ccccgtcaaggcgggagtggagaccaccacaccctccaaacaaagcaacaacaagtacgcggccagc<br>agctacctgagcctgacgcctgagcagtggaagtcccacagaagctacagctgccaggtcacgcatgaa<br>gggagcaccgtggagaagacagtggcccctacagaatgttca |
| SEQ ID NO: 70 | | | Cλ Light Chain Constant Region (IGLC3*04) Amino Acid Sequence | GQPKAAPSVTLFPPSSEELQANKATLVCLISDYPGAVTVAWKADSSPVKAGVETTT<br>PSKQSNNKYAASSYLSLTPEQWKSHRSYSCQVTHEGSTVEKTVAPTECS |
| SEQ ID NO: 71 | Human Cλ constant region | IGLC6* 01 | Cλ Light Chain Constant Region (IGLC6*01) Nucleotide Sequence | ggtcagcccaaggctgccccatcggtcactctgttcccgccctcctctgaggagcttcaagccaacaaggc<br>cacactggtgtgcctgatcagtgacttctacccgggagctgtgaaagtggcctggaaggcagatggcag<br>ccccgtcaacacgggagtggagaccaccacaccctccaaacagagcaacaacaagtacgcggccagc<br>agctacctgagcctgacgcctgagcagtggaagtcccacagaagctacagctgccaggtcacgcatgaa<br>gggagcaccgtggagaagacagtggcccctgcagaatgttca |

TABLE A-continued

| Sequences of human antibody constant regions | | | | |
|---|---|---|---|---|
| | | | Description | Sequence |
| SEQ ID NO: 72 | | | Cλ Light Chain Constant Region (IGLC6*01) Amino Acid Sequence | GQPKAAPSVTLFPPSSEELQANKATLVCLISDFYPGAVKVAWKADGSPVNTGVETTTPSKQSNNKYAASSYLSLTPEQWKSHRSYSCQVTHEGSTVEKTVAPAECS |
| SEQ ID NO: 73 | Human Cλ constant region | IGLC7*01 or IGLC7*02 | Cλ Light Chain Constant Region (IGLC7*01 or IGLC7*02) Nucleotide Sequence | ggtcagcccaaggctgccccatcggtcactctgttcccaccctcctctgaggagcttcaagccaacaaggccacactggtgtgtctcgtaagtgacttctacccgggagccgtgacagtggcctggaaggcagatggcagccccgtcaaggtgggagtggagaccaccaaaccctccaaacaaagcaacaacaagtatgcggccagcagctacctgagcctgacgcccgagcagtggaagtcccacagaagctacagctgccgggtcacgcatgaagggagcaccgtggagaagacagtggcccctgcagaatgctct |
| SEQ ID NO: 74 | | | Cλ Light Chain Constant Region (IGLC7*01) Amino Acid Sequence | GQPKAAPSVTLFPPSSEELQANKATLVCLVSDFYPGAVTVAWKADGSPVKVGVETTKPSKQSNNKYAASSYLSLTPEQWKSHRSYSCRVTHEGSTVEKTVAPAECS |
| SEQ ID NO: 75 | Human Cλ constant region | IGLC7*03 | Cλ Light Chain Constant Region (IGLC7*03) Nucleotide Sequence | GGTCAGCCCAAGGCTGCCCCCTCGGTCACTCTGTTCCCACCCTCCTCTGAGGAGCTTCAAGCCAACAAGGCCACACTGGTGTGTCTCGTAAGTGACTTCAACCCGGGAGCCGTGACAGTGGCCTGGAAGGCAGATGGCAGCCCCGTCAAGGTGGGAGTGGAGACCACCAAACCCTCCAAACAAAGCAACAACAAGTATGCGGCCAGCAGCTACCTGAGCCTGACGCCCGAGCAGTGGAAGTCCCACAGAAGCTACAGCTGCCGGGTCACGCATGAAGGGAGCACCGTGGAGAAGACAGTGGCCCCTGCAGAATGCTCT |
| SEQ ID NO: 76 | | | Cλ Light Chain Constant Region (IGLC7*03) Amino Acid Sequence | GQPKAAPSVTLFPPSSEELQANKATLVCLVSDFNPGAVTVAWKADGSPVKVGVETTKPSKQSNNKYAASSYLSLTPEQWKSHRSYSCRVTHEGSTVEKTVAPAECS |

TABLE B

Further Sequences

| Sequence ID | Sequence info | Sequence |
|---|---|---|
| SEQ ID NO: 77 | Truncated human λ5 coding region | GTGTTTGGCAGCGGGACCCAGCTCACCGTTTTAAGTCAGCCCAAGGCCACCCCCTCGGTCACTCTGTTCCCGCCG<br>TCCTCTGAGGAGCTCCAAGCCAACAAGGCTACACTGGTGTGTCTCATGAATGACTTTTATCCGGGAATCTTGACG<br>GTGACCTGGAAGGCAGATGGTACCCCCATCACCCAGGGCGTGGAGATGACCACGCCCTCCAAACAGAGCAACAA<br>CAAGTACGCGGCCAGCAGCTACCTGAGCCTGACGCCCGAGCAGTGGAGGTCCCGCAGAAGCTACAGCTGCCAGG<br>TCATGCACGAAGGGAGCACCGTGGAGAAGACGGTGGCCCCTGCAGAATGTTCATAG |
| SEQ ID NO: 78 | Human Kappa promoter and leader with intron including Human kappa intronic enhancer (human Vκ1-5 derived | ATGGACATGAGGGTCCCCGCTCAGCTCCTGGGGCTCCTGCTGCTCTGGCTCCCAGGTAAGTAATTTTTCACTATT<br>GTCTTCTGAAATTTGGGTCTGATGGCCAGTATTGACTTTTAGAGGCTTAAATAGGAGTTTGGTAAAGATTGGTAA<br>ATGAGGGCATTTAAGATTTGCCATGGGTTGCAAAAGTTAAACTCAGCTTCAAAAATGGATTTGGAGAAAAAAAGA<br>TTAAATTGCTCTAAACTGAATGACACAAAGTAAAAAAAAAAAGTGTAACTAAAAAGGAACCCTTGTATTTCTAAGG<br>AGCAAAAGTAAATTTATTTTTGTTCACTCTTGCCAAATATTGTATTGGTTGTTGCTGATTATGCATGATACAGAAA<br>AGTGGAAAAATACATTTTTTAGTCTTTCTCCCTTTTGTTTGATAAATTATTTTGTCAGACAACAATAAAAATCAAT<br>AGCACGCCCTAAGAAAAATCAGGGAAAAGTGAAGTGTACCTATTTGCTATGTAGAAGAGGCAGCTTACTTGAAAA<br>TCAGCAGCAATGTTGTTTTTAGAGTCTGTAATAAGTAATAAACTCAAAAAGACACATTCTATAGGAATAAGGGCTT<br>CACAGATAGAGCTCATTTTTTAAAAATCCAATTTGTACATTAGACTAAACGTGAAATTATCTCTTATTGTAATGGT<br>GGAAAGGTGGTTATTCCCAAAAGCTCAATCTCAAAGAAATGTGTTTAAATGAAAAAAAGTAAATAATTGCATTTTT<br>TAATGACCGTGGGTCTGTGAAAAAAATAGGAAATATTTTAAAGAGTATGTTCTTTCATTATCCTCTGTTATTACTT<br>GTCTACATTTTTATTCTGCCAAGAAGGCCGTGGCACCGCGAGCTGTAGACAGAGCCGCGGTCTTTCTCGATTGAG<br>TGGCTTTGGTGGCCATGCCACCGCGCTCTTGGGGCAGCCGCCTTGCCGCTAGTGGCCGTGGCCACCCTGTGTCT<br>GCCCGATTGATGCTGCCGTAGCCAGCTTTCCTGATGCACAGTGATACAAATAATGCCACTAAGGGAAAGAGAACA<br>GAAACGTAATGGGCGCTGAGCTGGGAAAACCAGGGAGAAGACTGATTTATTAGAGATTTCAGAAATAAAATTCAC<br>ATTCATTATGATATCTCATTAGTGAAAATTTCCATTAGGGGATTGTAAATAATTTAAAGCTTTTTTTTTTTTCAGT<br>GCTATTTAATTATTTCAATATCCTCTCATCAAATGTATTTAAATAACAAAAGCTCAACCAAAAAGAAAGAAATATG<br>TAATTCTTTCAGAGTAAAAATCACACCCATGACCTGGCCACTGAGGGCTTGATCAATTCACTTTGAATTTGGCATT<br>AAATACCATTAAGGTATATTAACTGATTTTAAAATAAGATATATTCGTGACCATGTTTTTAACTTTCAAAAATGTA<br>GCTGCCAGTGTGTGATTTTATTTCAGTTGTACAAAATATCTAAACCTATAGCAATGTGATTAATAAAAACTTAAAC<br>ATATTTTCCAGTACCTTAATTCTGTGATAGGAAAATTTTAATCTGAGTATTTTAATTTCATAATCTCTAAAATAGTT<br>TAATGATTTGTCATTGTGTTGCTGTCGTTTACCCCAGCTGATCTCAAAAGTGATATTTAAGGAGATTATTTTGGTC<br>TGCAACAACTTGATAGGACTATTTTAGGGCCTTTTTAAAGCTCTATTAAAACTAACTTACAACGATTCAAAACTGT<br>TTTAAACTATTTCAAAATGATTTTAGAGCCTTTTGAAAACTCTTTTAAACACTTTTTAAACTCTATTAAAACTAATA<br>AGATAACTTGAAATAATTTTCATGTCAAATACATTAACTGTTTAATGTTTAAATGCCAGATGAAAAATGTAAAGCT<br>ATCAAGAATTCACCCAGATAGGAGTATCTTCATAGCATGTTTTTCCCTGCTTATTTTCCAGTGATCACATTATTTT<br>GCTACCATGGTTATTTTATACAATTATCTGAAAAAAATTAGTTATGAAGATTAAAAGAGAAGAAAATATTAAACAT<br>AAGAGATTCAGTCTTTCATGTTGAACTGCTTGGTTAACAGTGAAGTTAGTTTTAAAAAAAAAAAAAACTATTTCTG<br>TTATCAGCTGACTTCTCCCTATCTGTTGACTTCTCCCAGCAAAAGATTCTTATTTTACATTTTAACTACTGCTCTCC<br>CACCCAACGGGTGGAATCCCCCAGAGGGGGATTTCCAAGAGGCCACCTGGCAGTTGCTGAGGGTCAGAAGTGAA<br>GCTAGCCACTTCCTCTTAGGCAGGTGGCCAAGATTACAGTTGACCTCTCCTGGTATGGCTGAAAATTGCTGCATA<br>TGGTTACAGGCCTTGAGGCCTTTGGGAGGGCTTAGAGAGTTGCTGGAACAGTCAGAAGGTGGAGGGGCTGACAC<br>CACCCAGGCGCAGAGGCAGGGCTCAGGGCCTGCTCTGCAGGGAGGTTTTAGCCCAGCCCAGCCAAAGTAACCCC<br>CGGGAGCCTGTTATCCCAGCACAGTCCTGGAAGAGGCACAGGGGAAATAAAAGCGGACGGAGGCTTTCCTTGAC<br>TCAGCCGCTGCCTGGTCTTCTTCAGACCTGTTCTGAATTCTAAACTCTGAGGGGGTCGGATGACGTGGCCATTCT<br>TTGCCTAAAGCATTGAGTTTACTGCAAGGTCAGAAAAGCATGCAAAGCCCTCAGAATGGCTGCAAAGAGCTCCAA<br>CAAAACAATTTAGAACTTTATTAAGGAATAGGGGGAAGCTAGGAAGAAACTCAAAACATCAAGATTTTAAATACG<br>CTTCTTGGTCTCCTTGCTATAATTATCTGGGATAAGCATGCTGTTTTCTGTCTGTCCCTAACATGCCCTGTGATTA<br>TCCGCAAACAACACACCCAAGGGCAGAACTTTGTTACTTAAACACCATCCTGTTTGCTTCTTTCCTCAGGTGCCAA<br>ATGT |

TABLE B-continued

| Further Sequences | | |
|---|---|---|
| Sequence ID | Sequence info | Sequence |
| SEQ ID NO: 79 | Full λ5 transgene plus homology arms | GCTGAATCTTGAATGACAGCTCAAGGGATAGGGAGGACAGGGTGTTCAGAAGCAGAGAAGATGCCTTGTAAATG TGGAAGGCTGTGGCAGGATTGGAAGGACTTTGGGGTGGTAGGAAGGGGATGGGAATGGGTGGTTACAAGAGAA ACAAGACTGTAGTAAATAAAGCTGAAACTCAAAGCAAGCTTTCAGCATCTTTAATTGGAGACACAAACTTCAAAGG TATCATGAATGTGGTTGATCTTGGTGAAAGTTGAGCTTCACCTGTCCTAACAACAGACCAATCCATGAGTGAAAG CTTATCTTTCTCCTTTATTAATGGTTGCTGTTGTATCCATAACTCAATTCCAAAGGATATGAACCTTAACATATAG ATATAATTTTGTGTACCTTCTATGAAACAGCATTAAAGCAAAGAAGTTCAAATAGAAAGACTGGCTTAGTTATTAT TAACTAAGAGATGCTAGTGAGTTCTAAATTAATACCATTTAAAATTTATAATTTGCAGAATTACCACCACCACCAC CACTCAGCCCAGGAAAAGTTACAAAGAACTGGCTATCCAATTTGTTTGTTTTCCTCCTTTTTAGAGTTCTTTTATT TATGTGTGAGTGAATGCCATGTACTTATGGATGCAGAGGCTGTCAGATTCCTTGCAGCTGGAGTAATAGACAGTT GTGAGCTACTTATAGTACTAGAACTAAGATCCTATGGAAGAGCAGCGAGTGCCACTAACTGCTGAGCCACCTCTC CAGCCCATTTCTTTATTTTTCAATGAACAAATAATAAGCAGTCCTATGTGACATGCTTCTAAAGCAAAAGATATAA TATTTAGTATTATATACATTAATAATAAAATACATTATCTTCTAAGAATTGAAGTCTCAACTATGAAAATCAGCAG TTCTCTGTCAGAGAAGATGTCCAGTTTCATCTGGATCCAACTGATTTCTCCATGTACATAGACAATTGCTTGATAA GAGATTGAGTATGTTTTTCCTAAAGGTGTTAACAGGGAGGCTGGTGTCTGGGTCAGGATGATGTCCCCATGCAC TGATAAAAAGTATAAGAAGAAAGTGTCATTGATGGTGCATGGCAGGGACATGCTCCGTGCAGTGGCCACCCTCAC TAAGACAGATGAACTTTGGGAAATAATACCCAATGGCAGAAAAGAAGGTAGACTATGAAGGTACCCAAAACAAGA ATAAGGTGCACCTCATTTAGTCTCTGGGTATTAAAGAGACCTGCAGTTCTTGATAGTGGTGGATCTGTGAGTGCT GCATGCATGGAGACAACACGGTATCATCTTTGTATATCTGTAATAAATTGCTTGATCTAATACTAGTAAGAACAAA GGCATAACACCATTACCTAATACTTACAAATATATAGCATCATGCCGATACATTTTATTTTTAATTTTTTTTAGAAA GGAACAATGTTAAACTCACAGAAATGTTGCAGGTATAGCACAATTACCCCCTTCCCTACCCGGAATCTTATGAGA GTCTTTTGAAGACTTGAGAATCCTACCATCTAACATTTTACTATGTGTTTCCTACAAACAAGAATATTCTCCTAAA TAATCCTGATACACCAATGAAATACATTACTCTATCGGCTCCTGAGGAATATTTAAAATTCTCAAAAAAATACCTA AAAATTGTTTCTCATAATAAAATAGTCCCCAGTAGAAACACATTCTCTGCAGACAAATTTGTGCTACCCTGGTCTT ACCTGGGACACCTGGGGACACTGAGCTGGTGCTGAGTTACTGAGATGAGCCAGCTCTGCAGCTGTGCCCAGCCT GCCCCATCCCCTGCTCATTTGCATGTTCCCAGAGCACAACCTCCTGCCCTGAAGCCTTATTAATAGGCTGGTCACA CTTTGTGCAGGAGTCAGACCCAGTCAGGACACAGCATGGACATGAGGGTCCCCGCTCAGCTCCTGGGGCTCCTG CTGCTCTGGCTCCCAGGTAAGTAATTTTTCACTATTGTCTTCTGAAATTTGGGTCTGATGGCCAGTATTGACTTTT AGAGGCTTAAATAGGAGTTTGGTAAAGATTGGTAAATGAGGGCATTTAAGATTTGCCATGGGTTGCAAAAGTTAA ACTCAGCTTCAAAAATGGATTTGGAGAAAAAAAGATTAAATTGCTCTAAACTGAATGACACAAAGTAAAAAAAAAA AGTGTAACTAAAAAGGAACCCTTGTATTTCTAAGGAGCAAAAGTAAATTTATTTTTGTTCACTCTTGCCAAATATT GTATTGGTTGTTGCTGATTATGCATGATACAGAAAAGTGGAAAAATACATTTTTTAGTCTTTCTCCCTTTTGTTTG ATAAATTATTTTGTCAGACAACAATAAAAATCAATAGCACGCCCTAAGAAAAATCAGGGAAAAGTGAAGTGTACCT ATTTGCTATGTAGAAGAGGCAGCTTACTTGAAAATCAGCAGCAATGTTGTTTTTAGAGTCTGTAATAAGTAATAA ACTCAAAAAGACACATTCTATAGGAATAAGGGCTTCACAGATAGAGCTCATTTTTTAAAAATCCAATTTGTACATT AGACTAAACGTGAAATTATCTCTTATTGTAATGGTGGAAAGGTGGTTATTCCCAAAAGCTCAATCTCAAAGAAAT GTGTTTAAATGAAAAAAAGTAAATAATTGCATTTTTTAATGACCGTGGGTCTGTGAAAAAAAATAGGAAATATTTTA AAGAGTATGTTCTTTCATTATCCTCTGTTATTACTTGTCTACATTTTTATTCTGCCAAGAAGGCCGTGGCACCGCG AGCTGTAGACAGAGCCGCGGTCTTTCTCGATTGAGTGGCTTTGGTGGCCATGCCACCGCGCTCTTGGGGCAGCC GCCTTGCCGCTAGTGGCCGTGGCCACCCTGTGTCTGCCCGATTGATGCTGCCGTAGCCAGCTTTCCTGATGCACA GTGATACAAATAATGCCACTAAGGGAAAGAGAACAGAAACGTAATGGGCGCTGAGCTGGGAAAACCAGGGAGAA GACTGATTTATTAGAGATTTCAGAAATAAAATTCACATTCATTATGATATCTCATTAGTGAAAATTTCCATTAGGG GATTGTAAATAATTTAAAGCTTTTTTTTTTTTCAGTGCTATTTAATTATTTCAATATCCTCTCATCAAATGTATTTA AATAACAAAAGCTCAACCAAAAAGAAAGAAATATGTAATTCTTTCAGAGTAAAAATCACACCCATGACCTGGCCAC TGAGGGCTTGATCAATTCACTTTGAATTTGGCATTAAATACCATTAAGGTATATTAACTGATTTTAAAATAAGATA TATTCGTGACCATGTTTTTAACTTTCAAAAATGTAGCTGCCAGTGTGTGATTTTATTTCAGTTGTACAAAATATCT AAACCTATAGCAATGTGATTAATAAAAACTTAAACATATTTTCCAGTACCTTAATTCTGTGATAGGAAAATTTTAA TCTGAGTATTTTAATTTCATAATCTCTAAAATAGTTTAATGATTTGTCATTGTGTTGCTGTCGTTTACCCCAGCTG ATCTCAAAAGTGATATTTAAGGAGATTATTTTGGTCTGCAACAACTTGATAGGACTATTTTAGGGCCTTTTTAAAG CTCTATTAAAACTAACTTACAACGATTCAAAACTGTTTTAAACTATTTCAAAATGATTTTAGAGCCTTTTGAAAACT |

TABLE B-continued

| Further Sequences | | |
|---|---|---|
| Sequence ID | Sequence info | Sequence |
| | | CTTTTAAACACTTTTTAAACTCTATTAAAACTAATAAGATAACTTGAAATAATTTTCATGTCAAATACATTAACTGT<br>TTAATGTTTAAATGCCAGATGAAAAATGTAAAGCTATCAAGAATTCACCCAGATAGGAGTATCTTCATAGCATGTT<br>TTTCCCTGCTTATTTTCCAGTGATCACATTATTTTGCTACCATGGTTATTTTATACAATTATCTGAAAAAAATTAGT<br>TATGAAGATTAAAAGAGAAGAAAATATTAAACATAAGAGATTCAGTCTTTCATGTTGAACTGCTTGGTTAACAGT<br>GAAGTTAGTTTTAAAAAAAAAAAAAACTATTTCTGTTATCAGCTGACTTCTCCCTATCTGTTGACTTCTCCCAGCA<br>AAAGATTCTTATTTTACATTTTAACTACTGCTCTCCCACCCAACGGGTGGAATCCCCCAGAGGGGGATTTCCAAG<br>AGGCCACCTGGCAGTTGCTGAGGGTCAGAAGTGAAGCTAGCCACTTCCTCTTAGGCAGGTGGCCAAGATTACAG<br>TTGACCTCTCCTGGTATGGCTGAAAATTGCTGCATATGGTTACAGGCCTTGAGGCCTTTGGGAGGGCTTAGAGA<br>GTTGCTGGAACAGTCAGAAGGTGGAGGGGCTGACACCACCCAGGCGCAGAGGCAGGGCTCAGGGCCTGCTCTGC<br>AGGGAGGTTTTAGCCCAGCCCAGCCAAAGTAACCCCCGGGAGCCTGTTATCCCAGCACAGTCCTGGAAGAGGCA<br>CAGGGGAAATAAAAGCGGACGGAGGCTTTCCTTGACTCAGCCGCTGCCTGGTCTTCTTCAGACCTGTTCTGAATT<br>CTAAACTCTGAGGGGGTCGGATGACGTGGCCATTCTTTGCCTAAAGCATTGAGTTTACTGCAAGGTCAGAAAAGC<br>ATGCAAAGCCCTCAGAATGGCTGCAAAGAGCTCCAACAAAACAATTTAGAACTTTATTAAGGAATAGGGGGAAGC<br>TAGGAAGAAACTCAAAACATCAAGATTTTAAATACGCTTCTTGGTCTCCTTGCTATAATTATCTGGGATAAGCATG<br>CTGTTTTCTGTCTGTCCCTAACATGCCCTGTGATTATCCGCAAACAACACACCCAAGGGCAGAACTTTGTTACTTA<br>AACACCATCCTGTTTGCTTCTTTCCTCAGGTGCCAAATGTGTGTTTGGCAGCGGGACCCAGCTCACCGTTTTAAG<br>TCAGCCCAAGGCCACCCCCTCGGTCACTCTGTTCCCGCCGTCCTCTGAGGAGCTCCAAGCCAACAAGGCTACACT<br>GGTGTGTCTCATGAATGACTTTTATCCGGGAATCTTGACGGTGACCTGGAAGGCAGATGGTACCCCCATCACCCA<br>GGGCGTGGAGATGACCACGCCCTCCAAACAGAGCAACAACAAGTACGCGGCCAGCAGCTACCTGAGCCTGACGC<br>CCGAGCAGTGGAGGTCCCGCAGAAGCTACAGCTGCCAGGTCATGCACGAAGGGAGCACCGTGGAGAAGACGGTG<br>GCCCCTGCAGAATGTTCATAGAGACAAAGGTCCTGAGACGCCACCACCAGCTCCCCAGCTCCATCCTATCTTCCC<br>TTCTAAGGTCTTGGAGGCTTCCCCACAAGCGACCTACCACTGTTGCGGTGCTCCAAACCTCCTCCCCACCTCCTTC<br>TCCTCCTCCTCCCTTTCCTTGGCTTTTATCATGCTAATATTTGCAGAAAATATTCAATAAAGTGAGTCTTTGCACT<br>TGAGATCTCTGTCTTTCTTACTAAATGGTAGTAATCAGTTGTTTTTCCAGTTACCTGGGTTTCTCTTCTAAAGAAG<br>TTAAATGTTTAGTTGCCCTGAAATCCACCACACTTAAAGGATAAATAAAACCCTCCACTTGCCCTGGTTGGCTGTC<br>CACTACATGGCAGTCCTTTCTAAGGTTCACGAGTACTATTCATGGCTTATTTCTCTGGGCCATGGTAGGTTTGAG<br>GAGGCATACTTCCTAGTTTTCTTCCCCTAAGTCGTCAAAGTCCTGAAGGGGGACAGTCTTTACAAGCACATGTTC<br>TGTAATCTGATTCAACCTACCCAGTAAACTTGGCGAAGCAAAGTAGAATCATTATCACAGGAAGCAAAGGCAACC<br>TAAATGTGCAAGCAATAGGAAAATGTGGAAGCCCATCATAGTACTTGGACTTCATCTGCTTTTGTGCCTTCACTA<br>AGTTTTTAAACATGAGCTGGCTCCTATCTGCCATTGGCAAGGCTGGGCACTACCCACAACCTACTTCAAGGACCT<br>CTATACCGTGAGATTACACACATACATCAAAATTTGGGAAAAGTTCTACCAAGCTGAGAGCTGATCACCCCACTCT<br>TAGGTGCTTATCTCTGTACACCAGAAACCTTAAGAAGCAACCAGTATTGAGAGAC |
| SEQ ID NO: 80 | Full λ5 targeting vector insert including positive/negative selection cassette) | GCTGAATCTTGAATGACAGCTCAAGGGATAGGGAGGACAGGGTGTTCAGAAGCAGAGAAGATGCCTTGTAAATG<br>TGGAAGGCTGTGGCAGGATTGGAAGGACTTTGGGGTGGTAGGAAGGGGATGGGAATGGGTGGTTACAAGAGAA<br>ACAAGACTGTAGTAAATAAAGCTGAAACTCAAAGCAAGCTTTCAGCATCTTTAATTGGAGACACAAACTTCAAAGG<br>TATCATGAATGTGGTTGATCTTGGTGAAAGTTGAGCTTCACCTGTCCTAACAACAGACCAATCCATGAGTGAAAG<br>CTTATCTTTCTCCTTTATTAATGGTTGCTGTTGTATCCATAACTCAATTCCAAAGGATATGAACCTTAACATATAG<br>ATATAATTTTGTGTACCTTCTATGAAACAGCATTAAAGCAAAGAAGTTCAAATAGAAAGACTGGCTTAGTTATTAT<br>TAACTAAGAGATGCTAGTGAGTTCTAAATTAATACCATTTAAAATTTATAATTTGCAGAATTACCACCACCACCAC<br>CACTCAGCCCAGGAAAAGTTACAAAGAACTGGCTATCCAATTTGTTTGTTTTCCTCCTTTTTAGAGTTCTTTTATT<br>TATGTGTGAGTGAATGCCATGTACTTATGGATGCAGAGGCTGTCAGATTCCTTGCAGCTGGAGTAATAGACAGTT<br>GTGAGCTACTTATAGTACTAGAACTAAGATCCTATGGAAGAGCAGCGAGTGCCACTAACTGCTGAGCCACCTCTC<br>CAGCCCATTTCTTTATTTTTCAATGAACAAATAATAAGCAGTCCTATGTGACATGCTTCTAAAGCAAAAGATATAA<br>TATTTAGTATTATATACATTAATAATAAAATACATTATCTTCTAAGAATTGAAGTCTCAACTATGAAAATCAGCAG<br>TTCTCTGTCAGAGAAGATGTCCAGTTTCATCTGGATCCAACTGATTTCTCCATGTACATAGACAATTCTTTTAACC<br>CTAGAAAGATAGTCTGCGTAAAATTGACGCATGCATTCTTGAAATATTGCTCTCTCTTTCTAAATAGCGCGAATCC<br>GTCGCTGTGCATTTAGGACATCTCAGTCGCCGCTTGGAGCTCCCGTGAGGCGTGCTTGTCAATGCGGTAAGTGT<br>CACTGATTTTGAACTATAACGACCGCGTGAGTCAAAATGACGCATGATTATCTTTTACGTGACTTTTAAGATTTAA |

TABLE B-continued

Further Sequences

| Sequence ID | Sequence info | Sequence |
|---|---|---|
| | | CTCATACGATAATTATATTGTTATTTCATGTTCTACTTACGTGATAACTTATTATATATATATTTTCTTGTTATAGA |
| | | TATCTACCGGGTAGGGGAGGCGCTTTTCCCAAGGCAGTCTGGAGCATGCGCTTTAGCAGCCCCGCTGGGCACTT |
| | | GGCGCTACACAAGTGGCCTCTGGCCTCGCACACATTCCACATCCACCGGTAGGCGCCAACCGGCTCCGTTCTTTG |
| | | GTGGCCCCTTCGCGCCACCTTCTACTCCTCCCCTAGTCAGGAAGTTCCCCCCCGCCCCGCAGCTCGCGTCGTGCA |
| | | GGACGTGACAAATGGAAGTAGCACGTCTCACTAGTCTCGTGCAGATGGACAGCACCGCTGAGCAATGGAAGCGG |
| | | GTAGGCCTTTGGGGCAGCGGCCAATAGCAGCTTTGCTCCTTCGCTTTCTGGGCTCAGAGGCTGGGAAGGGGTGG |
| | | GTCCGGGGGCGGGCTCAGGGGCGGGCTCAGGGGCGGGGCGGGCGCCCGAAGGTCCTCCGGAGGCCCGGCATTC |
| | | TGCACGCTTCAAAAGCGCACGTCTGCCGCGCTGTTCTCCTCTTCCTCATCTCCGGGCCTTTCGACCTGCAGCCAA |
| | | CGCCACCATGGGGACCGAGTACAAGCCCACGGTGCGCCTCGCCACCCGCGACGACGTCCCCCGGGCCGTACGCA |
| | | CCCTCGCCGCCGCGTTCGCCGACTACCCCGCCACGCGCCACACCGTCGACCCGGACCGCCACATCGAGCGGGTCA |
| | | CCGAGCTGCAAGAACTCTTCCTCACGCGCGTCGGGCTCGACATCGGCAAGGTGTGGGTCGCGGACGACGGCGCC |
| | | GCGGTGGCGGTCTGGACCACGCCGGAGAGCGTCGAAGCGGGGGCGGTGTTCGCCGAGATCGGCCCGCGCATGG |
| | | CCGAGTTGAGCGGTTCCCGGCTGGCCGCGCAGCAACAGATGGAAGGCCTCCTGGCGCCGCACCGGCCCAAGGAG |
| | | CCCGCGTGGTTCCTGGCCACCGTCGGCGTCTCGCCCGACCACCAGGGCAAGGGTCTGGGCAGCGCCGTCGTGCT |
| | | CCCCGGAGTGGAGGCGGCCGAGCGCGCCGGGGTGCCCGCCTTCCTGGAGACCTCCGCGCCCCGCAACCTCCCCT |
| | | TCTACGAGCGGCTCGGCTTCACCGTCACCGCCGACGTCGAGGTGCCCGAAGGACCGCGCACCTGGTGCATGACC |
| | | CGCAAGCCCGGTGCCGGATCCATGCCCACGCTACTGCGGGTTTATATAGACGGTCCTCACGGGATGGGGAAAAC |
| | | CACCACCACGCAACTGCTGGTGGCCCTGGGTTCGCGCGACGATATCGTCTACGTACCCGAGCCGATGACTTACTG |
| | | GCAGGTGCTGGGGGCTTCCGAGACAATCGCGAACATCTACACCACACAACACCGCCTCGACCAGGGTGAGATATC |
| | | GGCCGGGGACGCGGCGGTGGTAATGACAAGCGCCCAGATAACAATGGGCATGCCTTATGCCGTGACCGACGCCG |
| | | TTCTGGCTCCTCATATCGGGGGGGAGGCTGGGAGCTCACATGCCCCGCCCCCGGCCCTCACCCTCATCTTCGACC |
| | | GCCATCCCATCGCCGCCCTCCTGTGCTACCCGGCCGCGCGATACCTTATGGGCAGCATGACCCCCCAGGCCGTGC |
| | | TGGCGTTCGTGGCCCTCATCCCGCCGACCTTGCCCGGCACAAACATCGTGTTGGGGGCCCTTCCGGAGGACAGA |
| | | CACATCGACCGCCTGGCCAAACGCCAGCGCCCCGGCGAGCGGCTTGACCTGGCTATGCTGGCCGCGATTCGCCG |
| | | CGTTTACGGGCTGCTTGCCAATACGGTGCGGTATCTGCAGGGCGGCGGGTCGTGGCGGGAGGATTGGGGACAG |
| | | CTTTCGGGGACGGCCGTGCCGCCCCAGGGTGCCGAGCCCCAGAGCAACGCGGGCCCACGACCCCATATCGGGGA |
| | | CACGTTATTTACCCTGTTTCGGGCCCCCGAGTTGCTGGCCCCCAACGGCGACCTGTACAACGTGTTTGCCTGGGC |
| | | CTTGGACGTCTTGGCCAAACGCCTCCGTCCCATGCACGTCTTTATCCTGGATTACGACCAATCGCCCGCCGGCTG |
| | | CCGGGACGCCCTGCTGCAACTTACCTCCGGGATGGTCCAGACCCACGTCACCACCCCCGGCTCCATACCGACGAT |
| | | CTGCGACCTGGCGCGCACGTTTGCCCGGGAGATGGGGGAGGCTAACTGAGCTCTAGAGCTCGCTGATCAGCCTC |
| | | GACTGTGCCTTCTAGTTGCCAGCCATCTGTTGTTTGCCCCTCCCCCGTGCCTTCCTTGACCCTGGAAGGTGCCAC |
| | | TCCCACTGTCCTTTCCTAATAAAATGAGGAAATTGCATCGCATTGTCTGAGTAGGTGTCATTCTATTCTGGGGGG |
| | | TGGGGTGGGGCAGGACAGCAAGGGGGAGGATTGGGAAGACAATAGCAGGCATGCTGGGGATGCGGTGGGCTCT |
| | | ATGGCTTCTGAGGCGGAAAGAACCAGCTGGGGCTCGAGATCCACTAGTTAAAAGTTTTGTTACTTTATAGAAGAA |
| | | ATTTTGAGTTTTTGTTTTTTTTTAATAAATAAATAAACATAAATAAATTGTTTGTTGAATTTATTATTAGTATGTAA |
| | | GTGTAAATATAATAAAACTTAATATCTATTCAAATTAATAAATAAACCTCGATATACAGACCGATAAAACACATGC |
| | | GTCAATTTTACGCATGATTATCTTTAACGTACGTCACAATATGATTATCTTTCTAGGGTTAATCTAGTATAATTGC |
| | | TTGATAAGAGATTGAGTATGTTTTTCCTAAAGGTGTTAACAGGGAGGCTGGTGTCTGGGTCAGGATGATGTCCC |
| | | CATGCACTGATAAAAAGTATAAGAAGAAAGTGTCATTGATGGTGCATGGCAGGGACATGCTCCGTGCAGTGGCC |
| | | ACCCTCACTAAGACAGATGAACTTTGGGAAATAATACCCAATGGCAGAAAAGAAGGTAGACTATGAAGGTACCCA |
| | | AAACAAGAATAAGGTGCACCTCATTTAGTCTCTGGGTATTAAAGAGACCTGCAGTTCTTGATAGTGGTGGATCTG |
| | | TGAGTGCTGCATGCATGGAGACAACACGGTATCATCTTTGTATATCTGTAATAAATTGCTTGATCTAATACTAGTA |
| | | AGAACAAAGGCATAACACCATTACCTAATACTTACAAATATATAGCATCATGCCGATACATTTTATTTTTAATTTTT |
| | | TTTAGAAAGGAACAATGTTAAACTCACAGAAATGTTGCAGGTATAGCACAATTACCCCCTTCCCTACCCGGAATCT |
| | | TATGAGAGTCTTTTGAAGACTTGAGAATCCTACCATCTAACATTTTACTATGTGTTTCCTACAAACAAGAATATTC |
| | | TCCTAAATAATCCTGATACACCAATGAAATACATTACTCTATCGGCTCCTGAGGAATATTTAAAATTCTCAAAAAA |
| | | ATACCTAAAAATTGTTTCTCATAATAAAATAGTCCCCAGTAGAAACACATTCTCTGCAGACAAATTTGTGCTACCC |
| | | TGGTCTTACCTGGGACACCTGGGGACACTGAGCTGGTGCTGAGTTACTGAGATGAGCCAGCTCTGCAGCTGTGC |
| | | CCAGCCTGCCCCATCCCCTGCTCATTTGCATGTTCCCAGAGCACAACCTCCTGCCCTGAAGCCTTATTAATAGGCT |

TABLE B-continued

Further Sequences

| Sequence ID | Sequence info | Sequence |
|---|---|---|
| | | GGTCACACTTTGTGCAGGAGTCAGACCCAGTCAGGACACAGCATGGACATGAGGGTCCCCGCTCAGCTCCTGGG<br>GCTCCTGCTGCTCTGGCTCCCAGGTAAGTAATTTTTCACTATTGTCTTCTGAAATTTGGGTCTGATGGCCAGTAT<br>TGACTTTTAGAGGCTTAAATAGGAGTTTGGTAAAGATTGGTAAATGAGGGCATTTAAGATTTGCCATGGGTTGCA<br>AAAGTTAAACTCAGCTTCAAAAATGGATTTGGAGAAAAAAAGATTAAATTGCTCTAAACTGAATGACACAAAGTAA<br>AAAAAAAAAGTGTAACTAAAAAGGAACCCTTGTATTTCTAAGGAGCAAAAGTAAATTTATTTTTGTTCACTCTTGC<br>CAAATATTGTATTGGTTGTTGCTGATTATGCATGATACAGAAAAGTGGAAAAATACATTTTTTAGTCTTTCTCCCT<br>TTTGTTTGATAAATTATTTTGTCAGACAACAATAAAAATCAATAGCACGCCCTAAGAAAAATCAGGGAAAAGTGAA<br>GTGTACCTATTTGCTATGTAGAAGAGGCAGCTTACTTGAAAATCAGCAGCAATGTTGTTTTTAGAGTCTGTAATA<br>AGTAATAAACTCAAAAAGACACATTCTATAGGAATAAGGGCTTCACAGATAGAGCTCATTTTTTAAAAATCCAATT<br>TGTACATTAGACTAAACGTGAAATTATCTCTTATTGTAATGGTGGAAAGGTGGTTATTCCCAAAAGCTCAATCTCA<br>AAGAAATGTGTTTAAATGAAAAAAAGTAAATAATTGCATTTTTTAATGACCGTGGGTCTGTGAAAAAAATAGGAA<br>ATATTTTAAAGAGTATGTTCTTTCATTATCCTCTGTTATTACTTGTCTACATTTTTATTCTGCCAAGAAGGCCGTG<br>GCACCGCGAGCTGTAGACAGAGCCGCGGTCTTTCTCGATTGAGTGGCTTTGGTGGCCATGCCACCGCGCTCTTG<br>GGGCAGCCGCCTTGCCGCTAGTGGCCGTGGCCACCCTGTGTCTGCCCGATTGATGCTGCCGTAGCCAGCTTTCC<br>TGATGCACAGTGATACAAATAATGCCACTAAGGGAAAGAGAACAGAAACGTAATGGGCGCTGAGCTGGGAAAAC<br>CAGGGAGAAGACTGATTTATTAGAGATTTCAGAAATAAAATTCACATTCATTATGATATCTCATTAGTGAAAATTT<br>CCATTAGGGGATTGTAAATAATTTAAAGCTTTTTTTTTTTTCAGTGCTATTTAATTATTTCAATATCCTCTCATCAA<br>ATGTATTTAAATAACAAAAGCTCAACCAAAAAGAAAGAAATATGTAATTCTTTCAGAGTAAAAATCACACCCATGA<br>CCTGGCCACTGAGGGCTTGATCAATTCACTTTGAATTTGGCATTAAATACCATTAAGGTATATTAACTGATTTTAA<br>AATAAGATATATTCGTGACCATGTTTTTAACTTTCAAAAATGTAGCTGCCAGTGTGTGATTTTATTTCAGTTGTAC<br>AAAATATCTAAACCTATAGCAATGTGATTAATAAAAACTTAAACATATTTTCCAGTACCTTAATTCTGTGATAGGA<br>AAATTTTAATCTGAGTATTTTAATTTCATAATCTCTAAAATAGTTTAATGATTTGTCATTGTGTTGCTGTCGTTTA<br>CCCCAGCTGATCTCAAAAGTGATATTTAAGGAGATTATTTTGGTCTGCAACAACTTGATAGGACTATTTTAGGGC<br>CTTTTTAAAGCTCTATTAAAACTAACTTACAACGATTCAAAACTGTTTTAAACTATTTCAAAATGATTTTAGAGCCT<br>TTTGAAAACTCTTTTAAACACTTTTTAAACTCTATTAAAACTAATAAGATAACTTGAAATAATTTTCATGTCAAATA<br>CATTAACTGTTTAATGTTTAAATGCCAGATGAAAAATGTAAAGCTATCAAGAATTCACCCAGATAGGAGTATCTTC<br>ATAGCATGTTTTTCCCTGCTTATTTTCCAGTGATCACATTATTTTGCTACCATGGTTATTTTATACAATTATCTGA<br>AAAAAATTAGTTATGAAGATTAAAAGAGAAGAAAATATTAAACATAAGAGATTCAGTCTTTCATGTTGAACTGCTT<br>GGTTAACAGTGAAGTTAGTTTTAAAAAAAAAAAAAACTATTTCTGTTATCAGCTGACTTCTCCCTATCTGTTGACT<br>TCTCCCAGCAAAAGATTCTTATTTTACATTTTAACTACTGCTCTCCCACCCAACGGGTGGAATCCCCCAGAGGGG<br>GATTTCCAAGAGGCCACCTGGCAGTTGCTGAGGGTCAGAAGTGAAGCTAGCCACTTCCTCTTAGGCAGGTGGCC<br>AAGATTACAGTTGACCTCTCCTGGTATGGCTGAAAATTGCTGCATATGGTTACAGGCCTTGAGGCCTTTGGGAGG<br>GCTTAGAGAGTTGCTGGAACAGTCAGAAGGTGGAGGGGCTGACACCACCCAGGCGCAGAGGCAGGGCTCAGGG<br>CCTGCTCTGCAGGGAGGTTTTAGCCCAGCCCAGCCAAAGTAACCCCCGGGAGCCTGTTATCCCAGCACAGTCCTG<br>GAAGAGGCACAGGGGAAATAAAAGCGGACGGAGGCTTTCCTTGACTCAGCCGCTGCCTGGTCTTCTTCAGACCT<br>GTTCTGAATTCTAAACTCTGAGGGGGTCGGATGACGTGGCCATTCTTTGCCTAAAGCATTGAGTTTACTGCAAGG<br>TCAGAAAAGCATGCAAAGCCCTCAGAATGGCTGCAAAGAGCTCCAACAAAACAATTTAGAACTTTATTAAGGAAT<br>AGGGGGAAGCTAGGAAGAAACTCAAAACATCAAGATTTTAAATACGCTTCTTGGTCTCCTTGCTATAATTATCTG<br>GGATAAGCATGCTGTTTTCTGTCTGTCCCTAACATGCCCTGTGATTATCCGCAAACAACACACCCAAGGGCAGAA<br>CTTTGTTACTTAAACACCATCCTGTTTGCTTCTTTCCTCAGGTGCCAAATGTGTGTTTGGCAGCGGGACCCAGCT<br>CACCGTTTTAAGTCAGCCCAAGGCCACCCCCTCGGTCACTCTGTTCCCGCCGTCCTCTGAGGAGCTCCAAGCCAA<br>CAAGGCTACACTGGTGTGTCTCATGAATGACTTTTATCCGGGAATCTTGACGGTGACCTGGAAGGCAGATGGTAC<br>CCCCATCACCCAGGGCGTGGAGATGACCACGCCCTCCAAACAGAGCAACAACAAGTACGCGGCCAGCAGCTACCT<br>GAGCCTGACGCCCGAGCAGTGGAGGTCCCGCAGAAGCTACAGCTGCCAGGTCATGCACGAAGGGAGCACCGTGG<br>AGAAGACGGTGGCCCCTGCAGAATGTTCATAGAGACAAAGGTCCTGAGACGCCACCACCAGCTCCCCAGCTCCAT<br>CCTATCTTCCCTTCTAAGGTCTTGGAGGCTTCCCCACAAGCGACCTACCACTGTTGCGGTGCTCCAAACCTCCTCC<br>CCACCTCCTTCTCCTCCTCCTCCCTTTCCTTGGCTTTTATCATGCTAATATTTGCAGAAAATATTCAATAAAGTGA<br>GTCTTTGCACTTGAGATCTCTGTCTTTCTTACTAAATGGTAGTAATCAGTTGTTTTTCCAGTTACCTGGGTTTCTC<br>TTCTAAAGAAGTTAAATGTTTAGTTGCCCTGAAATCCACCACACTTAAAGGATAAATAAAACCCTCCACTTGCCCT |

TABLE B-continued

Further Sequences

| Sequence ID | Sequence info | Sequence |
|---|---|---|
| | | GGTTGGCTGTCCACTACATGGCAGTCCTTTCTAAGGTTCACGAGTACTATTCATGGCTTATTTCTCTGGGCCATG<br>GTAGGTTTGAGGAGGCATACTTCCTAGTTTTCTTCCCCTAAGTCGTCAAAGTCCTGAAGGGGGACAGTCTTTACA<br>AGCACATGTTCTGTAATCTGATTCAACCTACCCAGTAAACTTGGCGAAGCAAAGTAGAATCATTATCACAGGAAG<br>CAAAGGCAACCTAAATGTGCAAGCAATAGGAAAATGTGGAAGCCCATCATAGTACTTGGACTTCATCTGCTTTTG<br>TGCCTTCACTAAGTTTTTAAACATGAGCTGGCTCCTATCTGCCATTGGCAAGGCTGGGCACTACCCACAACCTAC<br>TTCAAGGACCTCTATACCGTGAGATTACACACATACATCAAAATTTGGGAAAAGTTCTACCAAGCTGAGAGCTGA<br>TCACCCCACTCTTAGGTGCTTATCTCTGTACACCAGAAACCTTAAGAAGCAACCAGTATTGAGAGAC |
| SEQ ID NO: 81 | λ5 transgene-predicted spliced coding sequence | ATGGACATGAGGGTCCCCGCTCAGCTCCTGGGGCTCCTGCTGCTCTGGCTCCCAGGTGCCAAATGTGTGTTTGG<br>CAGCGGGACCCAGCTCACCGTTTTAAGTCAGCCCAAGGCCACCCCCTCGGTCACTCTGTTCCCGCCGTCCTCTGA<br>GGAGCTCCAAGCCAACAAGGCTACACTGGTGTGTCTCATGAATGACTTTTATCCGGGAATCTTGACGGTGACCTG<br>GAAGGCAGATGGTACCCCCATCACCCAGGGCGTGGAGATGACCACGCCCTCCAAACAGAGCAACAACAAGTACGC<br>GGCCAGCAGCTACCTGAGCCTGACGCCCGAGCAGTGGAGGTCCCGCAGAAGCTACAGCTGCCAGGTCATGCACG<br>AAGGGAGCACCGTGGAGAAGACGGTGGCCCCTGCAGAATGTTCATAG |
| SEQ ID NO: 82 | λ5 transgene-predicted protein | MDMRVPAQLLGLLLLWLPGAKCVFGSGTQLTVLSQPKATPSVTLFPPSSEELQANKATLVCLMNDFYPGILTVTWKA<br>DGTPITQGVEMTTPSKQSNNKYAASSYLSLTPEQWRSRRSYSCQVMHEGSTVEKTVAPAECS. |
| SEQ ID NO: 83 | Vκ3-2 fragment locus-predicted spliced coding sequence | ATGGAGAAAGACACACTCCTGCTATGGGTCCTGCTTCTCTGGGTTCCAGGTTCCACAGGTGACATTGTGCTGAAA<br>CGGGCTGATGCTGCACCAACTGTATCCATCTTCCCACCATCCAGTGAGCAGTTAACATCTGGAGGTGCCTCAGTC<br>GTGTGCTTCTTGAACAACTTCTACCCCAAAGACATCAATGTCAAGTGGAAGATTGATGGCAGTGAACGACAAAAT<br>GGCGTCCTGAACAGTTGGACTGATCAGGACAGCAAAGACAGCACCTACGGCATGAGCAGCACCCTCACGTTGACC<br>AAGGACGAGTATGAACGACATAACAGCTATACCTGTGAGGCCACTCACAAGACATCAACTTCACCCATTGTCAAG<br>AGCTTCAACAGGAATGAGTGTTAG |
| SEQ ID NO: 84 | Vκ3-2 fragment locus-predicted protein | MEKDTLLLWVLLLWVPGSTGDIVLKRADAAPTVSIFPPSSEQLTSGGASVVCFLNNFYPKDINVKWKIDGSERQNGVL<br>NSWTDQDSKDSTYGMSSTLTLTKDEYERHNSYTCEATHKTSTSPIVKSFNRNEC. |
| SEQ ID NO: 85 | Vκ3-4 fragment locus-predicted spliced coding sequence | ATGGAGACAGACACAATCCTGCTATGGGTGCTGCTGCTCTGGGTTCCAGGCTCCACTGGTGACATTGTGCTGAAA<br>CGGGCTGATGCTGCACCAACTGTATCCATCTTCCCACCATCCAGTGAGCAGTTAACATCTGGAGGTGCCTCAGTC<br>GTGTGCTTCTTGAACAACTTCTACCCCAAAGACATCAATGTCAAGTGGAAGATTGATGGCAGTGAACGACAAAAT<br>GGCGTCCTGAACAGTTGGACTGATCAGGACAGCAAAGACAGCACCTACGGCATGAGCAGCACCCTCACGTTGACC<br>AAGGACGAGTATGAACGACATAACAGCTATACCTGTGAGGCCACTCACAAGACATCAACTTCACCCATTGTCAAG<br>AGCTTCAACAGGAATGAGTGTTAG |
| SEQ ID NO: 86 | Vκ3-4 fragment locus-predicted protein | METDTILLWVLLLWVPGSTGDIVLKRADAAPTVSIFPPSSEQLTSGGASVVCFLNNFYPKDINVKWKIDGSERQNGVL<br>NSWTDQDSKDSTYGMSSTLTLTKDEYERHNSYTCEATHKTSTSPIVKSFNRNEC. |
| SEQ ID NO: 87 | Vκ6-17 fragment locus-predicted spliced coding sequence | ATGGAGTCACAGATTCAGGTCTTTGTATTCGTGTTTCTCTGGTTGTCTGGTGTTGACGGAGACATTGTGCTGAAA<br>CGGGCTGATGCTGCACCAACTGTATCCATCTTCCCACCATCCAGTGAGCAGTTAACATCTGGAGGTGCCTCAGTC<br>GTGTGCTTCTTGAACAACTTCTACCCCAAAGACATCAATGTCAAGTGGAAGATTGATGGCAGTGAACGACAAAAT<br>GGCGTCCTGAACAGTTGGACTGATCAGGACAGCAAAGACAGCACCTACGGCATGAGCAGCACCCTCACGTTGACC<br>AAGGACGAGTATGAACGACATAACAGCTATACCTGTGAGGCCACTCACAAGACATCAACTTCACCCATTGTCAAG<br>AGCTTCAACAGGAATGAGTGTTAG |
| SEQ ID NO: 88 | Vκ6-17 fragment locus-predicted protein | MESQIQVFVFVFLWLSGVDGDIVLKRADAAPTVSIFPPSSEQLTSGGASVVCFLNNFYPKDINVKWKIDGSERQNGVL<br>NSWTDQDSKDSTYGMSSTLTLTKDEYERHNSYTCEATHKTSTSPIVKSFNRNEC. |

TABLE B-continued

| Further Sequences | | |
|---|---|---|
| Sequence ID | Sequence info | Sequence |
| SEQ ID NO: 89 | Vκ10-96 fragment locus-predicted spliced coding sequence | ATGATGTCCTCTGCTCAGTTCCTTGGTCTCCTGTTGCTCTGTTTTCAAGGTACCAGATGTGATATCCAGCTGAAA<br>CGGGCTGATGCTGCACCAACTGTATCCATCTTCCCACCATCCAGTGAGCAGTTAACATCTGGAGGTGCCTCAGTC<br>GTGTGCTTCTTGAACAACTTCTACCCCAAAGACATCAATGTCAAGTGGAAGATTGATGGCAGTGAACGACAAAAT<br>GGCGTCCTGAACAGTTGGACTGATCAGGACAGCAAAGACAGCACCTACGGCATGAGCAGCACCCTCACGTTGACC<br>AAGGACGAGTATGAACGACATAACAGCTATACCTGTGAGGCCACTCACAAGACATCAACTTCACCCATTGTCAAG<br>AGCTTCAACAGGAATGAGTGTTAG |
| SEQ ID NO: 90 | Vκ10-96 fragment locus-predicted protein | MMSSAQFLGLLLLCFQGTRCDIQLKRADAAPTVSIFPPSSEQLTSGGASVVCFLNNFYPKDINVKWKIDGSERQNGVL<br>NSWTDQDSKDSTYGMSSTLTLTKDEYERHNSYTCEATHKTSTSPIVKSFNRNEC. |
| SEQ ID NO: 91 | Vκ6-17 full transgene: promoter and leader, including intron and J5 fragment | GGGTTAGGTGCATCGATATCTCTGAATGAACACAGACCCAGCAGTACTCTTCTGTATGTGTGTTGGTGGCATCAT<br>ATCAGCTGGTGTATGCTGCCTGTTTGGTGATCCAGTGTTTGAGAGATCTCGGGGGTCCAGATTAATTGAGACAG<br>TTGGACTTCCTACAGGGTCACTGTCCTCCTCAACTTCTTTCAGTCTTTCCCTAATTCAACAACAGGAGTCAGCTGC<br>TTCTGTCCATTGGTTGGGTGCAAATACCTGCATCTAGCTCAACTGCTTGTTGTATCTTCTAGAGTGAGGTCATGC<br>TAGGTCCCTTTCTGTGAGTTCTTCATAGCCTCAATGATAGTGTCAGGCCTTGTGGCTGCCACTTGAGCTGGATTC<br>CACTTTGGACCTGTCGCTGGACCTTCTTTTCTTCAGGCTCCCCTCCATTTCCATCCCTGTAATTCTTTCAGACAGG<br>AACAATTATGGGTCAGAGTTGTAACTGTAGGATGGCACCCCCTCCCTCATTTGATGCCCTGTCTTCCTGCTGGAG<br>GTGGGCTCTAGAAGTTCCCTCTCCCTACTGTTGGGCATTTTATCCCTTTGATTCCTGAGAGTCTCTCACCTGCAA<br>GGTCTCTGGTGCATTCTGGAGGGTCCTCCCAACCTCCTACCTCCTGAGGTTGCCTGCTTCCATTCTTTCAGCTGG<br>CCCTCAGTGCTTCAGTCCTTTACCCTCACCCAATATCTGATTTTGATGGAAGCCTATCATGAGAGCATCTATACAC<br>TTGTGGTTTCAGAGCTTTAAATTGGTCCTTGAGCTTCTATTTTGACTTCCTTCCCAGTGATTACTTCCTGTCTTTG<br>GTTGTACTTTTGACTGTTTATTTAACCTGGATACTCTCAAACCGCTGTGTAATTTACTTCCTTATTTGATGACTCC<br>TTTGCATAGATCCCTAGAGGCCAGCCCAGCTGCTCATGATTTATAAACCAGGTCTTTGCAGTGAGATATGAAATG<br>CATCACACCAGCATGGGCATCAAAATGGAGTCACAGATTCAGGTCTTTGTATTCGTGTTTCTCTGGTTGTCTGGT<br>GAGACATGTAAAACTTTTATAATATCTTAAAAGTAATTCATTTAAATATCTATTTCCTATAAGAAGCCAATATTAG<br>GCAGACAATGCTATTAGATAAGACATTTTGGATTCTAACATTTGTATCATGAAGTCTTTGTATGTGTAAGTGTATA<br>CACATTATCTGTTTCTGTTTGCAGGTGTTGACGGAGACATTGTGCTGAAAC |
| SEQ ID NO: 92 | Vκ6-17 full targeting vector insert including homology arms | GCTGAATCTTGAATGACAGCTCAAGGGATAGGGAGGACAGGGTGTTCAGAAGCAGAGAAGATGCCTTGTAAATG<br>TGGAAGGCTGTGGCAGGATTGGAAGGACTTTGGGGTGGTAGGAAGGGGATGGGAATGGGTGGTTACAAGAGAA<br>ACAAGACTGTAGTAAATAAAGCTGAAACTCAAAGCAAGCTTTCAGCATCTTTAATTGGAGACACAAACTTCAAAGG<br>TATCATGAATGTGGTTGATCTTGGTGAAAGTTGAGCTTCACCTGTCCTAACAACAGACCAATCCATGAGTGAAAG<br>CTTATCTTTCTCCTTTATTAATGGTTGCTGTTGTATCCATAACTCAATTCCAAAGGATATGAACCTTAACATATAG<br>ATATAATTTTGTGTACCTTCTATGAAACAGCATTAAAGCAAAGAAGTTCAAATAGAAAGACTGGCTTAGTTATTAT<br>TAACTAAGAGATGCTAGTGAGTTCTAAATTAATACCATTTAAAATTTATAATTTGCAGAATTACCACCACCACCAC<br>CACTCAGCCCAGGAAAAGTTACAAAGAACTGGCTATCCAATTTGTTTGTTTTCCTCCTTTTTAGAGTTCTTTTATT<br>TATGTGTGAGTGAATGCCATGTACTTATGGATGCAGAGGCTGTCAGATTCCTTGCAGCTGGAGTAATAGACAGTT<br>GTGAGCTACTTATAGTACTAGAACTAAGATCCTATGGAAGAGCAGCGAGTGCCACTAACTGCTGAGCCACCTCTC<br>CAGCCCATTTCTTTATTTTTCAATGAACAAATAATAAGCAGTCCTATGTGACATGCTTCTAAAGCAAAAGATATAA<br>TATTTAGTATTATATACATTAATAATAAAATACATTATCTTCTAAGAATTGAAGTCTCAACTATGAAAATCAGCAG<br>TTCTCTGTCAGAGAAGGGGTTAGGTGCATCGATATCTCTGAATGAACACAGACCCAGCAGTACTCTTCTGTATGT<br>GTGTTGGTGGCATCATATCAGCTGGTGTATGCTGCCTGTTTGGTGATCCAGTGTTTGAGAGATCTCGGGGGTCC<br>AGATTAATTGAGACAGTTGGACTTCCTACAGGGTCACTGTCCTCCTCAACTTCTTTCAGTCTTTCCCTAATTCAAC<br>AACAGGAGTCAGCTGCTTCTGTCCATTGGTTGGGTGCAAATACCTGCATCTAGCTCAACTGCTTGTTGTATCTTC<br>TAGAGTGAGGTCATGCTAGGTCCCTTTCTGTGAGTTCTTCATAGCCTCAATGATAGTGTCAGGCCTTGTGGCTGC<br>CACTTGAGCTGGATTCCACTTTGGACCTGTCGCTGGACCTTCTTTTCTTCAGGCTCCCCTCCATTTCCATCCCTGT<br>AATTCTTTCAGACAGGAACAATTATGGGTCAGAGTTGTAACTGTAGGATGGCACCCCCTCCCTCATTTGATGCCC<br>TGTCTTCCTGCTGGAGGTGGGCTCTAGAAGTTCCCTCTCCCTACTGTTGGGCATTTTATCCCTTTGATTCCTGAG<br>AGTCTCTCACCTGCAAGGTCTCTGGTGCATTCTGGAGGGTCCTCCCAACCTCCTACCTCCTGAGGTTGCCTGCTT |

TABLE B-continued

| Further Sequences | | |
|---|---|---|
| Sequence ID | Sequence info | Sequence |
| | | CCATTCTTTCAGCTGGCCCTCAGTGCTTCAGTCCTTTACCCTCACCCAATATCTGATTTTGATGGAAGCCTATCAT GAGAGCATCTATACACTTGTGGTTTCAGAGCTTTAAATTGGTCCTTGAGCTTCTATTTTGACTTCCTTCCCAGTGA TTACTTCCTGTCTTTGGTTGTACTTTTGACTGTTTATTTAACCTGGATACTCTCAAACCGCTGTGTAATTTACTTC CTTATTTGATGACTCCTTTGCATAGATCCCTAGAGGCCAGCCCAGCTGCTCATGATTTATAAACCAGGTCTTTGCA GTGAGATATGAAATGCATCACACCAGCATGGGCATCAAAATGGAGTCACAGATTCAGGTCTTTGTATTCGTGTTT CTCTGGTTGTCTGGTGAGACATGTAAAACTTTTATAATATCTTAAAAGTAATTCATTTAAATATCTATTTCCTATA AGAAGCCAATATTAGGCAGACAATGCTATTAGATAAGACATTTTGGATTCTAACATTTGTATCATGAAGTCTTTGT ATGTGTAAGTGTATACACATTATCTGTTTCTGTTTGCAGGTGTTGACGGAGACATTGTGCTGAAACGTAAGTACA CTTTTCTCATCTTTTTTTATGTGTAAGACACAGGTTTTCATGTTAGGAGTTAAAGTCAGTTCAGAAAATCTTGAGA AAATGGAGAGGGCTCATTATCAGTTGACGTGGCATACAGTGTCAGATTTTCTGTTTATCAAGCTAGTGAGATTAG GGGCAAAAAGAGGCTTTAGTTGAGAGGAAAGTAATTAATACTATGGTCACCATCCAAGAGATTGGATCGGAGAAT AAGCATGAGTAGTTATTGAGATCTGGGTCTGACTGCAGGTAGCGTGGTCTTCTAGACGTTTAAGTGGGAGATTT GGAGGGGATGAGGAATGAAGGAACTTCAGGATAGAAAAGGGCTGAAGTCAAGTTCAGCTCCTAAAATGGATGTG GGAGCAAACTTTGAAGATAAACTGAATGACCCAGAGGATGAAACAGCGCAGATCAAAGAGGGGCCTGGAGCTCT GAGAAGAGAAGGAGACTCATCCGTGTTGAGTTTCCACAAGTACTGTCTTGAGTTTTGCAATAAAAGTGGGATAGC AGAGTTGAGTGAGCCGTAGGCTGAGTTCTCTCTTTTGTCTCCTAAGTTTTTATGACTACAAAAATCAGTAGTATG TCCTGAAATAATCATTAAGCTGTTTGAAAGTATGACTGCTTGCCATGTAGATACCATGGCTTGCTGAATAATCAG AAGAGGTGTGACTCTTATTCTAAAATTTGTCACAAAATGTCAAAATGAGAGACTCTGTAGGAACGAGTCCTTGAC AGACAGCTCAAGGGGTTTTTTTCCTTTGTCTCATTTCTACATGAAAGTAAATTTGAAATGATCTTTTTTATTATAA GAGTAGAAATACAGTTGGGTTTGAACTATATGTTTTAATGGCCACGGTTTTGTAAGACATTTGGTCCTTTGTTTT CCCAGTTATTACTCGATTGTAATTTTATATCGCCAGCAATGGACTGAAACGGTCCGCAACCTCTTCTTTACAACTG GGTGACCTCGCGGCTG |
| SEQ ID NO: 93 | Vκ10-96 full transgene: promoter and leader, including intron and J5 fragment | ACAGTGGGTAATAGTCTCTGGCAGGACAGCGCTGATGATCATGAGGGCTTCCTCTCAGCAATTAAAGACTACAAT GGGAACATATCCATAACACAGTGATCAGTGTTGACTGGTATACTAGGGATGTCCTTTTACACTGTGCTTAATTTT GTTGGGATTCATTATTTATCCAATCGTAGGAACCAAATGTAACATCCAGAGTACCCAGTAGCAGTGTTTTCTGTT ATAGTATTCAAGGATATCTTCACTAGTCAAACGTGTATGCTGAAGAATTGTGGTAAATATTAGCAAGTACAAGAA AAGTGTTTAAGTAGATGATCCCAAACTGAGCAAAGGGTACATCCCATTATTCCCAAGAGAATAAATATACTTTCAT ATTCATGTGGACAAAGAATTCCTTGTGATATAGGTTGCTGGGATCAGGAATTATATGTGCCCATATTTTGCATTT ACTCATTATACTGTATTAAACACGGCTAATTCTGTTAAATCTTACTTTTTAATTCACCAAAAAGAGTCCTGATAAA TTATACTCTTAATTAAAAGACATGATTACTCTAATCACACAAATGGTTCACAAGGATAATATGTAGTATTTTAAAA GCAATTGAATTATTAATCTGATTAATAATCTCCTGTTTGAATAATATTCCTAGAAACAAGATTGTTTTTTATATTAC ACCCAATGTATATTTGATATATAGTATTACAATTAGAGCTCATGTATAGTAGAATTTTTCAAATAACCTTCAAAAT GACATCTGTAATTTTAAAACCTTAAAAATGAAGTGTGATCTCCAAAGCCATATGTTCACTCTGACCTTGGGCAAAG AGGGGTCACTGTGCTTGTGCTAAGTCCTGAGAAGAGTTAGCCTTGCAGCTGTGCTCAGCCCTAAATAGTTCCCAA AAATTTGCATGCTCTCACTTCCTATCTTTGGGTACTTTTTCATATACCAGTCAGATTGTGAGCCATTGTAATTGAA GTCAAGACTCAGCCTGGACATGATGTCCTCTGCTCAGTTCCTTGGTCTCCTGTTGCTCTGTTTTCAAGGTAAAAT TTACTACAATGGGAATTTTGCTGTTGCACAGTGATTCTTGTTGACTGGAATTTTGGAGGGGTCCTTTCTTTTCCT GCTTAACTCTGTGGGTATTTATTATGTCTCCACTCCTAGGTACCAGATGTGATATCCAGCTGAAAC |
| SEQ ID NO: 94 | Vκ10-96 full targeting vector insert including homology arms | GCTGAATCTTGAATGACAGCTCAAGGGATAGGGAGGACAGGGTGTTCAGAAGCAGAGAAGATGCCTTGTAAATG TGGAAGGCTGTGGCAGGATTGGAAGGACTTTGGGGTGGTAGGAAGGGGATGGGAATGGGTGGTTACAAGAGAA ACAAGACTGTAGTAAATAAAGCTGAAACTCAAAGCAAGCTTTCAGCATCTTTAATTGGAGACACAAACTTCAAAGG TATCATGAATGTGGTTGATCTTGGTGAAAGTTGAGCTTCACCTGTCCTAACAACAGACCAATCCATGAGTGAAAG CTTATCTTTCTCCTTTATTAATGGTTGCTGTTGTATCCATAACTCAATTCCAAAGGATATGAACCTTAACATATAG ATATAATTTTGTGTACCTTCTATGAAACAGCATTAAAGCAAAGAAGTTCAAATAGAAAGACTGGCTTAGTTATTAT TAACTAAGAGATGCTAGTGAGTTCTAAATTAATACCATTTAAAATTTATAATTTGCAGAATTACCACCACCACCAC CACTCAGCCCAGGAAAAGTTACAAAGAACTGGCTATCCAATTTGTTTGTTTTCCTCCTTTTTAGAGTTCTTTTATT TATGTGTGAGTGAATGCCATGTACTTATGGATGCAGAGGCTGTCAGATTCCTTGCAGCTGGAGTAATAGACAGTT |

TABLE B-continued

| Further Sequences | | |
|---|---|---|
| Sequence ID | Sequence info | Sequence |
| | | GTGAGCTACTTATAGTACTAGAACTAAGATCCTATGGAAGAGCAGCGAGTGCCACTAACTGCTGAGCCACCTCTC<br>CAGCCCATTTCTTTATTTTTCAATGAACAAATAATAAGCAGTCCTATGTGACATGCTTCTAAAGCAAAAGATATAA<br>TATTTAGTATTATATACATTAATAATAAAATACATTATCTTCTAAGAATTGAAGTCTCAACTATGAAAATCAGCAG<br>TTCTCTGTCAGAGAAGACAGTGGGTAATAGTCTCTGGCAGGACAGCGCTGATGATCATGAGGGCTTCCTCTCAGC<br>AATTAAAGACTACAATGGGAACATATCCATAACACAGTGATCAGTGTTGACTGGTATACTAGGGATGTCCTTTTA<br>CACTGTGCTTAATTTTGTTGGGATTCATTATTTATCCAATCGTAGGAACCAAATGTAACATCCAGAGTACCCAGTA<br>GCAGTGTTTTCTGTTATAGTATTCAAGGATATCTTCACTAGTCAAACGTGTATGCTGAAGAATTGTGGTAAATAT<br>TAGCAAGTACAAGAAAAGTGTTTAAGTAGATGATCCCAAACTGAGCAAAGGGTACATCCCATTATTCCCAAGAGA<br>ATAAATATACTTTCATATTCATGTGGACAAAGAATTCCTTGTGATATAGGTTGCTGGGATCAGGAATTATATGTG<br>CCCATATTTTGCATTTACTCATTATACTGTATTAAACACGGCTAATTCTGTTAAATCTTACTTTTTAATTCACCAAA<br>AAGAGTCCTGATAAATTATACTCTTAATTAAAAGACATGATTACTCTAATCACACAAATGGTTCACAAGGATAATA<br>TGTAGTATTTTAAAAGCAATTGAATTATTAATCTGATTAATAATCTCCTGTTTGAATAATATTCCTAGAAACAAGA<br>TTGTTTTTTATATTACACCCAATGTATATTTGATATATAGTATTACAATTAGAGCTCATGTATAGTAGAATTTTTC<br>AAATAACCTTCAAAATGACATCTGTAATTTTAAAACCTTAAAAATGAAGTGTGATCTCCAAAGCCATATGTTCACT<br>CTGACCTTGGGCAAAGAGGGGTCACTGTGCTTGTGCTAAGTCCTGAGAAGAGTTAGCCTTGCAGCTGTGCTCAG<br>CCCTAAATAGTTCCCAAAAAATTTGCATGCTCTCACTTCCTATCTTTGGGTACTTTTTCATATACCAGTCAGATTGT<br>GAGCCATTGTAATTGAAGTCAAGACTCAGCCTGGACATGATGTCCTCTGCTCAGTTCCTTGGTCTCCTGTTGCTC<br>TGTTTTCAAGGTAAAATTTACTACAATGGGAATTTTGCTGTTGCACAGTGATTCTTGTTGACTGGAATTTTGGAG<br>GGGTCCTTTCTTTTCCTGCTTAACTCTGTGGGTATTTATTATGTCTCCACTCCTAGGTACCAGATGTGATATCCAG<br>CTGAAACGTAAGTACACTTTTCTCATCTTTTTTTATGTGTAAGACACAGGTTTTCATGTTAGGAGTTAAAGTCAGT<br>TCAGAAAATCTTGAGAAAATGGAGAGGGCTCATTATCAGTTGACGTGGCATACAGTGTCAGATTTTCTGTTTATC<br>AAGCTAGTGAGATTAGGGGCAAAAAGAGGCTTTAGTTGAGAGGAAAGTAATTAATACTATGGTCACCATCCAAGA<br>GATTGGATCGGAGAATAAGCATGAGTAGTTATTGAGATCTGGGTCTGACTGCAGGTAGCGTGGTCTTCTAGACG<br>TTTAAGTGGGAGATTTGGAGGGGATGAGGAATGAAGGAACTTCAGGATAGAAAAGGGCTGAAGTCAAGTTCAGC<br>TCCTAAAATGGATGTGGGAGCAAACTTTGAAGATAAACTGAATGACCCAGAGGATGAAACAGCGCAGATCAAAGA<br>GGGGCCTGGAGCTCTGAGAAGAGAAGGAGACTCATCCGTGTTGAGTTTCCACAAGTACTGTCTTGAGTTTTGCA<br>ATAAAAGTGGGATAGCAGAGTTGAGTGAGCCGTAGGCTGAGTTCTCTCTTTTGTCTCCTAAGTTTTTATGACTAC<br>AAAAATCAGTAGTATGTCCTGAAATAATCATTAAGCTGTTTGAAAGTATGACTGCTTGCCATGTAGATACCATGG<br>CTTGCTGAATAATCAGAAGAGGTGTGACTCTTATTCTAAAATTTGTCACAAAATGTCAAAATGAGAGACTCTGTA<br>GGAACGAGTCCTTGACAGACAGCTCAAGGGGTTTTTTTCCTTTGTCTCATTTCTACATGAAAGTAAATTTGAAAT<br>GATCTTTTTTATTATAAGAGTAGAAATACAGTTGGGTTTGAACTATATGTTTTAATGGCCACGGTTTTGTAAGACA<br>TTTGGTCCTTTGTTTTCCCAGTTATTACTCGATTGTAATTTTATATCGCCAGCAATGGACTGAAACGGTCCGCAAC<br>CTCTTCTTTACAACTGGGTGACCTCGCGGCTG |
| SEQ ID NO: 95 | Primer HCP428 | GCTCTGGCTCCCAGGAACTG |
| SEQ ID NO: 96 | Primer HCP431 | GTCCTGCTCTGTGACACTCT |
| SEQ ID NO: 97 | Primer HCP446 | TTTGTGCAGGAGTCAGACCCAG |
| SEQ ID NO: 98 | Primer HCP451 | AAAAGGGTCAGAGGCCAAAGGAT |
| SEQ ID NO: 99 | Primer HCP428 | GCTCTGGCTCCCAGGAACTG |

TABLE B-continued

| Further Sequences | | |
|---|---|---|
| Sequence ID | Sequence info | Sequence |
| SEQ ID NO: 100 | Mouse λ5 gene fragment, truncated to include just the J-segment-like and C-segment-like domains | GTCTTTGGTGGTGGGACCCAGCTCACAATCCTAGGTCAGCCCAAGTCTGACCCCTTGGTCACTCTGTTCCTGCCT TCCTTAAAGAATCTTCAGCCAACAAGGCCACACGTAGTGTGTTTGGTGAGCGAATTCTACCCAGGTACTTTGGTG GTGGACTGGAAGGTAGATGGGGTCCCTGTCACTCAGGGTGTAGAGACAACCCAACCCTCCAAACAGACCAACAAC AAATACATGGTCAGCAGCTACCTGACACTGATATCTGACCAGTGGATGCCTCACAGTAGATACAGCTGCCGGGTC ACTCATGAAGGAAACACTGTGGAGAAGAGTGTGTCACCTGCTGAGTGTTCTTAG |
| SEQ ID NO: 101 | Mouse λ5 gene fragment, truncated to include just the J-segment-like and C-segment-like domains-translated | VFGGGTQLTILGQPKSDPLVTLFLPSLKNLQANKATLVCLVSEFYPGTLVVDWKVDGVPVTQGVETTQPSKQTNNKY MVSSYLTLISDQWMPHSRYSCRVTHEGNTVEKSVSPAECS |

TABLE C

Example Human Alleles for Inclusion in loci of mice of the invention One, more or all of the following gene segments in (a) and (b) may be comprised by the heavy and light (kappa or lambda) loci respectively.

(a) Heavy Chain Locus

| Constant element | Allele |
|---|---|
| IGHA1 | |
| IGHA2 | 02 |
| IGHD | |
| IGHE | 04 |
| IGHG1 | 02 |
| IGHG2 | 06 |
| IGHG3 | 10 |
| IGHG4 | |
| IGHM | 03 |

| Variable element | Allele |
|---|---|
| JH6 | 02 |
| JH5 | 02 |
| JH4 | 02 |
| JH3 | 02 |
| JH2 | 01 |
| JH1 | 01 |
| D7-27 | 02 |
| D1-26 | 01 |
| D6-25 | 01 |
| D5-24 | 01 |
| D4-23 | 01 |
| D3-22 | 01 |
| D2-21 | 02 |
| D1-20 | 01 |
| D6-19 | 01 |
| D5-18 | 01 |
| D4-17 | 01 |
| D3-16 | 02 |
| D2-15 | 01 |
| D1-14 | 01 |
| D6-13 | 01 |
| D5-12 | 01 |
| D4-11 | 01 |
| D3-10 | 01 |
| D3-9 | 01 |
| D2-8 | 01 |
| D1-7 | 01 |
| D6-6 | 01 |
| D5-5 | 01 |
| D4-4 | 01 |
| D3-3 | 01 |
| D2-2 | 02 |
| D1-1 | 01 |

TABLE C-continued

Example Human Alleles for Inclusion in loci of mice of the invention One, more or all of the following gene segments in (a) and (b) may be comprised by the heavy and light (kappa or lambda) loci respectively.

| | |
|---|---|
| VH6-1 | 01 |
| VH1-2 | 02 |
| VH1-3 | 01 |
| VH4-4 | 02 |
| VH7-4 | 01 |
| VH2-5 | 10 |
| VH3-7 | 01 |
| VH1-8 | 01 |
| VH3-9 | 01 |
| VH3-11 | 01 |
| VH3-13 | 01 |
| VH3-15 | 01 |
| VH1-18 | 01 |
| VH3-20 | 01 or d01 |
| VH3-21 | 03 |
| VH3-23 | 04 |
| VH1-24 | 01 or d01 |
| VH2-26 | 01 or d01 |
| VH4-28 | 05 |
| VH3-30 | 18 |
| VH4-31 | 03 |
| VH3-33 | 01 |
| VH4-34 | 01 |
| VH4-39 | 01 |
| VH3-43 | 01 |
| VH1-45 | 02 |
| VH1-46 | 01 |
| VH3-48 | 01 |
| VH3-49 | 05 |
| VH5-51 | 01 |
| VH3-53 | 01 |
| VH1-58 | 01 |
| VH4-59 | 01 |
| VH4-61 | 01 |
| VH3-64 | 02 |
| VH3-66 | 03 |
| VH1-69 | 12 |
| VH2-70 | 04 |
| VH3-72 | 01 |
| VH3-73 | 02 |
| VH3-74 | 01 |

(b) Kappa constant domain shield

| Constant element | Allele |
|---|---|
| IGKC | 01 |

The invention claimed is:

1. A non-human animal or non-human animal cell having a genome comprising:

a plurality of human variable region gene segments capable of rearrangement to encode a variable domain, upstream of DNA encoding an immunoglobulin constant region comprising a CH1 domain, and (i) a gene encoding a CL domain which lacks functional expression of variable region gene segments, or (ii) a gene encoding the immunoglobulin domain of λ5.

2. The non-human animal or non-human animal cell of claim 1, wherein the non-human animal or non-human animal cell is a non-human animal cell, wherein the non-human animal cell is an embryonic stem cell or a zygote.

3. The non-human animal or non-human animal cell of claim 1, wherein the plurality of variable region gene segments comprises one or more V gene segments, one or more D gene segments, and one or more J gene segments capable of rearrangement to encode a VH domain.

4. The non-human animal or non-human animal cell of claim 3, wherein the one or more V gene segments, one or more D gene segments and one or more J gene segments comprise multiple human V gene segments, multiple human D gene segments and multiple human J gene segments.

5. The non-human animal or non-human animal cell of claim 1, wherein the plurality of variable region gene segments are at the endogenous immunoglobulin heavy chain locus.

6. The non-human animal or non-human animal cell of claim 1, wherein the CL domain is a human CL domain.

7. The non-human animal or non-human animal cell of claim 6, wherein the human CL domain is human Ck.

8. The non-human animal or non-human animal cell of claim 1, wherein the gene encoding the CL domain comprises an exon encoding a light chain variable region leader sequence and an exon encoding the CL domain, separated by an intron comprising a J-C intron enhancer element, wherein the encoded CL domain comprises an N-terminal signal peptide.

9. The non-human animal or non-human animal cell of claim 8, wherein the gene encoding the CL domain comprises an exon encoding a human Vκ leader sequence and an exon encoding a human Cκ domain, separated by an intron comprising a human J-CK intron enhancer element, wherein the encoded CL domain is a human Cκ domain comprising an N-terminal signal peptide.

10. The non-human animal or non-human animal cell of claim 9, wherein the human Cκ domain comprises SEQ ID NO: 4 or SEQ ID NO: 6.

11. The non-human animal or non-human animal cell of claim 10, wherein transcription of the gene encoding the CL domain produces nucleic acid comprising SEQ ID NO: 5.

12. The non-human animal or non-human animal cell of claim 11, wherein the gene encoding the CL domain is at an endogenous immunoglobulin light chain locus of the animal, and/or wherein the CL domain is at the endogenous Igκ locus.

13. The non-human animal or non-human animal cell of claim 1, wherein expression of endogenous immunoglobulin light chain variable region gene segments is inactivated, and/or expression of endogenous immunoglobulin light chains is inactivated.

14. The non-human animal or non-human animal cell of claim 1, wherein expression of endogenous immunoglobulin heavy chain variable region gene segments is inactivated, and/or expression of endogenous immunoglobulin heavy chains is inactivated.

15. The non-human animal or non-human animal cell of claim 1, wherein the animal is a mouse or a rat.

16. The non-human animal or non-human animal cell of claim 15, wherein the animal is a mouse, wherein a plurality of human variable region gene segments capable of rearrangement to encode a human variable domain, upstream of human DNA encoding an immunoglobulin constant region comprising a human CH1 domain, are inserted at the endogenous immunoglobulin heavy chain locus on mouse chromosome 12, and expression of mouse heavy chains is inactivated.

17. The non-human animal or non-human animal cell of claim 16, wherein a gene encoding a human Cκ domain is inserted at the endogenous Igκ light chain locus on mouse chromosome 6, and expression of mouse Igκ light chains is inactivated.

18. The non-human animal or non-human animal cell of claim 1, wherein the non-human animal or non-human animal cell is a non-human animal, wherein a B-lymphocyte of the animal expresses antibodies comprising an unpaired variable domain for binding a target antigen, wherein the unpaired variable domain is linked to a constant region, and wherein the constant region comprises a CH1 domain and a shield domain which binds the CH1 domain.

19. The non-human animal of claim 18, wherein, upon immunogenic stimulation, at least 50% of the antibody-expressing B-lymphocytes in the animal express antibodies comprising an unpaired variable domain for binding a target antigen, wherein the unpaired variable domain is linked to a constant region, wherein the constant region comprises a CH1 domain and a shield domain which binds the CH1 domain.

20. A method of generating a non-human animal comprising B-lymphocytes expressing an antibody comprising an unpaired human VH domain for a binding antigen, comprising:

(a) engineering the genome of a non-human animal cell to comprise:

a plurality of human variable region gene segments capable of rearrangement to encode a variable domain, upstream of DNA encoding an immunoglobulin constant region comprising a CH1 domain, and (i) a gene encoding a CL domain which lacks functional expression of variable region gene segments, or (ii) a gene encoding the immunoglobulin domain of λ5, and (b) generating an animal from the cell or from a group of cells comprising the cell.

* * * * *